US008658666B2

(12) United States Patent
Rice et al.

(10) Patent No.: US 8,658,666 B2
(45) Date of Patent: *Feb. 25, 2014

(54) SUBSTITUTED IMIDAZOQUINOLINES AND IMIDAZONAPHTHYRIDINES

(75) Inventors: Michael J. Rice, Oakdale, MN (US); Chad A. Haraldson, Apple Valley, MN (US); John F. Gerster, Saint Paul, MN (US); Joshua R. Wurst, Saint Paul, MN (US); Philip D. Heppner, Forest Lake, MN (US); Bryon A. Merrill, River Falls, WI (US); Tushar A. Kshirsagar, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1458 days.

This patent is subject to a terminal disclaimer.

(21) Appl. No.: 11/884,191

(22) PCT Filed: Feb. 10, 2006

(86) PCT No.: PCT/US2006/004713
§ 371 (c)(1),
(2), (4) Date: Aug. 25, 2008

(87) PCT Pub. No.: WO2006/091394
PCT Pub. Date: Aug. 31, 2006

(65) Prior Publication Data
US 2009/0099161 A1  Apr. 16, 2009

Related U.S. Application Data

(60) Provisional application No. 60/652,239, filed on Feb. 11, 2005.

(51) Int. Cl.
C07D 487/06 (2006.01)
A61K 31/437 (2006.01)
C07D 471/06 (2006.01)

(52) U.S. Cl.
USPC ............................................. 514/290; 546/80

(58) Field of Classification Search
USPC ............................................. 546/80; 514/290
See application file for complete search history.

(56) References Cited

U.S. PATENT DOCUMENTS

| | | | |
|---|---|---|---|
| 3,314,941 A | | 4/1967 | Littell et al. |
| 3,698,348 A * | | 10/1972 | Morgan ........................ 114/245 |
| 4,689,338 A * | | 8/1987 | Gerster ........................ 514/293 |
| 4,698,348 A | | 10/1987 | Gerster |
| 4,929,624 A | | 5/1990 | Gerster et al. |
| 4,988,815 A | | 1/1991 | Andre et al. |
| 5,037,986 A | | 8/1991 | Gerster |
| 5,175,296 A | | 12/1992 | Gerster |
| 5,238,944 A | | 8/1993 | Wick et al. |
| 5,266,575 A | | 11/1993 | Gerster |
| 5,268,376 A * | | 12/1993 | Gester ........................ 514/293 |
| 5,346,905 A * | | 9/1994 | Gerster ........................ 514/293 |
| 5,352,784 A | | 10/1994 | Nikolaides et al. |
| 5,367,076 A | | 11/1994 | Gerster |
| 5,389,640 A * | | 2/1995 | Gerster et al. ................ 514/293 |
| 5,395,937 A | | 3/1995 | Nikolaides et al. |
| 5,444,065 A | | 8/1995 | Nikolaides et al. |
| 5,446,153 A | | 8/1995 | Lindstrom et al. |
| 5,482,936 A | | 1/1996 | Lindstrom |
| 5,494,916 A | | 2/1996 | Lindstrom et al. |
| 5,525,612 A * | | 6/1996 | Gerster ........................ 514/293 |
| 5,605,899 A * | | 2/1997 | Gerster et al. ............. 514/232.8 |
| 5,627,281 A | | 5/1997 | Nikolaides et al. |
| 5,644,063 A | | 7/1997 | Lindstrom et al. |
| 5,648,516 A | | 7/1997 | Nikolaides et al. |
| 5,693,811 A | | 12/1997 | Lindstrom |
| 5,714,608 A * | | 2/1998 | Gerster ........................ 546/82 |
| 5,741,908 A | | 4/1998 | Gerster et al. |
| 5,741,909 A * | | 4/1998 | Gerster et al. ................ 546/82 |
| 5,756,747 A | | 5/1998 | Gerster et al. |
| 5,886,006 A | | 3/1999 | Nikolaides et al. |
| 5,939,090 A | | 8/1999 | Beaurline et al. |
| 5,977,366 A * | | 11/1999 | Gerster et al. ................ 546/159 |
| 6,039,969 A | | 3/2000 | Tomai et al. |
| 6,069,149 A | | 5/2000 | Nanba et al. |
| 6,083,505 A | | 7/2000 | Miller et al. |
| 6,110,929 A | | 8/2000 | Gerster et al. |
| 6,194,425 B1 | | 2/2001 | Gerster et al. |
| 6,200,592 B1 | | 3/2001 | Tomai et al. |
| 6,245,776 B1 | | 6/2001 | Skwierczynski et al. |
| 6,331,539 B1 | | 12/2001 | Crooks et al. |
| 6,348,462 B1 * | | 2/2002 | Gerster et al. ............. 514/232.8 |

(Continued)

FOREIGN PATENT DOCUMENTS

EP  0385630 A2  9/1990
EP  0 394 026  10/1990

(Continued)

OTHER PUBLICATIONS

Federal Registry p. 1766, Federal Register / vol. 76, No. 27 / Wednesday, Feb. 9, 2011.*
Wozniak et al., "The Amination of 3-nitro-1, 5-napthyridines by Liquid Ammonia/Potassium Permanganate[1,2]. A New and Convenient Amination Method.", *Journal of the Royal Netherlands Chemical Society*, 102, pp. 511-513, Dec. 12, 1983.
Brennan et al., "Automated Bioassay of Interferons in Micro-test Plates,", *Biotechniques*, Jun./Jul. 78, 1983.
Testerman et al., "Cytokine Induction by the Immunomodulators Imiquimod and S-27609.",*Journal of Leukocyte Biology*, vol. 58, pp. 365-372, Sep. 1995.

(Continued)

Primary Examiner — Rita Desai

(57) ABSTRACT

Imidazoquinolines and imidazonaphthyridines with a substituent containing a functional group, e.g., an amide, sulfonamide, urea, or heterocyclyl group, at the 6, 7, 8, or 9-position, pharmaceutical compositions containing the compounds, intermediates, methods of making and methods of use of these compounds as immunomodulators, for inducing cytokine biosynthesis in animals and in the treatment of diseases including viral and neoplastic diseases are disclosed.

20 Claims, No Drawings

(56) References Cited

U.S. PATENT DOCUMENTS

| | | | |
|---|---|---|---|
| 6,365,166 B2 | 4/2002 | Beaurline et al. | |
| 6,376,669 B1 | 4/2002 | Rice et al. | |
| 6,440,992 B1 | 8/2002 | Gerster et al. | |
| 6,451,810 B1 * | 9/2002 | Coleman et al. | 514/293 |
| 6,486,168 B1 | 11/2002 | Skwierczynski et al. | |
| 6,514,985 B1 | 2/2003 | Gerster et al. | |
| 6,518,265 B1 | 2/2003 | Kato et al. | |
| 6,525,064 B1 | 2/2003 | Dellaria et al. | |
| 6,541,485 B1 | 4/2003 | Crooks et al. | |
| 6,545,016 B1 | 4/2003 | Dellaria et al. | |
| 6,545,017 B1 | 4/2003 | Dellaria et al. | |
| 6,558,951 B1 | 5/2003 | Tomai et al. | |
| 6,573,273 B1 | 6/2003 | Crooks et al. | |
| 6,610,319 B2 | 8/2003 | Tomai et al. | |
| 6,627,638 B2 | 9/2003 | Gerster et al. | |
| 6,627,640 B2 | 9/2003 | Gerster et al. | |
| 6,630,588 B2 | 10/2003 | Rice et al. | |
| 6,638,944 B2 | 10/2003 | Mickelson | |
| 6,656,938 B2 | 12/2003 | Crooks et al. | |
| 6,660,735 B2 | 12/2003 | Crooks et al. | |
| 6,660,747 B2 | 12/2003 | Crooks et al. | |
| 6,664,260 B2 | 12/2003 | Charles et al. | |
| 6,664,264 B2 | 12/2003 | Dellaria et al. | |
| 6,664,265 B2 | 12/2003 | Crooks et al. | |
| 6,667,312 B2 | 12/2003 | Bonk et al. | |
| 6,670,372 B2 | 12/2003 | Charles et al. | |
| 6,677,347 B2 | 1/2004 | Crooks et al. | |
| 6,677,348 B2 | 1/2004 | Heppner et al. | |
| 6,677,349 B1 | 1/2004 | Griesgraber | |
| 6,683,088 B2 | 1/2004 | Crooks et al. | |
| 6,696,076 B2 | 2/2004 | Tomai et al. | |
| 6,696,465 B2 | 2/2004 | Dellaria et al. | |
| 6,703,402 B2 | 3/2004 | Gerster et al. | |
| 6,706,728 B2 | 3/2004 | Hedenstrom et al. | |
| 6,716,988 B2 | 4/2004 | Dellaria et al. | |
| 6,720,333 B2 | 4/2004 | Dellaria et al. | |
| 6,720,334 B2 | 4/2004 | Dellaria et al. | |
| 6,720,422 B2 | 4/2004 | Dellaria et al. | |
| 6,743,920 B2 | 6/2004 | Lindstrom et al. | |
| 6,756,382 B2 | 6/2004 | Coleman et al. | |
| 6,797,718 B2 | 9/2004 | Dellaria et al. | |
| 6,800,624 B2 | 10/2004 | Crooks et al. | |
| 6,809,203 B2 | 10/2004 | Gerster et al. | |
| 6,818,650 B2 | 11/2004 | Griesgraber | |
| 6,825,350 B2 | 11/2004 | Crooks et al. | |
| 6,841,678 B2 | 1/2005 | Merli et al. | |
| 6,852,861 B2 | 2/2005 | Merli et al. | |
| 6,878,719 B2 | 4/2005 | Lindstrom et al. | |
| 6,888,000 B2 | 5/2005 | Crooks et al. | |
| 6,894,060 B2 | 5/2005 | Slade | |
| 6,897,221 B2 | 5/2005 | Crooks et al. | |
| 6,903,113 B2 | 6/2005 | Heppner et al. | |
| 6,916,925 B1 | 7/2005 | Rice et al. | |
| 6,921,826 B2 | 7/2005 | Dellaria et al. | |
| 6,924,293 B2 | 8/2005 | Lindstrom | |
| 6,943,225 B2 | 9/2005 | Lee et al. | |
| 6,949,649 B2 | 9/2005 | Bonk et al. | |
| 6,953,804 B2 | 10/2005 | Dellaria et al. | |
| 6,969,722 B2 | 11/2005 | Heppner et al. | |
| 6,989,389 B2 | 1/2006 | Heppner et al. | |
| 7,030,129 B2 | 4/2006 | Miller et al. | |
| 7,030,131 B2 | 4/2006 | Crooks et al. | |
| 7,038,053 B2 | 5/2006 | Lindstrom et al. | |
| 7,049,439 B2 | 5/2006 | Crooks et al. | |
| 7,078,523 B2 | 7/2006 | Crooks et al. | |
| 7,091,214 B2 | 8/2006 | Hays et al. | |
| 7,098,221 B2 | 8/2006 | Heppner et al. | |
| 7,112,677 B2 | 9/2006 | Griesgraber | |
| 7,115,622 B2 | 10/2006 | Crooks et al. | |
| 7,125,890 B2 | 10/2006 | Dellaria et al. | |
| 7,132,429 B2 | 11/2006 | Griesgraber et al. | |
| 7,132,438 B2 | 11/2006 | Frenkel et al. | |
| 7,148,232 B2 | 12/2006 | Gerster et al. | |
| 7,157,453 B2 | 1/2007 | Crooks et al. | |
| 7,163,947 B2 | 1/2007 | Griesgraber et al. | |
| 7,179,253 B2 | 2/2007 | Graham et al. | |
| 7,199,131 B2 | 4/2007 | Lindstrom | |
| 7,214,675 B2 | 5/2007 | Griesgraber | |
| 7,220,758 B2 | 5/2007 | Dellaria et al. | |
| 7,226,928 B2 | 6/2007 | Mitra et al. | |
| 7,276,515 B2 | 10/2007 | Dellaria et al. | |
| 7,288,550 B2 | 10/2007 | Dellaria et al. | |
| 7,301,027 B2 | 11/2007 | Colombo et al. | |
| 7,375,180 B2 | 5/2008 | Gorden et al. | |
| 7,387,271 B2 | 6/2008 | Noelle et al. | |
| 7,393,859 B2 | 7/2008 | Coleman et al. | |
| 7,427,629 B2 | 9/2008 | Kedl et al. | |
| 7,485,432 B2 | 2/2009 | Fink et al. | |
| 7,544,697 B2 | 6/2009 | Hays et al. | |
| 7,576,068 B2 | 8/2009 | Averett | |
| 7,578,170 B2 | 8/2009 | Mayer et al. | |
| 7,579,359 B2 * | 8/2009 | Krepski et al. | 514/293 |
| 7,598,382 B2 | 10/2009 | Hays et al. | |
| 7,612,083 B2 | 11/2009 | Griesgraber | |
| 7,648,997 B2 | 1/2010 | Kshirsagar et al. | |
| 7,655,672 B2 | 2/2010 | Statham et al. | |
| 7,687,628 B2 | 3/2010 | Gutman et al. | |
| 7,696,159 B2 | 4/2010 | Owens et al. | |
| 7,699,057 B2 | 4/2010 | Miller et al. | |
| 7,731,967 B2 | 6/2010 | O'Hagan et al. | |
| 7,799,800 B2 | 9/2010 | Wightman | |
| 7,879,849 B2 | 2/2011 | Hays et al. | |
| 7,884,207 B2 | 2/2011 | Stoermer et al. | |
| 7,888,349 B2 | 2/2011 | Kshirsagar et al. | |
| 7,897,597 B2 | 3/2011 | Lindstrom et al. | |
| 7,897,609 B2 | 3/2011 | Niwas et al. | |
| 7,897,767 B2 | 3/2011 | Kshirsagar et al. | |
| 7,902,209 B2 | 3/2011 | Statham et al. | |
| 7,902,210 B2 | 3/2011 | Statham et al. | |
| 7,902,211 B2 | 3/2011 | Statham et al. | |
| 7,902,212 B2 | 3/2011 | Statham et al. | |
| 7,902,213 B2 | 3/2011 | Statham et al. | |
| 7,902,214 B2 | 3/2011 | Statham et al. | |
| 7,902,215 B2 | 3/2011 | Statham et al. | |
| 7,902,216 B2 | 3/2011 | Statham et al. | |
| 7,902,242 B2 | 3/2011 | Statham et al. | |
| 7,902,243 B2 | 3/2011 | Statham et al. | |
| 7,902,244 B2 | 3/2011 | Statham et al. | |
| 7,902,245 B2 | 3/2011 | Statham et al. | |
| 7,902,246 B2 | 3/2011 | Statham et al. | |
| 7,906,506 B2 | 3/2011 | Griesgraber et al. | |
| 7,915,281 B2 | 3/2011 | Moser et al. | |
| 7,939,526 B2 | 5/2011 | Radmer et al. | |
| 7,943,609 B2 | 5/2011 | Griesgraber et al. | |
| 7,968,562 B2 | 6/2011 | Skwierczynski et al. | |
| 7,968,563 B2 | 6/2011 | Kshirsagar et al. | |
| 7,993,659 B2 | 8/2011 | Noelle et al. | |
| 8,017,779 B2 | 9/2011 | Merrill et al. | |
| 8,026,366 B2 | 9/2011 | Prince et al. | |
| 8,034,938 B2 | 10/2011 | Griesgraber et al. | |
| 2002/0055517 A1 | 5/2002 | Smith | |
| 2002/0058674 A1 | 5/2002 | Hedenstrom et al. | |
| 2002/0107262 A1 | 8/2002 | Lindstrom | |
| 2003/0133913 A1 | 7/2003 | Tomai et al. | |
| 2003/0139364 A1 | 7/2003 | Krieg et al. | |
| 2004/0014779 A1 | 1/2004 | Gorden et al. | |
| 2004/0132079 A1 | 7/2004 | Gupta et al. | |
| 2004/0175336 A1 | 9/2004 | Egging et al. | |
| 2004/0180919 A1 | 9/2004 | Lee et al. | |
| 2004/0191833 A1 | 9/2004 | Fink et al. | |
| 2004/0197865 A1 | 10/2004 | Gupta et al. | |
| 2004/0202720 A1 | 10/2004 | Wightman et al. | |
| 2004/0214851 A1 | 10/2004 | Birmachu et al. | |
| 2004/0258698 A1 * | 12/2004 | Wightman et al. | 424/178.1 |
| 2004/0265351 A1 | 12/2004 | Miller et al. | |
| 2005/0048072 A1 | 3/2005 | Kedl et al. | |
| 2005/0059072 A1 | 3/2005 | Birmachu et al. | |
| 2005/0070460 A1 | 3/2005 | Hammerbeck et al. | |
| 2005/0096259 A1 | 5/2005 | Tomai et al. | |
| 2005/0106300 A1 | 5/2005 | Chen et al. | |
| 2005/0158325 A1 | 7/2005 | Hammerbeck et al. | |
| 2005/0165043 A1 | 7/2005 | Miller et al. | |
| 2005/0171072 A1 | 8/2005 | Tomai et al. | |
| 2005/0239735 A1 | 10/2005 | Miller et al. | |

(56) References Cited

U.S. PATENT DOCUMENTS

| | | |
|---|---|---|
| 2005/0245562 A1 | 11/2005 | Garcia-Echeverria et al. |
| 2006/0045885 A1 | 3/2006 | Kedl et al. |
| 2006/0045886 A1 | 3/2006 | Kedl |
| 2006/0051374 A1 | 3/2006 | Miller et al. |
| 2006/0088542 A1 | 4/2006 | Braun |
| 2006/0142202 A1 | 6/2006 | Alkan et al. |
| 2006/0142235 A1 | 6/2006 | Miller et al. |
| 2006/0195067 A1 | 8/2006 | Wolter et al. |
| 2006/0216333 A1 | 9/2006 | Miller et al. |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0123559 A1 | 5/2007 | Statham et al. |
| 2007/0166384 A1 | 7/2007 | Zarraga et al. |
| 2007/0167479 A1 | 7/2007 | Busch et al. |
| 2007/0213355 A1 | 9/2007 | Capraro et al. |
| 2007/0219196 A1 | 9/2007 | Krepski et al. |
| 2007/0243215 A1 | 10/2007 | Miller et al. |
| 2007/0259881 A1 | 11/2007 | Dellaria et al. |
| 2007/0259907 A1 | 11/2007 | Prince |
| 2007/0292456 A1 | 12/2007 | Hammerbeck et al. |
| 2008/0015184 A1 | 1/2008 | Kshirsagar et al. |
| 2008/0039533 A1 | 2/2008 | Sahouani et al. |
| 2008/0063714 A1 | 3/2008 | Sahouani et al. |
| 2008/0119508 A1 | 5/2008 | Slade et al. |
| 2008/0188513 A1 | 8/2008 | Skwierczynski et al. |
| 2008/0193468 A1 | 8/2008 | Levy et al. |
| 2008/0193474 A1 | 8/2008 | Griesgraber et al. |
| 2008/0207674 A1 | 8/2008 | Stoesz et al. |
| 2008/0213308 A1 | 9/2008 | Valiante et al. |
| 2008/0262021 A1 | 10/2008 | Capraro et al. |
| 2008/0262022 A1 | 10/2008 | Lee et al. |
| 2008/0306252 A1 | 12/2008 | Crooks et al. |
| 2008/0306266 A1 | 12/2008 | Martin et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0023720 A1 | 1/2009 | Kshirsagar et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0035323 A1 | 2/2009 | Stoermer et al. |
| 2009/0062272 A1 | 3/2009 | Bonk et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0124652 A1 | 5/2009 | Ach et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0202443 A1 | 8/2009 | Miller et al. |
| 2009/0221551 A1 | 9/2009 | Kshirsagar et al. |
| 2009/0221556 A1 | 9/2009 | Kshirsagar et al. |
| 2009/0240055 A1 | 9/2009 | Krepski et al. |
| 2009/0246174 A1 | 10/2009 | Rook et al. |
| 2009/0253695 A1 | 10/2009 | Kshirsagar et al. |
| 2009/0270443 A1 | 10/2009 | Stoermer et al. |
| 2009/0298821 A1 | 12/2009 | Kshirsagar et al. |
| 2009/0306388 A1 | 12/2009 | Zimmerman et al. |
| 2010/0028381 A1 | 2/2010 | Gorski et al. |
| 2010/0056557 A1 | 3/2010 | Benninghoff et al. |
| 2010/0096287 A1 | 4/2010 | Stoesz et al. |
| 2010/0113565 A1 | 5/2010 | Gorden et al. |
| 2010/0152230 A1 | 6/2010 | Dellaria et al. |
| 2010/0158928 A1 | 6/2010 | Stoermer et al. |
| 2010/0173906 A1 | 7/2010 | Griesgraber |
| 2010/0180902 A1 | 7/2010 | Miller et al. |
| 2010/0240693 A1 | 9/2010 | Lundquist et al. |
| 2011/0021554 A1 | 1/2011 | Stoesz et al. |

FOREIGN PATENT DOCUMENTS

| | | | |
|---|---|---|---|
| EP | 1 104 764 | | 6/2001 |
| JP | 9-176116 | | 7/1997 |
| JP | 9-208584 | | 8/1997 |
| JP | 11-080156 | | 3/1999 |
| JP | 11-222432 | | 8/1999 |
| JP | 2000-247884 | | 9/2000 |
| WO | WO 93/05042 A1 | | 3/1993 |
| WO | WO 95/02598 A1 | | 1/1995 |
| WO | WO 02/36592 | | 5/2002 |
| WO | WO2004058759 | * | 7/2004 |
| WO | WO 2005/003084 | | 1/2005 |
| WO | WO 2006/028451 | | 3/2006 |
| WO | WO2006028451 | * | 3/2006 |
| WO | WO 2006/063072 | | 6/2006 |
| WO | WO 2006/121528 | | 11/2006 |
| WO | WO 2007/030775 | | 3/2007 |

OTHER PUBLICATIONS

Bachman et al., "Synthesis of Substituted Quinolylamines. Derivatives of 4-Amino-7-Chloroquinoline.", *J. Org. Chem.* 15, pp. 1278-1284 (1950).

Jain et al., "Chemical and Pharmacological Investigations of Some ω-Substituted Alkylamino-3-aminopryidines.", *J. Med. Chem.*, 11, pp. 87-92 (1968).

Baranov et al., "Pyrazoles, Imidazoles, and Other 5-Membered Rings.", *Chem. Abs.* 85, 94362, (1976).

Berényi et al., "Ring Transformation of Condensed Dihydro-astriazines.", *J. Heterocyclic Chem.*, 18, pp. 1537-1540 (1981).

Chollet et al., "Development of a Topically Active Imiquimod Formulation.", *Pharmaceutical Development and Technology*, 4(1), pp. 35-43 (1999).

Izumi et al., "1H-Imidazo[4,5-c]quinoline Derivatives as Novel Potent TNF-α Suppressors: Synthesis and Structure-Activity Relationship of 1-, 2- and 4-Substituted 1H-imidazo[4,5-c]pyridines.", *Bioorganic & Medicinal Chemistry*, 11, pp. 2541-2550 (2003).

Torrence and DeClerq, 'Inducers and Induction of Interferons' Pharmac Ther, 2, (1977) pp. 1-88.

* cited by examiner

SUBSTITUTED IMIDAZOQUINOLINES AND IMIDAZONAPHTHYRIDINES

CROSS REFERENCE TO RELATED APPLICATIONS

This application is a national stage filing under 35 U.S.C. §371 of PCT International application PCT/US2006/004713 designating the United States of America, and filed Feb. 10, 2006. This application claims the benefit under 35 U.S.C. §119(e) of U.S. provisional application Ser. No. 60/652,239, filed Feb. 11, 2005.

BACKGROUND

Certain compounds have been found to be useful as immune response modifiers (IRMs), rendering them useful in the treatment of a variety of disorders. However, there continues to be interest in and a need for compounds that have the ability to modulate the immune response, by induction of cytokine biosynthesis or other mechanisms.

SUMMARY

The present invention provides a new class of compounds that are useful in inducing cytokine biosynthesis in animals. Such compounds are of the following Formula I:

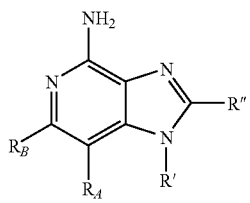

I wherein $R_A$, $R_B$, R', and R'' are as defined below.

The compounds of Formula I are useful as immune response modifiers due to their ability to induce cytokine biosynthesis (e.g., induces the synthesis of at least one cytokine) and otherwise modulate the immune response when administered to animals. This makes the compounds useful in the treatment of a variety of conditions such as viral diseases and tumors that are responsive to such changes in the immune response.

The invention further provides pharmaceutical compositions containing an effective amount of a compound of Formula I and methods of inducing cytokine biosynthesis in an animal, treating a viral infection or disease and/or treating a neoplastic disease in an animal by administering an effective amount of a compound of Formula I to the animal.

In addition, methods of synthesizing compounds of Formula I and intermediates useful in the synthesis of these compounds are provided.

As used herein, "a," "an," "the," "at least one," and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formulas I through VII:

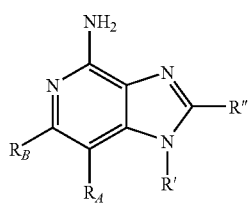

I

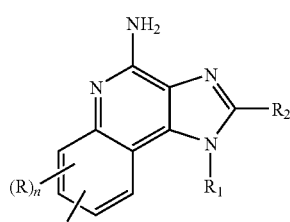

II

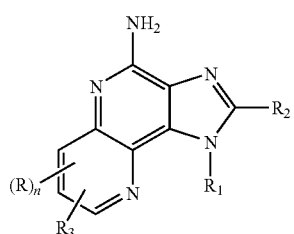

III

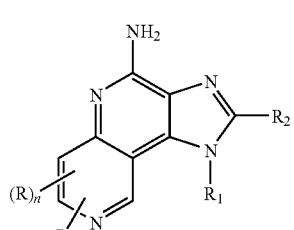

IV

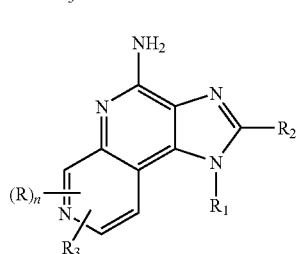

V

-continued

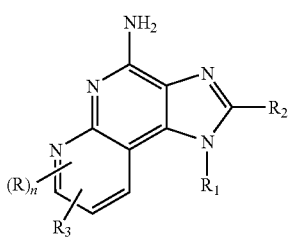

VI

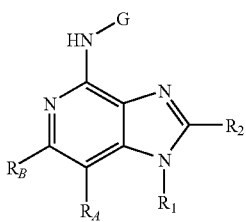

VII as well as intermediates of the following Formulas X and XI:

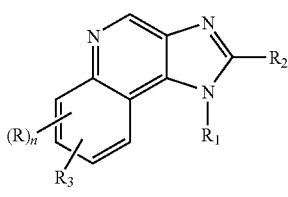

X

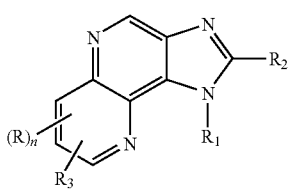

XI wherein $R_A$, $R_B$, R', R", R, $R_1$, $R_2$, $R_3$, G, and n are as defined below;

and pharmaceutically acceptable salts thereof.

In one embodiment, the present invention provides a compound of Formula I:

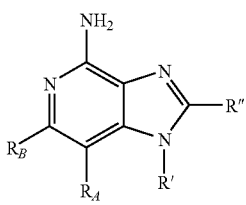

I wherein:

$R_A$ and $R_B$ taken together form a fused benzene ring or fused pyridine ring wherein the benzene ring or pyridine ring is substituted by one $R_3$ group, or substituted by one $R_3$ group and one R group;

$R_3$ is selected from the group consisting of:
-Z-Y-$R_4$,
-Z-Y-X-Y-$R_4$,
-Z-$R_5$,
-Z-Het,
-Z-Het'-$R_4$, and
-Z-Het'-Y-$R_4$;

R is selected from the group consisting of alkyl, alkoxy, hydroxy, halogen, and trifluoromethyl;

R' and R" are independently selected from the group consisting of hydrogen and non-interfering substitutents;

Z is selected from the group consisting of a bond, alkylene, alkenylene, and alkynylene; wherein alkylene, alkenylene, and alkynylene can be optionally interrupted with one or more —O— groups;

Y is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
C($R_6$)—N($R_8$)—,
—O—C($R_6$)—N($R_8$)—,
—C($R_6$)—N(OR$_9$)—,

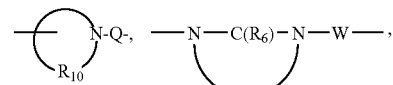

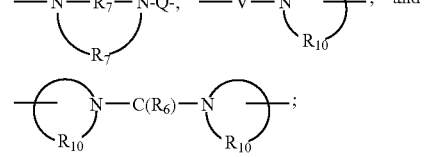

Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;

Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, cyano, amino, alkylamino, dialkylamino, and oxo;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

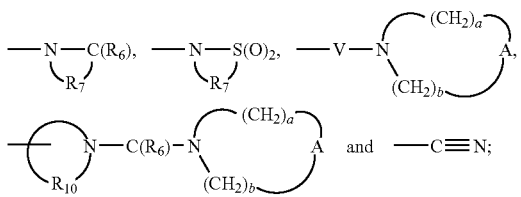

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, arylalkylenyl, and heteroarylalkylenyl;
$R_9$ is selected from the group consisting of hydrogen and alkyl;
$R_{10}$ is $C_{3-8}$ alkylene;
A is selected from the group consisting of —O—, —CH$_2$—, —C(O)—, —S(O)$_{0-2}$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_9$)—, —C(R$_6$)—O—, and —C(R$_6$)—N(OR$_5$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;

with the proviso that when R' is heterocyclyl, then heterocyclyl is attached to the imidazo ring by an atom in heterocyclyl other than a nitrogen atom; and with the proviso that Z is other than a bond when:
$R_3$ is -Z-Y-R$_4$ or -Z-Y-X-Y-R$_4$, and the Y group bonded to Z is —O—, —O—C(R$_6$)—, —OC(O)—O—, —O—C(R$_6$)—N(R$_8$)—,

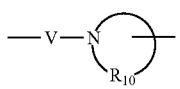

wherein V is —O—C(R$_6$)—,

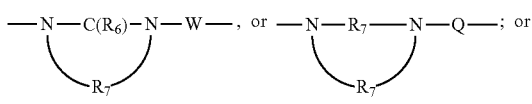

$R_3$ is -Z-R$_5$, and $R_5$ is

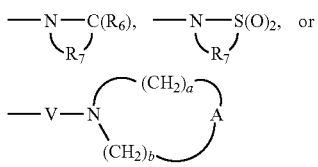

wherein V is —O—C(R$_6$)—; or $R_3$ is -Z-Het, -Z-Het'-R$_4$, or -Z-Het'-Y-R$_4$, and Z is attached to a nitrogen atom in Het or Het';

and with the further proviso that $R_3$ is other than —NH$_2$;

or a pharmaceutically acceptable salt thereof.

In another embodiment, the present invention provides a compound of Formula II:

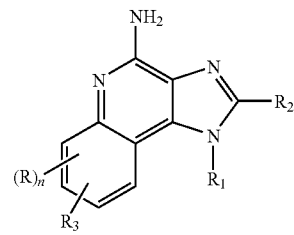

II wherein:
$R_3$ is selected from the group consisting of:
-Z-Y-R$_4$,
-Z-Y-X-Y-R$_4$,
-Z-R$_5$,
-Z-Het,
-Z-Het'-R$_4$, and
-Z-Het'-Y-R$_4$;
R is selected from the group consisting of alkyl, alkoxy, hydroxy, halogen, and trifluoromethyl;
n is 0 or 1;
$R_1$ is selected from the group consisting of:
-R$_4$,
-X-R$_4$,
-X-Y-R$_4$,
-X-Y-X-Y-R$_4$, and
-X-R$_5$;
$R_2$ is selected from the group consisting of:
-R$_4$,
-X-R$_4$,
-X-Y-R$_4$, and
-X-R$_5$;
Z is selected from the group consisting of a bond, alkylene, alkenylene, and alkynylene; wherein alkylene, alkenylene, and alkynylene can be optionally interrupted with one or more —O— groups;
Y is selected from the group consisting of:
—O—,
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

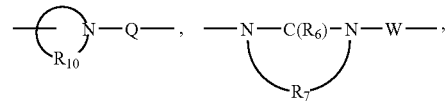

-continued

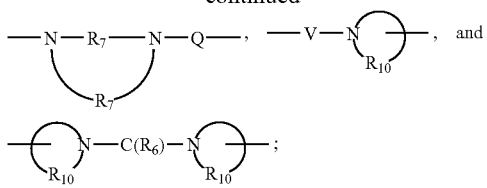

Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, allylamino, diallylamino, and oxo;

Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, cyano, amino, alkylamino, dialkylamino, and oxo;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

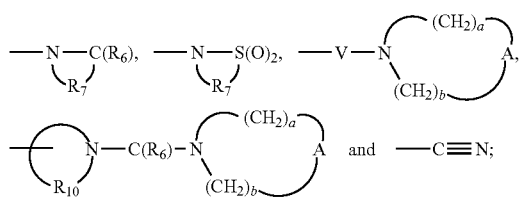

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, arylalkylenyl, and heteroarylalklenyl;
$R_9$ is selected from the group consisting of hydrogen and alkyl;
$R_{10}$ is $C_{3-8}$ alkylene;
A is selected from the group consisting of —O—, —CH$_2$—, —C(O)—, —S(O)$_{0-2}$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7;

with the proviso that when $R_1$ is $R_4$, and $R_4$ is heterocyclyl, then heterocyclyl is attached to the imidazo ring by an atom in heterocyclyl other than a nitrogen atom; and with the proviso that Z is other than a bond when:

$R_3$ is -Z-Y-$R_4$ or -Z-Y-X-Y-$R_4$, and the Y group bonded to Z is —O—, —O—C(R$_6$)—, —OC(O)—O—, —O—C(R$_6$)—N(R$_8$)—,

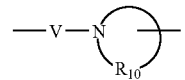

wherein V is —O—C(R$_6$)—,

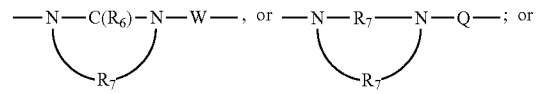

$R_3$ is -Z-$R_5$, and $R_5$ is

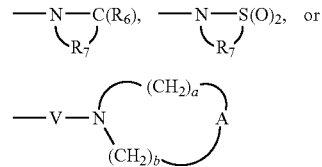

wherein V is —O—C(R$_6$)—; or $R_3$ is -Z-Het, -Z-Het'-$R_4$, or -Z-Het'-Y-$R_4$, and Z is attached to a nitrogen atom in Het or Het';

and with the further proviso that $R_3$ is other than —NH$_2$;

or a pharmaceutically acceptable salt thereof.

In another embodiment, the present invention provides a compound selected from the group consisting Formulas III, IV, V, and VI:

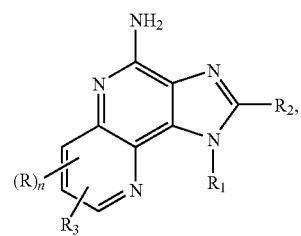

III

-continued

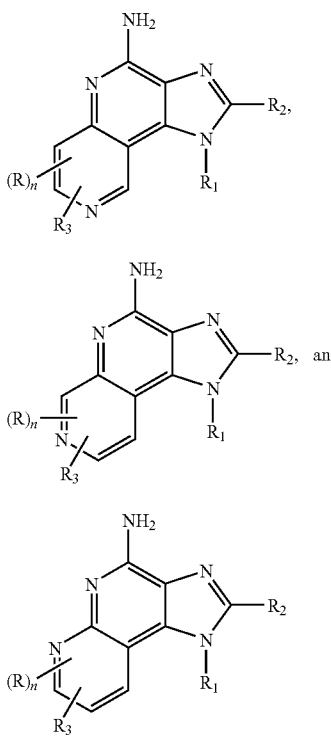

wherein:
R₃ is selected from the group consisting of:
-Z-Y-R₄,
-Z-Y-X-Y-R₄,
-Z-R₅,
-Z-Het,
-Z-Het'-R₄, and
-Z-Het'-Y-R₄;
R is selected from the group consisting of alkyl, alkoxy, hydroxy, halogen, and trifluoromethyl;
n is 0 or 1;
R₁ is selected from the group consisting of:
-R₄,
-X-R₄,
-X-Y-R₄,
-X-Y-X-Y-R₄, and
-X-R₅;
R₂ is selected from the group consisting of:
-R₄,
-X-R₄,
-X-Y-R₄, and
-X-R₅;
Z is selected from the group consisting of a bond, alkylene, alkenylene, and alkynylene; wherein alkylene, alkenylene, and alkynylene can be optionally interrupted with one or more —O— groups;
Y is selected from the group consisting of:
—O—,
—S(O)₀₋₂—,
—S(O)₂—N(R₈)—,
—C(R₆)—,
—C(R₆)—O—,
—O—C(R₆)—,
—O—C(O)—O—,
—N(R₈)-Q-,
—C(R₆)—N(R₈)—,
—O—C(R₆)—N(R₈)—,
—C(R₆)—N(OR₉)—,

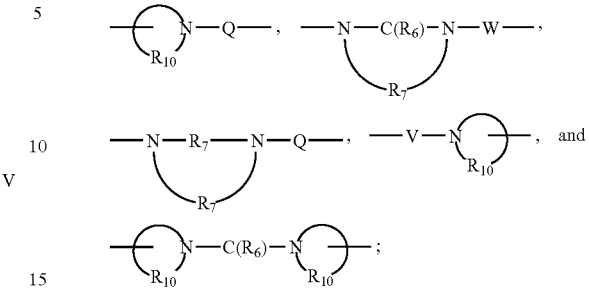

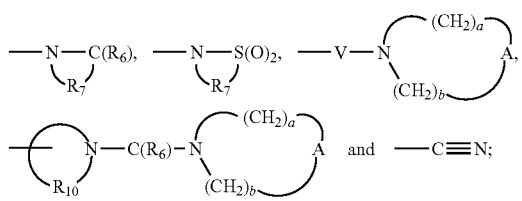

Het is heterocyclyl which can be unsubstituted or substituted by one or more substituents independently selected from the group consisting of alkyl, alkoxy, haloalkyl, haloalkoxy, halogen, nitro, hydroxy, hydroxyallyl, cyano, hydroxyalkyleneoxyalkylenyl, amino, alkylamino, diallylamino, and oxo;

Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, cyano, amino, alkylamino, dialkylamino, and oxo;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

R₄ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R₅ is selected from the group consisting of:

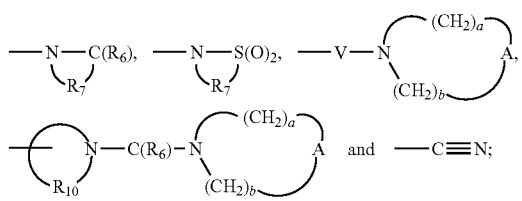

R₆ is selected from the group consisting of =O and =S;
R₇ is C₂₋₇ alkylene;
R₈ is selected from the group consisting of hydrogen, alkyl, alkoxyalkylenyl, hydroxyalkylenyl, arylalkylenyl, and heteroarylalklenyl;

$R_9$ is selected from the group consisting of hydrogen and alkyl;

$R_{10}$ is $C_{3-8}$ alkylene;

A is selected from the group consisting of —O—, —CH$_2$—, —C(O)—, —S(O)$_{0-2}$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—; and a and b are independently integers from 1 to 6 with the proviso that a+b is ≤7;

with the proviso that Z is other than a bond when:

$R_3$ is -Z-Y-R$_4$ or -Z-Y-X-Y-R$_4$, and the Y group bonded to Z is —O—, —O—C(R$_6$)—, —OC(O)—O—, —O—C(R$_6$)—N(R$_8$)—,

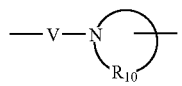

wherein V is —O—C(R$_6$)—,

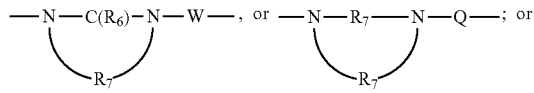

$R_3$ is -Z-R$_5$, and R$_5$ is

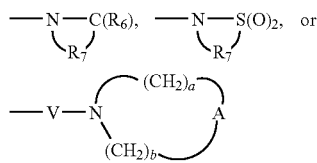

wherein V is —O—C(R$_6$)—; or $R_3$ is -Z-Het, -Z-Het'-R$_4$, or -Z-Het'-Y-R$_4$, and Z is attached to a nitrogen atom in Het or Het';

or a pharmaceutically acceptable salt thereof.

In another embodiment, the present invention provides a compound of Formula VII, which is a prodrug:

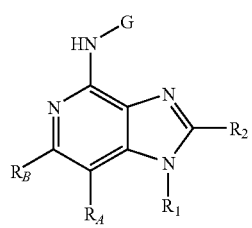

VII wherein:

G is selected from the group consisting of:
—C(O)—R''',
α-aminoacyl,
α-aminoacyl-α-aminoacyl,
—C(O)—O—R''',
—C(O)—N(R'''')R''',
—C(=NY$_1$)—R''',
—CH(OH)—C(O)—OY$_1$,
—CH(OC$_{1-4}$ alkyl)Y$_0$,
—CH$_2$Y$_2$, and
—CH(CH$_3$)Y$_2$;

R''' and R'''' are independently selected from the group consisting of C$_{1-10}$ alkyl, C$_{3-7}$ cycloalkyl, phenyl, and benzyl, each of which may be unsubstituted or substituted by one or more substituents independently selected from the group consisting of halogen, hydroxy, nitro, cyano, carboxy, C$_{1-6}$ alkyl, C$_{1-4}$ alkoxy, aryl, heteroaryl, aryl-C$_{1-4}$ alkylenyl, heteroaryl-C$_{1-4}$ alkylenyl, halo-C$_{1-4}$ alkylenyl, halo-C$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R'''' can also be hydrogen;

α-aminoacyl is an α-aminoacyl group derived from an α-amino acid selected from the group consisting of racemic, D-, and L-amino acids;

Y$_1$ is selected from the group consisting of hydrogen, C$_{1-6}$ alkyl, and benzyl;

Y$_0$ is selected from the group consisting of C$_{1-6}$ alkyl, carboxy-C$_{1-6}$ alkylenyl, amino-C$_{1-4}$ alkylenyl, mono-N—C$_{1-6}$ alkylamino-C$_{1-4}$ alkylenyl, and di-N,N—C$_{1-6}$ alkylamino-C$_{1-4}$ alkylenyl;

Y$_2$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl;

R$_A$ and R$_B$ are defined as in Formula I above;

R$_1$ and R$_2$ are as defined as in Formula II above;

or a pharmaceutically acceptable salt thereof.

In one embodiment, the present invention provides an intermediate compound of Formula X:

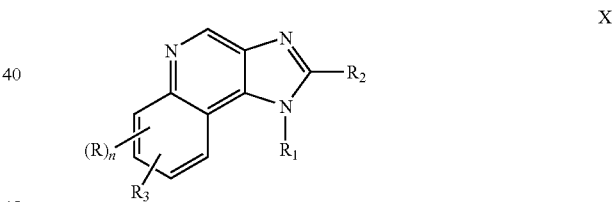

X wherein:

R$_3$ is selected from the group consisting of:
-Z-Y-R$_4$,
-Z-Y-X-Y-R$_4$,
-Z-R$_5$,
-Z-Het,
-Z-Het'-R$_4$, and
-Z-Het'-Y-R$_4$;

R is selected from the group consisting of alkyl, alkoxy, hydroxy, halogen, and trifluoromethyl;

n is 0 or 1;

R$_1$ is selected from the group consisting of:
-R$_4$,
-X-R$_4$,
-X-Y-R$_4$,
-X-Y-X-Y-R$_4$, and
-X-R$_5$;

R$_2$ is selected from the group consisting of:
-R$_4$,
-X-R$_4$,
-X-Y-R$_4$, and

-X-R$_5$;

Z is selected from the group consisting of a bond, alkylene, alkenylene, and alkynylene; wherein alkylene, alkenylene, and alkynylene can be optionally interrupted with one or more —O— groups;

Y is selected from the group consisting of:
—O—,
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

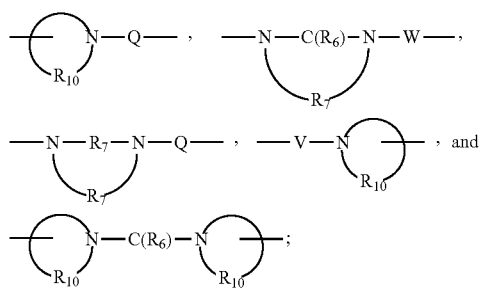

Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;

Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, cyano, amino, alkylamino, dialkylamino, and oxo;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino) alkyleneoxy, and in the case of alkyl, alkenyl, alkynyl, and heterocyclyl, oxo;

R$_5$ is selected from the group consisting of:

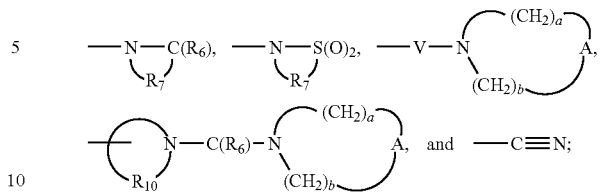

R$_6$ is selected from the group consisting of =O and =S;
R$_7$ is C$_{2-7}$ alkylene;
R$_8$ is selected from the group consisting of hydrogen, alkyl, alkoxyalkylenyl, hydroxyalkylenyl, arylalkylenyl, and heteroarylalklenyl;
R$_9$ is selected from the group consisting of hydrogen and alkyl;
R$_{10}$ is C$_{3-8}$ alkylene;
A is selected from the group consisting of —O—, —CH$_2$—, —C(O)—, —S(O)$_{0-2}$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≤7;

with the proviso that Z is other than a bond when:
R$_3$ is -Z-Y-R$_4$ or -Z-Y-X-Y-R$_4$, and the Y group bonded to Z is —O—, —O—C(R$_6$)—, —OC(O)—O—, —O—C(R$_6$)—N(R$_8$)—,

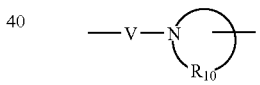

wherein V is —O—C(R$_6$)—,

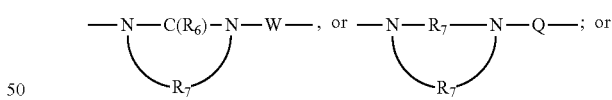

R$_3$ is -Z-R$_5$, and R$_5$ is

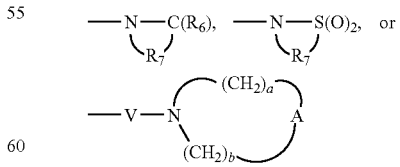

wherein V is —O—C(R$_6$)—; or
R$_3$ is -Z-Het, -Z-Het'-R$_4$, or -Z-Het'-Y-R$_4$, and Z is attached to a nitrogen atom in Het or Het';
and with the further proviso that R$_3$ is other than —NH$_2$; or a pharmaceutically acceptable salt thereof.

In one embodiment, the present invention provides an intermediate compound of Formula XI:

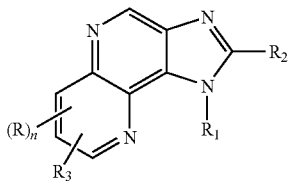

wherein:
$R_3$ is selected from the group consisting of:
-Z-Y-$R_4$,
-Z-Y-X-Y-$R_4$,
-Z-$R_5$,
-Z-Het,
-Z-Het'-$R_4$, and
-Z-Het'-Y-$R_4$;
R is selected from the group consisting of alkyl, alkoxy, hydroxy, halogen, and trifluoromethyl;
n is 0 or 1;
$R_1$ is selected from the group consisting of:
-$R_4$,
-X-$R_4$,
-X-Y-$R_4$,
-X-Y-X-Y-$R_4$, and
-X-$R_5$;
$R_2$ is selected from the group consisting of:
-$R_4$,
-X-$R_4$,
-X-Y-$R_4$, and
-X-$R_5$;
Z is selected from the group consisting of a bond, alkylene, alkenylene, and alkynylene; wherein alkylene, alkenylene, and alkynylene can be optionally interrupted with one or more —O— groups;
Y is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
N($R_8$)-Q-,
—C($R_6$)—N($R_8$)—,
—O—C($R_6$)—N($R_8$)—,
—C($R_6$)—N(O$R_9$)—,

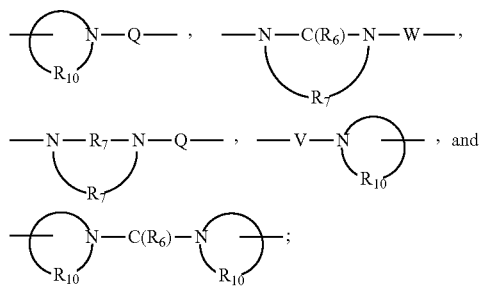

Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, dialkylamino, and oxo;
Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, cyano, amino, alkylamino, dialkylamino, and oxo;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino) alkyleneoxy, and in the case of alkyl, alkenyl, alkynyl, and heterocyclyl, oxo;
$R_5$ is selected from the group consisting of:

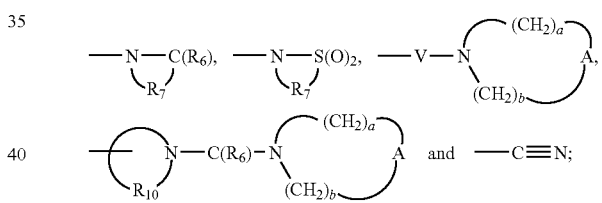

$R_6$ is selected from the group consisting of =O and =S;
$R_7$ is C$_{2-7}$ alkylene;
$R_8$ is selected from the group consisting of hydrogen, alkyl, alkoxyalkylenyl, hydroxyalkylenyl, arylalkylenyl, and heteroarylalklenyl;
$R_9$ is selected from the group consisting of hydrogen and alkyl;
$R_{10}$ is C$_{3-8}$ alkylene;
A is selected from the group consisting of —O—, —CH$_2$—, —C(O)—, —S(O)$_{0-2}$—, and —N($R_4$)—;
Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_5$)—;
V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—; and
a and b are independently integers from 1 to 6 with the proviso that a+b is ≤7,
with the proviso that Z is other than a bond when:
$R_3$ is -Z-Y-$R_4$ or -Z-Y-X-Y-$R_4$; and the Y group bonded to Z is —O—, —O—C($R_6$)—, —OC(O)—O—, —O—C($R_6$)—N($R_8$)—,

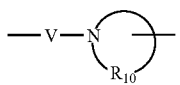

wherein V is —O—C(R₆)—,

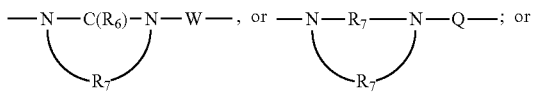

R₃ is -Z-R₅, and R₅ is

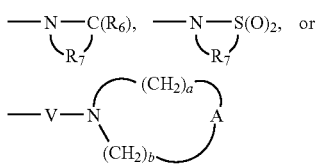

wherein V is —O—C(R₆)—; or

R₃ is -Z-Het, -Z-Het'-R₄, or -Z-Het'-Y-R₄, and Z is attached to a nitrogen atom in Het or Het';

or a pharmaceutically acceptable salt thereof.

Herein, "non-interfering" means that the ability of the compound or salt, which includes a non-interfering substituent, to modulate the biosynthesis of one or more cytokines is not destroyed by the non-interfering substitutent. For certain embodiments, R' is hydrogen or a non-interfering substituent. Illustrative non-interfering R' groups include those described above for $R_1$. For certain embodiments, R" is hydrogen or a non-interfering substituent. Illustrative non-interfering R" groups include those described above for $R_2$.

As used herein, the terms "alkyl," "alkenyl," "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "alkenylene," and "alkynylene" are the divalent forms of the "alkyl," "alkenyl," and "alkynyl" groups defined above. The terms, "alkylenyl," "alkenylenyl," and "alkynylenyl" are use when "alkylene," "alkenylene," and "alkynylene," respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl(azepanyl), 1,4-oxazepanyl, homopiperazinyl(diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, 1,1-dioxidotetrahydrothien-3-yl, 2-oxopyrrolidin-1-yl, and the like.

The term "heterocyclyl" includes bicyclic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom unless otherwise indicated.

The terms "arylene," "heteroarylene," and "heterocyclylene" are the divalent forms of the "aryl," "heteroaryl," and "heterocyclyl" groups defined above. The terms, "arylenyl," "heteroarylenyl," and "heterocyclylenyl" are used when "arylene," "heteroarylene," and "heterocyclylene," respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula —N(R₈)—C(R₆)—N(R₈)— each R₈ group is independently selected. In another example, when an R₂ and an R₃ group both contain an R₄ group, each R₄ group is independently selected. In a further example, when more than one Y group is present and each Y group contains one or more R₈ groups, then each Y group is independently selected, and each R₈ group is independently selected.

The invention is inclusive of the compounds described herein in any of their pharmaceutically acceptable forms, including isomers (e.g., diastereomers and enantiomers), salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

The term "prodrug" means a compound that can be transformed in vivo to yield an immune response modifying compound, including any of the salt, solvated, polymorphic, or isomeric forms described above. The prodrug, itself, may be an immune response modifying compound, including any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

For any of the compounds presented herein, each one of the following variables (e.g., Z, Y, X, $R_A$, $R_B$, R, $R_1$, $R_2$, $R_3$, Q, n, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments of Formulas I or VII, $R_A$ and $R_B$ taken together form a fused benzene ring or fused pyridine ring wherein the benzene ring or pyridine ring is substituted by one $R_3$ group, or substituted by one $R_3$ group and one R group.

For certain embodiments of Formulas I or VII, $R_A$ and $R_B$ are taken together to form a fused benzene ring wherein the benzene ring is substituted by one $R_3$ group, or substituted by one $R_3$ group and one R group. In certain of these embodiments, the fused benzene ring is substituted by one $R_3$ group.

For certain embodiments of Formulas I or VII, $R_A$ and $R_B$ are taken together to form a fused pyridine ring wherein the pyridine ring is substituted by one $R_3$ group, or substituted by one $R_3$ group and one R group. In certain of these embodiments, the fused pyridine ring is substituted by one $R_3$ group.

For certain embodiments, including any one of the above embodiments of Formula I, R' is $R_1$; wherein $R_1$ is selected from the group consisting of:
-$R_4$,
-X-$R_4$,
-X-Y-$R_4$,
-X-Y-X-Y-$R_4$, and
-X-$R_5$;
with the proviso that when $R_1$ is $R_4$, and $R_4$ is heterocyclyl, then heterocyclyl is attached to the imidazo ring by an atom in heterocyclyl other than a nitrogen atom.

For certain embodiments, including any one of the above embodiments of Formula I, R" is $R_2$; wherein $R_2$ is selected from the group consisting of:
-$R_4$,
-X-$R_4$,
-X-Y-$R_4$, and
-X-$R_5$.

For certain embodiments, the compound selected from the group consisting of Formulas III, IV, V, and VI, or a pharmaceutically acceptable salt thereof is the compound of Formula III:

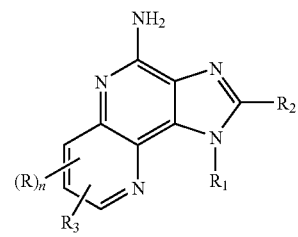

or a pharmaceutically acceptable salt thereof.

For certain embodiments, n is 0 in the above embodiments of Formulas II, III, IV, V, or VI.

For certain embodiments, R is selected from the group consisting of alkyl, alkoxy, hydroxy, halogen, and trifluoromethyl.

For certain embodiments, R' is hydrogen or a non-interfering substituent.

For certain embodiments, R' is a non-interfereing substituent.

For certain embodiments, R' is $R_1$; wherein $R_1$ is selected from the group consisting of -$R_4$, -X-$R_4$, -X-Y-$R_4$, -X-Y-X-Y-$R_4$, and -X-$R_5$.

For certain embodiments, R' is $R_1$; wherein $R_1$ is selected from the group consisting of alkyl, arylalkylenyl, aryloxyalkylenyl, hydroxyalkyl, dihydroxyalkyl, alkoxyalkylenyl, alkylsulfonylalkylenyl, -X-Y-$R_4$, -X-$R_5$, and heterocyclylalkylenyl; wherein the heterocyclyl of the heterocyclylalkylenyl group is optionally substituted by one or more alkyl groups; wherein X is alkylene; Y is —N($R_8$)—C(O)—, —N($R_8$)—S(O)$_2$—, —N($R_8$)—C(O)—N($R_8$)—, or

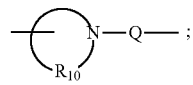

$R_4$ is alkyl, aryl, or heteroaryl; and $R_5$ is

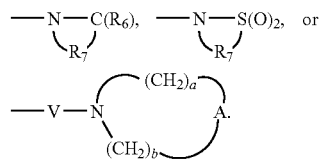

For certain embodiments, R" is hydrogen or a non-interfering substituent.

For certain embodiments, R" is a non-interfering substituent.

For certain embodiments, R" is $R_2$; wherein $R_2$ is selected from the group consisting of -$R_4$, -X-$R_4$, -X-Y'-$R_4$, and -X-$R_5$'.

For certain embodiments, R" is $R_2$; wherein $R_2$ is selected from the group consisting of hydrogen, alkyl, alkoxyalkylenyl, and hydroxyalkylenyl.

For certain embodiments, $R_1$ is selected from the group consisting of -$R_4$, -X-$R_4$, -X-Y-$R_4$, -X-Y-X-Y-$R_4$, and -X-$R_5$.

For certain embodiments, including any one of the above embodiments wherein $R_1$ is present, $R_1$ is selected from the group consisting of alkyl, arylalkylenyl, aryloxyalkylenyl, hydroxyalkyl, dihydroxyalkyl, alkoxyalkylenyl, alkylsulfonylalkylenyl, -X-Y-$R_4$, -X-$R_5$, and heterocyclylalkylenyl;

wherein the heterocyclyl of the heterocyclylalkylenyl group is optionally substituted by one or more alkyl groups; wherein X is alkylene; Y is —N($R_8$)—C(O)—, —N($R_8$)—S(O)$_2$—, —N($R_8$)—C(O)—N($R_8$)—, or

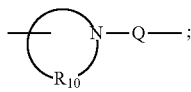

$R_4$ is alkyl, aryl, or heteroaryl; and $R_5$ is

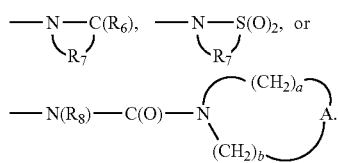

For certain embodiments, including any one of the above embodiments wherein $R_1$ is present, $R_1$ is selected from the group consisting of 2-hydroxy-2-methylpropyl, 2-methylpropyl, propyl, ethyl, methyl, 2,3-dihydroxypropyl, 3-isopropoxypropyl, 2-phenoxyethyl, 4-[(methylsulfonyl)amino]butyl, 2-methyl-2-[(methylsulfonyl)amino]propyl, 2-(acetylamino)-2-methylpropyl, 2-{[(isopropylamino)carbonyl]amino}-2-methylpropyl, 4-{[(isopropylamino)carbonyl]amino)}butyl, 4-(1,1-dioxidoisothiazolidin-2-yl)butyl, tetrahydro-2H-pyran-4-ylmethyl, and (2,2-dimethyl-1,3-dioxolan-4-yl)methyl.

For certain embodiments, including any one of the above embodiments wherein $R_1$ is present except where excluded, $R_1$ is selected from the group consisting of 2-[(methylsulfonyl)amino]ethyl, 2-(1,1-dioxidoisothiazolidin-2-yl)ethyl, 3-(2-oxopyrrolidin-1-yl)propyl, and 2-{[(isopropylamino)carbonyl]amino}ethyl.

For certain embodiments of Formulas III, IV, V, VI, or XI, when $R_1$ is $R_4$, and $R_4$ is heterocyclyl, then heterocyclyl is bonded to the imidazo ring by an atom in heterocyclyl that is other then nitrogen.

For certain embodiments, $R_2$ is selected from the group consisting of -$R_4$, -X-$R_4$, -X-Y-$R_4$, and -X-$R_5$.

For certain embodiments, including any one of the above embodiments wherein $R_2$ is present, $R_2$ is selected from the group consisting of hydrogen, alkyl, alkoxyalkylenyl, and hydroxyalkylenyl. For certain embodiments, $R_2$ is selected from the group consisting of hydrogen, alkyl, and alkoxyalkylenyl. For certain embodiments, $R_2$ is selected from the group consisting of alkyl and alkoxyalkylenyl. For certain embodiments, $R_2$ is selected from the group consisting of hydrogen, methyl, ethyl, propyl, butyl, ethoxymethyl, methoxymethyl, 2-methoxyethyl, hydroxymethyl, and 2-hydroxyethyl. For certain embodiments, $R_2$ is selected from the group consisting of methyl, ethyl, n-propyl, n-butyl, ethoxymethyl, methoxymethyl, and 2-methoxyethyl.

For certain embodiments, $R_3$ is selected from the group consisting of -Z-Y-$R_4$, -Z-Y-X-Y-$R_4$, -Z-$R_5$, -Z-Het, -Z-Het'-$R_4$, and -Z-Het'-Y-$R_4$.

For certain embodiments, including any one of the above embodiments, $R_3$ is -Z-Y-$R_4$ or -Z-Y-X-Y-$R_4$. For certain of these embodiments, $R_3$ is -Z-Y-$R_4$. In certain of these embodiments, Y is —N($R_8$)-Q-, and $R_4$ is alkyl, aryl, heteroaryl, or heterocyclyl. In certain of these embodiments, Q is —C($R_6$)—, —S(O)$_2$—, or —C($R_6$)—N($R_8$)—. For certain of these embodiments, Q is —C($R_6$)—. Alternatively, for certain of these embodiments, Q is —S(O)$_2$—. Alternatively, for certain of these embodiments, Q is —C($R_6$)—N($R_8$)—. Alternatively, for certain of these embodiments, Q is —C($R_6$)—O—. Alternatively, for certain of these embodiments, Q is —S(O)$_2$—N($R_8$)—. For certain of these embodiments where $R_3$ is -Z-Y-$R_4$ or -Z-Y-X-Y-$R_4$, $R_3$ is -Z-Y-X-Y-$R_4$.

In certain embodiments, including any one of the above embodiments wherein $R_3$ is -Z-Y-$R_4$ or -Z-Y-X-Y-$R_4$, except where excluded, Y is —C($R_6$)—N($R_8$)—, and $R_4$ is alkyl, aryl, arylalkylenyl, heteroaryl, heteroarylalkylenyl, or heterocyclyl. For certain of these embodiments, Y in -Y-$R_4$ is —C($R_6$)—N($R_8$)—. For certain of these embodiments, $R_6$ is =O, $R_8$ is $C_{1-4}$ alkyl, and $R_4$ is $C_{1-4}$ alkyl. For certain of these embodiments, $C_{1-4}$ alkyl is methyl.

In certain embodiments, including any one of the above embodiments wherein $R_3$ is -Z-Y-$R_4$ or -Z-Y-X-Y-$R_4$, except where excluded, -Y-$R_4$ is —C(O)—NH$_2$.

In certain embodiments, including any one of the above embodiments wherein $R_3$ is -Z-Y-X-Y-$R_4$, except where excluded, Y in -Z-Y- is —C(O)—, and Y in -Y-$R_4$ is selected from the group consisting of —C(O)—NH—, —C(O)—, and —C(O)—O—. For certain of these embodiments, $R_4$ is alkyl, and when Y in -Y-$R_4$ is —C(O)—NH—, then $R_4$ can also be hydrogen. For certain of these embodiments, X is heterocyclylene or heterocyclylene-alkylene.

In certain embodiments, including any one of the above embodiments wherein $R_3$ is -Z-Y-$R_4$ or -Z-Y-X-Y-$R_4$, except where excluded, Y is —C(O)— and $R_4$ is heterocyclyl.

In certain embodiments, including any one of the above embodiments wherein $R_3$ is -Z-Y-$R_4$, except where excluded, Y is —C(O)—, and $R_4$ is heterocyclyl which is unsubstituted or substituted by one or more substituents independently selected from the group consisting of alkyl, hydroxy, and oxo.

In certain embodiments, including any one of the above embodiments wherein $R_3$ is -Z-Y-$R_4$, except where excluded, Y is —C(O)—NH—, and $R_4$ is heterocyclyl which is unsubstituted or substituted by one or more substituents independently selected from the group consisting of alkyl, hydroxy, and oxo, or $R_4$ is alkyl which is unsubstituted or substituted by one or more substituents independently selected from the group consisting of hydroxy, alkoxy, heteroaryl, and heterocyclyl.

For certain embodiments, including any one of the above embodiments wherein $R_4$ is heterocyclyl, heterocyclyl is selected from the group consisting of tetrahydropyranyl, tetrahydrofuranyl, 1,3-dioxolanyl, pyrrolidinyl, piperidinyl, morpholinyl, thiomorpholinyl, 1,1-dioxothiomorpholinyl, thiazolidinyl, azepanyl, 1,4-oxazepanyl, diazepanyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and piperazinyl. For certain of these embodiments, heterocyclyl is pyrrolidinyl or piperidinyl. Alternatively, for certain of these embodiments, heterocyclyl is 1,1-dioxidotetrahydrothien-3-yl, or 2-oxopyrrolidin-1-yl.

In certain embodiments, including any one of the above embodiments wherein $R_3$ is -Z-Y-$R_4$, except where excluded, Y is selected from the group consisting of —C(O)—O—, —S(O)$_2$—, and —S(O)$_2$—N($R_8$)—. For certain of these embodiments, Y is —S(O)$_2$—. For certain of these embodiments, Y is —S(O)$_2$—N($R_8$). For certain of these embodiments, Y is —C(O)—O—. For certain of these embodiments, $R_4$ is alkyl.

In certain embodiments, including any one of the above embodiments wherein $R_3$ is -Z-Y-$R_4$, except where excluded, Y is —O—, and $R_4$ is hydrogen.

In certain embodiments, including any one of the above embodiments wherein R$_3$ is -Z-Y-R$_4$, except where excluded, Y is

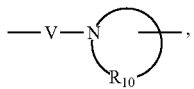

V is —C(O)—, and R$_4$ is hydroxyalkyl.

For certain embodiments, including any one of the above embodiments not excluding this definition, R$_3$ is -Z-R$_5$. In certain of these embodiments, R$_5$ is

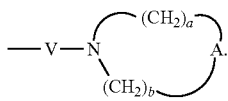

In certain of these embodiments, V is —NH—C(O)— or —C(O)—; A is —O—, —CH$_2$—, —S—, or —SO$_2$—; a is 1, 2, or 3; and b is 2.

For certain embodiments wherein R$_3$ is -Z-R$_5$, R$_5$ is —C≡N. In certain of these embodiments, Z is other than a bond. In certain of these embodiments, Z is alkylene. Alternatively, in certain of these embodiments, R$_3$ is —CH═CH—C≡N.

For certain embodiments, including any one of the above embodiments not excluding this definition, R$_3$ is -Z-Het or -Z-Het'-R$_4$. In certain of these embodiments, Het and Het' are, respectively, selected from the group consisting of the monovalent and divalent forms of tetrahydropyranyl, tetrahydrofuranyl, 1,3-dioxolanyl, pyrrolidinyl, piperidinyl, morpholinyl, thiomorpholinyl, 1,1-dioxothiomorpholinyl, thiazolidinyl, azepanyl, 1,4-oxazepanyl, diazepanyl, dihydroisoquinolin-(1)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and piperazinyl, each of which is unsubstituted or substituted by one or more substitutents. For certain of these embodiments, Het and Het' are, respectively, selected from the group consisting of the monovalent and divalent forms of pyrrolidinyl, piperidinyl, and morpholinyl, each of which is unsubstituted or substituted by one or more substitutents. For certain of these embodiments, Het is unsubstituted. For certain of these embodiments, Het' is unsubstituted. For certain of these embodiments, R$_4$ is heterocyclyl. For certain of these embodiments, Het is substituted by one or more substituents selected from the group consisting of alkyl, hydroxyl, hydroxyalkyl, hydroxyalkyleneoxyalkylenyl, and dialkylamino.

For certain embodiments, including any one of the above embodiments, except where excluded, Z is C$_{1-4}$ alkylene or C$_{2-4}$ alkenylene. For certain of these embodiments, Z is C$_{2-4}$ alkylene. For certain of these embodiments, Z is ethylene.

For certain embodiments, including any one of the above embodiments not excluded by the proviso for Formulas I through VI, and which does not exclude this definition, Z is a bond.

For certain embodiments, including any one of the above embodiments, R$_3$ is at the 7-position.

For certain embodiments, R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo.

For certain embodiments, R$_4$ is selected from the group consisting of alkyl, aryl, arylalkylenyl, alkylheteroarylenyl, heteroarylalkylenyl, heteroaryl, and heterocyclyl; wherein alkyl is unsubstituted or substituted by one or more substituents selected from the group consisting of hydroxy, alkoxy, and aryl; wherein aryl and arylalkylenyl are unsubstituted or substituted by one or more substituents selected from the group consisting of alkyl, halogen, cyano, dialkylamino, and alkoxy; and wherein heterocyclyl is unsubstituted or substituted by one or more alkyl substituents.

For certain embodiments, R$_4$ is alkyl, aryl, arylalkylenyl, heteroaryl, heteroarylalkylenyl, or heterocyclyl.

For certain embodiments, R$_4$ is alkyl, aryl, heteroaryl, or heterocyclyl.

For certain embodiments, R$_4$ is alkyl, aryl, or heteroaryl.

For certain embodiments, R$_4$ is alkyl substituted by heterocyclyl. For certain of these embodiments, heterocyclyl is substituted by one or two oxo groups.

For certain embodiments, R$_4$ is heterocyclyl.

For certain embodiments, R$_4$ is hydrogen or alkyl.

For certain embodiments, R$_4$ is alkyl.

For certain embodiments, R$_4$ is C$_{1-4}$ alkyl.

For certain embodiments, R$_4$ is methyl.

For certain embodiments, R$_4$ is hydrogen.

For certain embodiments, R$_5$ is selected from the group consisting of:

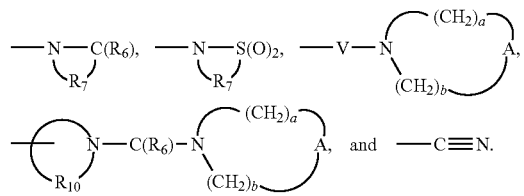

For certain embodiments, R$_5$ is selected from the group consisting of:

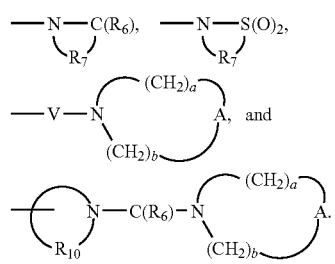

For certain embodiments, $R_5$ is

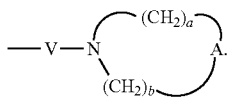

For certain embodiments, $R_5$ is

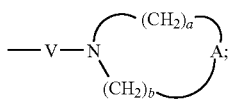

V is —NH—C(O)— or —C(O)—; A is —O—, —CH$_2$—, —S—, or —SO$_2$—; a is 1, 2, or 3; and b is 2.

For certain embodiments, $R_5$ is —C≡N.

For certain embodiments, $R_6$ is selected from the group consisting of =O and =S.

For certain embodiments, $R_6$ is =O.

For certain embodiments, $R_7$ is $C_{2-7}$ alkylene.

For certain embodiments, $R_7$ is $C_{2-4}$ alkylene.

For certain embodiments, $R_8$ is selected from the group consisting of hydrogen, alkyl, hydroxyalkylenyl, alkoxyalkylenyl, arylalkylenyl, and heteroarylalkylenyl.

For certain embodiments, $R_8$ is selected from the group consisting of hydrogen, $C_{1-4}$ alkyl, and $C_{1-4}$ alkoxy$C_{1-4}$ alkylenyl.

For certain embodiments, $R_8$ is hydrogen or $C_{1-4}$ alkyl.

For certain embodiments, $R_8$ is $C_{1-4}$ alkyl.

For certain embodiments, $R_8$ is methyl.

For certain embodiments, $R_8$ is hydrogen.

For certain embodiments, $R_9$ is selected from the group consisting of hydrogen and alkyl.

For certain embodiments, $R_{10}$ is $C_{3-8}$ alkylene.

For certain embodiments, $R_{10}$ is $C_{4-6}$ alkylene.

For certain embodiments, $R_{10}$ is $C_{4-5}$ alkylene.

For certain embodiments, A is selected from the group consisting of —O—, —CH$_2$—, —C(O)—, —S(O)$_{0-2}$—, and —N(R$_4$)—.

For certain embodiments, A is —O—, —CH$_2$—, —S—, or —S(O)$_2$—.

For certain embodiments, A is —O— or —S(O)$_2$—.

For certain embodiments, A is —S—.

For certain embodiments, A is —O—.

For certain embodiments, including any one of the above embodiments of Formula VII, G is selected from the group consisting of —C(O)—R''', α-aminoacyl, α-aminoacyl-α-aminoacyl, —C(O)—O—R''', —C(O)—N(R'''')R''', —C(=NY$_1$)—R''', —CH(OH)—C(O)—OY$_1$, —CH(OC$_{14}$ alkyl)Y$_0$, —CH$_2$Y$_2$, and —CH(CH$_3$)Y$_2$. For certain of these embodiments, R''' and R'''' are independently selected from the group consisting of $C_{1-10}$ alkyl, $C_{3-7}$ cycloalkyl, phenyl, and benzyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R'''' can also be hydrogen; α-aminoacyl is an α-aminoacyl group derived from an α-amino acid selected from the group consisting of racemic, D-, and L-amino acids; Y$_1$ is selected from the group consisting of hydrogen, $C_{1-6}$ alkyl, and benzyl; Y$_0$ is selected from the group consisting of $C_{1-6}$ alkyl, carboxy-$C_{1-6}$ alkylenyl, amino-$C_{1-4}$ alkylenyl, mono-N—$C_{1-6}$ alkylamino-$C_{1-4}$ alkylenyl, and di-N,N—$C_{1-6}$ alkylamino-$C_{1-4}$ alkylenyl; and Y$_2$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl.

For certain embodiments, including any one of the above embodiments of Formula VII, G is selected from the group consisting of —C(O)—R''', α-aminoacyl, and —C(O)—O—R'''.

For certain embodiments, including any one of the above embodiments of Formula VII, G is selected from the group consisting of —C(O)—R''', α-amino-$C_{2-11}$ acyl, and —C(O)—O—R'''. α-Amino-$C_{2-11}$ acyl includes α-amino acids containing a total of at least 2 carbon atoms and a total of up to 11 carbon atoms, and may also include one or more heteroatoms selected from the group consisting of O, S, and N. For certain of these embodiments, R''' contains one to ten carbon atoms.

For certain embodiments, including any one of the above embodiments which include an α-aminoacyl group, α-aminoacyl is an α-aminoacyl group derived from a naturally occurring α-amino acid selected from the group consisting of racemic, D-, and L-amino acids.

For certain embodiments, including any one of the above embodiments which include an α-aminoacyl group, α-aminoacyl is an α-aminoacyl group derived from an α-amino acid found in proteins, wherein the α-amino acid is selected from the group consisting of racemic, D-, and L-amino acids.

In certain embodiments, Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_9$)—, —C(R$_6$)—O—, and —C(R$_6$)—N(OR$_9$)—.

In certain embodiments, Q is selected from the group consisting of —C(R$_6$)—, —C(R$_6$)—C(R$_6$)—, —S(O)$_2$—, —C(R$_6$)—N(R$_8$)—W—, —S(O)$_2$—N(R$_5$)—, —C(R$_6$)—O—, and —C(R$_6$)—N(OR$_9$)—.

In certain embodiments, Q is other than a bond when $R_3$ is -Z-Y-$R_4$ and Y is —N(R$_5$)-Q-.

In certain embodiments, Q is selected from the group consisting of a bond, —C(R$_6$)—, —S(O)$_2$—, and —C(R$_6$)—N(R$_8$)—.

In certain embodiments, Q is —C(O)—NH—, —C(O)—, or —C(O)—O—.

In certain embodiments, Q is —C(R$_6$)—.

In certain embodiments, Q is —C(O)—.

In certain embodiments, Q is —S(O)$_2$—.

In certain embodiments, Q is —C(R$_6$)—N(R$_8$)—.

In certain embodiments, Q is —C(O)—NH—.

In certain embodiments, Q is —C(R$_6$)—O—.

In certain embodiments, Q is —S(O)$_2$—N(R$_8$)—.

In certain embodiments, Q is a bond.

In certain embodiments, V is selected from the group consisting of —C(R$_6$)—, O—C(R$_6$)—, —N(R$_8$)—C(R$_6$)—, and —S(O)$_2$—.

In certain embodiments, V is selected from the group consisting of —C(O)— and —NH—C(O)—.

In certain embodiments, W is selected from the group consisting of a bond, —C(O)—, and —S(O)$_2$—.

In certain embodiments, W is a bond or —C(O)—.

In certain embodiments, W is a bond.

In certain embodiments, X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups.

In certain embodiments, X is alkylene.

In certain embodiments, X is heteroarylene-alkylene. For certain of these embodiments, heteroarylene is thiazoldiyl.

In certain embodiments, X is heterocyclylene. For certain of these embodiments, heterocyclylene is piperidin-1,4-diyl or piperazin-1,4-diyl.

In certain embodiments, Y is selected from the group consisting of —O—, —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—,

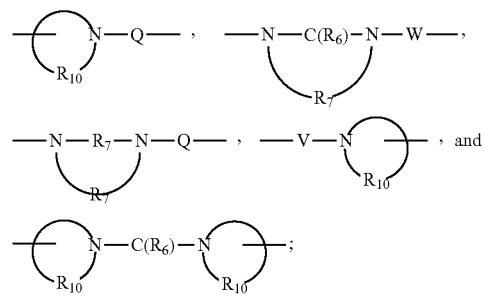

In certain of these embodiments, including any one of the above embodiments wherein Y is present, Y is other than —O—.

In certain embodiments, Y is —N(R$_8$)—C(O)—, —N(R$_8$)—S(O)$_2$—, —N(R$_8$)—C(O)—N(R$_8$)—, or

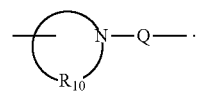

In certain embodiments, Y is —N(R$_8$)-Q-.

In certain embodiments, Y is —N(R$_8$)-Q-, and Q is —C(R$_6$)—, S(O)$_2$—, or —C(R$_6$)—N(R$_8$)—.

In certain embodiments, Y is —N(R$_8$)—C(R$_6$)—.

In certain embodiments, Y is —NH—C(O)—.

In certain embodiments, Y is —NH—S(O)$_2$—.

In certain embodiments, Y is —NH—C(O)—NH—.

In certain embodiments, Y is —NH—C(O)—O—.

In certain embodiments, Y is —NH—S(O)$_2$—N(R$_8$)—.

In certain embodiments, Y is —C(R$_6$)—N(R$_8$)—.

In certain embodiments, Y is —C(O)—NH—.

In certain embodiments, Y is —C(O)—.

In certain embodiments, Y is —C(O)—O—.

In certain embodiments, Y is —C(O)—NH—, —C(O)—, or —C(O)—O—.

In certain embodiments, Z is selected from the group consisting of a bond, alkylene, alkenylene, and alkynylene, wherein alkylene, alkenylene, and alkynylene can be optionally interrupted with one or more —O— groups; with the proviso that Z is other than a bond when:

R$_3$ is -Z-Y-R$_4$ or -Z-Y-X-Y-R$_4$, and the Y group bonded to Z is —O—, —O—C(R$_6$)—, —OC(O)—O—, —O—C(R$_6$)—N(R$_8$)—,

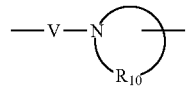

wherein V is —O—C(R$_6$)—,

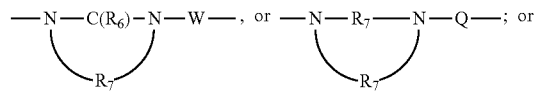

R$_3$ is -Z-R$_5$, and R$_5$ is

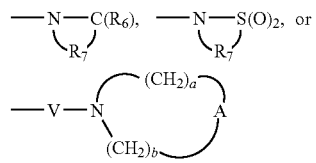

wherein V is —O—C(R$_6$)—; or

R$_3$ is -Z-Het, -Z-Het'-R$_4$, or -Z-Het'-Y-R$_4$, and Z is attached to a nitrogen atom in Het or Het'. In certain of these embodiments, Z is other than a bond further when R$_5$ is —C≡N. In certain of these embodiments, Z is other than a bond further when R$_3$ is -Z-Y-R$_4$, Y is —C(O)— or —C(O)—O—, and R$_4$ is alkyl.

In certain embodiments, Z is a bond except where excluded by the above proviso.

In certain embodiments, Z is C$_{1-4}$ alkylene or C$_{2-4}$ alkenylene.

In certain embodiments, Z is C$_{2-4}$ alkylene.

In certain embodiments, Z is ethylene.

In certain embodiments, Het is heterocyclyl which can be unsubstituted or substituted by one or more substituents independently selected from the group consisting of alkyl, alkoxy, haloalkyl, haloalkoxy, halogen, nitro, hydroxy, hydroxyalkyl, cyano, hydroxyalkyleneoxyalkylenyl, amino, alkylamino, diallylamino, and oxo.

In certain embodiments, Het is selected from the group consisting of tetrahydropyranyl, tetrahydrofuranyl, 1,3-dioxolanyl, pyrrolidinyl, piperidinyl, morpholinyl, thiomorpholinyl, 1,1-dioxothiomorpholinyl, thiazolidinyl, azepanyl, 1,4-oxazepanyl, diazepanyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and piperazinyl, each of which is unsubstituted or substituted by one or more substitutents.

In certain embodiments, Het is substituted by one or more substituents selected from the group consisting of alkyl, hydroxyl, hydroxyalkyl, hydroxyalkyleneoxyalkylenyl, and dialkylamino.

In certain embodiments, Het is unsubstituted.

In certain embodiments, Het' is heterocyclylene which can be unsubstituted or substituted by one or more substituents independently selected from the group consisting of alkyl, alkoxy, haloalkyl, haloalkoxy, halogen, nitro, hydroxy, hydroxyalkyl, cyano, amino, alkylamino, dialkylamino, and oxo.

In certain embodiments, Het' is selected from the group consisting of the divalent forms of tetrahydropyranyl, tetrahydrofuranyl, 1,3-dioxolanyl, pyrrolidinyl, piperidinyl, morpholinyl, thiomorpholinyl, 1,1-dioxothiomorpholinyl, thiazolidinyl, azepanyl, 1,4-oxazepanyl, diazepanyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and piperazinyl, each of which is unsubstituted or substituted by one or more substitutents.

In certain embodiments, Het' is unsubstituted (except by -R$_4$ or -Y-R$_4$).

In certain embodiments, a and b are independently integers from 1 to 6 with the proviso that a+b is ≤7.

In certain embodiments, a and b are each independently 1 to 3.

In certain embodiments, a and b are each 2.

In certain embodiments, a is 1, 2, or 3, and b is 2.

In certain embodiments, n is 0 or 1.

In certain embodiments, n is 0.

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v. 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of compounds of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic Synthesis*, John Wiley & Sons, New York, USA, 1991.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

For some embodiments, compounds of the invention can be prepared according to Reaction Scheme I, wherein R$_1$, R$_2$, R, and n are as defined above; Hal is —Br or —I; R$_{3a}$ is selected from the group consisting of —C(H)=C(H)—Z$_a$—Y—R$_4$, —C(H)=C(H)—Z$_a$—Y—X—Y—R$_4$, —C(H)=C(H)—Z$_a$—R$_5$, —C(H)=C(H)—Z$_a$-Het, —C(H)=C(H)—Z$_a$-Het'-R$_4$, —C(H)=C(H)—Z$_a$-Het'-Y—R$_4$, —N(R$_8$)—C(R$_6$)—R$_4$, —N(R$_8$)—SO$_2$—R$_4$, and

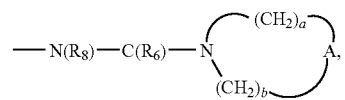

wherein R$_8$, R$_6$, R$_5$, R$_4$, Y, X, Het, and Het' are as defined above, and Z$_a$ is selected from the group consisting of a bond and alkylene, wherein alkylene can be optionally interrupted with one or more —O— groups; and R$_{3b}$ is selected from the group consisting of —CH$_2$—CH$_2$—Z$_a$—Y—R$_4$, —CH$_2$—CH$_2$—Z$_a$—Y—X—Y—R$_4$, —CH$_2$—CH$_2$—Z$_a$—R$_5$, —CH$_2$—CH$_2$—Z$_a$-Het, —CH$_2$—CH$_2$—Z$_a$-Het'-R$_4$, and —CH$_2$—CH$_2$—Z$_a$-Het'-Y—R$_4$, wherein R$_5$, R$_4$, Z$_a$, Y, X, Het, and Het' are as defined above. Numerous compounds of Formula XV are known; see, for example, U.S. Patent Application Publication No. US 2004/0147543 and the documents cited therein.

The Heck reaction is used in step (1) of Reaction Scheme I to provide compounds of Formula IIa, wherein R$_{3a}$ is selected from the group consisting of —C(H)=C(H)—Z$_a$—Y—R$_4$, —C(H)=C(H)—Z$_a$—Y—X—Y—R$_4$, —C(H)=C(H)—Z$_a$—R$_5$, —C(H)=C(H)—Z$_a$-Het, C(H)=C(H)—Z$_a$-Het'-R$_4$, and —C(H)=C(H)—Z$_a$-Het'-Y—R$_4$. The Heck reaction is carried out by coupling a 1H-imidazo[4,5-c]quinolin-4-amine of Formula XV with a compound of the Formula H$_2$C=C(H)—Z$_a$—Y—R$_4$, H$_2$C=C(H)—Z$_a$—Y—X—Y—R$_4$, H$_2$C=C(H)—Z$_a$—R$_5$, H$_2$C=C(H)—Z$_a$-Het, H$_2$C=C(H)—Z$_a$-Het'-R$_4$, or H$_2$C=C(H)—Z$_a$-Het'-Y—R$_4$. Several of these vinyl-substituted compounds are commercially available; others can be prepared by known methods. For example, vinyl-substituted compounds are readily prepared from aldehydes, primary alcohols, or primary allyl halides using a variety of conventional methods. The reaction is conveniently carried out by combining the compound of Formula XV and the vinyl-substituted compound in the presence of palladium (II) acetate, triphenylphosphine or tri-ortho-tolylphosphine, and a base such as triethylamine or cesium carbonate in a suitable solvent such as acetonitrile, toluene, or N,N-dimethylformamide (DMF). The reaction can be carried out at an elevated temperature such as 85° C. to 125° C. under an inert atmosphere. The product of Formula IIa, a subgenus of Formulas I and II, or pharmaceutically acceptable salt thereof can be isolated using conventional methods. The Heck reaction can also be carried out on a trifluoromethanesulfonate-substituted 1H-imidazo[4,5-c]quinolin-4-amine, in which Hal in Formula XV is replaced by —O(SO)$_2$—CF$_3$. It is understood by one skilled in the art that certain substrates are not compatible with Heck reaction chemistry; see, R. F. Heck, in *Comprehensive Organic Synthesis*, Vol. 4 (Eds.: B. M. Trost, I. Fleming), Pergamon Press, Oxford, p. 833, (1991). For example, it is understood by one skilled in the art that for the Heck reaction described above, $Z_a$ is other than a bond when a Y group bonded to $Z_a$ is —O—, —O—C($R_6$)—, —OC(O)—O—, —O—C($R_6$)—N($R_8$)—,

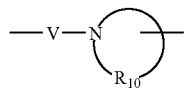

wherein V is —O—C($R_6$)—, or

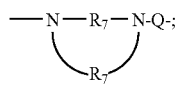

or when the $R_5$ bonded to $Z_a$ is

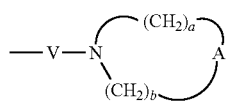

wherein V is —O—C($R_6$)—; or when $Z_a$ is attached to a nitrogen atom in Het or Het'.

A copper-mediated coupling reaction can be used to prepare compounds of Formula IIa, wherein $R_{3a}$ is —N($R_8$)—C($R_6$)—$R_4$, —N($R_8$)—SO$_2$-$R_4$, or

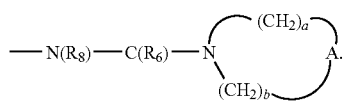

The reaction is conveniently carried out by combining the 1H-imidazo[4,5-c]quinolin-4-amine of the Formula XV and an amide, sulfonamide, or urea of formula HN($R_8$)-Q-$R_4$ or

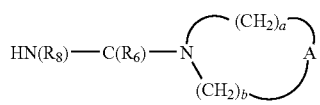

in the presence of copper (I) iodide, potassium phosphate, and racemic trans-1,2-diaminocyclohexane in a suitable solvent such as 1,4-dioxane. The reaction can be carried out at an elevated temperature such as 110° C. Many amides, sulfonamides, and ureas are commercially available; others can be made by conventional methods. The compound or a pharmaceutically acceptable salt thereof can be isolated using conventional methods.

The compounds of Formula IIa prepared by the Heck reaction, can undergo reduction of the alkenylene group present in step (2) of Reaction Scheme I to provide compounds of Formula IIb. The reduction can be carried out by hydrogenation using a conventional heterogeneous hydrogenation catalyst such as palladium on carbon. The reaction can conveniently be carried out on a Parr apparatus in a suitable solvent such as ethanol, methanol, or mixtures thereof. The product of Formula IIb, a subgenus of Formulas I and II, or a pharmaceutically acceptable salt thereof can be isolated using conventional methods.

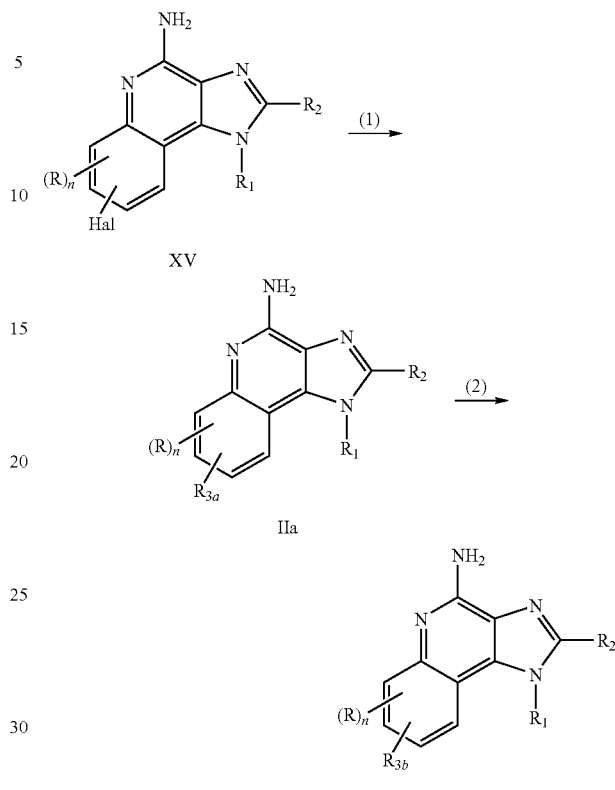

Reaction Scheme I

For some embodiments, compounds of the invention can be prepared according to Reaction Scheme II, wherein $R_1$, $R_2$, $R_{3a}$, $R_{3b}$, R, Hal, and n are as defined above. In steps (1) and (2) of Reaction Scheme II, a 1H-imidazo[4,5-c]quinoline of Formula XVI undergoes a metal-mediated coupling reaction to provide a compound of Formula Xa, which may be reduced in step (2) to a compound of Formula Xb. Compounds of Formula Xa and Xb are subgenera of Formula X. Steps (1) and (2) of Reaction Scheme II can be carried out according to the methods described in steps (1) and (2) of Reaction Scheme I. Numerous compounds of Formula XVI are known; see, for example, U.S. Patent Publication Application No. US 2004/0147543 and the documents cited therein.

In steps (3a) and (3b) of Reaction Scheme II, 1H-imidazo[4,5-c]quinolines of Formula Xa and Xb are oxidized to provide 1H-imidazo[4,5-c]quinoline-5N-oxides of Formulas XVII and XVIII, respectively, using a conventional oxidizing agent capable of forming N-oxides. The reaction is conveniently carried out by adding 3-chloroperoxybenzoic acid at room temperature to a solution of a compound of Formula Xa or Xb in a solvent such dichloromethane or chloroform. Alternatively, the oxidation can be carried out by heating a solution of a compound of Formula Xa or Xb in a suitable solvent such as ethyl acetate with peracetic acid at a temperature such as 50° C. and then adding sodium metabisulfite.

In steps (4a) and (4b) of Reaction Scheme II, 1H-imidazo[4,5-c]quinoline-5N-oxides of Formulas XVII and XVIII are aminated to provide 1H-imidazo[4,5-c]quinolin-4-amines of Formulas IIa and IIb, respectively. The amination can be carried out by the activation of an N-oxide of Formula XVII or XVIII by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide followed by p-toluenesulfonyl chloride to a solution of the N-oxide of Formula XVII or XVIII in a suitable solvent such as chloroform or dichloromethane at room temperature. The reaction may also be carried out by adding ammonium hydroxide and p-toluenesulfonyl chloride to the reaction mixture from step (3a) or (3b) without isolating the N-oxide of Formula XVII or XVIII. The product or a pharmaceutically acceptable salt thereof can be isolated using conventional methods.

Alternatively step (4a) or (4b) can be carried out by the reaction of a 1H-imidazo[4,5-c]quinoline-5N-oxide of Formula XVII or XVIII with trichloroacetyl isocyanate followed by hydrolysis of the resulting intermediate to provide a compound of Formula IIa or IIb. The reaction is conveniently carried out in two steps by (i) adding trichloroacetyl isocyanate to a solution of the N-oxide of Formula XVII or XVIII in a solvent such as dichloromethane and stirring at room temperature to provide an isolable amide intermediate. In step (ii), a solution of the intermediate in methanol is treated with a base such as sodium methoxide or ammonium hydroxide at ambient temperature. The product or a pharmaceutically acceptable salt thereof can be isolated using conventional methods.

An $R_{3a}$ or $R_{3b}$ group in a compound of Formula Xa or Xb may contain a —S— functional group, which can be oxidized to —S(O)$_2$— in step (3a) or (3b) of Reaction Scheme II using an excess of the oxidizing agent. Step (4a) or (4b) of Reaction Scheme II may then be carried out to provide a compound of Formula IIa or IIb, wherein $R_{3a}$ or $R_{3b}$ contains a —S(O)$_2$— functional group.

Reaction Scheme II

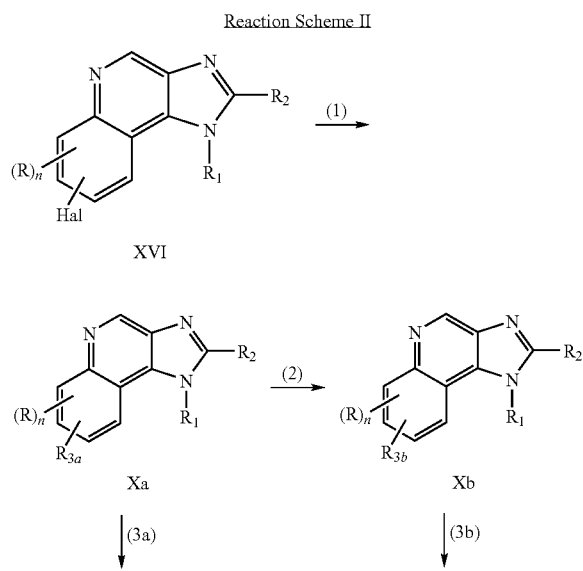

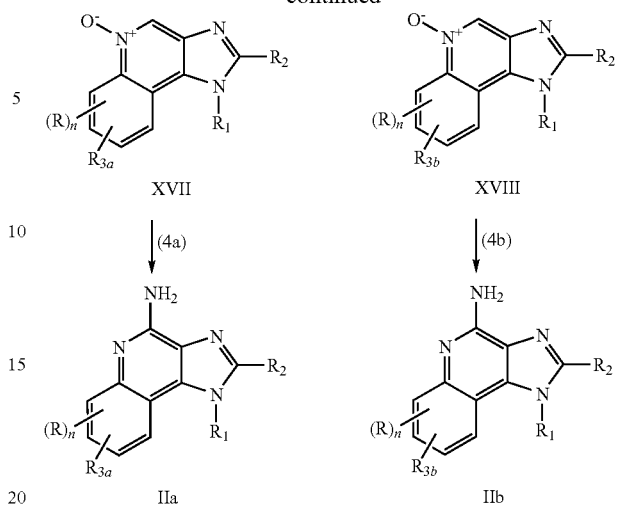

For some embodiments, compounds of the invention can be prepared according to Reaction Scheme III, wherein $R_1$, $R_2$, $R_4$, $R_8$, A, R, $Z_a$, Hal, a, b, and n are as defined above. In step (1) of Reaction Scheme III, a 1H-imidazo[4,5-c]quinolin-4-amine of Formula XV is coupled with an ester of formula $H_2C=C(H)—C(O)—Oalkyl$ to provide an ester-substituted 1H-imidazo[4,5-c]quinolin-4-amine of Formula XIX, a subgenus of Formulas I and II. The reaction can be carried out under the Heck reaction conditions described in step (1) of Reaction Scheme I. Some esters of formula $H_2C=C(H)—C(O)—O$-alkyl, for example methyl acrylate, are commercially available; others can be prepared by known methods. The conditions described in step (2) of Reaction Scheme I may then be used to reduce the double bond in a compound of Formula XIX in step (2) of Reaction Scheme III to provide an ester-substituted 1H-imidazo[4,5-c]quinolin-4-amine of Formula XX, a subgenus of Formulas I and II.

In step (3) of Reaction Scheme III, the ester group of a 1H-imidazo[4,5-c]quinolin-4-amine of Formula XX undergoes base-promoted hydrolysis to the carboxylic acid of Formula XXI. The hydrolysis reaction is conveniently carried out by combining a compound of Formula XX with a base such as potassium hydroxide or sodium hydroxide in a suitable solvent mixture such as an alcohol/water mixture, preferably a methanol/water mixture. The reaction can be carried out at room temperature, and the product of Formula XXI, a subgenus of Formulas I and II, or a pharmaceutically acceptable salt thereof can be isolated by conventional methods.

A carboxylic acid of Formula XXI is converted into an amide of Formula IIg or IIh in step (4) or (4a) of Reaction Scheme III using conventional methods. The reaction is conveniently carried out by treating a solution of a carboxylic acid of Formula XXI with a secondary amine of formula $HN(R_8)R_4$ or

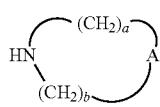

and a coupling agent, such as 1-[3-(dimethylamino)propyl-3-ethylcarbodiimide hydrochloride, in the presence of 1-hydroxybenzotriazole. The reaction can be carried out at room temperature in a suitable solvent such as DMF, and the product of Formula IIg or IIh, which are subgenera of Formulas I and II, or a pharmaceutically acceptable salt thereof, can be isolated by conventional methods. Numerous secondary amines are commercially available; others can be prepared by known synthetic methods.

In step (1) of Reaction Scheme IV, a 1H-imidazo[4,5-c]quinoline of Formula XVI undergoes a Heck coupling reaction, according to the method described in step (1) of Reaction Scheme I, with an alkenyl-substituted phthalimide of formula

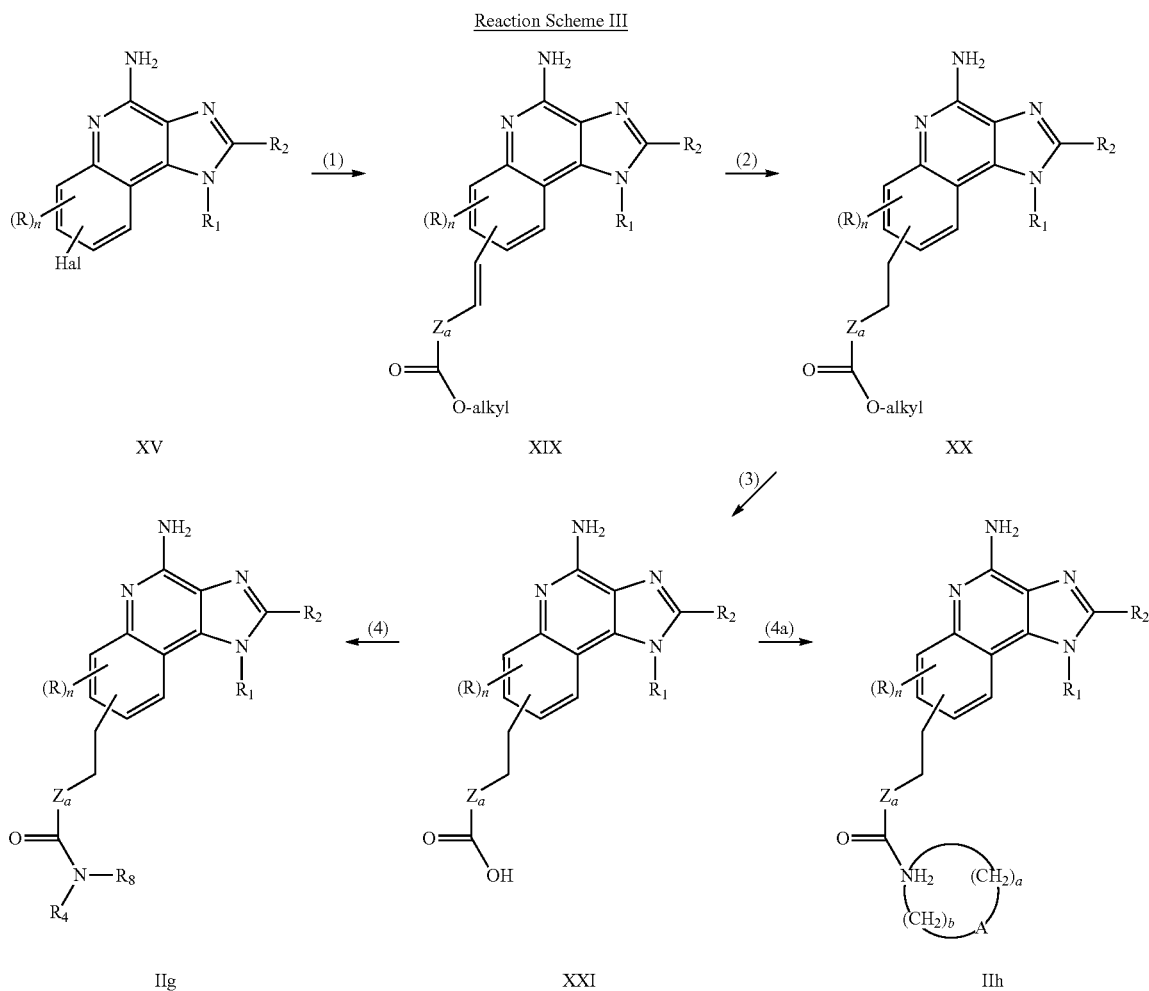

Reaction Scheme III

For some embodiments, compounds of the invention can be prepared according to Reaction Scheme IV, wherein $R_1$, $R_2$, $R_4$, $R_8$, Q, R, $Z_a$, Hal, and n are as defined above; and $R_{5a}$ is

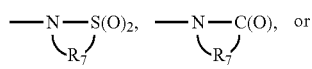

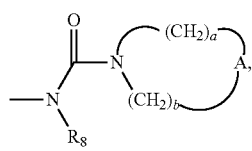

wherein A, a, b, $R_7$, and $R_8$ are as defined above.

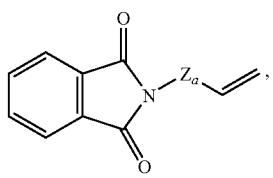

which is commercially available or can be prepared by known methods. The resulting compound of Formula XXIII may then be reduced in step (2) according to the method described in step (2) of Reaction Scheme I. Compounds of Formula XXIII and XXIV are subgenera of Formula X and can be isolated by conventional methods.

In steps (3) and (4) of Reaction Scheme IV, a phthalimide-substituted 1H-imidazo[4,5-c]quinoline of Formula XXIV is first oxidized to a 5N-oxide of Formula XXV, which is then aminated to provide a phthalimide-substituted 1H-imidazo[4,5-c]quinolin-4-amine of Formula XXVI, a subgenus of Formulas I and II. Steps (3) and (4) of Reaction Scheme IV can be carried out according to the methods described in steps (3a) and (4a) of Reaction Scheme II, and the product or a pharmaceutically acceptable salt thereof can be isolated by conventional methods.

In step (5) of Reaction Scheme IV, the phthalimide group of a 1H-imidazo[4,5-c]quinolin-4-amine of Formula XXVI is removed to provide an amino-substituted 1H-imidazo[4,5-c] quinolin-4-amine of Formula XXVII, a subgenus of Formulas I and II. The reaction is conveniently carried out by adding hydrazine or hydrazine hydrate to a solution or suspension of a compound of Formula XXVI in a suitable solvent such as ethanol. The reaction can be carried out at room temperature or at an elevated temperature, such as the reflux temperature of the solvent. The product or a pharmaceutically acceptable salt thereof can be isolated by conventional methods.

In step (6) or (6a) of Reaction Scheme IV, an amino-substituted 1H-imidazo[4,5-c]quinolin-4-amine of Formula XXVII is converted to a 1H-imidazo[4,5-c]quinolinyl compound of Formula XXVIII or XXIX, subgenera of Formulas I and II, using conventional methods. For example, an amino-substituted 1H-imidazo[4,5-c]quinolin-4-amine of Formula XXVII can react with an acid chloride of Formula $R_4C(O)Cl$ to provide a compound of Formula XXVIII in which $-QR_4$ is $—C(O)—R_4$. In addition, a 1H-imidazo[4,5-c]quinolin-4-amine of Formula XXVII can react with sulfonyl chloride of Formula $R_4S(O)_2Cl$ or a sulfonic anhydride of Formula $(R_4S(O)_2)_2O$ to provide a compound of Formula XXVIII in which $-QR_4$ is $—S(O)_2—R_4$. Numerous acid chlorides of Formula $R_4C(O)Cl$, sulfonyl chlorides of Formula $R_4S(O)_2Cl$, and sulfonic anhydrides of Formula $(R_4S(O)_2)_2O$ are commercially available; others can be readily prepared using known synthetic methods. The reaction is conveniently carried out by adding the acid chloride of Formula $R_4C(O)Cl$, sulfonyl chloride of Formula $R_4S(O)_2Cl$, or sulfonic anhydride of Formula $(R_4S(O)_2)_2O$ to a solution of the amino-substituted 1H-imidazo[4,5-c]quinolin-4-amine of Formula XXVII in a suitable solvent such as chloroform, dichloromethane, or 1-methyl-2-pyrrolidinone. Optionally a base such as triethylamine, pyridine, or N,N-diisopropylethylamine, or a combination thereof can be added. The reaction can be carried out at room temperature or initially at a sub-ambient temperature such as 0° C. and then warming to room temperature. The product or a pharmaceutically acceptable salt thereof can be isolated using conventional methods.

Compounds of Formula XXIX where $R_{5a}$ is

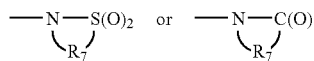

can be prepared by treating an amino-substituted 1H-imidazo [4,5-c]quinolin-4-amine of Formula XXVII with a chloroalkanesulfonyl chloride of Formula $C_1$-$R_7S(O)_2Cl$ or a chloroalkanoyl chloride of Formula $C_1$-$R_7C(O)Cl$. The reaction is conveniently carried out by adding the chloroalkanesulfonyl chloride or chloroalkanoyl chloride to a solution of the amino-substituted 1H-imidazo[4,5-c]quinolin-4-amine of Formula XXVII in a suitable solvent such as chloroform at ambient temperature. The isolable intermediate chloroalkanesulfonamide or chloroalkanamide can then be treated with a base such as 1,8-diazabicyclo[5.4.0]undec-7-ene in a suitable solvent such as DMF to effect the cyclization. The product or a pharmaceutically acceptable salt thereof can be isolated using conventional methods.

Ureas of Formula XXVIII, where $-QR_4$ is $—C(R_6)—NH—W—R_4$, $R_6$ is $=O$, and W is a bond, can be prepared by reacting an amino-substituted 1H-imidazo[4,5-c]quinolin-4-amine of Formula XXVII with isocyanates of Formula $R_4N=C=O$. Numerous isocyanates of Formula $R_4N=C=O$ are commercially available; others can be readily prepared using known synthetic methods. The reaction can be conveniently carried out by adding the isocyanate of Formula $R_4N=C=O$ to a solution of the amino-substituted 1H-imidazo[4,5-c]quinolin-4-amine of Formula XXVII in a suitable solvent such as dichloromethane or chloroform. Optionally a base such as triethylamine can be added. The reaction can be carried out at room temperature or initially at a sub-ambient temperature such as 0° C. and then warming to room temperature. Alternatively, a compound of Formula XXVII can be treated with an isocyanate of Formula $R_4(CO)N=C=O$, a thioisocyanate of Formula $R_4N=C=S$, a sulfonyl isocyanate of Formula $R_4S(O)_2N=C=O$, or a carbamoyl chloride of Formula $R_4N—(R_8)—C(O)Cl$, or

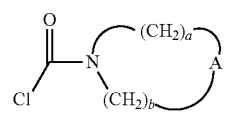

to provide a compound of Formula XXVIII, wherein $-QR_4$ is $—C(R_6)—N(R_8)—W—$, where $R_6$, $R_8$, and W are as defined above, or a compound of Formula XXIX wherein $R_{5a}$ is

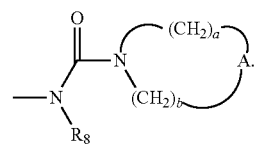

The product or a pharmaceutically acceptable salt thereof can be isolated using conventional methods.

Sulfamides of Formula XXVIII, where $-QR_4$ is $—S(O)_2—N(R_8)—R_4$ can be prepared by reacting a compound of Formula XXVII with sulfuryl chloride to generate a sulfamoyl chloride in situ, and then reacting the sulfamoyl chloride with an amine of formula $HN(R_8)R_4$. Alternatively, sulfamides of Formula XXVIII can be prepared by reacting a compound of Formula XXVII with a sulfamoyl chloride of formula $R_4(R_8)N—S(O)_2Cl$. The product or a pharmaceutically acceptable salt thereof can be isolated using conventional methods. Many amines of Formula $HN(R_8)R_4$ and some sulfamoyl chlorides of formula $R_4(R_8)N—S(O)_2Cl$ are commercially available; others can be prepared using known synthetic methods.

Compounds of Formula XXVIII, wherein $R_8$ is other than hydrogen can be prepared by reductive alkylation of the amino-substituted 1H-imidazo[4,5-c]quinolin-4-amine of Formula XXVII. The alkylation is conveniently carried out in two parts by (i) adding an aldehyde or ketone to a solution of an amino-substituted 1H-imidazo[4,5-c]quinolin-4-amine of Formula XXVII or a salt thereof in a suitable solvent such as DMF in the presence of a base such as N,N-diisopropylethylamine. In part (ii) the reduction is carried out by adding a suitable reducing agent such as the borane-pyridine complex. Both part (i) and part (ii) can be carried out at ambient temperature, and the product or a pharmaceutically acceptable salt thereof can be isolated using conventional methods. The resulting compound can undergo reaction with an acid chloride, sulfonyl chloride, sulfonic anhydride, isocyanate, or carbamoyl chloride as described above to provide a compound of Formula XXVIII, wherein $R_8$ is other than hydrogen.

one or more —O— groups, and X, Y, $R_4$, $R_5$, Het, and Het' are as defined above; and $R_{3d}$ is -Het, -Het'-$R_4$, -Het'-Y-$R_4$, —S—$R_4$, —S(O)$_2$—$R_4$, or Reaction Scheme IV

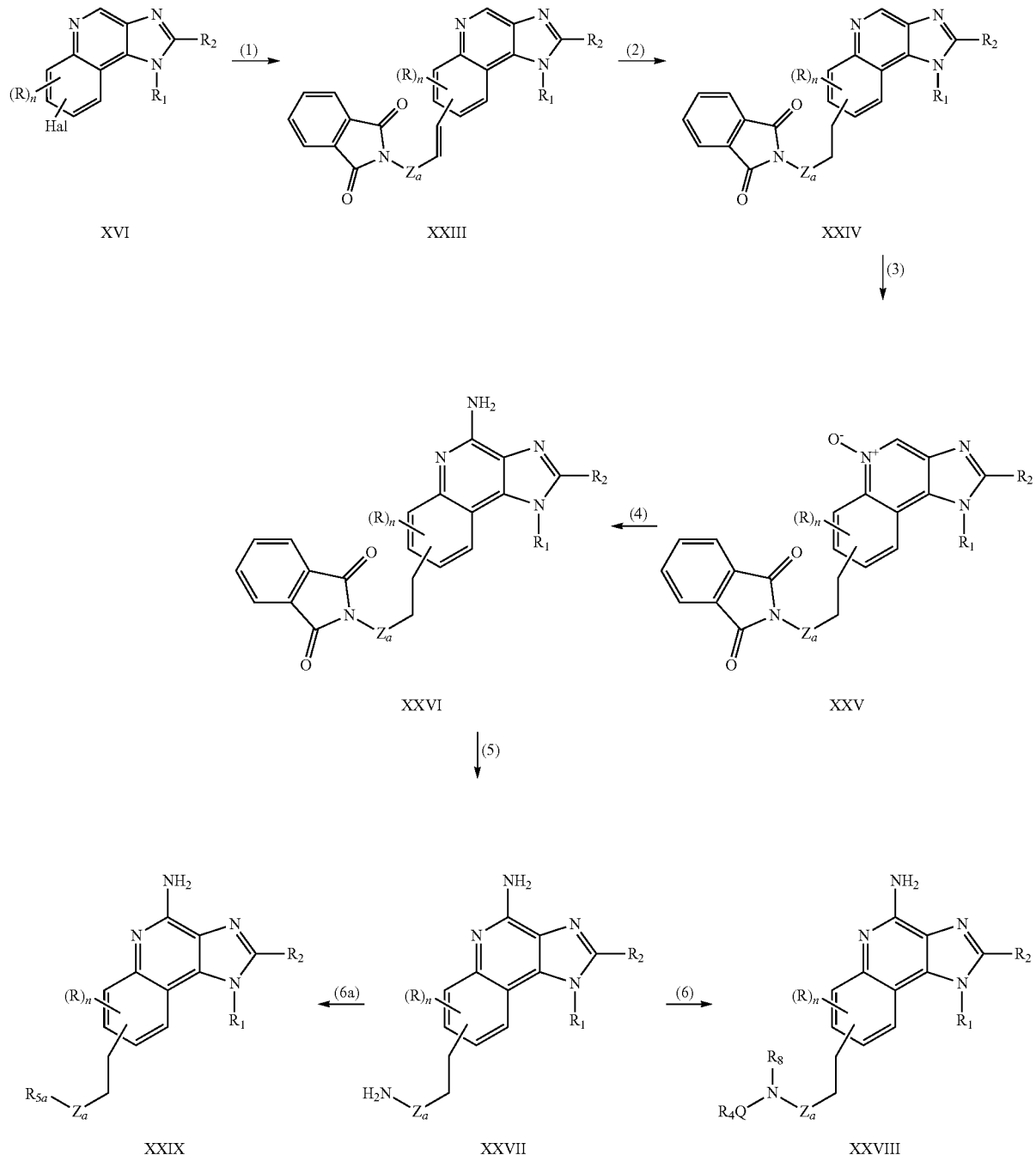

For some embodiments, compounds of the invention can be prepared according to Reaction Scheme V, wherein $R_1$, $R_2$, $Z_a$, R, and n are as defined above; LG is a leaving group such as —Cl, —Br, —I, —O(SO)$_2$CH$_3$, or —O(SO)$_2$CF$_3$; $R_{3c}$ is -$Z_b$-Y-$R_4$, -$Z_b$-Y-X-Y-$R_4$, -$Z_b$-$R_5$, -$Z_b$-Het, -$Z_b$-Het'-$R_4$, and -$Z_b$-Het'-Y-$R_4$, wherein $Z_b$ is selected from the group consisting of alkylene, alkenylene, and alkynylene interrupted with

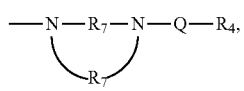

wherein Y, $R_4$, $R_7$, Q, Het, and Het' are as defined above.

In step (1) of Reaction Scheme V, an ester-substituted compound of Formula XX is reduced to a hydroxyalkyl-substituted 1H-imidazo[4,5-c]quinolin-4-amine of Formula XXX using conventional methods. For example, the reduction may be carried out at room temperature with lithium borohydride in a suitable solvent such as THF. The product or a pharmaceutically acceptable salt thereof can be isolated by conventional methods.

In step (2a) of Reaction Scheme V, a hydroxy-substituted compound of Formula XXX is converted to an ether substituted 1H-imidazo[4,5-c]quinolin-4-amine of Formula XXXI, which is a subgenus of Formulas I and II, using a Williamson-type ether synthesis. The reaction is effected by treating a compound of Formula XXX with a halide of Formula Halide—$R_{3c}$ in the presence of a base. The reaction can be carried out by combining the halide with a compound of Formula XXX in a suitable solvent such as DMF in the presence of a base such as cesium carbonate. The reaction can be carried out at ambient temperature or at an elevated temperature, for example, 60 to 85° C. Alternatively, the reaction can be carried out by treating a solution of a compound of Formula XXX in a suitable solvent such as DMF with sodium hydride and then adding the halide.

In step (2) of Reaction Scheme V, a hydroxy-substituted compound of Formula XXX is converted to a leaving group in a compound of Formula XXXII using a variety of conventional methods. For example, a hydroxy-substituted compound of Formula XXX can be chlorinated to provide a compound of Formula XXXII wherein LG is —Cl. Conventional chlorinating reagents can be used. The reaction is conveniently carried out by combining a compound of Formula XXX with thionyl chloride in a suitable solvent such as dichloromethane and heating. Alternatively, the reaction may be run neat. A hydroxy-substituted compound of Formula XXX can also be treated with methanesulfonic anhydride to provide a compound of Formula XXXII wherein LG is —O(SO)$_2$CH$_3$.

In step (3) of Reaction Scheme V, the chloro group on a compound of Formula XXXII can be displaced by a thiol under basic conditions to provide a compound of Formula XXXIII wherein $R_{3d}$ is —S—$R_4$. The reaction is conveniently carried out by adding a thiol to a solution of a compound of Formula XXXII in the presence of a base such as potassium tert-butoxide in a suitable solvent such as DMF. The product or a pharmaceutically acceptable salt thereof can be isolated by conventional methods. A compound of Formula XXXIII where $R_{3d}$ is —S—$R_4$ can then be oxidized to a compound of Formula XXXIII where $R_{3d}$ is —S(O)$_2$—$R_4$ using conventional oxidizing agents. The reaction is conveniently carried out by adding peracetic acid to the compound of Formula XXXIII where $R_{3d}$ is —S—$R_4$ in a suitable solvent. The conversion of a compound of Formula XXXII to a compound of Formula XXXIII where $R_{3d}$ is —S(O)$_2$—$R_4$ can conveniently be carried out in one pot without isolating the thioether from the reaction mixture. The product or a pharmaceutically acceptable salt thereof can be isolated by conventional methods.

The chloro group on a compound of Formula XXXII can also be displaced by an amine of Formula

H—N—R$_7$—N—Q—R$_4$,
       \\___R$_7$___/ several of which are commercially available. Other amines of this formula can be prepared by conventional methods. The reaction is conveniently carried out by combining a compound of Formula XXXII with the amine in the presence of a base such as potassium carbonate and in a suitable solvent such as DMF. Catalytic sodium iodide can optionally be added. The reaction can be carried out at an elevated temperature such as 50° C. or 90-100° C., and the product can be isolated by conventional methods. These reaction conditions can also be used employing a variety of cyclic secondary amines, such as substituted or unsubstituted pyrrolidines, piperidines, or morpholines, to provide compounds of Formula XXXIII wherein $R_{3d}$ is -Het, -Het'-$R_4$, or -Het'-Y-$R_4$, wherein Het or Het' is attached to the —CH$_2$— group at a nitrogen atom.

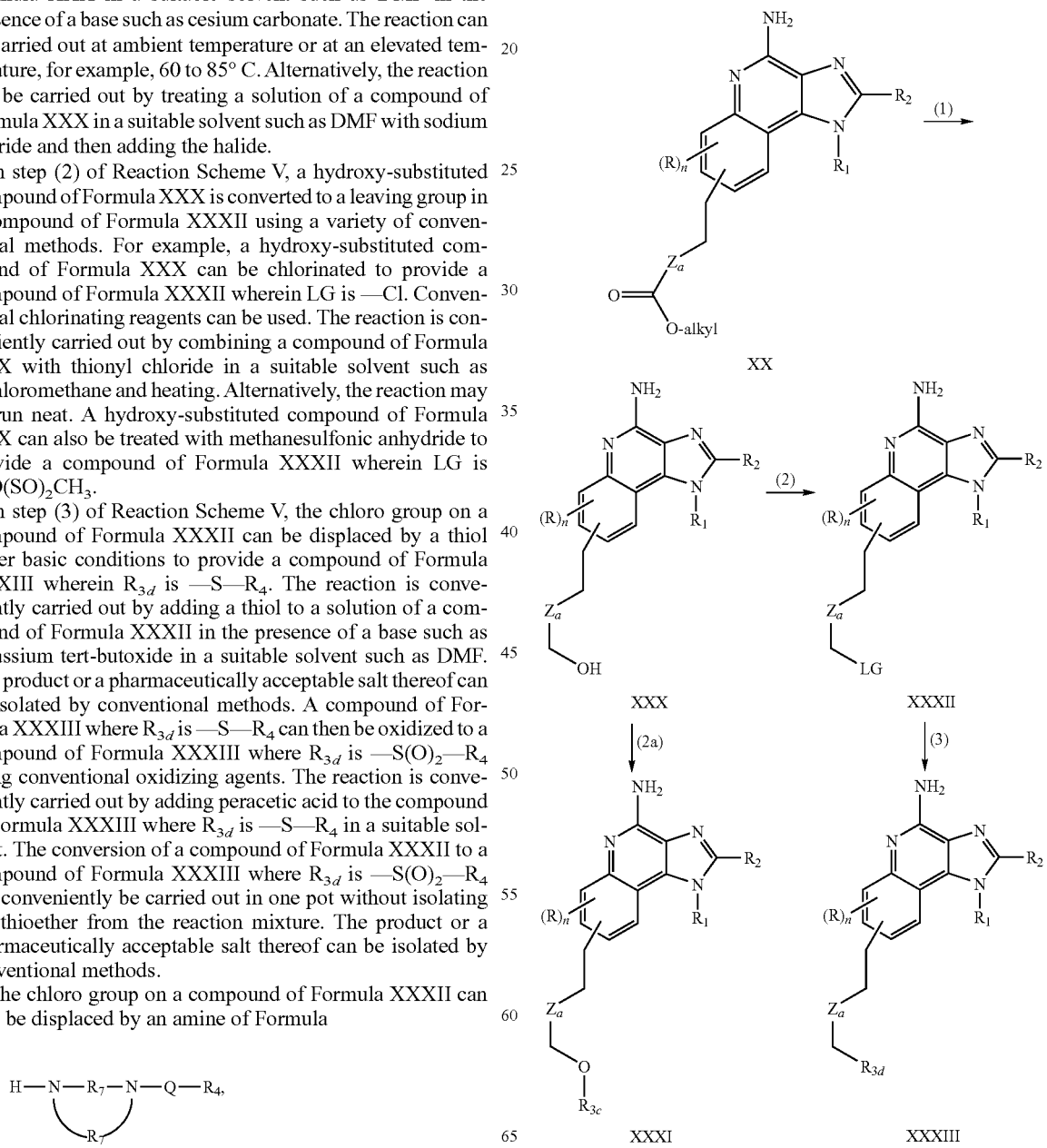

Reaction Scheme V

For some embodiments, compounds of the invention can be prepared according to Reaction Scheme VI wherein $R_1$, $R_2$, $R_{3a}$, $R_{3b}$, R, Hal, and n are as defined above. In step (1) of Reaction Scheme VI, an aminopyridine of Formula XXXIV is treated with the condensation product generated from 2,2-dimethyl-1,3-dioxane-4,6-dione (Meldrum's acid) and triethyl orthoformate to provide an imine of Formula XXXV. The reaction is conveniently carried out by adding a solution of an aminopyridine of Formula XXXIV to a heated mixture of Meldrum's acid and triethyl orthoformate and heating the reaction at an elevated temperature such as 70° C.

In step (2) of Reaction Scheme VI, an imine of Formula XXXV undergoes thermolysis and cyclization to provide a [1,5]naphthyridin-4-ol of Formula XXXVI. The reaction is conveniently carried out in a medium such as DOWTHERM A heat transfer fluid at a temperature in the range of 200 to 250° C.

In step (3) of Reaction Scheme VI, the [1,5]naphthyridin-4-ol of Formula XXXVI is nitrated under conventional nitration conditions to provide a 3-nitro[1,5]naphthyridin-4-ol of Formula XXXVII. The reaction is conveniently carried out by heating the [1,5]naphthyridin-4-ol of Formula XXXVI in nitric acid at an elevated temperature such as 90° C.

In step (4) of Reaction Scheme VI, a 3-nitro[1,5]naphthyridin-4-ol of Formula XXXVII is chlorinated using conventional chlorination chemistry to provide a 4-chloro-3-nitro[1,5]naphthyridine of Formula XXXVIII. The reaction is conveniently carried out by treating the 3-nitro[1,5]naphthyridin-4-ol of Formula XXXVII with phosphorous oxychloride in a suitable solvent such as DMF. The reaction can be carried out at ambient temperature or at an elevated temperature such as 100° C.

In step (5) of Reaction Scheme VI, a 4-chloro-3-nitro[1,5]naphthyridine of Formula XXXVIII is treated with an amine of Formula $R_1$—$NH_2$ to provide a 3-nitro[1,5]naphthyridin-4-amine of Formula XXXIX. Several amines of Formula $R_1$—$NH_2$ are commercially available; others can be prepared by known synthetic methods. The reaction is conveniently carried out by adding the amine of Formula $R_1$—$NH_2$ to a solution of the 4-chloro-3-nitro[1,5]naphthyridine of Formula XXXIX in a suitable solvent such as dichloromethane or methanol in the presence of a tertiary amine such as triethylamine. The reaction can be carried out at ambient temperature or at a sub-ambient temperature such as, for example, 0° C.

In step (6) of Reaction Scheme VI, a 3-nitro[1,5]naphthyridin-4-amine of Formula XXXIX is reduced to provide a [1,5]naphthyridine-3,4-diamine of Formula XL. The reaction can be carried out by hydrogenation using a heterogeneous hydrogenation catalyst such as platinum on carbon. The hydrogenation is conveniently carried out in a Parr apparatus in a suitable solvent such as toluene, methanol, or acetonitrile. The reaction can be carried out at ambient temperature.

Alternatively, the reduction in step (6) can be carried out using a one- or two-phase sodium dithionite reduction. The reaction is conveniently carried out using the conditions described by Park, K. K.; Oh, C. H.; and Joung, W. K.; *Tetrahedron Lett.*, 34, pp. 7445-7446 (1993) by adding sodium dithionite to a compound of Formula XXXIX in a mixture of dichloromethane and water at ambient temperature in the presence of potassium carbonate and ethyl viologen dibromide, ethyl viologen diiodide, or 1,1'-di-n-octyl-4,4'-bipyridinium dibromide.

In step (7) of Reaction Scheme VI, a [1,5]naphthyridine-3,4-diamine of Formula XL is treated with a carboxylic acid equivalent to provide a 1H-imidazo[4,5-c][1,5]naphthyridine of Formula XLI. Suitable carboxylic acid equivalents include orthoesters of Formula $R_2C(O-alkyl)_3$, 1,1-dialkoxyalkyl alkanoates of Formula $R_2C(O-alkyl)_2(O-C(O)-alkyl)$, and acid chlorides of Formula $R_2C(O)Cl$. The selection of the carboxylic acid equivalent is determined by the desired substituent at $R_2$. For example, triethyl orthoformate will provide a compound where $R_2$ is hydrogen, and trimethyl orthovalerate will provide a compound where $R_2$ is a butyl group. The reaction is conveniently carried out by adding the carboxylic acid equivalent to a [1,5]naphthyridine-3,4-diamine of Formula XL in a suitable solvent such as toluene or xylenes. Optionally, catalytic pyridine hydrochloride can be added. The reaction is carried out at a temperature high enough to drive off alcohol or water formed during the reaction. Conveniently, a Dean-Stark trap can be used to collect the volatiles.

Alternatively, step (7) can be carried out in two steps when an acid chloride of Formula $R_2C(O)Cl$ is used as the carboxylic acid equivalent. Part (i) of step (7) is conveniently carried out by adding the acid chloride to a solution of a [1,5]naphthyridine-3,4-diamine of Formula XL in a suitable solvent such as dichloromethane or acetonitrile to afford an amide. Optionally, a tertiary amine such as triethylamine, pyridine, or 4-dimethylaminopyridine can be added. The reaction can be carried out at room temperature. The amide product can be isolated and optionally purified using conventional techniques. Part (ii) of step (7) involves heating the amide prepared in part (i) to provide a 1H-imidazo[4,5-c][1,5]naphthyridine of Formula XLI. The reaction is conveniently carried out in a suitable solvent such as toluene at a temperature sufficient to drive off water formed during the reaction. The reaction can also be carried out in a solvent such as ethanol or methanol in the presence of a base such as triethylamine.

In steps (8) and (9) of Reaction Scheme VI, a 1H-imidazo[4,5-c][1,5]naphthyridine of Formula XLI is first oxidized to a 5N-oxide of Formula XLII, which is then aminated to provide a 1H-imidazo[4,5-c][1,5]naphthyridin-4-amine of Formula XLIII. Steps (8) and (9) of Reaction Scheme VI can be carried out according to the methods described in steps (3a) and (4a) of Reaction Scheme II.

In step (10) of Reaction Scheme VI a 1H-imidazo[4,5-c][1,5]naphthyridin-4-amine of Formula XLIII undergoes a metal-mediated coupling reaction to provide a compound of Formula IIIa, which may be reduced, when appropriate, in step (11) to a compound of Formula IIIb. Compounds of Formula IIIa and IIIb are subgenera of Formula III. Steps (10) and (11) of Reaction Scheme VI can be carried out according to the methods described in steps (1) and (2) of Reaction Scheme I, and the products or pharmaceutically acceptable salts thereof can be isolated by conventional methods.

Isomers of the compound of Formula XXXIV or Formula XXXVI can also be synthesized and can be used to prepare compounds of Formulas IV, V, and VI according to the methods shown in Reaction Scheme VI.

For some embodiments, compounds in Reaction Scheme VI can be further elaborated using conventional synthetic methods. For example, an amine of Formula $R_1$—$NH_2$ may be substituted by a hydroxy or second amino group, which may be further functionalized before step (7) of Reaction Scheme VI. Several examples of synthetic elaborations of an $R_1$ group on an imidazo ring compound are known. See, for example, U.S. Patent Publication Application No. US 2004/0147543 and the documents cited therein.

Similar synthetic transformations can be made at $R_2$ if, for example, the acid chloride used in step (7) of Reaction Scheme VI contains a protected hydroxy or amino group. Several acid chlorides of this type, for example acetoxyacetyl chloride, are commercially available. Others can be prepared by known synthetic methods. For examples of synthetic elaborations of an $R_2$ group on an imidazo ring compound, see U.S. Pat. No. 5,389,640 (Gerster et al.).

1H-imidazo[4,5-c]quinoline of Formula XLIV. The reaction can be carried out as described in step (1) of Reaction Scheme I.

Reaction Scheme VI

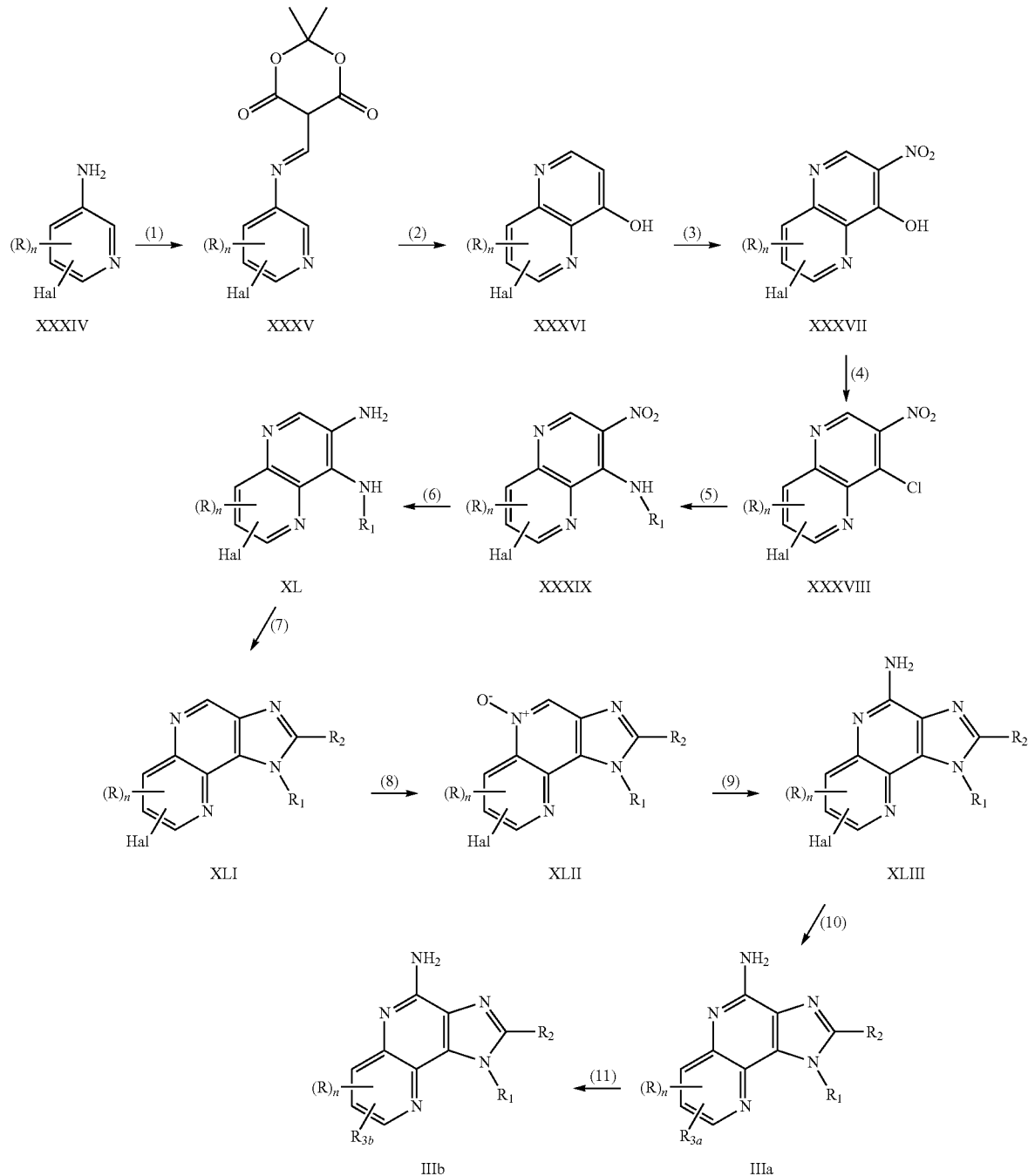

In some embodiments, compounds of the invention can be prepared according to Reaction Scheme VII, wherein R, $R_1$, $R_2$, $R_4$, $R_8$, Q, Hal, and n are as described above.

In step (1) of Reaction Scheme VII, the Heck reaction is used to couple a halogen substituted 1H-imidazo[4,5-c] quinoline of Formula XV with acrylonitrile to provide a In step (2) of Reaction Scheme VII, both the nitrile and the alkenylene groups in a 1H-imidazo[4,5-c]quinoline of Formula XLIV are reduced to provide an aminoalkyl substituted 1H-imidazo[4,5-c]quinoline of Formula XLV. The reduction can be carried out by hydrogenation using a conventional heterogeneous hydrogenation catalyst such as palladium on carbon. The reaction can be carried out on a Parr apparatus in a suitable solvent mix, such as methanol and trifluoroacetic acid.

In step (3) of Reaction Scheme VII, the amino group of a 1H-imidazo[4,5-c]quinoline of Formula XLV is further elaborated using the methods described in step (6) of Reaction Scheme IV to provide a 1H-imidazo[4,5-c]quinoline of Formula XLVI, which is a subgenus of Formulas I and II. The product or a pharmaceutically acceptable salt thereof can be isolated using conventional methods.

In step (2) of Reaction Scheme VIII, the nitrile group in a 1H-imidazo[4,5-c]quinoline of Formula XLVII is hydrolyzed to provide a 1H-imidazo[4,5-c]quinoline of Formula XLVIII, which is a subgenus of Formulas I and II The reaction can be carried out by treating a solution of a compound of Formula XLVII in a suitable solvent such as methanol with aqueous sodium hydroxide and aqueous hydrogen peroxide. The reaction can be carried out at an elevated temperature, such as for example, 50° C., and the product or a pharmaceutically acceptable salt thereof can be isolated using conventional methods.

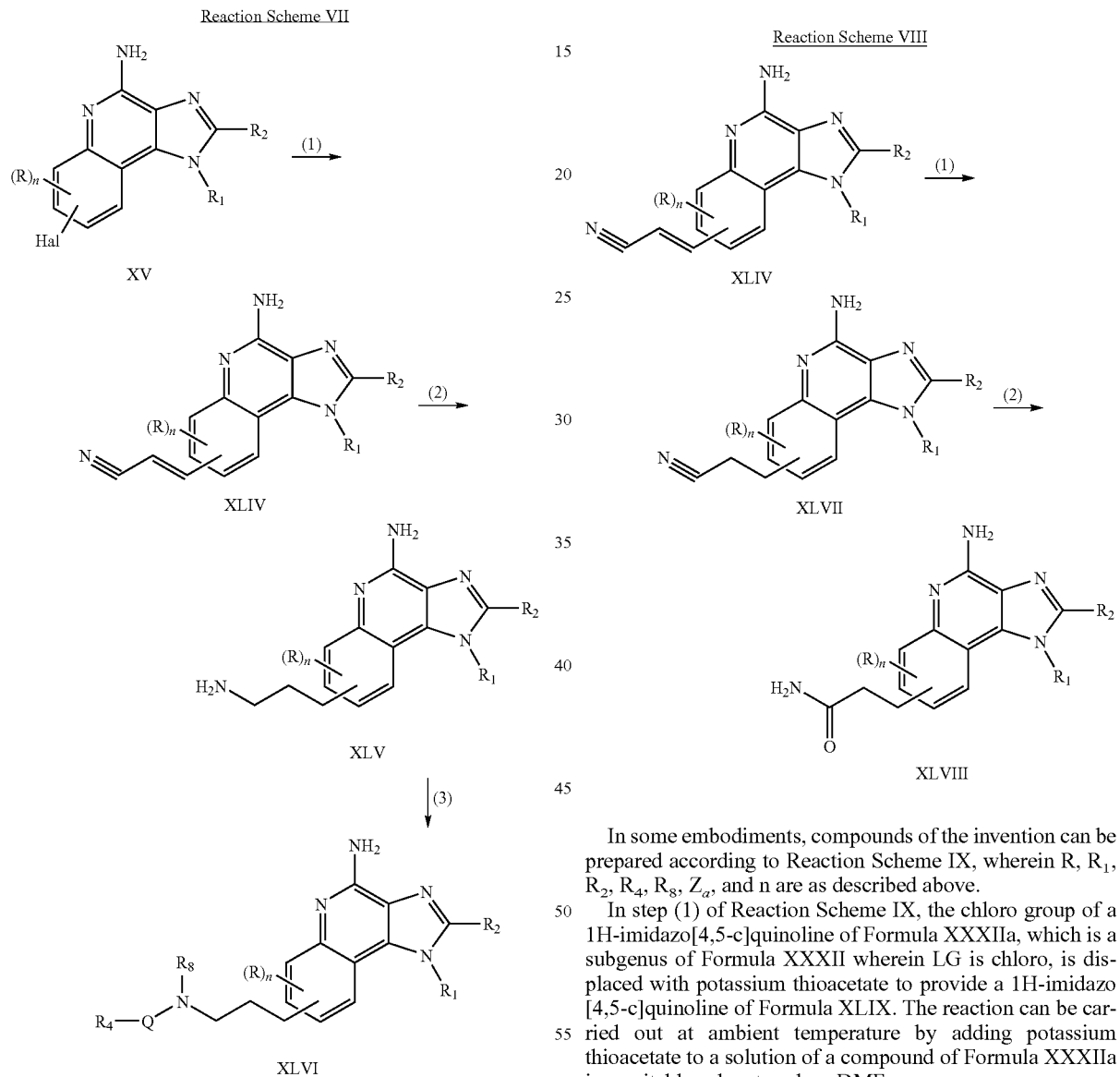

In some embodiments, compounds of the invention can be prepared according to Reaction Scheme VIII, wherein R, $R_1$, $R_2$, and n are as described above.

In step (1) of Reaction Scheme VIII, the alkenylene bond in a 1H-imidazo[4,5-c]quinoline of Formula XLIV is reduced to provide a 1H-imidazo[4,5-c]quinoline of Formula XLVII. The reduction can be carried out as described in step (2) of Reaction Scheme I.

In some embodiments, compounds of the invention can be prepared according to Reaction Scheme IX, wherein R, $R_1$, $R_2$, $R_4$, $R_8$, $Z_a$, and n are as described above.

In step (1) of Reaction Scheme IX, the chloro group of a 1H-imidazo[4,5-c]quinoline of Formula XXXIIa, which is a subgenus of Formula XXXII wherein LG is chloro, is displaced with potassium thioacetate to provide a 1H-imidazo [4,5-c]quinoline of Formula XLIX. The reaction can be carried out at ambient temperature by adding potassium thioacetate to a solution of a compound of Formula XXXIIa in a suitable solvent such as DMF.

In step (2) of Reaction Scheme IX, the thioacetate group of a 1H-imidazo[4,5-c]quinoline of Formula XLIX is hydrolyzed under basic conditions to provide a thiol substituted 1H-imidazo[4,5-c]quinoline of Formula L. The reaction can be carried out by adding a solution of sodium methoxide in methanol to a solution of a compound of Formula XLIX in a suitable solvent such as methanol. The reaction can be carried out at ambient temperature.

In step (3) of Reaction Scheme IX, the thiol group of a 1H-imidazo[4,5-c]quinoline of Formula L is oxidized to provide a sulfonyl chloride substituted 1H-imidazo[4,5-c]quinoline of Formula LI. The reaction can be carried out by adding a solution of sodium chlorate in water to a solution of a compound of Formula L in hydrochloric acid. The reaction can be carried out at a sub-ambient temperature, such as for example, 0° C.

In step (4) of Reaction Scheme IX, a sulfonyl chloride substituted 1H-imidazo[4,5-c]quinoline of Formula LI is treated with an amine to provide a sulfonamide substituted 1H-imidazo[4,5-c]quinoline of Formula LII, which is a subgenus of Formulas I and II. The reaction can be carried out by adding an amine of Formula $HN(R_4)(R_8)$ to a compound of Formula LI in a suitable solvent such as dichloromethane or pyridine. The reaction can be carried out at ambient temperature.

Formula LV. The reaction can be carried out by treating a solution of a compound of Formula LIV in a suitable solvent such as THF with sodium borohydride. The reduction can be carried out at ambient temperature or at a sub-ambient temperature, such as 0° C.

In step (3) of Reaction Scheme X, a hydroxy substituted 1H-imidazo[4,5-c]quinoline of Formula LV is chlorinated using conventional methods to provide a chloro substituted 1H-imidazo[4,5-c]quinoline of Formula LVI. The reaction can be carried out by treating a solution of a compound of Formula LV in a suitable solvent such as dichloromethane with thionyl chloride.

In step (4) of Reaction Scheme X, the chloro group of a 1H-imidazo[4,5-c]quinoline of Formula LVI is displaced to

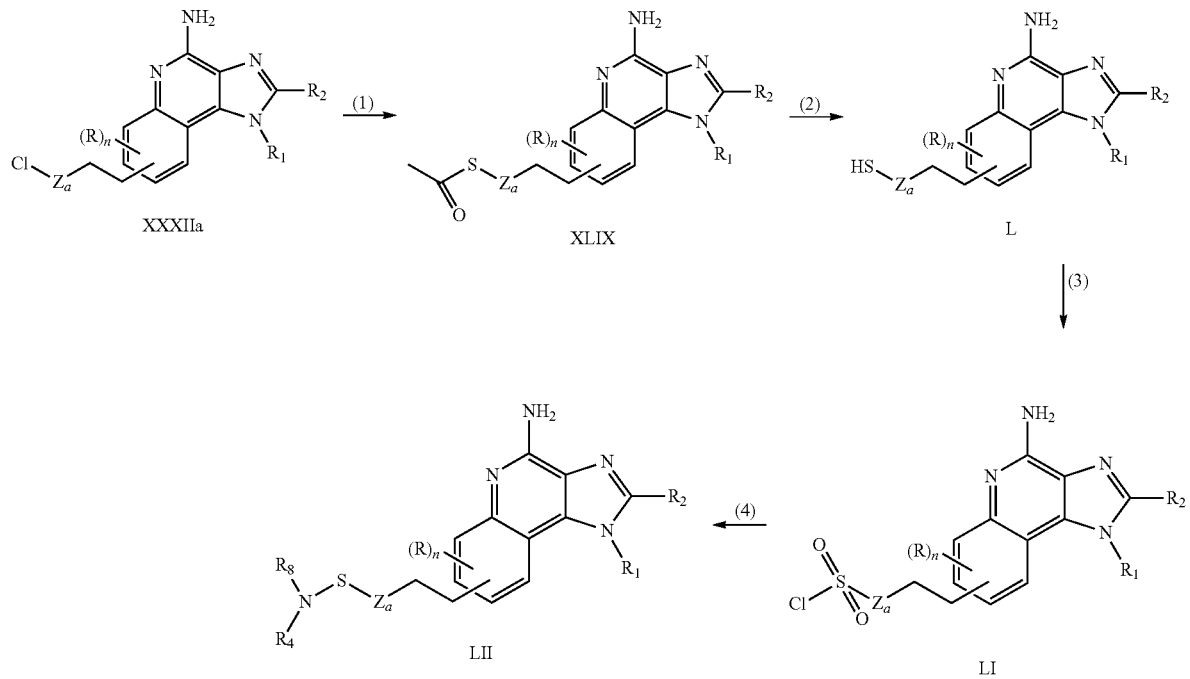

Reaction Scheme IX

In some embodiments, compounds of the invention can be prepared according to Reaction Scheme X, wherein R, $R_1$, $R_2$, $R_4$, $R_8$, Q, and n are as described above.

In step (1) of Reaction Scheme X, a vinyl substituted 1H-imidazo[4,5-c]quinoline of Formula LIII undergoes ozonolysis to provide an aldehyde substituted 1H-imidazo[4,5-c]quinoline of Formula LIV. The reaction can be carried out by bubbling ozone through a solution of a compound of Formula LIII in a suitable solvent such as dichloromethane and then quenching with triphenylphosphine. The reaction can be carried out at a sub-ambient temperature, such as 0° C. Some vinyl substituted 1H-imidazo[4,5-c]quinolines of Formula LIII are known; others can be prepared using known synthetic methods. See for example, U.S. Patent Application No. 2004/0147543 and the documents cited therein.

In step (2) of Reaction Scheme X, an aldehyde substituted 1H-imidazo[4,5-c]quinoline of Formula LIV is reduced to provide a hydroxy substituted 1H-imidazo[4,5-c]quinoline of provide an azido substituted 1H-imidazo[4,5-c]quinoline of Formula LVII. The reaction can be carried out by treating a solution of a compound of Formula LVI in a suitable solvent such as DMF with sodium azide.

In step (5) of Reaction Scheme X, the azido group of a 1H-imidazo[4,5-c]quinoline of Formula LVII is reduced to provide an aminomethyl substituted 1H-imidazo[4,5-c]quinoline of Formula LVIII. The reduction can be carried out using conventional methods such as, for example, catalytic hydrogenation.

In step (6) of Reaction Scheme X, the amino group of a 1H-imidazo[4,5-c]quinoline of Formula LVIII is further elaborated using the methods described in step (6) of Reaction Scheme IV to provide 1H-imidazo[4,5-c]quinoline of Formula LIX, which is a subgenus of Formulas I and II. The product or a pharmaceutically acceptable salt thereof can be isolated using conventional methods.

Reaction Scheme X

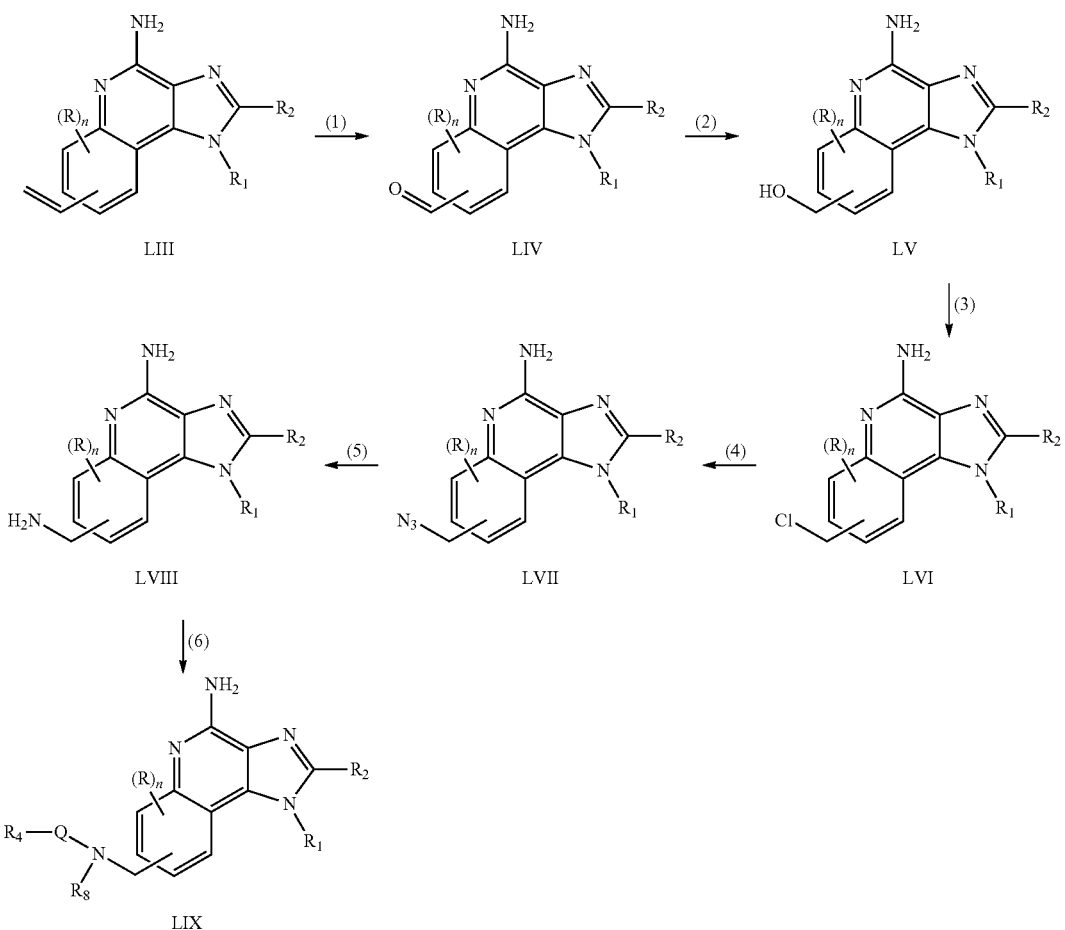

For certain embodiments, compounds of the invention can be prepared according to Reaction Scheme XI, wherein $R_A$, $R_B$, $R_1$, $R_2$, and G are as defined above. Compounds of Formula Ia can be prepared according to the methods described above. The amino group of a compound of Formula Ia can be converted by conventional methods to a functional group such as an amide, carbamate, urea, amidine, or another hydrolyzable group. A compound of this type can be made by the replacement of a hydrogen atom in an amino group with a group such as —C(O)—R''', α-aminoacyl, α-aminoacyl-α-aminoacyl, —C(O)—O—R''', —C(O)—N(R'''')—R''', —C(=NY')—R''', —CH(OH)—C(O)—OY', —CH(OC$_{1-4}$ alkyl)Y$_0$, —CH$_2$Y$_1$, or —CH(CH$_3$)Y$_1$; wherein R''' and R'''' are each independently C$_{1-10}$ alkyl, C$_{3-7}$ cycloalkyl, phenyl, or benzyl, each of which may be unsubstituted or substituted by one or more substituents independently selected from the group consisting of halogen, hydroxy, nitro, cyano, carboxy, C$_{1-6}$ alkyl, C$_{1-4}$ alkoxy, aryl, heteroaryl, arylC$_{1-4}$ alkylenyl, heteroarylC$_{1-4}$ alkylenyl, haloC$_{1-4}$ alkylenyl, haloC$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$; with the proviso that R'''' may also be hydrogen; each α-aminoacyl group is independently selected from racemic, D, or L-amino acids; Y' is hydrogen, C$_{1-6}$ alkyl, or benzyl; Y$_0$ is C$_{1-6}$ alkyl, carboxyC$_{1-6}$ alkylenyl, aminoC$_{1-4}$ alkylenyl, mono-N—C$_{1-6}$ alkylaminoC$_{1-4}$ alkylenyl, or di-N,N—C$_{1-6}$ alkylaminoC$_{1-4}$ alkylenyl; and Y$_1$ is mono-N—C$_{1-6}$ alkylamino, di-N,N—C$_{1-6}$ alkylamino, morpholin-4-yl, piperidin-1-yl, pyrrolidin-1-yl, or 4-C$_{1-4}$ alkylpiperazin-1-yl. Particularly useful compounds of Formula XVI are amides derived from carboxylic acids containing one to ten carbon atoms, amides derived from amino acids, and carbamates containing one to ten carbon atoms. The reaction can be carried out, for example, by combining a compound of Formula Ia with a chloroformate or acid chloride, such as ethyl chloroformate or acetyl chloride, in the presence of a base such as triethylamine in a suitable solvent such as dichloromethane at room temperature.

Reaction Scheme X

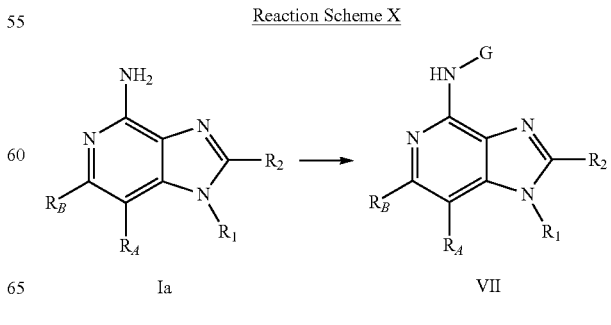

Compounds of the invention can also be prepared using variations of the synthetic routes shown in Reaction Schemes I through X that would be apparent to one of skill in the art. For example, the synthetic routes shown in Reaction Schemes II through V for the preparation of imidazoquinolines can be used to prepare imidazo[1,5]naphthyridines by using a compound of Formula XLIII or XLI in lieu of a compound of Formula XV or XVI. Also, the reduction shown in step (2) of Reaction Scheme III or IV may be eliminated to provide compounds of the invention, wherein Z contains a carbon-carbon double bond. Compounds of the invention can also be prepared using the synthetic routes described in the EXAMPLES below.

Pharmaceutical Compositions and Biological Activity

Pharmaceutical compositions of the invention contain a therapeutically effective amount of a compound or salt described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. The exact amount of compound or salt used in a pharmaceutical composition of the invention will vary according to factors known to those of skill in the art, such as the physical and chemical nature of the compound or salt, the nature of the carrier, and the intended dosing regimen.

In some embodiments, the compositions of the invention will contain sufficient active ingredient or prodrug to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject.

In other embodiments, the compositions of the invention will contain sufficient active ingredient or prodrug to provide a dose of, for example, from about 0.01 mg/m$^2$ to about 5.0 mg/m$^2$, computed according to the Dubois method, in which the body surface area of a subject (m$^2$) is computed using the subject's body weight: m$^2$=(wt kg$^{0.425}$×height cm$^{0.725}$)× 0.007184, although in some embodiments the methods may be performed by administering a compound or salt or composition in a dose outside this range. In some of these embodiments, the method includes administering sufficient compound to provide a dose of from about 0.1 mg/m$^2$ to about 2.0 mg/m$^2$ to the subject, for example, a dose of from about 0.4 mg/m$^2$ to about 1.2 mg/m$^2$.

A variety of dosage forms may be used, such as tablets, lozenges, capsules, parenteral formulations, syrups, creams, ointments, aerosol formulations, transdermal patches, transmucosal patches and the like. These dosage forms can be prepared with conventional pharmaceutically acceptable carriers and additives using conventional methods, which generally include the step of bringing the active ingredient into association with the carrier.

The compounds or salts of the invention can be administered as the single therapeutic agent in the treatment regimen, or the compounds or salts described herein may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the tests set forth below. These results indicate that the compounds or salts are useful for modulating the immune response in a number of different ways, rendering them useful in the treatment of a variety of disorders.

Cytokines whose production may be induced by the administration of compounds or salts of the invention generally include interferon-α (IFN-α) and tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt of the invention to the animal. The animal to which the compound or salt is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts described herein can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts described herein can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt or composition and other component or components may be administered separately; together but independently such as in a solution; or together and associated with one another such as (a) covalently linked or (b) non-covalently associated, e.g., in a colloidal suspension.

Conditions for which compounds or salts or compositions identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus

*Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such as chlamydia, fungal diseases including but not limited to candidiasis, aspergillosis, histoplasmosis, cryptococcal meningitis, or parasitic diseases including but not limited to malaria, pneumocystis carnii pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to acute myeloid leukemia, acute lymphocytic leukemia, chronic myeloid leukemia, chronic lymphocytic leukemia, multiple myeloma, Hodgkin's lymphoma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia greata; and (g) diseases associated with wound repair such as, for example, inhibition of keloid formation and other types of scarring (e.g., enhancing wound healing, including chronic wounds).

Additionally, a compound or salt identified herein may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts identified herein may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An animal may also be vaccinated by administering an effective amount of a compound or salt described herein, as a vaccine adjuvant. In one embodiment, there is provided a method of vaccinating an animal comprising administering an effective amount of a compound or salt described herein to the animal as a vaccine adjuvant.

An amount of a compound or salt effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) over a background level of such cytokines. The precise amount will vary according to factors known in the art but is expected to be a dose of about 100 ng/kg to about 50 mg/kg, preferably about 10 µg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments the induction or inhibition of cytokine biosynthesis may be performed by administering a compound or salt in a dose outside this range. In some of these embodiments, the method includes administering sufficient compound or salt or composition to provide a dose of from about 0.1 mg/m$^2$ to about 2.0 mg/m$^2$ to the subject, for example, a dose of from about 0.4 mg/m$^2$ to about 1.2 mg/m$^2$.

The invention also provides a method of treating a viral infection in an animal and a method of treating a neoplastic disease in an animal comprising administering an effective amount of a compound or salt of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments either of these methods may be performed by administering a compound or salt in a dose outside this range. In some of these embodiments, the method includes administering sufficient compound or salt to provide a dose of from about 0.1 mg/m$^2$ to about 2.0 mg/m$^2$ to the subject, for example, a dose of from about 0.4 mg/m$^2$ to about 1.2 mg/m$^2$.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

Example 1

2-Ethoxymethyl-1-(3-isopropoxypropyl)-7-[(E)-2-(phenylthio)ethenyl]-1H-imidazo[4,5-c]quinolin-4-amine

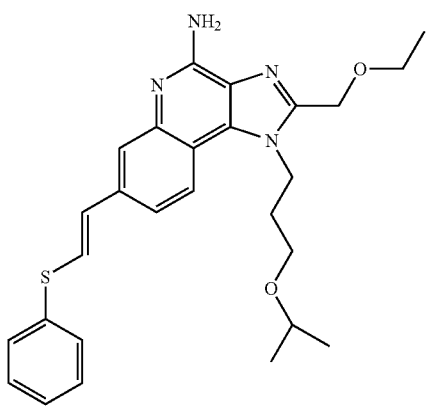 [SMILES: CCOCc1nc2c(N)nc3cc(/C=C/Sc4ccccc4)ccc3c2n1CCCOC(C)C]

Part A

7-Bromo-4-chloro-3-nitroquinoline (40 g) was dissolved in dichloromethane (1.4 L) and triethylamine (23.3 mL). 3-Isopropoxypropylamine (19.3 mL) was added dropwise. After 48 hours, the reaction mixture was washed successively with water and saturated aqueous sodium chloride. The organic fraction was dried over anhydrous sodium sulfate, filtered and concentrated under reduced pressure. (7-Bromo-3-nitroquinolin-4-yl)-(3-isopropoxypropyl)amine was isolated as a tan solid (51.2 g).

Part B

(7-Bromo-3-nitroquinolin-4-yl)-(3-isopropoxypropyl)amine (51 g) was slurried in acetonitrile (750 mL) and added to a Parr flask containing 5% platinum on carbon (5 g). The flask was degassed three times, then charged with hydrogen (30 psi) and shaken for 4 hours with replenishment of the hydrogen as necessary. The platinum catalyst was removed by filtration through a bed of CELITE filter agent. The filtrate was evaporated to afford 7-bromo-$N^4$-(3-isopropoxypropyl)quinoline-3,4-diamine as a yellow oil (45 g).

Part C

7-Bromo-$N^4$-(3-isopropoxypropyl)quinoline-3,4-diamine (45 g) was dissolved in acetonitrile (1.3 L) and triethylamine (19.4 mL). Ethoxyacetyl chloride (18.0 g) was added dropwise to the solution and the reaction was stirred for 16 hours. The solvent was removed under reduced pressure to afford a tan solid. The solid was added to a solution of ethanol (1 L) and triethylamine (77.5 mL) and heated at reflux for 4 hours. The solvent was removed under reduced pressure. Water was added to the solid residue and the crude product was recovered by filtration. Recrystallization from acetonitrile yielded 36.25 g of 7-bromo-2-ethoxymethyl-1-(3-isopropoxypropyl)-1H-imidazo[4,5-c]quinoline as a tan crystalline solid.

Part D

7-Bromo-2-ethoxymethyl-1-(3-isopropoxypropyl)-1H-imidazo[4,5-c]quinoline (20 g) was dissolved in chloroform (400 mL). 3-Chloroperoxybenzoic acid (60% pure, 17.1 g) was added in 2 g portions over a 5 minute period and the reaction was stirred for 1 hour. Ammonium hydroxide (300 mL) was added and the mixture was cooled to 5° C. with an ice/water bath. p-Toluenesulfonyl chloride (9.4 g) was added at the rate of 1 g/min to minimize gas evolution. After stirring for 16 hours, the layers were separated and the aqueous fraction was extracted with chloroform. The combined organic fractions were sequentially washed with 5% aqueous sodium bicarbonate, water and brine; dried over anhydrous sodium sulfate, filtered and concentrated under reduced pressure. The residue was purified by flash column chromatography on silica gel. The polar component of the eluent was chloroform:methanol:ammonium hydroxide 80:18:2 (CMA). The purification was carried out eluting with chloroform:CMA in a gradient from 98:2 to 88:12. The material recovered from the column was recrystallized from acetonitrile to yield 7.0 g of 7-bromo-2-ethoxymethyl-1-(3-isopropoxypropyl)-1H-imidazo[4,5-c]quinolin-4-amine as a tan granular powder.

Part E

7-Bromo-2-ethoxymethyl-1-(3-isopropoxypropyl)-1H-imidazo[4,5-c]quinolin-4-ylamine (1.00 g, 2.46 mmol), tris(2-tolyl)phosphine (16 mg, 0.05 mmol) and a stir bar were added to a pressure vessel. Palladium(II) acetate (6 mg, 0.025 mmol), phenyl vinyl sulfide (0.330 mL, 2.53 mmol) and triethylamine (0.685 mL, 4.92 mmol) were subsequently added, followed by toluene (5 mL). The vessel was sealed with a TEFLON cap and the reaction was heated at 110° C. for 40 hours. The reaction mixture was cooled to ambient temperature and concentrated under reduced pressure. The residue was purified by flash column chromatography (silica gel, eluting with a linear gradient of 1-7% methanol in dichloromethane), followed by recrystallization from acetonitrile to provide 0.35 g of 2-ethoxymethyl-1-(3-isopropoxypropyl)-7-[(E)-2-(phenylthio)ethenyl]-1H-imidazo[4,5-c]quinolin-4-amine hydrobromide as yellow-orange crystals, mp 220-221° C.

$^1$H NMR (300 MHz, DMSO-$d_6$) δ 13.16 (s, 1H), 9.2-8.1 (br s, 2H), 8.29 (d, J=9.1 Hz, 1H), 7.93-7.73 (m, 2H), 7.57-7.32 (m, 6H), 6.90 (d, J=15.6 Hz, 1H), 4.83 (s, 2H), 4.72-4.67 (m, 2H), 3.64-3.51 (m, 5H), 2.15-2.02 (m, 2H), 1.18 (t, J=7.0 Hz, 3H), 1.14 (d, J=6.1 Hz, 6H);

HRMS (ESI) m/z 477.2323 (477.2324 calcd. for $C_{27}H_{32}N_4O_2S$, M+H);

Anal. Calcd. for $C_{27}H_{32}N_4O_2S \cdot HBr$: C, 58.16; H, 5.97; N, 10.05; Br, 14.33. Found: C, 58.42; H, 6.49; N, 10.06; Br, 14.28.

Example 2

2-Ethoxymethyl-1-(3-isopropoxypropyl)-7-[(E)-2-(phenylsulfonyl)ethenyl]-1H-imidazo[4,5-c]quinolin-4-amine

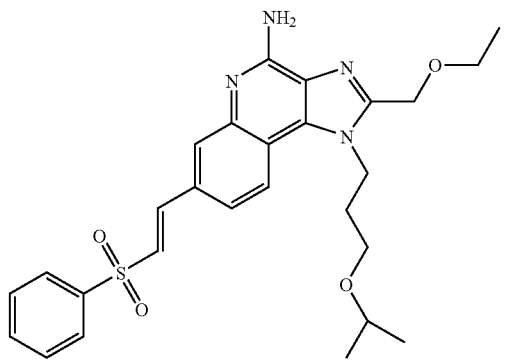 [SMILES: CCOCc1nc2c(N)nc3cc(/C=C/S(=O)(=O)c4ccccc4)ccc3c2n1CCCOC(C)C]

Part A

7-Bromo-2-ethoxymethyl-1-(3-isopropoxypropyl)-1H-imidazo[4,5-c]quinoline (1.00 g, 2.46 mmol), phenyl vinyl sulfone (0.852 g, 5.06 mmol), palladium(II) acetate (12 mg, 0.05 mmol), and tris(2-tolyl)phosphine (32 mg, 0.10 mmol) were added to a pressure tube. Triethylamine (1.37 mL, 9.84 mmol) and acetonitrile (5 mL) were added. The tube was flushed with nitrogen, sealed with a TEFLON plug and heated at 100° C. for 96 hours. The reaction mixture was cooled to ambient temperature and concentrated under reduced pressure. The residue was initially purified by flash column chromatography (silica gel, eluting with a gradient of 50%-100% ethyl acetate in hexanes, followed by a gradient of 2%-6% methanol in ethyl acetate). Recrystallization of the resulting solid from acetonitrile provided 0.600 g 7-(2-benzenesulfonylvinyl)-2-ethoxymethyl-1-(3-isopropoxypropyl)-1H-imidazo[4,5-c]quinoline as a yellow crystalline solid.

Part B 7-(2-Benzenesulfonylvinyl)-2-ethoxymethyl-1-(3-isopropoxypropyl)-1H-imidazo[4,5-c]quinoline (0.600 g, 1.22 mmol) was dissolved in chloroform (12 mL). 3-Chloroperoxybenzoic acid (60% purity, 0.351 g, 1.22 mmol) was added. The reaction was stirred for 30 minutes. Ammonium hydroxide (8 mL) was added and the mixture was stirred for 10 minutes. p-Toluenesulfonyl chloride (0.232 g, 1.22 mmol) was added in one portion and the reaction was stirred for an additional 16 hours. The layers were separated and the aqueous fraction was extracted with chloroform. The combined organic fractions were sequentially washed with water and saturated aqueous sodium chloride, dried over anhydrous sodium sulfate, filtered, and concentrated under reduced pressure. The residue was purified by column chromatography using a Horizon HPFC system (an automated, modular high-performance flash purification product available from Biotage, Inc.; Charlottesville, Va., USA). The polar component of the eluent was chloroform:methanol:ammonium hydroxide 80:18:2 (CMA). The purification was carried out with a silica cartridge eluting with a linear gradient of 1-22% CMA in chloroform. The resulting material was subsequently recrystallized from acetonitrile to yield 0.320 g 2-ethoxymethyl-1-(3-isopropoxypropyl)-7-[(E)-2-(phenylsulfonyl)ethenyl]-1H-imidazo[4,5-c]quinolin-4-amine as green needles, mp 188.5-190.0° C.

$^1$H NMR (300 MHz, DMSO-$d_6$) δ 8.20 (d, J=8.6 Hz, 1H), 7.98-7.92 (m, 3H), 7.81-7.60 (m, 6H), 6.76 (s, 2H), 4.78 (s, 2H), 4.67-4.62 (m, 2H), 3.63-3.44 (m, 5H), 2.13-1.98 (m, 2H), 1.16 (t, J=7.0 Hz, 3H), 1.15 (d, J=6.1 Hz, 6H);

HRMS (ESI) m/z 509.2218 (509.2223 calcd. for $C_{27}H_{32}N_4O_4S$, M+H);

Anal. Calcd. for $C_{27}H_{32}N_4O_4S \cdot 0.8H_2O$: C, 62.02; H, 6.47; N, 10.72; S, 6.13. Found: C, 62.03; H, 6.52; N, 10.73; S, 6.12.

Example 3

N-[4-Amino-2-ethoxymethyl-1-(3-isopropoxypropyl)-1H-imidazo[4,5-c]quinolin-7-yl]-2-methylpropanamide

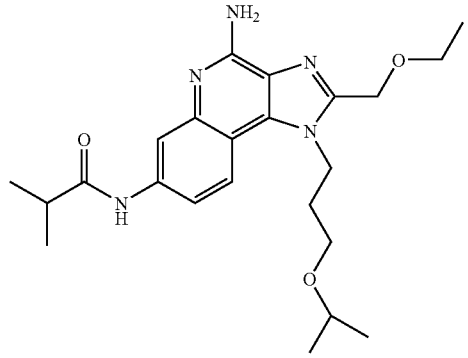 [SMILES: CCOCc1nc2c(N)nc3cc(NC(=O)C(C)C)ccc3c2n1CCCOC(C)C]

Part A

7-Bromo-2-ethoxymethyl-1-(3-isopropoxypropyl)-1H-imidazo[4,5-c]quinoline (0.5 g, 1.23 mmol), potassium phosphate (0.548 g, 2.58 mmol), isobutyramide (0.128 g, 1.48 mmol), copper(I) iodide (46 mg, 0.246 mmol), and trans-(±)-1,2-diaminocyclohexane were added to a 2 dram vial. Dioxane (1.2 mL) and a stir bar were added and the vial was sealed with a TEFLON lined cap. The vial was heated at 110° C. for 16 hours. The reaction was cooled to ambient temperature and then diluted with water and chloroform. The layers were separated and the organic fraction was washed with water and saturated aqueous sodium chloride. The organic fraction was dried over anhydrous sodium sulfate, filtered, and concentrated under reduced pressure. Purification using a HORIZON HPFC system (silica cartridge, eluting with a linear gradient of 2-23% CMA in chloroform) provided 0.402 g of N-[2-ethoxymethyl-1-(3-isopropxypropyl)-1H-imidazo[4,5-c]quinolin-7-yl]-2-methylpropanamide as a yellowish waxy solid.

Part B

N-[2-ethoxymethyl-1-(3-isopropxypropyl)-1H-imidazo[4,5-c]quinolin-7-yl]-2-methylpropanamide (0.400 g, 0.98 mmol) was dissolved in chloroform (10 mL). 3-Chloroperoxybenzoic acid (60% purity, 0.532 g, 1.85 mmol) was added in two portions 30 minutes apart. The reaction was stirred for an additional 30 minutes. Ammonium hydroxide (10 mL) was added and the reaction was stirred for 10 minutes. Benzenesulfonyl chloride (0.236 mL, 1.8 mmol) was added in one portion and the reaction was stirred for 72 hours. The layers were separated and the aqueous fraction was extracted with chloroform. The combined organic fractions were sequentially washed with water and saturated aqueous sodium chloride, dried over anhydrous sodium sulfate, filtered, and concentrated under reduced pressure. Purification using a HORIZON HPFC system (silica cartridge, eluting with a linear gradient of 2-25% CMA in chloroform), followed by recrystallization from acetonitrile provided 0.130 g of N-[4-amino-2-ethoxymethyl-1-(3-isopropxypropyl)-1H-imidazo[4,5-c]quinolin-7-yl]-2-methylpropanamide as a beige solid, mp 214-215° C.

$^1$H NMR (300 MHz, DMSO-$d_6$) δ 9.88 (s, 1H), 8.11 (d, J=8.9 Hz, 1H), 7.96 (d, J=2.1 Hz, 1H), 7.51 (dd, J=8.9, 2.1 Hz, 1H), 6.52 (s, 2H), 4.75 (s, 2H), 4.62-4.57 (m, 2H), 3.65-3.48 (m, 5H), 2.73-2.58 (m, 1H), 2.15-2.00 (m, 2H), 1.18-1.12 (m, 15H);

$^{13}$C NMR (75 MHz, DMSO-$d_6$) δ 175.2, 152.2, 148.3, 145.9, 138.3, 133.1, 120.7, 115.0, 114.0, 110.4, 70.7, 65.3, 64.0, 63.9, 42.8, 35.0, 30.3, 22.0, 19.5, 14.9;

MS (ESI) m/z 428.2657 (428.2662 calcd. for $C_{23}H_{33}N_5O_3$, M+H);

Anal. Calcd. for $C_{23}H_{33}N_5O_3 \cdot 0.25H_2O$: C, 63.94; H, 7.82; N, 16.21. Found: C, 64.02; H, 8.10; N, 16.25.

Example 4

N-[4-Amino-2-ethoxymethyl-1-(2-hydroxy-2-methylpropyl)-1H-imidazo[4,5-c]quinolin-7-yl]ethanesulfonamide

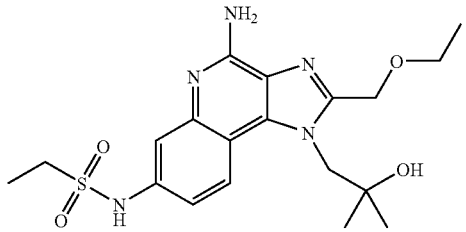 [SMILES: CCOCc1nc2c(N)nc3cc(NS(=O)(=O)CC)ccc3c2n1CC(C)(C)O]

The general method described in Part A of Example 3 was followed using 7-bromo-2-ethoxymethyl-1-(2-hydroxy-2-methylpropyl)-1H-imidazo[4,5-c]quinolin-4-amine (U.S. Patent Application Publication No. US 2004/0147543, Examples 125-135) in lieu of 7-bromo-2-ethoxymethyl-1-(3-isopropoxypropyl)-1H-imidazo[4,5-c]quinoline and ethanesulfonamide in lieu of isobutyramide. Purification using a HORIZON HPFC system (silica cartridge, eluting with a linear gradient of 2-25% CMA in chloroform), followed by recrystallization from acetonitrile afforded 0.108 g of N-[4-amino-2-ethoxymethyl-1-(2-hydroxy-2-methylpropyl)-1H-imidazo[4,5-c]quinolin-7-yl]ethanesulfonamide as white crystals, mp 124.0-127.0° C.

$^1$H NMR (300 MHz, DMSO-$d_6$) δ 9.85 (s, 1H), 8.21 (d, J=9.0 Hz, 1H), 7.44 (d, J=2.4 Hz, 1H), 7.11 (dd, J=8.9, 2.3 Hz, 1H), 6.56 (s, 2H), 5.05-4.73 (br s, 1H), 4.86 (s, 2H), 4.62 (s, 2H), 3.50 (q, J=7.0 Hz, 2H), 3.11 (q, J=7.3 Hz, 2H), 1.21 (t, J=7.3 Hz, 3H), 1.17 (br s, 6H), 1.13 (t, J=7.0 Hz, 3H);

$^{13}$C NMR (125 MHz, DMSO-$d_6$) δ 152.4, 150.4, 146.2, 136.9, 134.2, 125.4, 122.5, 114.7, 113.1, 111.6, 70.6, 65.2, 64.8, 54.7, 44.9, 27.5, 15.0, 8.0;

MS (APCI) m/z 422 (M+H)$^+$;

Anal. Calcd. for $C_{19}H_{27}N_5O_4S \cdot 0.25H_2O$: C, 53.57; H, 6.51; N, 16.44; S, 7.53. Found: C, 53.28; H, 6.72; N, 16.58; S, 7.42.

Example 5

N-{4-[4-Amino-2-ethoxymethyl-1-(3-isopropxypropyl)-1H-imidazo[4,5-c]quinolin-7-yl]butyl}acetamide

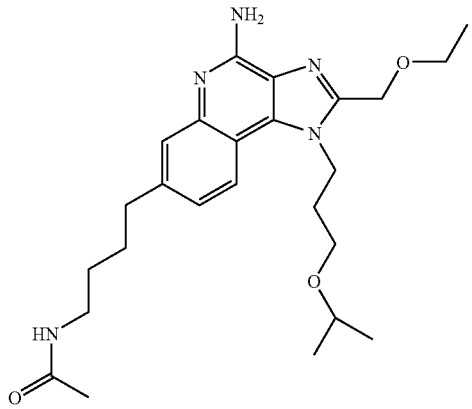 [SMILES: CCOCc1nc2c(N)nc3cc(CCCCNC(C)=O)ccc3c2n1CCCOC(C)C]

Part A

7-Bromo-2-ethoxymethyl-1-(3-isopropoxypropyl)-1H-imidazo[4,5-c]quinoline (1.9 g, 4.68 mmol), 2-but-3-enyl-1H-isoindole-1,3(2H)-dione (1.04 g, 5.15 mmol), cesium carbonate (3.05 g, 9.36 mmol), triphenylphosphine (0.246 g, 0.94 mmol), palladium(II) acetate (0.105 g, 0.47 mmol), and N,N-dimethylformamide (DMF) (28 mL) were added to a pressure tube. The vessel was sealed with a TEFLON cap and heated at 140° C. for 2.5 hours. The reaction was cooled to ambient temperature. The reaction was diluted with ethyl acetate and washed multiple times with water. The initial water wash was extracted with ethyl acetate. The organic fractions were combined and washed with water once again. The organic fractions were concentrated under reduced pressure and the residue was purified using a HORIZON HPFC system (silica cartridge, eluting with a linear gradient of 2-20% CMA in chloroform) to yield 1.9 g of 2-{(3E)-4-[2-ethoxymethyl-1-(3-isopropoxypropyl)-1H-imidazo[4,5-c]quinolin-7-yl]but-3-enyl}-1H-isoindole-1,3(2H)-dione as a pale yellow oil.

Part B

2-{(3E)-4-[2-ethoxymethyl-1-(3-isopropoxypropyl)-1H-imidazo[4,5-c]quinolin-7-yl]but-3-enyl}-1H-isoindole-1,3(2H)-dione (1.9 g, 3.6 mmol) was dissolved in ethanol (50 mL) and added to a Parr flask containing 10% palladium on carbon (0.3 g) wetted with ethanol. The flask was degassed three times, charged with hydrogen (50 psi) and shaken for 16 hours. The catalyst was removed by filtration through CELITE filter agent. Concentration of the filtrate under reduced pressure provided 1.9 g of 2-{4-[2-ethoxymethyl-1-(3-isopropoxypropyl)-1H-imidazo[4,5-c]quinolin-7-yl]butyl}-1H-isoindole-1,3(2H)-dione as a pale yellow oil.

Part C

2-{4-[2-(ethoxymethyl)-1-(3-isopropoxypropyl)-H-imidazo[4,5-c]quinolin-7-yl]butyl}-1H-isoindole-1,3(2H)-dione (1.5 g, 2.84 mmol) was dissolved in ethyl acetate (15 mL) and heated to 50° C. 33% Peracetic acid in acetic acid (0.60 mL, 2.84 mmol) was added and the solution was stirred for 3 hours. Another 0.2 mL peracetic acid was added and the reaction was stirred for 1 hour. The mixture was cooled to ambient temperature and quenched with aqueous sodium metabisulfite (0.593 g in 1.2 mL water). The solution was made basic with saturated aqueous sodium carbonate. The mixture was diluted with water and the layers were separated. The aqueous fraction was extracted with ethyl acetate. The organic fractions were combined and concentrated under reduced pressure. The resulting yellow foam was dissolved in dichloromethane (15 mL) and ammonium hydroxide (10 mL). p-Toluenesulfonyl chloride (0.541 g, 2.84 mmol) was added in one portion. The mixture was stirred for 70 hours. The layers were separated and the aqueous fraction was extracted with dichloromethane. The organic fractions were combined and concentrated under reduced pressure to yield 0.525 g of 2-{4-[4-amino-2-ethoxymethyl-1-(3-isopropoxypropyl)-1H-imidazo[4,5-c]quinolin-7-yl]butyl}-1H-isoindole-1,3(2H)-dione as a yellow oil.

Part D

2-{4-[4-amino-2-ethoxymethyl-1-(3-isopropoxypropyl)-1H-imidazo[4,5-c]quinolin-7-yl]butyl}-1H-isoindole-1,3(2H)-dione (1.15 g, 2.1 mmol) was dissolved in ethanol (36 mL. Hydrazine (0.372 mL, 11.4 mmol) was added and the solution was heated at reflux temperature for 1 hour. The resulting white slurry was cooled to ambient temperature and filtered. The solid showed 40% product by NMR. The solid was saved and used in Part E. The filtrate was concentrated under reduced pressure and purified using a HORIZON HPFC system (silica cartridge, eluting with a linear gradient of 2-20% CMA in chloroform) to provide 0.211 g of 7-(4-aminobutyl)-2-ethoxymethyl-1-(3-isopropoxypropyl)-1H-imidazo[4,5-c]quinolin-4-amine as a white solid.

Part E

The crude mixture of 7-(4-aminobutyl)-2-ethoxymethyl-1-(3-isopropoxypropyl)-1H-imidazo[4,5-c]quinolin-4-amine from Part D was slurried in chloroform (7 mL) and triethylamine (0.185 mL, 1.32 mmol). Acetic anhydride (0.061 mL, 1.32 mmol) was added and the mixture was stirred for 16 hours. The resulting solution was concentrated under reduced pressure and the residue was purified using a HORIZON HPFC system (silica cartridge, eluting with a linear gradient of 1-20% CMA in chloroform). The diacylated product was dissolved in methanol (10 mL) and concentrated hydrochloric acid (2 mL). The mixture was heated to reflux for 2 hours and then cooled to ambient temperature. Saturated aqueous sodium carbonate was added to make the reaction basic. The methanol was evaporated under reduced pressure and the residue was extracted with dichloromethane (2×100 mL). The combined organic fractions were dried over sodium sulfate, filtered, and concentrated under reduced pressure. The residue was purified using a HORIZON HPFC system (silica cartridge, eluting with a linear gradient of 2-15% CMA in chloroform). Subsequent crystallization from ethyl acetate and hexanes provided 0.192 g of N-{4-[4-amino-2-ethoxymethyl-1-(3-isopropxypropyl)-1H-imidazo[4,5-c]quinolin-7-yl]butyl}acetamide as flocculent white crystals, mp 122-124° C.

$^1$H NMR (300 MHz, DMSO-$d_6$) δ 8.10 (d, J=8.4 Hz, 1H), 7.79 (t, J=4.8 Hz, 1H), 7.42 (d, J=1.1 Hz, 1H), 7.09 (dd, J=8.3, 1.3 Hz, 1H), 6.51 (s, 2H), 4.76 (s, 2H), 4.64-4.59 (m, 2H), 3.64-3.47 (m, 5H), 3.09-3.03 (m, 2H), 2.69 (t, J=7.4 Hz, 2H), 2.15-2.01 (m, 2H), 1.78 (s, 3H), 1.68-1.59 (m, 2H), 1.48-1.36 (m, 2H), 1.16 (t, J=7.0 Hz, 3H), 1.15 (d, J=6.2 Hz, 6H);

$^{13}$C NMR (125 MHz, DMSO-$d_6$) δ 168.8, 152.0, 148.5, 145.3, 140.7, 133.1, 125.8, 125.3, 122.0, 120.4, 112.6, 70.8, 65.4, 64.1, 63.9, 42.8, 38.3, 34.8, 30.3, 28.8, 28.3, 22.6, 22.0, 14.9;

MS (ESI) m/z 456 (M+H)$^+$;

Anal. Calcd. for $C_{25}H_{37}N_5O_3$: C, 65.91; H, 8.19; N, 15.37. Found: C, 65.62; H, 7.94; N, 15.42.

Example 6

N-{4-[4-Amino-2-ethoxymethyl-1-(3-isopropxypropyl)-1H-imidazo[4,5-c]quinolin-7-yl]butyl}-N'-propylurea

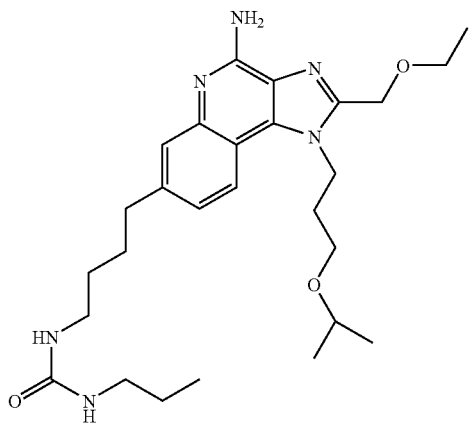 [SMILES: CCCNC(=O)NCCCCc1ccc2c(c1)nc(N)c1nc(COCC)n(CCCOC(C)C)c12]

7-(4-Aminobutyl)-2-ethoxymethyl-1-(3-isopropoxypropyl)-1H-imidazo[4,5-c]quinolin-4-amine (0.250 g, 0.604 mmol) was dissolved in dichloromethane. Propyl isocyanate (0.060 mL, 0.604 mmol) was added and the reaction was stirred for 16 hours. A feathery solid was produced. The dichloromethane was removed under reduced pressure. The residue was diluted (not dissolved) in acetonitrile. This altered the solid to a more granular form. The solid was filtered, washed with acetonitrile, and dried to yield 0.090 g of N-{4-[4-Amino-2-ethoxymethyl-1-(3-isopropxypropyl)-1H-imidazo[4,5-c]quinolin-7-yl]butyl}-N'-propylurea as an off-white solid, mp 134.5-135.5° C. $^1$H NMR (300 MHz, DMSO-$d_6$) δ 8.10 (d, J=8.4 Hz, 1H), 7.42 (s, 1H), 7.09 (dd, J=8.3, 1.2 Hz, 1H), 6.50 (s, 2H), 5.75 (t, J=5.4 Hz, 1H), 5.71 (t, J=5.7 Hz, 1H), 4.76 (s, 2H), 4.63-4.60 (m, 2H), 3.62-3.54 (m, 3H), 3.49 (t, J=5.5 Hz, 2H), 3.03-2.99 (m, 2H), 2.92 (q, J=6.5 Hz, 2H), 2.68 (t, J=7.5 Hz, 2H), 2.11-2.04 (m, 2H), 1.65-1.59 (m, 2H), 1.44-1.31 (m, 4H), 1.77-1.15 (m, 9H), 0.81 (t, J=7.4 Hz, 3H);

$^{13}$C NMR (125 MHz, DMSO-$d_6$) δ 158.0, 151.9, 148.5, 145.4, 140.8, 133.1, 125.8, 125.3, 122.1, 120.4, 112.5, 70.8, 65.3, 64.1, 63.9, 42.8, 41.0, 34.9, 30.3, 29.7, 28.3, 23.2, 22.0, 14.9, 11.3;

MS (APCI) m/z 499 (M+H)$^+$;

Anal. Calcd. for $C_{27}H_{42}N_6O_3$: C, 65.03; H, 8.49; N, 16.85. Found: C, 64.90; H, 8.38; N, 16.84.

Example 7

2-Ethoxymethyl-1-(3-methoxypropyl)-7-methylsulfonyl-1H-imidazo[4,5-c]quinolin-4-amine

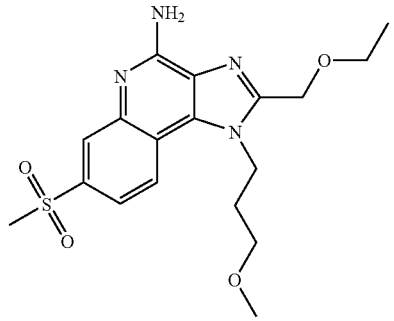 [SMILES: CCOCc1nc2c(N)nc3cc(S(C)(=O)=O)ccc3c2n1CCCOC]

Part A

7-Bromo-2-ethoxymethyl-1-(3-methoxypropyl)-1H-imidazo[4,5-c]quinoline (U.S. Patent Application Publication No. US 2004/0147543 Examples 163-175, 1.0 g, 2.64 mmol) and sodium thiomethoxide (0.185 g, 2.64 mmol) were dissolved in N,N-dimethylformamide (25 mL). The reaction mixture was stirred at ambient temperature for 20 minutes and then heated at 55° C. for 16 hours. The reaction was cooled to ambient temperature and the solvent was removed under reduced pressure. The residue was dissolved in dichloromethane and sequentially washed with water and saturated aqueous sodium chloride, dried over anhydrous sodium sulfate, filtered, and concentrated under reduced pressure. 2-Ethoxymethyl-1-(3-methoxypropyl)-7-methylthio-1H-imidazo[4,5-c]quinoline was isolated as 1.1 g of a pale yellow oil.

Part B

The crude oil from Part A was dissolved in chloroform (20 mL). 3-Chloroperoxybenzoic acid (60% pure, 1.96 g, 6.84 mmol) was added in one portion. After 30 minutes, an additional 0.5 g of 3-chloroperoxybenzoic acid and 5 mL of chloroform was added. After 20 minutes, the reaction mixture was poured into a separatory funnel and washed with saturated aqueous sodium carbonate. The aqueous fraction was extracted sequentially with dichloromethane, chloroform, and 9:1 chloroform/methanol. The combined organic fractions were sequentially washed with water and saturated aqueous sodium chloride, dried over sodium sulfate, filtered, and concentrated under reduced pressure. The residue was purified using a HORIZON HPFC system (silica cartridge, eluting with a linear gradient of 2-30% CMA in chloroform). Fractions containing oxidized product were combined and concentrated. The residue was dissolved dichloromethane (15 mL) and diluted with ammonium hydroxide (10 mL). p-Toluenesulfonyl chloride was added to the mixture and the reaction was stirred for 120 hours. The layers were separated and the aqueous fraction was extracted with dichloromethane. The combined organic fractions were sequentially washed with water and saturated aqueous sodium chloride, dried over sodium sulfate, filtered, and concentrated under reduced pressure. Purification using a HORIZON HPFC system (silica cartridge, eluting with a linear gradient of 1-20% CMA in chloroform), followed by recrystallization from acetonitrile yielded 0.357 g of 2-ethoxymethyl-1-(3-methoxypropyl)-7-methylsulfonyl-1H-imidazo[4,5-c]quinolin-4-amine as white needles, mp 166.5-167.5° C.

$^1$H NMR (300 MHz, DMSO-$d_6$) δ 8.34 (d, J=8.7 Hz, 1H), 8.07 (d, J=2.0 Hz, 1H), 7.70 (dd, J=8.6, 1.9 Hz, 1H), 7.03 (s, 2H), 4.80 (s, 2H), 4.71-4.66 (m, 2H), 3.57 (q, J=7.0 Hz, 2H), 3.47 (t, J=5.6 Hz, 2H), 3.31 (s, 3H), 3.28 (s, 3H), 2.15-2.07 (m, 2H), 1.17 (t, J=7.0 Hz, 3H);

$^{13}$C NMR (75 MHz, DMSO-$d_6$) δ 153.3, 150.3, 144.6, 138.5, 132.3, 127.8, 124.9, 121.8, 117.8, 117.7, 68.6, 65.5, 64.0, 58.1, 43.7, 43.0, 29.7, 14.9;

MS (ESI) m/z 393.1602 (393.1597 calcd. for $C_{18}H_{24}N_4O_4S$, M+H);

Anal. Calcd. for $C_{18}H_{24}N_4O_4S$: C, 55.09; H, 6.16; N, 14.28; S, 8.17. Found: C, 55.12; H, 6.02; N, 14.32; S, 8.26.

Example 8

Methyl(2E)-3-[4-amino-2-butyl-1-(2-methylpropyl)-1H-imidazo[4,5-c]quinolin-7-yl]prop-2-enoate

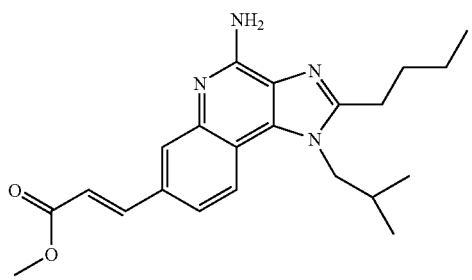 [SMILES: CCCCc1nc2c(N)nc3cc(/C=C/C(=O)OC)ccc3c2n1CC(C)C]

A thick walled glass tube, equipped with stir bar, was charged with palladium (II) acetate (18 mg, 0.08 mmol), acetonitrile (2 mL), methyl acrylate (69 mg, 0.8 mmol), triethylamine (240 mg, 2.4 mmol), tri-o-tolylphosphine (49 mg, 0.16 mmol) and 7-bromo-2-butyl-1-(2-methylpropyl)-1H-imidazo[4,5-c]quinolin-4-amine (U.S. Patent Application Publication No. US 2004/0147543 Example 1, 300 mg, 0.8 mmol). The reaction mixture was purged with nitrogen and the tube was sealed and heated to 100° C. in an oil bath. The mixture became an amber homogeneous solution after approximately 5 minutes. The reaction was maintained at 100° C. for 32 hours and then concentrated to dryness. The reaction mixture was taken up in water and dichloromethane. Saturated aqueous potassium carbonate solution was added, adjusting to pH 11. The organic layer was separated and concentrated to a golden syrup. The crude product was purified by flash chromatography on silica gel (eluting with 5% methanol/dichloromethane). The resulting tan solid (230 mg) was recrystallized from acetonitrile to give 220 mg of Methyl (2E)-3-[4-amino-2-butyl-1-(2-methylpropyl)-1H-imidazo[4,5-c]quinolin-7-yl]prop-2-enoate as a pale gold solid, mp 193-194° C.

MS (APCI) m/z 381.5 (M+H)$^+$.

Example 9

Methyl(2E)-3-[4-amino-1-[4-(1,1-dioxidoisothiazolidin-2-yl)butyl]-2-(ethoxymethyl)-1H-imidazo[4,5-c]quinolin-7-yl]prop-2-enoate

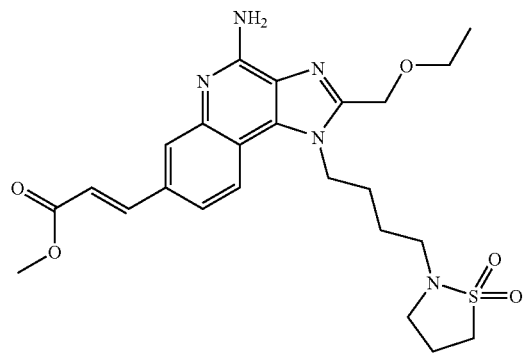 [SMILES: CCOCc1nc2c(N)nc3cc(/C=C/C(=O)OC)ccc3c2n1CCCCN1CCCS1(=O)=O]

A 50-mL thick walled glass vessel was charged with palladium (II) acetate (67 mg, 0.3 mmol), acetonitrile (2 mL), methyl acrylate (0.26 g, 3.0 mmol), triethylamine (0.9 g, 9.0 mmol), tri-o-tolylphosphine (0.18 g, 0.6 mmol) and 7-bromo-1-[4-(1,1-dioxidoisothiazolidin-2-yl)butyl]-2-(ethoxymethyl)-1H-imidazo[4,5-c]quinolin-4-amine (U.S. Patent Application Publication No. US 2004/0147543 Example 152-156, 1.5 g, 3.0 mmol). An additional 13 mL of acetonitrile was added. The reaction mixture was purged with nitrogen then heated to 90° C. The turbid orange mixture was maintained at 90° C. overnight. Anhydrous DMF (30 mL) was added to dissolve the 7-bromoquinoline starting material. The reaction was then heated at 120° C. overnight. The reaction mixture was filtered to remove the catalyst then concentrated to dryness. The desired product was isolated by column chromatography on silica gel (eluting with a gradient of 2%-8% methanol in dichloromethane). The resulting peach solid was taken up in saturated potassium carbonate solution and dichloromethane and stirred overnight at ambient temperature. The organic layer was separated and concentrated to dryness. The residue was recrystallized from acetonitrile to yield 0.65 g of Methyl(2E)-3-[4-amino-1-[4-(1,1-dioxidoisothiazolidin-2-yl)butyl]-2-(ethoxymethyl)-1H-imidazo[4,5-c]quinolin-7-yl]prop-2-enoate as a pale yellow solid, mp 162-163° C.

MS (ACPI) m/z 502.2 (M+H)$^+$.

Anal. Calcd. for $C_{24}H_{31}N_5O_5S$: C, 57.47; H, 6.23; N, 13.96. Found: C, 57.21; H, 6.38; N, 14.14.

Example 10

1-{3-[4-Amino-1-(2-methylpropyl)-1H-imidazo[4,5-c]quinolin-8-yl]propyl}pyrrolidin-2-one

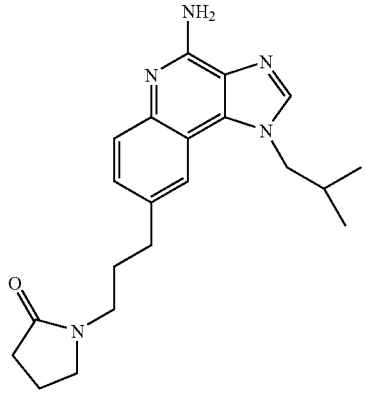 [SMILES: CC(C)Cn1cnc2c(N)nc3ccc(CCCN4CCCC4=O)cc3c21]

Part A

A thick walled glass tube, equipped with stir bar, was charged with palladium (II) acetate (67 mg, 0.3 mmol), acetonitrile (15 mL), N-allyl-2-pyrrolidone (650 mg, 5.17 mmol), triethylamine (2.1 ml, 15.65 mmol), tri-o-tolylphosphine (275 mg, 0.9 mmol) and 8-bromo-1-(2-methylpropyl)-1H-imidazo[4,5-c]quinolin-4-amine (U.S. Patent Application Publication No. US 2004/0147543 Example 11, 1.5 g, 4.7 mmol). The reaction mixture was purged with nitrogen, sealed and heated at 120° C. for 24 hours. The reaction mixture was concentrated to dryness. The reaction mixture was slurried in a mixture of 1% aqueous sodium carbonate (75 mL) and chloroform (100 mL). The layers were separated. The aqueous layer was extracted with chloroform (2×25 mL). The combined organic fractions were concentrated to dryness and purified by chromatography using a HORIZON HPFC system (silica cartridge, eluting with 0-8% methanol/dichloromethane) to provide 1-{(2E)-3-[4-amino-1-(2-methylpropyl)-1H-imidazo[4,5-c]quinolin-8-yl]prop-2-enyl}pyrrolidin-2-one.

Part B

A glass Parr vessel was charged with 10% palladium on carbon catalyst (0.1 g), methanol (50 mL), ethanol (50 mL) and 1-{(2E)-3-[4-amino-1-(2-methylpropyl)-1H-imidazo[4,5-c]quinolin-8-yl]prop-2-enyl}pyrrolidin-2-one. The vessel was evacuated and charged with hydrogen gas (51 psi, 3.4× $10^5$ Pa). The reaction was shaken at ambient temperature overnight (approximately 18 hours). The reaction mixture was filtered to remove the catalyst and concentrated to dryness. The crude product was purified by chromatography using a HORIZON HPFC system (silica cartridge, eluting with 0-8% methanol in dichloromethane) followed by recrystallization from acetonitrile to yield 300 mg of 1-{3-[4-amino-1-(2-methylpropyl)-1H-imidazo[4,5-c]quinolin-8-yl]propyl}pyrrolidin-2-one as a white solid, mp 174-175° C.

MS (APCI) m/z=366 (M+H)$^+$;

Anal. Calcd. for $C_{21}H_{27}N_5O$: C, 69.01; H, 7.45; N, 19.16. Found: C, 68.83; H, 7.71; N, 19.42.

Example 11

Methyl(2E)-3-[4-amino-2-(ethoxymethyl)-1-(2-hydroxy-2-methylpropyl)-1H-imidazo[4,5-c]quinolin-7-yl]prop-2-enoate

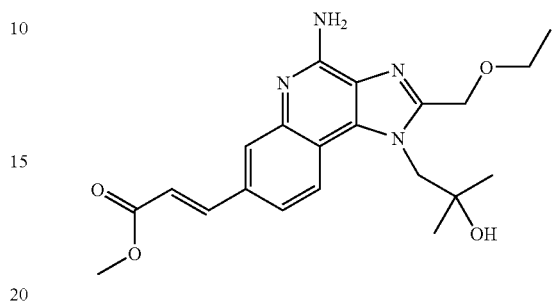

A thick walled glass reaction vessel was charged with anhydrous DMF (2 mL), palladium (II) Acetate (0.01 equivalents (eq)), tri-o-tolylphosphine (0.02 eq) and triethylamine (3 eq). To this orange solution was added a solution of 1-[4-amino-7-bromo-2-(ethoxymethyl)-1H-imidazo[4,5-c]quinolin-1-yl]-2-methylpropan-2-ol in 50 mL anhydrous DMF followed by the addition of methyl acrylate (1.0 eq). The reaction mixture was purged with nitrogen, sealed and heated at 120° C. overnight, and slowly cooled to room temperature. The reaction mixture was concentrated to dryness and then slurried in water (50 mL). Saturated potassium carbonate solution (25 mL) was added. The mixture was extracted with dichloromethane (4×50 mL). The combined extracts were concentrated under reduced pressure and purified by chromatography using a HORIZON HPFC system (silica cartridge, eluting with 0-25% CMA in chloroform) to provide Methyl(2E)-3-[4-amino-2-(ethoxymethyl)-1-(2-hydroxy-2-methylpropyl)-1H-imidazo[4,5-c]quinolin-7-yl]prop-2-enoate as a white solid.

Example 12

Methyl 3-[4-amino-2-(ethoxymethyl)-1-(2-hydroxy-2-methylpropyl)-1H-imidazo[4,5-c]quinolin-7-yl]propanoate

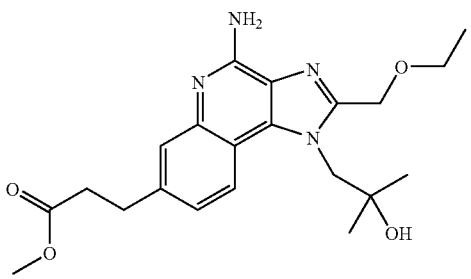 [SMILES: CCOCc1nc2c(N)nc3cc(CCC(=O)OC)ccc3c2n1CC(C)(C)O]

A glass Parr vessel was charged with 10% palladium on carbon catalyst (0.35 g, 0.1 eq. weight/weight (w/w)), methanol (50 mL) ethanol (50 ml) and Methyl(2E)-3-[4-amino-2-(ethoxymethyl)-1-(2-hydroxy-2-methylpropyl)-1H-imidazo[4,5-c]quinolin-7-yl]prop-2-enoate (3.5 g, 8.8 mmol). The vessel was evacuated and charged with hydrogen gas (45 psi, 3.1×10⁵ Pa). The reaction was shaken at ambient temperature overnight (approximately 18 hours). The reaction mixture was filtered to remove the catalyst and concentrated to dryness. The crude product was purified by chromatography using a HORIZON HPFC system (silica cartridge, eluting with 0-30% CMA in chloroform) followed by recrystallization from acetonitrile to provide methyl 3-[4-amino-2-(ethoxymethyl)-1-(2-hydroxy-2-methylpropyl)-1H-imidazo[4,5-c]quinolin-7-yl]propanoate as a white solid.

Example 13

3-[4-Amino-2-(ethoxymethyl)-1-(2-hydroxy-2-methylpropyl)-1H-imidazo[4,5-c]quinolin-7-yl]propanoic acid

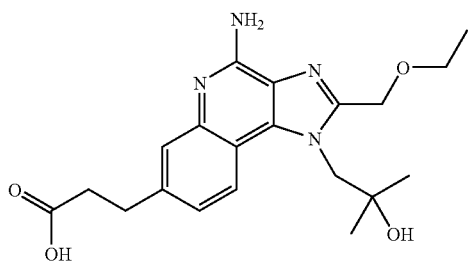 [SMILES: CCOCc1nc2c(N)nc3cc(CCC(=O)O)ccc3c2n1CC(C)(C)O]

A 100-mL round bottom flask was charged with methyl 3-[4-amino-2-(ethoxymethyl)-1-(2-hydroxy-2-methylpropyl)-1H-imidazo[4,5-c]quinolin-7-yl]propanoate (0.28 g, 0.7 mmol) and Claisen's alkali (4.0 mL), and the reaction was stirred at ambient temperature for one hour and then concentrated to a colorless syrup. Citric acid solution (25 mL of 10% aqueous) was added. A white precipitate formed. The mixture was stirred for 15 minutes, and then the solid was collected by vacuum filtration to yield 0.25 g of 3-[4-amino-2-(ethoxymethyl)-1-(2-hydroxy-2-methylpropyl)-1H-imidazo[4,5-c]quinolin-7-yl]propanoic acid.

Example 14

1-[4-Amino-2-(ethoxymethyl)-7-(3-morpholin-4-yl-3-oxopropyl)-1H-imidazo[4,5-c]quinolin-1-yl]-2-methylpropan-2-ol

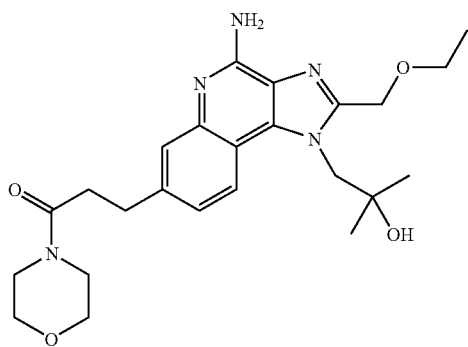 [SMILES: CCOCc1nc2c(N)nc3cc(CCC(=O)N4CCOCC4)ccc3c2n1CC(C)(C)O]

A 20-ml glass vial was charged with anhydrous DMF (1 mL), 3-[4-amino-2-(ethoxymethyl)-1-(2-hydroxy-2-methylpropyl)-1H-imidazo[4,5-c]quinolin-7-yl]propanoic acid (165 mg, 0.43 mmol), N-(3-dimethylaminopropyl)-N''-ethyl-carbodiimide hydrochloride (100 mg, 0.52 mmol, 1.3 eq), 1-hydroxybenzotriazole (70.3 mg, 0.52 mmol, 1.3 eq), and morpholine (110 mg, 1.29 mmol, 3.0 eq). The reaction was maintained at ambient temperature overnight. The reaction mixture was poured into water (10 mL), and the resulting mixture was extracted with dichloromethane (3×10 mL). The chloroform fractions were combined and concentrated, and the residue was purified by chromatography using a HORIZON HPFC system (silica cartridge, eluting with 0-30% CMA in chloroform) followed by recrystallization from acetonitrile to provide 1-[4-amino-2-(ethoxymethyl)-7-(3-morpholin-4-yl-3-oxopropyl)-1H-imidazo[4,5-c]quinolin-1-yl]-2-methylpropan-2-ol as a white solid, mp 118-119° C. MS (APCI) m/z 456 (M+H)⁺.

Example 15

Methyl(2E)-3-[4-amino-1-(2-hydroxy-2-methylpropyl)-1H-imidazo[4,5-c]quinolin-7-yl]prop-2-enoate

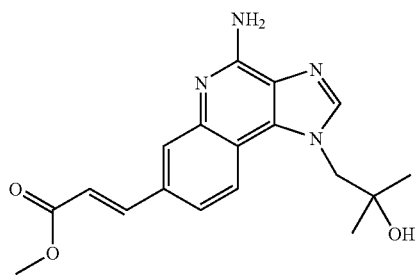 [SMILES: COC(=O)/C=C/c1ccc2c(c1)nc(N)c1ncn(CC(C)(C)O)c12]

Part A

To a suspension of 7-bromo-4-chloro-3-nitroquinoline (U.S. Patent Application Publication No. US 2004/0147543 Example 1, 54.2 g, 0.19 mol) in dichloromethane (1 L) was added triethylamine (100 mL, 0.72 mol., 3.8 eq) in one portion. To the resulting solution was slowly added hydroxyisobutylamine (18.44 g, 0.21 mol, 1.1 eq). The reaction was complete within two hours. The reaction mixture was concentrated to dryness, and the residue was slurried in a solution of 1% aqueous sodium carbonate (600 mL) for two hours. The resulting bright yellow solid was collected by vacuum filtration and dried on the filter funnel overnight to provide 57 g of 1-(7-bromo-3-nitroquinolin-4-ylamino)-2-methylpropan-2-ol.

Part B

A glass Parr vessel was charged with 5% platinum on carbon catalyst (5 g), 1-(7-bromo-3-nitroquinolin-4-ylamino)-2-methylpropan-2-ol (57 g, 0.17 mol), and a 1:1 solution of acetonitrile/toluene (1800 mL). The vessel was evacuated, charged with hydrogen gas (50 psi, 3.4×10⁵ Pa), and shaken for 5 hours. The reaction mixture was then filtered through a 0.2 micron polytetrafluoroethylene (PTFE) membrane filter. The filtrate was concentrated to provide 49 g of 1-[(3-amino-7-bromoquinolin-4-yl)amino]-2-methylpropan-2-ol as a bright yellow-orange solid.

Part C

A 2-L round bottom flask was charged with 1-[(3-amino-7-bromoquinolin-4-yl)amino]-2-methylpropan-2-ol (25.5 g, 82.2 mmol), toluene (1 L), pyridine-HCl (0.1 g, 0.82 mmol, 0.01 eq) and triethylorthoformate (13.4 g, 90.4 mmol, 1.1 eq), and the reaction was heated at reflux for 2 hours. The reaction mixture was concentrated to dryness. The resulting pale yellow solid was slurried in 1% aqueous sodium carbonate solution (250 mL), collected by vacuum filtration, and air-dried on the funnel overnight to provide 25 g of 1-(7-bromo-1H-imidazo[4,5-c]quinolin-1-yl)-2-methylpropan-2-ol.

Part D

A 1-liter round bottom flask was charged with 1-(7-bromo-1H-imidazo[4,5-c]quinolin-1-yl)-2-methylpropan-2-ol (25.0 g, 78.0 mmol), dichloromethane (400 mL) and chloroform (100 mL). To this solution was slowly added in small portions 3-chloroperoxybenxzoic acid (34.0 g of 60% purity, 117 mmol, 1.5 eq). The reaction was maintained at room temperature for 2 hours and then concentrated ammonium hydroxide solution (200 mL) was added. The mixture was vigorously stirred as p-toluenesulfonyl chloride (22.4 g, 117 mmol) was slowly added in small portions. The reaction was complete within 1 hour but was left to stir at room temperature overnight. The reaction mixture was filtered to collect a pale yellow solid. The product was purified by chromatography using a HORIZON HPFC system (silica cartridge, eluting with 0-30% CMA in chloroform). The resulting pale yellow solid was slurried in cold acetonitrile, isolated by filtration, and air-dried on the vacuum filter to provide 17.2 g of 1-(4-amino-7-bromo-1H-imidazo[4,5-c]quinolin-1-yl)-2-methylpropan-2-ol. The filtrate was transferred to a separatory funnel and the layers were separated. The aqueous layer was extracted with chloroform (3×100 mL). The chloroform fractions were combined, washed with brine (100 mL), dried over magnesium sulfate and concentrated to dryness to provide an additional 0.8 g of 1-(4-amino-7-bromo-1H-imidazo[4,5-c]quinolin-1-yl)-2-methylpropan-2-ol, mp>250° C.

MS (ESI) m/z 335, m/z 337 (M+H)$^+$;

Anal. Calcd. for $C_{14}H_{15}BrN_4O$: C, 50.17; H, 4.51; N, 16.71. Found: C, 49.96; H, 4.44; N, 16.75.

Part E

A thick walled glass reaction vessel was charged with anhydrous DMF (2 mL), palladium (II) acetate (34 mg, 0.15 mmol, 0.005 eq), tri-o-tolylphosphine (91 mg, 0.3 mmol, 0.01 eq) and triethylamine (12.4 ml, 89.4 mmol, 3 eq). To this orange solution was added a solution of 1-(4-amino-7-bromo-1H-imidazo[4,5-c]quinolin-1-yl)-2-methylpropan-2-ol (10.0 g, 29.8 mmol) in 100 mL anhydrous DMF followed by the addition of methyl acrylate (2.82 g, 32.8 mmol, 1.1 eq). The reaction mixture was purged with nitrogen, sealed and heated at 120° C. overnight. The heat was turned off and the dark orange reaction mixture was slowly cooled to room temperature. The reaction mixture was poured into a solution of water (600 mL), saturated aqueous potassium carbonate (200 mL) and saturated aqueous sodium chloride 100 mL). An orange precipitate crashed out of solution. The solid was collected by vacuum filtration to provide 7.9 g of product. A small amount of product was purified by chromatography using a HORIZON HPFC system (silica cartridge, eluting with 20% methanol in dichloromethane:dichloromethane in a gradient from 1-15% over 300 mL, 15-40% over 1700 mL, and 40% for 1000 mL). The resulting material was recrystallized from 75:25 acetonitrile/methanol and dried to provide Methyl(2E)-3-[4-amino-1-(2-hydroxy-2-methylpropyl)-1H-imidazo[4,5-c]quinolin-7-yl]prop-2-enoate, mp>250° C.

MS (APCI) m/z 341 (M+H)$^+$;

Anal. Calcd. for $C_{18}H_{20}N_4O_3$ 0.5 $CH_3OH$: C, 62.35; H, 6.22; N, 15.72. Found: C, 62.24; H, 6.26; N, 16.10.

Example 16

Methyl 3-[4-amino-1-(2-hydroxy-2-methylpropyl)-1H-imidazo[4,5-c]quinolin-7-yl]propanoate

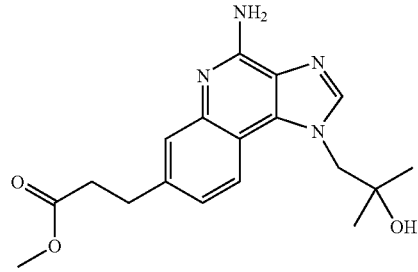 [SMILES: COC(=O)CCc1ccc2c(c1)nc(N)c1ncn(CC(C)(C)O)c12]

A Parr vessel was charged 10% palladium on carbon catalyst (3.0 g), and a slurry of Methyl(2E)-3-[4-amino-1-(2-hydroxy-2-methylpropyl)-1H-imidazo[4,5-c]quinolin-7-yl]prop-2-enoate (7.5 g, 22.0 mmol) in 1:1 methanol/ethanol solution (200 mL). The vessel was evacuated and charged with hydrogen gas (50 psi, 3.4×10$^5$ Pa). The vessel was shaken for 3 days. The reaction was not complete. The reaction was charged with additional catalyst (1 g), placed under hydrogen pressure, and shaken overnight. The reaction was still not complete. The reaction was placed under hydrogen pressure and heated at 50° C. overnight. The reaction was now complete. The catalyst was removed by filtering the reaction mixture through a 0.2 micron PTFE membrane filter. The filtrate was concentrated to dryness. The residue was purified by chromatography using a HORIZON HPFC system (silica cartridge, eluting with a CMA:CHCl$_3$ gradient: 0-8% over 200 mL, 3-30% over 3200 mL, and 30% for 2400 mL). The pure fractions were combined and concentrated to give one lot of product. The impure fractions were combined and concentrated, and the residue was slurried in acetonitrile, collected by vacuum filtration, and combined with the first lot to provide 2.7 g of white solid. A small portion of this material was further purified by chromatography using a HORIZON HPFC system (eluting with a 20% methanol/dichloromethane in dichloromethane gradient: 0-40% over 2400 mL). The pure fractions were combined, concentrated under reduced pressure, recrystallized from acetonitrile, filtered, and dried on the vacuum funnel to provide methyl 3-[4-amino-1-(2-hydroxy-2-methylpropyl)-1H-imidazo[4,5-c]quinolin-7-yl]propanoate as a white solid, mp 201-205° C.

MS (ESI) m/z 343 (M+H)$^+$;

Anal. Calcd. for $C_{18}H_{22}N_4O_3$: C, 63.14; H, 6.48; N, 16.36. Found: C, 63.02; H, 6.56; N, 16.37.

Example 17

Methyl(2E)-3-[4-amino-2-ethyl-1-(2-hydroxy-2-methylpropyl)-1H-imidazo[4,5-c]quinolin-7-yl]prop-2-enoate

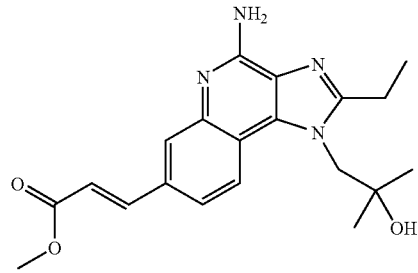 [SMILES: CCc1nc2c(N)nc3cc(/C=C/C(=O)OC)ccc3c2n1CC(C)(C)O]

A thick walled glass reaction vessel was charged with anhydrous DMF (2 mL), palladium (II) acetate (19 mg, 0.085 mmol, 0.005 eq), tri-o-tolylphosphine (51 mg, 0.17 mmol, 0.01 eq) and triethylamine (7.25 g, 52.02 mmol, 3 eq). To this orange solution was added a solution of 1-(4-amino-7-bromo-2-ethyl-1H-imidazo[4,5-c]quinolin-1-yl)-2-methylpropan-2-ol (U.S. Patent Application Publication No. US 2004/0147543 Example 142-144, 6.3 g, 17.34 mmol) in 100 mL anhydrous DMF followed by methyl acrylate (1.64 g, 19.08 mmol, 1.1 eq). The reaction mixture was purged with nitrogen, sealed and heated to 120° C. overnight. The heat was turned off and the dark orange reaction mixture was slowly cooled to room temperature. The reaction mixture was poured into a solution of water (600 mL), saturated aqueous potassium carbonate (200 mL) and saturated aqueous sodium chloride (100 mL). The mixture was transferred to a separatory funnel and extracted with chloroform. The chloroform fractions were combined and concentrated to dryness. The product was purified by chromatography using a HORIZON HPFC system (silica cartridge, eluting with a CMA:chloroform gradient: 0-5% over 200 mL, 5-30% over 3200 mL, and then 30% for 2400 mL) to provide approximately 4 g of product. A small portion was further purified by chromatography using a HORIZON HPFC system (silica cartridge, eluting with a 20% methanol/dichloromethane in dichloromethane gradient: 0-10% over 200 mL, 10-40% over 1650 mL, and then 40% for 500 mL) followed by recrystallization from acetonitrile/methanol to provide Methyl(2E)-3-[4-amino-2-ethyl-1-(2-hydroxy-2-methylpropyl)-1H-imidazo[4,5-c]quinolin-7-yl]prop-2-enoate, mp 238-240° C.

MS (ESI) m/z 369 (M+H)$^+$;

Anal. Calcd. for $C_{20}H_{24}N_4O_3$ 1.0 $CH_3OH$: C, 62.99; H, 7.05; N, 14.00. Found: C, 63.00; H, 7.12; N, 13.67.

Example 18

Methyl(2E)-3-[4-amino-1-(2-hydroxy-2-methylpropyl)-1H-imidazo[4,5-c]quinolin-8-yl]prop-2-enoate

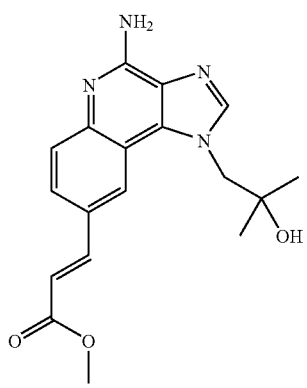 [SMILES: COC(=O)/C=C/c1ccc2nc(N)c3ncn(CC(C)(C)O)c3c2c1]

Part A

A 2-liter round bottom flask was charged with 1-(4-amino-1H-imidazo[4,5-c]quinolin-1-yl)-2-methylpropan-2-ol (50.0 g, 0.195 mol.) and DMF (1 L). To this stirred suspension was added a solution of N-bromosuccinimide (41.7 g, 0.234 mol, 1.2 eq) in DMF (200 mL). The reaction was stirred at ambient temperature overnight. The dark red solution was poured into 2% aqueous potassium carbonate solution (8 L). After 30 minutes the resulting mixture was filtered through a layer of CELITE filter agent followed by a rinse of 4 L of deionized water and 1 L of DMF. The aqueous filtrate was divided into five 2.5 L fractions and each was extracted with chloroform (3×600 mL), diluted with DMF (200 mL), and extracted again with chloroform (3×600 mL). The combined organic extracts were dried over magnesium sulfate, filtered and concentrated to dryness. After drying overnight under high vacuum, a reddish brown solid remained (50 g). This material was slurried in concentrated sodium bisulfite (200 mL) for 30 minutes and then filtered, rinsed with water, and dried on vacuum funnel overnight to provide 50 g of product. A small sample was purified by chromatography using a HORIZON HPFC system (silica cartridge, eluting with a gradient of chloroform/CMA; 0-8% over 200 mL, 8-20% over 2000 mL, 20-30% over 1000 mL, 30% over 2400 mL) followed by trituration with hot acetonitrile. The resulting bright yellow solid was further purified by chromatography using a HORIZON HPFC system (silica cartridge, eluting with a gradient of 20% methanol/dichloromethane in dichloromethane: 0-10% over 200 mL, 10-40% over 2400 mL, and 40% over 1200 mL) followed by recrystallization from acetonitrile/methanol to provide 0.65 g of 1-(4-amino-8-bromo-1H-imidazo[4,5-c]quinolin-1-yl)-2-methylpropan-2-ol as an off-white solid, mp 197-198° C.

MS (APCI) m/z 335, 337 (M+H)$^+$;

Anal. Calcd. for $C_{14}H_{15}BrN_4O$: C, 50.17; H, 4.51; N, 16.71. Found: C, 50.24; H, 4.57; N, 16.62.

Part B

The method described in Example 15 Part E can be used to couple 1-(4-amino-8-bromo-1H-imidazo[4,5-c]quinolin-1-yl)-2-methylpropan-2-ol with methyl acrylate to provide Methyl(2E)-3-[4-amino-1-(2-hydroxy-2-methylpropyl)-1H-imidazo[4,5-c]quinolin-8-yl]prop-2-enoate.

Examples 19-24

A solution of 7-bromo-2-ethoxymethyl-1-(3-isopropoxypropyl)-1H-imidazo[4,5-c]quinolin-4-amine (42 mg, 0.1 mmol, Example 1 Parts A-D) in 1,4-dioxane (1 mL) was added to a test tube containing copper iodide (8 mg), potassium phosphate (42 mg), and a reagent (0.12 mmol) from the table below and the tube was purged with nitrogen. Trans-1,2-diaminocyclohexane (7 μL) was added to the tube. The tube was purged with nitrogen and then heated with stirring in a sand bath at 110° C. for about 6 days. The reaction mixture was filtered and the filtrate was concentrated by vacuum centrifugation. The compounds were purified by preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. The table below shows the reagent used for each example, the structure of the resulting compound, and the observed accurate mass for the isolated trifluoroacetate salt.

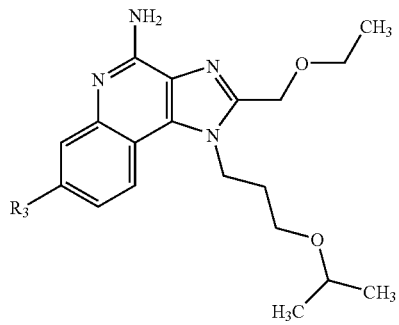

| Example | Reagent | R₃ | Measured Mass (M + H) |
|---|---|---|---|
| 19 | Methyl Carbamate | H₃C-O-C(=O)-NH- | 416.2328 |
| 20 | Methanesulfonamide | H₃C-S(=O)₂-NH- | 436.2006 |
| 21 | 3-Methylbutanamide | (CH₃)₂CH-CH₂-C(=O)-NH- | 442.2820 |
| 22 | (S)-(+)-2,2-Dimethylcyclopropanecarboxamide | 2,2-dimethylcyclopropyl-C(=O)-NH- | 454.2854 |
| 23 | 3,4-Difluorobenzamide | 3,4-F₂-C₆H₃-C(=O)-NH- | 498.2300 |
| 24 | Benzenesulfonamide | C₆H₅-S(=O)₂-NH- | 498.2155 |

Examples 25 and 26

A solution of N-[4-(4-amino-7-bromo-2-ethoxymethyl-1H-imidazo[4,5-c]quinolin-yl)butyl]methanesulfonamide (50 mg, 0.1 mmol, U.S. Patent Application Publication No. US2004/0147543, examples 612-642) in 1,4-dioxane (1 mL) was added to a test tube containing copper iodide (19 mg), potassium phosphate (16 mg), and a reagent (0.2 mmol) from the table below and the tube was purged with nitrogen. Trans-1,2-diaminocyclohexane (18 μL) was added to the tube. The tube was purged with nitrogen, capped, and then heated with stirring in a sand bath at 110° C. for about 16 hours. The reaction mixture was filtered and the filtrate was concentrated by vacuum centrifugation. The compounds were purified using the method described in Examples 19-24. The table below shows the reagent used for each example, the structure of the resulting compound, and the observed accurate mass for the isolated trifluoroacetate salt.

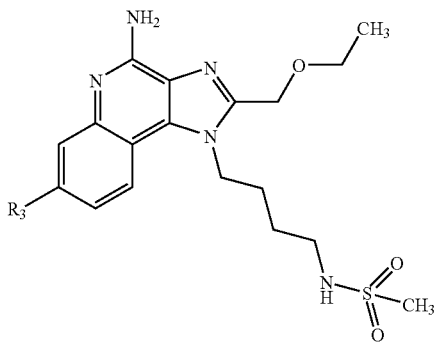

| Example | Reagent | R₃ | Measured Mass (M + H) |
|---|---|---|---|
| 25 | Cyclopropanecarboxamide | | 475.2153 |
| 26 | 1,1-Dimethylurea | | 478.2241 |

Examples 27-41

A solution of 1-{3-[4-amino-8-(2-aminoethyl)-2-(2-methoxyethyl)-1H-imidazo[4,5-c]quinolin-1-yl]propyl}pyrrolidin-2-one (41 mg, 0.16 mmol, 1.0 eq) in a mixture of N,N-dimethylacetamide (1 mL) and N,N-diisopropylethylamine (34 μL) was added to a test tube containing a reagent from the table below (1.1 eq). The tube was vortexed overnight at ambient temperature and then the reaction was quenched with water (100 μL). The solvent was removed by vacuum centrifugation and the compound was purified using the method described in Examples 19-24. The table below shows the reagent used for each example, the structure of the resulting compound, and the observed accurate mass for the isolated trifluoroacetate salt.

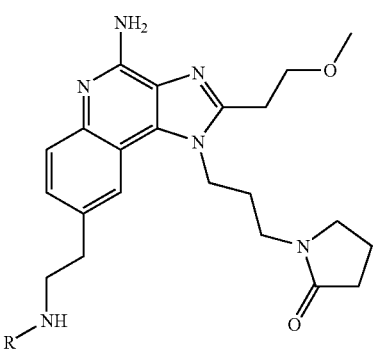

| Example | Reagent | R | Measured Mass (M + H) |
|---|---|---|---|
| 27 | Acetyl chloride | | 453.2643 |
| 28 | Cyclopropanecarbonyl chloride | | 479.2805 |
| 29 | Isobutyryl chloride | | 481.2954 |
| 30 | Benzoyl chloride | | 515.2795 |
| 31 | Nicotinoyl chloride hydrochloride | | 516.2712 |
| 32 | Methanesulfonyl chloride | | 489.2295 |
| 33 | Isopropylsulfonyl chloride | | 517.2607 |
| 34 | Dimethylsulfamoyl chloride | | 518.2574 |

-continued

| Example | Reagent | R | Measured Mass (M + H) |
|---|---|---|---|
| 27 | Acetyl chloride | 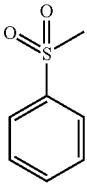 | 453.2643 |
| 35 | Benzenesulfonyl chloride | 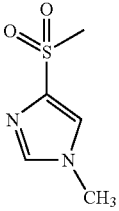 | 551.2482 |
| 36 | 1-Methylimidazole-4-sulfonyl chloride | 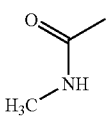 | 555.2527 |
| 37 | Methyl isocyanate | 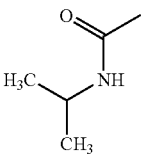 | 468.2766 |
| 38 | Isopropyl isocyanate |  | 496.3044 |

-continued

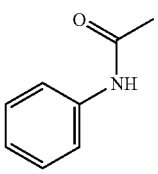

| Example | Reagent | R | Measured Mass (M + H) |
|---|---|---|---|
| 27 | Acetyl chloride | 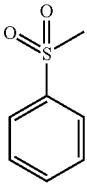 | 453.2643 |
| 39 | Phenyl isocyanate | 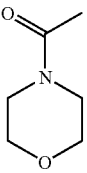 | 530.2836 |
| 40 | 4-Morpholinylcarbonyl chloride | 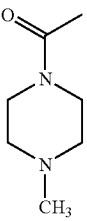 | 524.3011 |
| 41 | 4-Methyl-1-Piperazinecarbonyl chloride | | 537.3329 |

Examples 42-78

A solution of 1-[4-amino-7-(3-aminopropyl)-2-(methoxymethyl)-1H-imidazo[4,5-c]quinolin-1-yl]-2-methylpropan-2-ol (35 mg, 0.1 mmol, 1.0 eq) in a mixture of chloroform (1 mL), N,N-dimethylacetamide (about 80 µL), and N,N-diisopropylethylamine (36 µL) was added to a test tube containing a reagent from the table below (1.1 eq). The tube was vortexed overnight at ambient temperature and then the reaction was quenched with water (50 µL). The solvent was removed by vacuum centrifugation and the compound was purified using the method described in Examples 19-24. The table below shows the reagent used for each example, the structure of the resulting compound, and the observed accurate mass for the isolated trifluoroacetate salt.

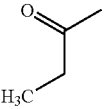
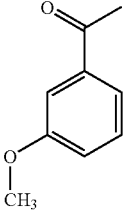

| Example | Reagent | R | Measured Mass (M + H) |
|---|---|---|---|
| 42 | Propionyl chloride | 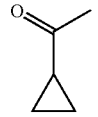 | 414.2485 |
| 43 | Cyclopropanecarbonyl chloride | | 426.2527 |
| 44 | Butyryl chloride | | 428.2683 |
| 45 | Isobutyryl chloride | | 428.2637 |
| 46 | Cyclopentanecarbonyl chloride | | 454.2795 |
| 47 | Cyclohexanecarbonyl chloride | | 468.2937 |
| 48 | Dimethylaminoacetyl chloride hydrochloride | | 443.2772 |

| Example | Reagent | R | Measured Mass (M + H) |
|---|---|---|---|
| 49 | 3-Methoxybenzoyl chloride | 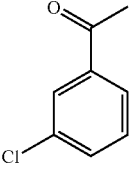 | 492.2614 |
| 50 | 3-Chlorobenzoyl chloride | | 496.2090 |
| 51 | 4-Chlorobenzoyl chloride | | 496.2094 |
| 52 | Methanesulfonyl chloride | | 436.1988 |
| 53 | Ethanesulfonyl chloride | | 450.2188 |
| 54 | 1-Propanesulfonyl chloride | | 464.2343 |

-continued

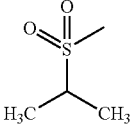

| Example | Reagent | R | Measured Mass (M + H) |
|---|---|---|---|
| 55 | Isopropylsulfonyl chloride | 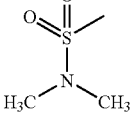 | 464.2345 |
| 56 | Dimethylsulfamoyl chloride | 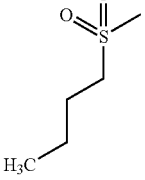 | 465.2298 |
| 57 | 1-Butanesulfonyl chloride | 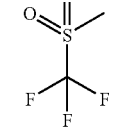 | 478.2488 |
| 58 | Trifluoromethanesulfonyl chloride | 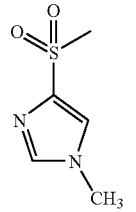 | 490.1765 |
| 59 | 1-Methylimidazole-4-sulfonyl chloride | 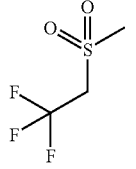 | 502.2260 |
| 60 | 2,2,2-Trifluoroethanesulfonyl chloride | 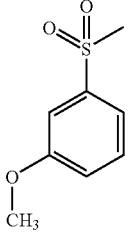 | 504.1884 |

-continued

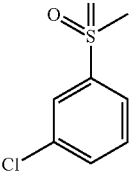

| Example | Reagent | R | Measured Mass (M + H) |
|---|---|---|---|
| 61 | 3-Methoxybenzenesulfonyl chloride | 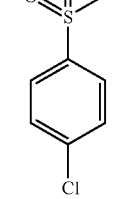 | 528.2272 |
| 62 | 3-Chlorobenzenesulfonyl chloride | 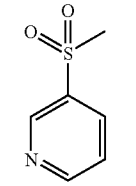 | 532.1821 |
| 63 | 4-Chlorobenzenesulfonyl chloride | 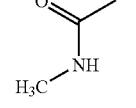 | 532.1793 |
| 64 | 3-Pyridine sulfonyl chloride hydrochloride | 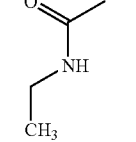 | 499.2130 |
| 65 | Methyl isocyanate | | 415.2461 |
| 66 | Ethyl isocyanate | | 429.2572 |

-continued

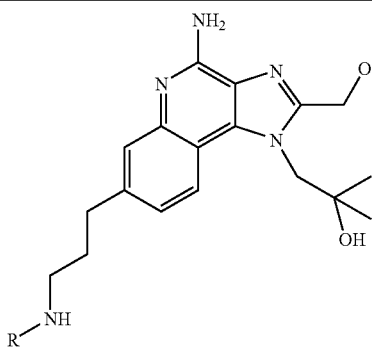

| Example | Reagent | R | Measured Mass (M + H) |
|---|---|---|---|
| 67 | Isopropyl isocyanate | [isopropyl-NH-C(=O)-] | 443.2747 |
| 68 | n-Propyl isocyanate | [n-propyl-NH-C(=O)-] | 443.2764 |
| 69 | Phenyl isocyanate | [phenyl-NH-C(=O)-] | 477.2596 |
| 70 | Cyclohexyl isocyanate | [cyclohexyl-NH-C(=O)-] | 483.3073 |
| 71 | 3-Methoxyphenyl isocyanate | [3-methoxyphenyl-NH-C(=O)-] | 507.2736 |
| 72 | 4-Methoxyphenyl isocyanate | [4-methoxyphenyl-NH-C(=O)-] | 507.2714 |

-continued

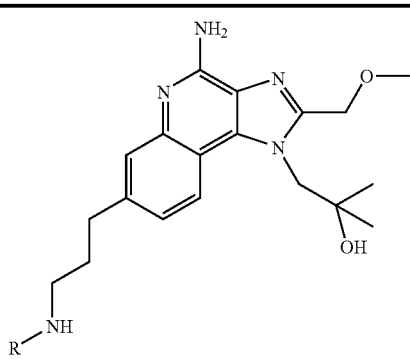

| Example | Reagent | R | Measured Mass (M + H) |
|---|---|---|---|
| 73 | 3-Chlorophenyl isocyante | [3-chlorophenyl-NH-C(=O)-] | 511.2195 |
| 74 | 4-Chlorophenyl isocyante | [4-chlorophenyl-NH-C(=O)-] | 511.2211 |
| 75 | 1-Pyrrolidinecarbonyl chloride | [pyrrolidin-1-yl-C(=O)-] | 455.2779 |
| 76 | 1-Piperidinecarbonyl chloride | [piperidin-1-yl-C(=O)-] | 469.2917 |
| 77 | 4-Morpholinylcarbonyl chloride | [morpholin-4-yl-C(=O)-] | 471.2733 |
| 78 | 4-Methyl-1-piperazinecarbonyl chloride | [4-methylpiperazin-1-yl-C(=O)-] | 484.2990 |

Examples 79-95

A solution of 3-[4-amino-1-(2-hydroxy-2-methylpropyl)-2-(methoxymethyl)-1H-imidazo[4,5-c]quinolin-7-yl]propanoic acid (20 mg, 0.1 mmol, 1 eq) in 1:1 methanol:dichloromethane (2 mL) was placed in a test tube. The solvent was removed by vacuum centrifugation. A solution of 1-hydroxybenzotriazole (29 mg) in pyridine (1 mL) was added to the tube. The tube was sonicated for 15 minutes to provide a uniform suspension. A solution of N-(3-dimethylaminopropyl)-N'-ethylcarbodiimide (350 mg) in pyridine (100 μL) was added to the tube and the mixture was stirred for about 30 minutes. A reagent (2 eq) from the table below was added, the reaction mixture was stirred at ambient temperature overnight, and then the reaction was quenched with water (100 μL). The solvent was removed by vacuum centrifugation and the compound was purified using the method described in Examples 19-24. The table below shows the reagent used for each example, the structure of the resulting compound, and the observed accurate mass for the isolated trifluoroacetate salt.

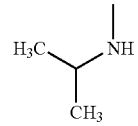

| Example | Reagent | R | Measured Mass (M + H) |
|---|---|---|---|
| 79 | Isopropylamine | 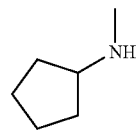 | 414.2520 |
| 80 | Cyclopentylamine | 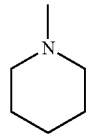 | 440.2655 |
| 81 | Piperidine | 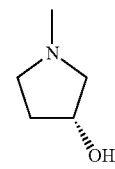 | 440.2705 |
| 82 | (R)-3-Hydroxypyrrolidine | 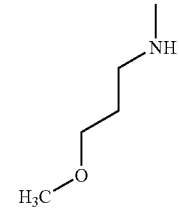 | 442.2455 |
| 83 | 3-Methoxypropylamine | | 444.2607 |

-continued
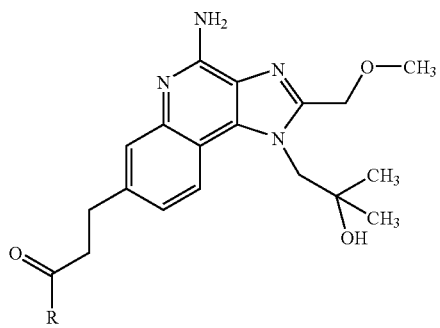
| Example | Reagent | R | Measured Mass (M + H) |
|---|---|---|---|
| 84 | 2-Methylpiperidine | 2-methylpiperidin-1-yl | 454.2857 |
| 85 | Tetrahydrofurfurylamine | (tetrahydrofuran-2-ylmethyl)amino | 456.2646 |
| 86 | 3,5-Dimethylpiperidine | 3,5-dimethylpiperidin-1-yl | 468.2977 |
| 87 | Thiophene-2-ethylamine | [2-(thiophen-2-yl)ethyl]amino | 482.2198 |
| 88 | Nipecotamide | 3-carbamoylpiperidin-1-yl | 483.2740 |
| 89 | 1-Acetylpiperazine | 4-acetylpiperazin-1-yl | 483.2754 |

-continued
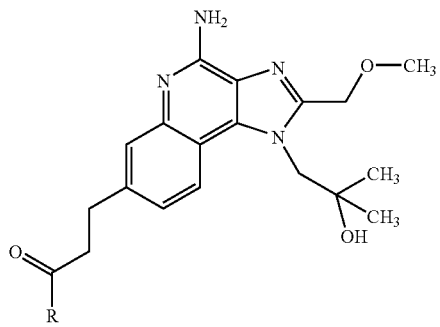
| Example | Reagent | R | Measured Mass (M + H) |
|---|---|---|---|
| 90 | 4-Piperidineethanol | 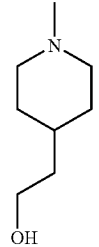 | 484.2943 |
| 91 | 1,1-Dioxidotetrahydrothien-3-ylamine | 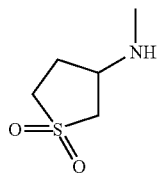 | 490.2134 |
| 92 | 1-(3-Aminopropyl)-2-pyrrolidinone | 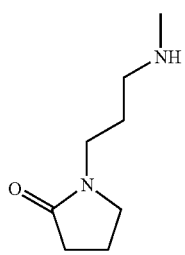 | 497.2887 |
| 93 | Methyl isonipecotate | 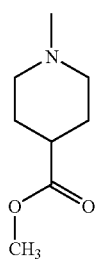 | 498.2765 |
| 94 | 1-Adamantanamine | 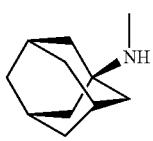 | 506.3137 |

-continued

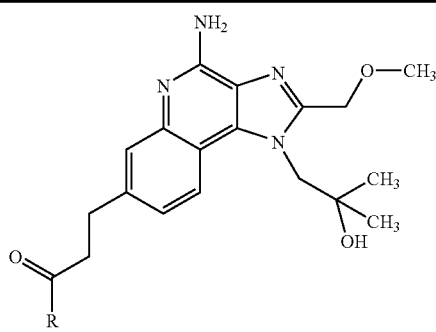

| Example | Reagent | R | Measured Mass (M + H) |
|---|---|---|---|
| 95 | Ethyl 2-amino-4-thiazoleacetate | ![R group structure] | 541.2277 |

Example 96

2-(4-Amino-1-isobutyl-1H-imidazo[4,5-c]quinolin-8-yl)ethanol

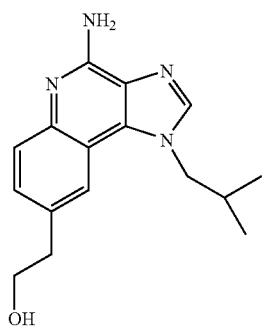 [SMILES: CC(C)Cn1cnc2c(N)nc3ccc(CCO)cc3c21]

Part A

8-Bromo-1-isobutyl-1H-imidazo[4,5-c]quinolin-4-amine (22.0 g, 68.9 mmol), triethylamine (19.20 mL, 137.8 mmol), dichloro[1,1'-bis(diphenylphosphino)ferrocene]palladium (II) dichloromethane (1.00 g, 1.37 mmol), and potassium vinyltrifluoroborate (10.15 g, 75.81 mmol) were dissolved in n-propanol (20 mL/g). The amber colored solution was heated at reflux temperature for 18 hours and then cooled to ambient temperature. The reaction was concentrated under reduced pressure. The resulting solid was slurried in 1% aqueous sodium carbonate and a fine powder was collected by filtration. The powder was sequentially washed with acetonitrile (5 mL/g) and 10% sodium hydroxide (500 mL). A final purification using a HORIZON HPFC system (silica cartridge, eluting with 4% methanol/dichloromethane) provided 10 g of 1-isobutyl-8-vinyl-1H-imidazo[4,5-c]quinolin-4-amine as an off-white solid, MS (APCI) m/z 267 (M+H)$^+$.

Part B

A 500 mL round bottom flask was charged with 1-isobutyl-8-vinyl-1H-imidazo[4,5-c]quinolin-4-amine (850 mg, 3.2 mmol) and 200 mL of tetrahydrofuran. The flask was purged with nitrogen. A solution of 9-borabicyclo[3.3.1]nonane (0.5M in tetrahydrofuran, 8.5 mL, 4.25 mmol) was added in one portion and the reaction was stirred overnight. Additional 9-borabicyclo[3.3.1]nonane (0.5M in tetrahydrofuran, 12.5 mL, 6.25 mmol) was added and the mixture was stirred for approximately 24 hours. The reaction was cooled to 0° C. with an ice/water bath and 30% $H_2O_2$ (2 mL) was added dropwise. After 5 minutes, 10% NaOH (5 mL) was added dropwise. The reaction was stirred for 30 minutes, diluted with water (100 mL) and then extracted with chloroform (3×100 mL). The combined organic fractions were concentrated under reduced pressure and purified by chromatography using a HORIZON HPFC system (silica cartridge, eluting with a gradient of 0-30% CMA in chloroform) followed by recrystallization from acetonitrile to provide 580 mg of 2-(4-amino-1-isobutyl-1H-imidazo[4,5-c]quinolin-8-yl)ethanol as an off-white solid, mp 214-216° C.

$^1$H NMR (500 MHz, DMSO-d$_6$) δ 8.15 (s, 1H), 7.82 (m, 1H), 7.54 (d, J=8.4 Hz, 1H), 7.31 (dd, J=8.4, 1.4 Hz, 1H), 6.47 (br s, 2H), 4.68 (t, J=5.2 Hz, 1H), 4.39 (d, J=7.3 Hz, 2H), 3.71-3.68 (m, 2H), 2.87 (t, J=7.0 Hz, 2H), 2.18 (septet, J=6.8 Hz, 1H), 0.93 J=6.6 Hz, 6H);

$^{13}$C NMR (125 MHz, DMSO-d$_6$) δ 151.5, 143.3, 143.0, 132.1, 131.4, 128.1, 128.0, 125.8, 119.9, 114.5, 62.2, 53.3, 38.8, 28.3, 19.1;

MS (ESI) m/z 285 (M+H)$^+$;

Anal. Calcd. for $C_{16}H_{20}N_4O$: C, 67.58; H, 7.09; N, 19.70. Found: C, 67.51; H, 7.36; N, 19.74.

Example 97

3-[4-Amino-1-(2-hydroxy-2-methylpropyl)-1H-imidazo[4,5-c]quinolin-7-yl]-1-(morpholin-4-yl)propan-1-one

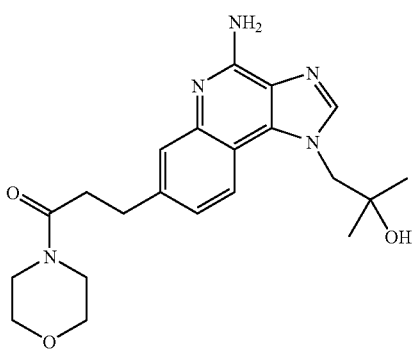 [SMILES: CC(C)(O)Cn1cnc2c(N)nc3cc(CCC(=O)N4CCOCC4)ccc3c21]

Part A

Methyl 3-[4-amino-1-(2-hydroxy-2-methylpropyl)-1H-imidazo[4,5-c]quinolin-7-yl]propanoate (2.3 g, 6.7 mmol) was stirred in Claisen's alkali (50 mL) for 30 minutes. The solution was concentrated under reduced pressure. The resulting white solid was dissolved in water (200 mL) and washed with chloroform (4×50 mL). Citric acid was added to the aqueous fraction until the pH was 5-6. A fine white precipitate formed that was obtained by filtration to provide 2.5 g of wet 3-[4-amino-1-(2-hydroxy-2-methylpropyl)-1H-imidazo[4,5-c]quinolin-7-yl]propanoic acid as a white solid. MS (ESI) m/z 329 (M+H)$^+$.

Part B

3-[4-Amino-1-(2-hydroxy-2-methylpropyl)-1H-imidazo[4,5-c]quinolin-7-yl]propanoic acid (500 mg, 1.5 mmol), anhydrous N,N-dimethylformamide (25 mL), and 1-hydroxybenzotriazole (250 mg, 1.8 mmol) were combined and the reaction was stirred for 15 minutes. 1-(3-Dimethylaminopropyl)-3-ethylcarbodiimide (350 mg, 1.8 mmol) was added and the reaction mixture was stirred for an additional 30 minutes. Morpholine (400 mg, 2.3 mmol) was added to the reaction slurry. After five hours 1-hydroxybenzotriazole (250 mg, 1.8 mmol), 1-(3-Dimethylaminopropyl)-3-ethylcarbodiimide (350 mg, 1.8 mmol), and morpholine (400 mg, 2.3 mmol) were added and the mixture was heated at 70° C. for 2 hours. After cooling to ambient temperature, the solvent was removed under reduced pressure and the residue was partitioned between chloroform (100 ml) and 1% aqueous sodium carbonate (50 mL). The fractions were separated and organic fraction was washed 1% aqueous sodium carbonate (2×50 mL). The combined aqueous fractions were back extracted with chloroform (50 mL). The combined organic fractions were dried (MgSO$_4$), filtered, and concentrated under reduced pressure. The resulting off-white solid was purified by chromatography using a HORIZON HPFC system (silica cartridge, eluting with a CMA:chloroform gradient; 0-5% CMA over 75 mL, 5-35% over 1500 mL, and 35% for 600 mL) followed by recrystallization from acetonitrile to provide 335 mg of 3-[4-amino-1-(2-hydroxy-2-methylpropyl)-1H-imidazo[4,5-c]quinolin-7-yl]-1-(morpholin-4-yl)propan-1-one as an off-white solid, mp 217-218° C.

$^1$H NMR (500 MHz, DMSO-d$_6$) δ 8.20 (d, J=8.4 Hz, 1H), 8.03 (s, 1H), 7.45 (d, J=1.3 Hz, 1H), 7.10 (dd, J=8.4, 1.5 Hz, 1H), 6.50 (br s, 2H), 4.83 (s, 1H), 4.51 (s, 2H), 3.51-3.40 (m, 8H), 2.92 (m, 2H), 2.69 (m, 2H), 1.16 (s, 6H);

MS (APCI) m/z 398 (M+H)$^+$;

Anal. Calcd. for C$_{21}$H$_{27}$N$_5$O$_3$: C, 63.46; H, 6.85; N, 17.62. Found: C, 63.29; H, 6.97; N, 17.83.

Example 98

3-[4-Amino-2-ethyl-1-(2-hydroxy-2-methylpropyl)-1H-imidazo[4,5-c]quinolin-7-yl]-1-(morpholin-4-yl)propan-1-one

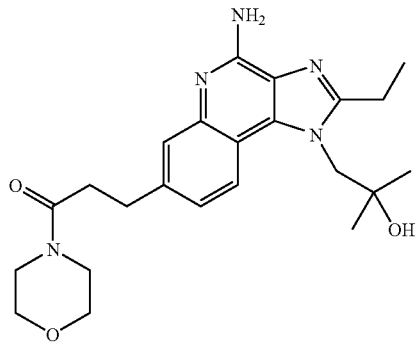 [SMILES: CCc1nc2c(N)nc3cc(CCC(=O)N4CCOCC4)ccc3c2n1CC(C)(C)O]

3-[4-Amino-2-ethyl-1-(2-hydroxy-2-methylpropyl)-1H-imidazo[4,5-c]quinolin-7-yl]propanoic acid (500 mg, 1.4 mmol), chloroform (100 mL) and 1-hydroxybenzotriazole (575 mg, 4.26 mmol) were combined and then stirred for 30 minutes. 1-(3-Dimethylaminopropyl)-3-ethylcarbodiimide (1.00 g, 5.2 mmol) was added and the reaction was stirred for 30 minutes. Morpholine (10 mL) was added in one portion. After 4 hours, 1% aqueous sodium carbonate (100 mL) was added and the mixture was stirred. The fractions were separated and the organic fraction was sequentially washed with 1% aqueous sodium carbonate (50 mL), dried (MgSO$_4$), filtered, and concentrated to a white solid. Recrystallization from acetonitrile provided 225 mg of 3-[4-amino-2-ethyl-1-(2-hydroxy-2-methyl-propyl)-1H-imidazo[4,5-c]quinolin-7-yl]-1-(morpholin-4-yl)propan-1-one as a white solid, mp 237-239° C.

$^1$H NMR (500 MHz, DMSO-d$_6$) δ 8.14 (d, J=8.5 Hz, 1H), 7.42 (d, J=1.5 Hz, 1H), 7.08 (dd, J=8.5, 1.7 Hz, 1H), 6.30 (br s, 2H), 4.76 (s, 1H), 4.51 (br s, 2H), 3.51-3.40 (m, 8H), 3.04 (quartet, J=7.4 Hz, 2H), 2.91 (m, 2H), 2.68 (m, 2H), 1.34 (t, J=7.4 Hz, 3H), 1.16 (br s, 6H);

MS (APCI) m/z 426 (M+H)$^+$;

Anal. Calcd. for C$_{23}$H$_{31}$N$_5$O$_3$: C, 64.92; H, 7.34; N, 16.46. Found: C, 64.93; H, 7.31; N, 16.60.

Example 99

1-{4-Amino-7-[2-(methylsulfonyl)ethyl])-1H-imidazo[4,5-c]quinolin-1-yl}-2-methylpropan-2-ol

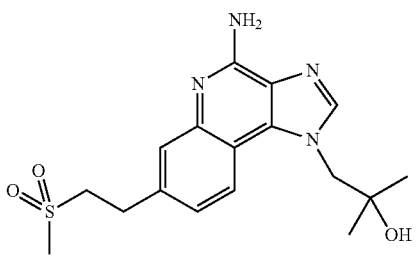 [SMILES: CC(C)(O)Cn1cnc2c(N)nc3cc(CCS(C)(=O)=O)ccc3c21]

Part A

A thick walled glass tube, equipped with a stir bar, was charged with palladium (II) acetate (15 mg, 0.07 mmol), acetonitrile (50 mL), methyl vinyl sulfone (268 mg, 2.52 mmol), triethylamine (1.00 mL, 7.17 mmol), tri-o-tolylphosphine (45 mg, 0.21 mmol) and 1-(4-amino-7-bromo-1H-imidazo[4,5-c]quinolin-1-yl)-2-methylpropan-2-ol (800 mg, 2.39 mmol). The reaction mixture was purged with nitrogen and the tube was sealed and heated at 120° C. in an oil bath. The reaction was maintained at 120° C. for 12 hours, cooled to ambient temperature, and then concentrated under reduced pressure to yield a dark brown oil. The oil was partitioned between chloroform (75 mL) and a solution comprised of a 1:1 combination of 10% aqueous potassium carbonate and 10% sodium hydroxide. A precipitate formed. The mixture was filtered and the recovered solid was purified by chromatography using a HORIZON HPFC system (silica cartridge, eluting with 20% methanol in dichloromethane. The filtrate was also concentrated and the residue purified by chromatography using a HORIZON HPFC system (silica cartridge, eluting with a 0-8% gradient of methanol in dichloromethane). The two lots of purified product were combined to provide 380 mg of 1-{4-amino-7-[2-(methylsulfonyl)ethenyl]-1H-imidazo[4,5-c]quinolin-1-yl}-2-methylpropan-2-ol as a pale yellow solid. MS (APCI) m/z 361 (M+H)$^+$.

Part B

A glass Parr vessel was charged with 10% palladium on carbon (0.1 g), methanol (50 mL) and 1-{4-amino-7-[2-(methylsulfonyl)ethenyl]-1H-imidazo[4,5-c]quinolin-1-yl}-2-methylpropan-2-ol (380 mg, 1.05 mmol). The vessel was evacuated and charged with hydrogen gas (40 psi, 2.8×10$^5$ Pa). The reaction was shaken at 50° C. for approximately 18 hours. The reaction was cooled to ambient temperature, filtered, and then concentrated under reduced pressure. The resulting crude product was purified by chromatography using a HORIZON HPFC system (silica cartridge, eluting with a 0-35% gradient of CMA in chloroform) followed by recrystallization from acetonitrile to provide 176 mg of 1-{4-amino-7-[2-(methylsulfonyl)ethyl]-1H-imidazo[4,5-c]quinolin-1-yl}-2-methylpropan-2-ol as an off-white solid, mp 269-271° C.

$^1$H NMR (500 MHz, DMSO-$d_6$) δ 8.25 (d, J=8.5 Hz, 1H), 8.05 (s, 1H), 7.50 (d, J=1.5 Hz, 1H), 7.15 (dd, J=8.4, 1.7 Hz, 1H), 6.54 (br s, 2H), 4.83 (s, 1H), 4.52 (s, 2H), 3.52-3.49 (m, 2H), 3.13-3.10 (m, 2H), 3.00 (s, 3H), 1.16 (s, 6H);

$^{13}$C NMR (125 MHz, DMSO-$d_6$) δ 152.1, 145.2, 143.8, 136.3, 132.6, 127.1, 125.3, 121.5, 121.1, 113.6, 69.4, 56.1, 54.3, 40.1, 27.7, 27.0;

MS (APCI) m/z 363 (M+H)$^+$;

Anal. Calcd. for $C_{17}H_{22}N_4O_3S \cdot 0.33CH_3CN$: C, 56.42; H, 6.16; N, 16.13. Found: C, 56.23; H, 6.17; N, 16.16.

Example 100

3-[4-Amino-2-ethyl-1-(2-hydroxy-2-methylpropyl)-1H-imidazo[4,5-c]quinolin-7-yl]-N,N-dimethylpropanamide

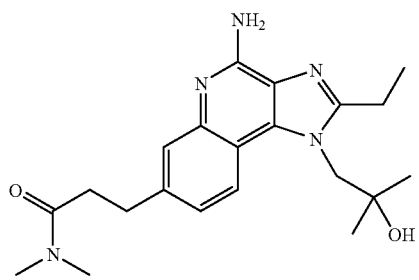 [SMILES: CCc1nc2c(N)nc3cc(CCC(=O)N(C)C)ccc3c2n1CC(C)(C)O]

Part A

A thick walled glass tube, equipped with a stir bar, was charged with palladium (II) acetate (50 mg, 0.22 mmol), acetonitrile (50 mL), triethylamine (1.80 mL, 13.0 mmol), tri-o-tolylphosphine (200 mg, 0.65 mmol), N,N-dimethylacrylamide (511 mg, 5.16 mmol) and 1-(7-bromo-2-ethyl-1H-imidazo[4,5-c]quinolin-1-yl)-2-methylpropan-2-ol (1.50 g, 4.30 mmol). The reaction mixture was purged with nitrogen and the tube was sealed and heated at 120° C. in an oil bath. The reaction was maintained at 120° C. for 18 hours and then cooled to ambient temperature. Upon cooling a precipitate formed that was dissolved by the addition of methanol and chloroform. The remaining insoluble material was removed by filtration through a 0.2 micron PTFE membrane filter. The filtrate was concentrated under reduced pressure and purified by chromatography using a HORIZON HPFC system (silica, eluting with a 0-25% gradient of CMA in chloroform). The resulting product was washed with 1% aqueous sodium carbonate and filtered to provide 1.37 g of 3-[2-ethyl-1-(2-hydroxy-2-methylpropyl)-1H-imidazo[4,5-c]quinolin-7-yl]-N,N-dimethylprop-2-enamide as an off-white solid, mp 196-198° C.

$^1$H NMR (500 MHz, DMSO-$d_6$) δ 9.15 (s, 1H), 8.61 (d, J=8.9 Hz, 1H), 8.33 (d, J=1.3 Hz, 1H), 8.00 (dd, J=8.9, 1.5 Hz, 1H), 7.66 (d, J=15.4 Hz, 1H), 7.38 (d, J=15.4 Hz, 1H), 4.81 (s, 1H), 4.64 (br s, 2H), 3.21 (s, 3H), 3.10 (m, 2H), 2.96 (s, 3H), 1.39 (t, J=7.4 Hz, 3H), 1.20 (s, 6H);

MS (ESI) m/z 367 (M+H)$^+$;

Anal. Calcd. for $C_{21}H_{26}N_4O_2 \cdot H_2O$: C, 67.99; H, 7.20; N, 15.10. Found: C, 68.00; H, 7.25; N, 15.22.

Part B

A glass Parr vessel was charged with 10% palladium on carbon (0.14 g), methanol (50 mL) and 3-[2-ethyl-1-(2-hydroxy-2-methylpropyl)-1H-imidazo[4,5-c]quinolin-7-yl]-N,N-dimethylprop-2-enamide (1.20 g, 3.27 mmol). The vessel was evacuated and charged with hydrogen gas (40 psi, 2.8× 10$^5$ Pa). The reaction was shaken at 50° C. for approximately 19 hours. After cooling to ambient temperature, the reaction mixture was filtered and the filtrate concentrated to dryness to provide crude 3-[2-ethyl-1-(2-hydroxy-2-methylpropyl)-1H-imidazo[4,5-c]quinolin-7-yl]-N,N-dimethylpropanamide as a white semi-solid. MS (APCI) m/z 369 (M+H)$^+$.

Part C

To a stirring solution of crude 3-[2-ethyl-1-(2-hydroxy-2-methylpropyl)-1H-imidazo[4,5-c]quinolin-7-yl]-N,N-dimethylpropanamide, (1.2 g, 3.3 mmol) in dichloromethane (75 mL) was added 3-chloroperoxybenzoic acid (60% pure, 941 mg, 3.6 mmol). After 18 hours concentrated ammonium hydroxide (50 mL) was added and the reaction was vigorously stirred for 10 minutes. p-Toluenesulfonyl chloride (690 mg, 3.6 mmol) was then added in one portion and the reaction was stirred for one hour. The fractions were separated and the aqueous fraction was extracted with chloroform (3×50 mL). The combined organic fractions were concentrated under reduced pressure. Purification of the residue by chromatography using a HORIZON HPFC system (silica cartridge, eluting with 0-6% gradient of methanol in dichloromethane) followed by recrystallization from acetonitrile provided 651 mg of 3-[4-amino-2-ethyl-1-(2-hydroxy-2-methylpropyl)-1H-imidazo[4,5-c]quinolin-7-yl]-N,N-dimethylpropanamide as an off-white solid, mp 234-237° C.

$^1$H NMR (500 MHz, DMSO-$d_6$) δ 8.14 (d, J=8.5 Hz, 1H), 7.42 (d, J=1.6 Hz, 1H), 7.08 (dd, J=8.5, 1.7 Hz, 1H), 6.30 (br s, 2H), 4.76 (s, 1H), 4.51 (br s, 2H), 3.04 (q, J=7.4 Hz, 2H), 2.94 (s, 3H), 2.89 (m, 2H), 2.83 (s, 3H), 2.66 (m, 2H), 1.34 (t, J=7.4 Hz, 3H), 1.16 (br s, 6H);

$^{13}$C NMR (75 MHz, DMSO-$d_6$) δ 171.2, 155.5, 151.5, 144.9, 139.0, 133.5, 125.6, 125.1, 121.2, 120.8, 113.4, 70.6, 54.4, 36.5, 34.7, 33.9, 30.5, 27.5, 20.3, 12.0;

MS (ESI) m/z 384 (M+H)$^+$;

Anal. Calcd. for $C_{21}H_{29}N_5O_2$: C, 65.77; H, 7.62; N, 18.26. Found: C, 65.76; H, 7.67; N, 18.35.

Example 101

1-{3-[4-Amino-2-(2-methoxyethyl)-8-(3-morpholin-4-yl-3-oxo-propyl)-1H-imidazo[4,5-c]quinolin-1-yl]propyl}pyrrolidin-2-one

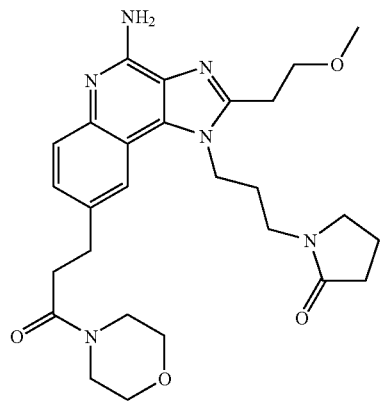 [SMILES: COCCc1nc2c(N)nc3ccc(CCC(=O)N4CCOCC4)cc3c2n1CCCN1CCCC1=O]

Part A

A thick walled glass tube, equipped with a stir bar, was charged with palladium (II) acetate (8 mg, 0.04 mmol), acetonitrile (50 mL), triethylamine (0.9 mL, 5.2 mmol), tri-o-tolylphosphine (30 mg, 0.10 mmol), 4-acryloylmorpholine (271 mg, 1.91 mmol) and 1-{3-[8-bromo-2-(2-methoxyethyl)-1H-imidazo[4,5-c]quinolin-1-yl]propyl}pyrrolidin-2-one (0.75 g, 1.7 mmol). The reaction mixture was purged with nitrogen and the tube was sealed and heated at 120° C. in an oil bath. The reaction was maintained at 120° C. for 15 hours and then cooled to ambient temperature. Upon cooling a precipitate formed that was dissolved by the addition of methanol and chloroform. The remaining insoluble material was removed by filtration through a 0.2 micron PTFE membrane filter. The filtrate was concentrated to dryness and purified by chromatography using a HORIZON HPFC system (silica cartridge, eluting with a 0-6% gradient of methanol in dichloromethane) to provide an off-white solid.

A glass Parr vessel was charged with 10% palladium on carbon (0.08 g), methanol (50 mL) and the solid. The vessel was evacuated and charged with hydrogen gas (40 psi, 2.8× $10^5$ Pa). The mixture was shaken at 50° C. for approximately 19 hours. After cooling to ambient temperature, the reaction mixture was filtered and the filtrate was concentrated to dryness to provide crude 1-{3-[2-(2-methoxyethyl)-8-(3-morpholin-4-yl-3-oxopropyl)-1H-imidazo[4,5-c]quinolin-1-yl]propyl}pyrrolidin-2-one as a white semi-solid. MS (ESI) m/z 494 (M+H)$^+$.

Part B

To a stirring solution of crude 1-{3-[2-(2-methoxyethyl)-8-(3-morpholin-4-yl-3-oxopropyl)-1H-imidazo[4,5-c]quinolin-1-yl]propyl}pyrrolidin-2-one, (0.85 g) in dichloromethane (75 mL) was added 3-chloroperoxybenzoic acid (60% pure, 500 mg, 1.91 mmol). After 18 hours concentrated ammonium hydroxide (50 mL) was added and the reaction was vigorously stirred for 10 minutes. p-Toluenesulfonyl chloride (690 mg, 3.60 mmol) was added in one portion and the mixture was stirred for one hour. The fractions were separated and aqueous fraction was extracted with chloroform (3×50 mL). The combined organic fractions were concentrated under reduced pressure. Purification by chromatography using a HORIZON HPFC system (silica cartridge, eluting with a gradient of 0-30% CMA in chloroform) followed by recrystallization from acetonitrile provided 75 mg of 1-{3-[4-amino-2-(2-methoxyethyl)-8-(3-morpholin-4-yl-3-oxopropyl)-1H-imidazo[4,5-c]quinolin-1-yl]propyl}pyrrolidin-2-one as a pale yellow solid, mp 168-170° C.

$^1$H NMR (300 MHz, DMSO-$d_6$) δ 7.84 (s, 1H), 7.53 (d, J=8.5 Hz, 1H), 7.32 (dd, J=8.5, 1.5 Hz, 1H), 6.35 (br s, 2H), 4.53 (m, 2H), 3.81 (t, J=6.6 Hz, 2H), 3.50-3.33 (m, 12H), 3.29 (s, 3H), 3.18 (t, J=6.7 Hz, 2H), 2.98 (m, 2H), 2.72 (m, 2H), 2.23 (m, 2H), 2.05-1.87 (m, 4H);

MS (APCI) m/z 509 (M+H)$^+$;

Anal. Calcd. for $C_{27}H_{36}N_6O_4$: C, 63.76; H, 7.13; N, 16.52. Found: C, 63.55; H, 6.87; N, 16.41.

Example 102

3-{4-Amino-2-(2-methoxyethyl)-1-[3-(2-oxo-pyrrolidin-1-yl)propyl]-1H-imidazo[4,5-c]quinolin-8-yl}-N,N-dimethylpropanamide

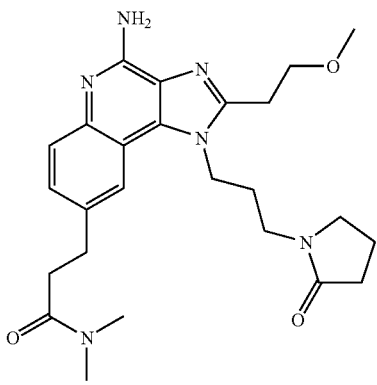 [SMILES: COCCc1nc2c(N)nc3ccc(CCC(=O)N(C)C)cc3c2n1CCCN1CCCC1=O]

Part A

A thick walled glass tube, equipped with a stir bar, was charged with palladium (II) acetate (8 mg, 0.04 mmol), acetonitrile (50 mL), triethylamine (0.9 mL, 5.22 mmol), tri-o-tolylphosphine (30 mg, 0.10 mmol), N,N-dimethylacrylamide (189 mg, 1.91 mmol) and 1-{3-[8-bromo-2-(2-methoxyethyl)-1H-imidazo[4,5-c]quinolin-1-yl]propyl}pyrrolidin-2-one (0.75 g, 1.7 mmol). The reaction mixture was purged with nitrogen and the tube was sealed and heated at 120° C. in an oil bath. The reaction was maintained at 120° C. for 18 hours and then cooled to ambient temperature. Upon cooling a precipitate formed that was dissolved by the addition of methanol and chloroform. The remaining insoluble material was removed by filtration through a 0.2 micron PTFE membrane filter. The filtrate was concentrated under reduced pressure and purified by chromatography using a HORIZON HPFC system (silica cartridge, eluting with a 0-7% gradient of methanol in dichloromethane) to provide 660 mg of 3-{2-(2-methoxyethyl)-1-[3-(2-oxopyrrolidin-1-yl)propyl]-1H-imidazo[4,5-c]quinolin-8-yl}-N,N-dimethylprop-2-enamide as an off-white solid.

Part B

A glass Parr vessel was charged with 10% palladium on carbon (0.07 g), methanol (50 mL) and 3-{2-(2-methoxyethyl)-1-[3-(2-oxopyrrolidin-1-yl)propyl]-1H-imidazo[4,5-c]quinolin-8-yl}-N,N-dimethylprop-2-enamide (0.66 g, 1.47 mmol). The vessel was evacuated and charged with hydrogen gas (40 psi, $2.8 \times 10^5$ Pa). The mixture was shaken at 50° C. for approximately 72 hours. The reaction mixture was cooled to ambient temperature and filtered. The filtrate was concentrated under reduced pressure to provide 720 mg of crude 3-{2-(2-methoxyethyl)-1-[3-(2-oxopyrrolidin-1-yl)propyl]-1H-imidazo[4,5-c]quinolin-8-yl}-N,N-dimethylpropanamide as a white semi-solid. MS (ESI) m/z 452 (M+H)$^+$.

Part C

To a stirring solution of 3-{2-(2-methoxyethyl)-1-[3-(2-oxopyrrolidin-1-yl)propyl]-1H-imidazo[4,5-c]quinolin-8-yl}-N,N-dimethylpropanamide, (0.66 g) in dichloromethane (75 mL) was added 3-chloroperoxybenzoic acid (60% pure, 423 mg, 1.62 mmol). After 18 hours concentrated ammonium hydroxide (50 mL) was added and the reaction was vigorously stirred for 10 minutes. p-Toluenesulfonyl chloride (311 mg, 1.62 mmol) was then added in one portion. The fractions were separated and aqueous fraction was extracted with chloroform (3×50 mL). The combined organic fractions were concentrated under reduced pressure and purified by chromatography using a HORIZON HPFC system (silica cartridge, eluting with a 0-30% gradient of CMA in chloroform). The resulting product was washed with a 1% aqueous sodium carbonate and then recrystallized from acetonitrile to provide 75 mg of 3-{4-amino-2-(2-methoxyethyl)-1-[3-(2-oxopyrrolidin-1-yl)propyl]-1H-imidazo[4,5-c]quinolin-8-yl}-N,N-dimethylpropanamide as an off-white solid, mp 184-186° C.

$^1$H NMR (300 MHz, DMSO-d$_6$) δ 7.84 (d, J=1.0 Hz, 1H), 7.53 (d, J=8.5 Hz, 1H), 7.32 (dd, J=8.5, 1.5 Hz, 1H), 6.35 (br s, 2H), 4.53 (m, 2H), 3.81 (t, J=6.7 Hz, 2H), 3.42-3.34 (m, 4H), 3.30 (s, 3H), 3.18 (t, J=6.7 Hz, 2H), 3.00-2.92 (m, 5H), 2.82 (s, 3H), 2.70 (m, 2H), 2.23 (m, 2H), 2.06-1.86 (m, 4H); MS (ESI) m/z 467 (M+H)$^+$;

Anal. Calcd for C$_{25}$H$_{34}$N$_6$O$_3$: C, 64.36; H, 7.35; N, 18.01. Found: C, 64.47; H, 7.33; N, 18.11.

Example 103

1-{4-Amino-2-ethyl-7-[3-oxo-3-(1,3-thiazolidin-3-yl)propyl]-1H-imidazo[4,5-c]quinolin-1-yl}-2-methylpropan-2-ol

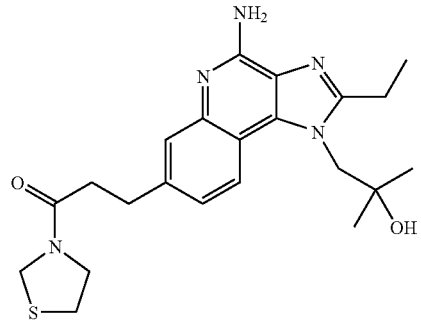 [SMILES: CCc1nc2c(N)nc3cc(CCC(=O)N4CCSC4)ccc3c2n1CC(C)(C)O]

Part A

A glass Parr vessel was charged with 10% palladium on carbon (1.0 g), methanol (75 mL), ethanol (75 mL) and methyl 3-[4-amino-2-ethyl-1-(2-hydroxy-2-methylpropyl)-1H-imidazo[4,5-c]quinolin-7-yl]prop-2-enoate (approximately 4 g, 10.8 mmol). The vessel was evacuated and charged with hydrogen gas (40 psi, $2.8 \times 10^5$ Pa). The mixture was shaken at 50° C. for approximately 18 hours. The reaction mixture was cooled to ambient temperature and filtered. The filtrate was concentrated under reduced pressure to provide 3.55 g of methyl 3-[4-amino-2-ethyl-1-(2-hydroxy-2-methylpropyl)-1H-imidazo[4,5-c]quinolin-7-yl]propanate as an off-white solid. MS (ESI) m/z 371 (M+H)$^+$.

Part B

Methyl 3-[4-amino-2-ethyl-1-(2-hydroxy-2-methylpropyl)-1H-imidazo[4,5-c]quinolin-7-yl]propanate was slurried in Claisen's alkali (50 mL) for 30 minutes and then concentrated to dryness. The resulting solid was dissolved in water (200 mL) and citric acid was slowly added until the pH reached 5-6. A fine off-white precipitate formed. Filtration provided 2.83 g of 3-[4-amino-2-ethyl-1-(2-hydroxy-2-methylpropyl)-1H-imidazo[4,5-c]quinolin-7-yl]propanoic acid as an off-white solid. MS (ESI) m/z 357 (M+H)$^+$.

Part C

A round bottom flask, equipped with a stir bar, was charged with 3-[4-amino-2-ethyl-1-(2-hydroxy-2-methylpropyl)-

1H-imidazo[4,5-c]quinolin-7-yl]propanoic acid (500 mg, 1.40 mmol), anhydrous pyridine (50 mL) and 1-hydroxybenzotriazole (379 mg, 2.80 mmol). After 30 minutes of stirring 1-(3-dimethylaminopropyl)-3-ethylcarbodiimide (537 mg, 2.80 mmol) was added to the reaction mixture in two portions. After 15 minutes, thiazolidine (250 mg, 2.80 mmol) was added in one portion. The pale yellow solution was stirred for 18 hours and then concentrated under reduced pressure. The resulting foam was dissolved in dichloromethane and washed with 1% aqueous sodium carbonate (2×15 mL). The combined aqueous fractions were extracted with chloroform (3×30 mL). The combined organic fractions were purified by chromatography using a HORIZON HPFC system (silica cartridge, eluting with a 0-25% gradient of CMA in chloroform) followed by recrystallization from acetonitrile to provide 516 mg of 1-{4-amino-2-ethyl-7-[3-oxo-3-(1,3-thiazolidin-3-yl)propyl]-1H-imidazo[4,5-c]quinolin-1-yl}-2-methylpropan-2-ol as a white solid, mp 210-212° C.

$^1$H NMR (300 MHz, DMSO-$d_6$) δ 8.15 (d, J=8.5 Hz, 1H), 7.44 (d, J=1.7 Hz, 1H), 7.09 (dd, J=8.5, 1.8 Hz, 1H), 6.35 (br s, 2H), 4.76 (s, 1H), 4.60-4.44 (m, 4H), 3.72-3.63 (m, 2H), 3.08-2.88 (m, 6H), 2.73 (m, 2H), 1.34 (t, J=7.5 Hz, 3H), 1.17 (br s, 6H);

MS (ESI) m/z 428 (M+H)$^+$;

Anal. Calcd. for $C_{22}H_{29}N_5O_2S$: C, 61.80; H, 6.84; N, 16.38. Found: C, 61.55; H, 6.92; N, 16.50.

Example 104

1-{4-Amino-2-(methoxymethyl)-7-[2-(methylsulfonyl)ethyl]-1H-imidazo[4,5-c]quinolin-1-yl}-2-methylpropan-2-ol

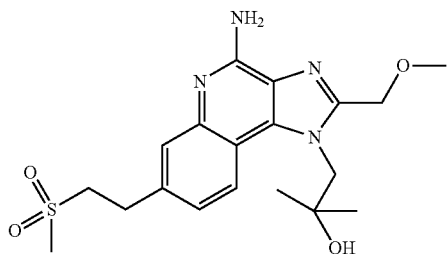 [SMILES: COCc1nc2c(N)nc3cc(CCS(C)(=O)=O)ccc3c2n1CC(C)(C)O]

Part A

A thick walled glass tube, equipped with a stir bar, was charged with palladium (II) acetate (12 mg, 0.05 mmol), acetonitrile (20 mL), N,N-dimethylformamide (15 mL) triethylamine (1.10 mL, 7.92 mmol), tri-o-tolylphosphine (48 mg, 0.16 mmol), methyl vinyl sulfone (294 mg, 2.77 mmol) and 1-[4-amino-7-bromo-2-(methoxymethyl)-1H-imidazo[4,5-c]quinolin-1-yl)-2-methylpropan-2-ol (1.00 g, 2.64 mmol). The reaction mixture was purged with nitrogen. The tube was sealed and heated at 120° C. in an oil bath. The reaction was maintained at 120° C. for 18 hours and then cooled to ambient temperature. The reaction was filtered and the filtrate was concentrated under reduced pressure. The resulting solid was partitioned between chloroform (100 mL) and aqueous 1% sodium carbonate (100 mL). The fractions were separated and the aqueous fraction was extracted with chloroform (5×50 mL). The combined organic fractions were concentrated and purified by chromatography using a HORIZON HPFC system (silica cartridge, eluting with 0-6% gradient of methanol in dichloromethane) to provide 750 mg of 1-{4-amino-2-(methoxymethyl)-7-[2-(methylsulfonyl)ethenyl]-1H-imidazo[4,5-c]quinolin-1-yl}-2-methylpropan-2-ol as a yellow semi-solid. MS (ESI) m/z 405 (M+H)$^+$.

Part B

A glass Parr vessel was charged with 10% palladium on carbon (200 mg), methanol (12.5 mL), ethanol (12.5 mL) and 1-{4-amino-2-(methoxymethyl)-7-[2-(methylsulfonyl)ethenyl]-1H-imidazo[4,5-c]quinolin-1-yl}-2-methylpropan-2-ol (750 mg, 1.85 mmol). The vessel was evacuated and charged with hydrogen gas (40 psi, 2.8×10$^5$ Pa). The mixture was shaken at 50° C. for approximately 18 hours and then cooled to ambient temperature. The reaction mixture was sequentially filtered through a 0.2 micron PTFE membrane filter, concentrated under reduced pressure, and purified by chromatography using a HORIZON HPFC system (silica cartridge, eluting with 0-7% gradient of methanol in dichloromethane) to provide 195 mg of 1-{4-amino-2-(methoxymethyl)-7-[2-(methylsulfonyl)ethyl]-1H-imidazo[4,5-c]quinolin-1-yl}-2-methylpropan-2-ol as a white solid, mp 210-212° C.

$^1$H NMR (500 MHz, DMSO-$d_6$) δ 8.22 (d, J=8.5 Hz, 1H), 7.51 (d, J=1.7 Hz, 1H), 7.15 (dd, J=8.5, 1.8 Hz, 1H), 6.63 (br s, 2H), 5.20-4.50 (m, 5H), 3.51 (m, 2H), 3.30 (s, 3H), 3.12 (m, 2H), 3.00 (s, 3H), 1.16 (br s, 6H);

$^{13}$C NMR (125 MHz, DMSO-$d_6$) δ 151.9, 150.3, 145.2, 136.4, 134.1, 125.8, 125.3, 121.5, 121.1, 113.6, 70.5, 66.5, 57.6, 54.7, 54.2, 40.1, 27.6, 27.5;

MS (APCI) m/z 407 (M+H)$^+$;

Anal. Calcd. for $C_{19}H_{26}N_4O_4S \cdot CH_3CN$: C, 56.35; H, 6.53; N, 15.56. Found: C, 56.10; H, 6.55; N, 15.56.

Example 105

1-{4-Amino-2-(hydroxymethyl)-7-[2-(methylsulfonyl)ethyl]-1H-imidazo[4,5-c]quinolin-1-yl}-2-methylpropan-2-ol

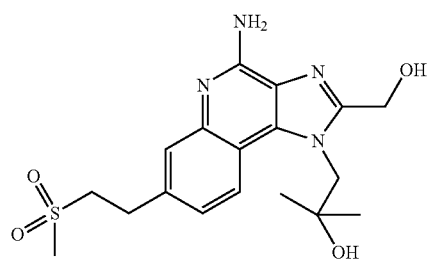 [SMILES: CC(C)(O)Cn1c(CO)nc2c(N)nc3cc(CCS(C)(=O)=O)ccc3c21]

A stirring solution of 1-{4-amino-2-(methoxymethyl)-7-[2-(methylsulfonyl)ethyl]-1H-imidazo[4,5-c]quinolin-1-yl}-2-methylpropan-2-ol (340 mg, 0.84 mmol) in dichloromethane (40 mL) was sealed with a septum and purged with nitrogen gas. The solution was cooled in an ice/water bath and a 1.0 M solution of boron tribromide in dichloromethane (4.2 mL) was added via syringe. The resulting mixture was stirred for 18 hours while warming to ambient temperature. The mixture was cooled back to 0° C. in an ice/water bath and the second portion of boron tribromide (1.0 M, 4.2 mL) was added. The reaction was stirred for 3 hours while warming to ambient temperature. Methanol (30 mL) was added and the mixture was concentrated to a purple foam. The foam was dissolved in 10% aqueous hydrochloric acid (30 ml) and washed with chloroform (2×25 mL). The aqueous fraction was neutralized by the slow addition of solid potassium carbonate until the pH reached 11. The aqueous fraction was extracted with chloroform (2×50 mL) and allowed to stand overnight. The resulting solid was recovered by filtration to provide 126 mg of 1-{4-amino-2-(hydroxymethyl)-7-[2-(methylsulfonyl)ethyl]-1H-imidazo[4,5-c]quinolin-1-yl}-2-methylpropan-2-ol as a white crystalline solid, mp 221-223° C.

$^1$H NMR (300 MHz, DMSO-$d_6$) δ 8.21 (d, J=8.5 Hz, 1H), 7.49 (d, J=1.6 Hz, 1H), 7.14 (dd, J=8.5, 1.8 Hz, 1H), 6.51 (br s, 2H), 5.48 (br s, 1H), 5.12-4.77 (m, 3H), 4.69 (br s, 2H), 3.51 (m, 2H), 3.11 (m, 2H), 3.00 (s, 3H), 1.17 (br s, 6H);

$^{13}$C NMR (125 MHz, DMSO-$d_6$) δ 153.6, 152.0, 145.3, 136.1, 133.9, 125.7, 125.4, 121.4, 121.0, 113.8, 70.5, 56.5, 54.6, 54.3, 40.1, 27.6, 27.5;

MS (APCI) m/z 393 (M+H)$^+$;

Anal. Calcd. for $C_{18}H_{24}N_4O_4S \cdot 0.75H_2O$: C, 53.25; H, 6.33; N, 13.80. Found: C, 53.05; H, 6.51; N, 13.62.

Example 106

1-[4-Amino-2-(methoxymethyl)-7-(3-morpholin-4-yl-3-oxopropyl)-1H-imidazo[4,5-c]quinolin-1-yl]-2-methylpropan-2-ol

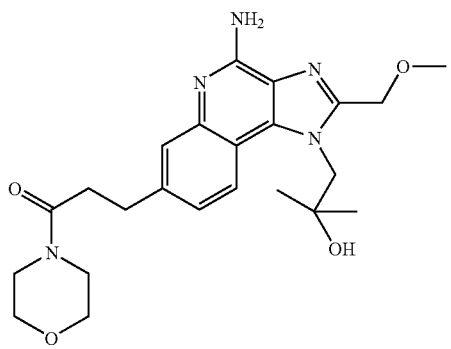 [SMILES: COCc1nc2c(N)nc3cc(CCC(=O)N4CCOCC4)ccc3c2n1CC(C)(C)O]

Part A

A thick walled glass tube, equipped with a stir bar, was charged with palladium (II) acetate (150 mg, 0.66 mmol), acetonitrile (50 mL), N,N-dimethylformamide (20 mL) triethylamine (5.50 mL, 39.54 mmol), tri-o-tolylphosphine (600 mg, 1.98 mmol), methyl acrylate (294 mg, 2.77 mmol) and 1-[4-amino-7-bromo-2-(methoxymethyl)-1H-imidazo[4,5-c]quinolin-1-yl]-2-methylpropan-2-ol (5.00 g, 13.2 mmol). The reaction mixture was purged with nitrogen and the tube was sealed and heated at 120° C. for 18 hours. The reaction was cooled to ambient temperature and then concentrated to dryness under reduced pressure. The resulting solid was partitioned between chloroform (300 mL) and aqueous 1% sodium carbonate (100 mL). The fractions were separated and the aqueous fraction was extracted with chloroform (4×100 mL). The combined organic fractions were concentrated and purified by chromatography using a HORIZON HPFC system (silica cartridge, eluting with 0-8% gradient of methanol in dichloromethane) to provide a yellow semi-solid.

The intermediate product was added to a Parr vessel with 10% palladium on carbon (700 mg), methanol (12.5 mL), and ethanol (12.5 mL). The vessel was evacuated and charged with hydrogen gas (40 psi, 2.8×10$^5$ Pa). The mixture was shaken at 50° C. for approximately 18 hours followed by cooling to ambient temperature. The mixture was filtered through a 0.2 micron PTFE membrane filter and the filtrate was concentrated under reduced pressure to provide crude methyl 3-[4-amino-1-(2-hydroxy-2-methylpropyl)-2-(methoxymethyl)-1H-imidazo[4,5-c]quinolin-7-yl]propanoate as a white solid. MS (APCI) m/z 387 (M+H)$^+$.

Part B

Methyl 3-[4-amino-1-(2-hydroxy-2-methylpropyl)-2-(methoxymethyl)-1H-imidazo[4,5-c]quinolin-7-yl]propanoate was slurried in Claisen's alkali (50 mL) for 30 minutes and then concentrated to dryness. The resulting solid was dissolved in water (200 mL) and citric acid was slowly added until the pH reached 5-6. A fine off-white precipitate formed. Filtration provided 7.58 g of wet 3-[4-amino-1-(2-hydroxy-2-methylpropyl)-2-(methoxymethyl)-1H-imidazo[4,5-c]quinolin-7-yl]propanoic acid as a white solid. MS (APCI) m/z 373 (M+H)$^+$.

Part C

3-[4-Amino-1-(2-hydroxy-2-methylpropyl)-2-(methoxymethyl)-1H-imidazo[4,5-c]quinolin-7-yl]propanoic acid (1.25 g, 3.30 mmol), anhydrous pyridine (75 mL) and 1-hydroxybenzotriazole (892 mg, 6.60 mmol) were combined and the reaction was stirred for 30 minutes. 1-(3-Dimethylaminopropyl)-3-ethylcarbodiimide (1.27 g, 6.60 mmol) was added and the reaction mixture was stirred for an additional 15 minutes. Morpholine (581 mg, 6.60 mmol) was added in one portion. After stirring for 18 hours the solution was concentrated under reduced pressure. The resulting foam was dissolved in chloroform (50 mL) and washed with 1% aqueous sodium carbonate (2×15 mL). The combined aqueous washes were extracted with chloroform. The combined organic fractions were concentrated under reduced pressure and then purified by chromatography using a HORIZON HPFC system (silica cartridge, eluting with a CMA:chloroform gradient; 0-20% CMA over 1500 mL, followed by 20-25% CMA over 500 mL, and finally 25-30% CMA over 500 mL). A final recrystallization from acetonitrile provided 913 mg of 3-[4-amino-2-(methoxymethyl)-7-(3-morpholin-4-yl-3-oxopropyl)-1H-imidazo[4,5-c]quinolin-1-yl]-2-methylpropan-2-ol as an off-white solid, mp 215-217° C.

$^1$H NMR (500 MHz, DMSO-$d_6$) δ 8.15 (d, J=8.5 Hz, 1H), 7.45 (d, J=1.6 Hz, 1H), 7.11 (dd, J=8.5, 1.8 Hz, 1H), 6.55 (br s, 2H), 5.15-4.50 (br s, 2H), 4.89 (s, 1H), 4.63 (br s, 2H), 3.51-3.39 (m, 8H), 3.30 (s, 3H), 2.92 (t, J=7.6 Hz, 2H), 2.69 (t, J=7.6 Hz, 2H), 1.16 (br s, 6H);

MS (ESI) m/z 442 (M+H)$^+$;

Anal. Calcd. for $C_{23}H_{31}N_5O_4$: C, 62.57; H, 7.08; N, 15.86. Found: C, 62.42; H, 6.90; N, 15.92.

Example 107

1-[4-Amino-7-[3-(1,1-dioxidothiomorpholin-4-yl)-3-oxopropyl]-2-(methoxymethyl)-1H-imidazo[4,5-c]quinolin-1-yl]-2-methylpropan-2-ol

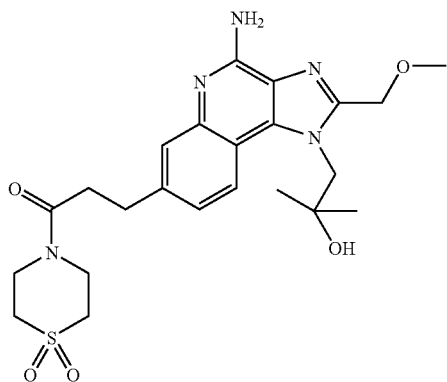 [SMILES: COCc1nc2c(N)nc3cc(CCC(=O)N4CCS(=O)(=O)CC4)ccc3c2n1CC(C)(C)O]

3-[4-Amino-1-(2-hydroxy-2-methylpropyl)-2-(methoxymethyl)-1H-imidazo[4,5-c]quinolin-7-yl]propanoic acid (1.25 g, 3.30 mmol), anhydrous pyridine (75 mL) and 1-hydroxybenzotriazole (892 mg, 6.60 mmol) were combined and the reaction was stirred for 30 minutes. 1-(3-Dimethylaminopropyl)-3-ethylcarbodiimide (1.27 g, 6.60 mmol) was added and the reaction mixture was stirred for an additional 15 minutes. Thiomorpholine 1,1-dioxide (895 mg, 6.60 mmol) was added in one portion. After stirring for 18 hours the solution was concentrated under reduced pressure and the residual foam was dissolved in chloroform (50 mL) and washed with 1% aqueous sodium carbonate (2×25 mL). The combined aqueous washes were extracted with chloroform. The combined organic fractions were concentrated under reduced pressure and purified by chromatography using a HORIZON HPFC system (silica cartridge, eluting with a CMA:chloroform gradient; 0-25% CMA over 1500 mL, followed by 25-30% CMA over 500 mL, finally 30% CMA over 1000 mL). The resulting material was subjected to a second chromatography purification using a HORIZON HPFC system (silica cartridge, eluting with CMA:chloroform gradient; 0-25% CMA over 1500 mL, followed by 25-30% CMA over 500 mL) followed by recrystallization from acetonitrile to provide 1.07 g of 1-[4-amino-7-[3-(1,1-dioxidothiomorpholin-4-yl)-3-oxopropyl]-2-(methoxymethyl)-1H-imidazo[4,5-c]quinolin-1-yl]-2-methylpropan-2-ol as a white solid, mp 190-192° C.

$^1$H NMR (500 MHz, DMSO-$d_6$) δ 8.16 (d, J=8.5 Hz, 1H), 7.46 (d, J=1.4 Hz, 1H), 7.11 (dd, J=8.5, 1.6 Hz, 1H), 6.53 (br s, 2H), 5.14-4.50 (br s, 2H), 4.88 (s, 1H), 4.64 (br s, 2H), 3.90-3.83 (m, 4H), 3.30 (s, 3H), 3.13 (m, 2H), 3.07 (m, 2H), 2.93 (t, J=7.5 Hz, 2H), 2.81 (t, J=7.5 Hz, 2H), 1.16 (br s, 6H);

MS (ESI) m/z 490 (M+H)$^+$;

Anal. Calcd. for $C_{23}H_{31}N_5O_5S$: C, 56.43; H, 6.38; N, 14.30. Found: C, 56.44; H, 6.33; N, 14.29.

Example 108

3-[4-Amino-1-(2-hydroxy-2-methylpropyl)-2-(methoxymethyl)-1H-imidazo[4,5-c]quinolin-7-yl]-N,N-dimethylpropanamide

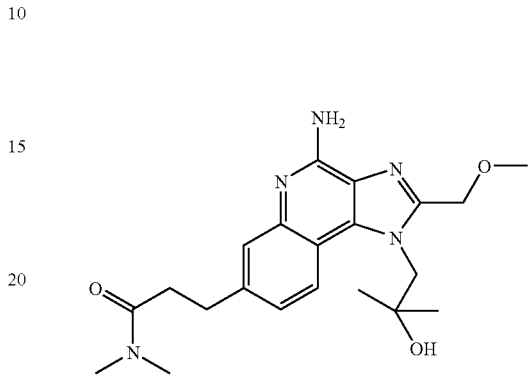

3-[4-Amino-1-(2-hydroxy-2-methylpropyl)-2-(methoxymethyl)-1H-imidazo[4,5-c]quinolin-7-yl]propanoic acid (1.25 g, 3.30 mmol), anhydrous pyridine (75 mL) and 1-hydroxybenzotriazole (892 mg, 6.60 mmol) were combined and the reaction was stirred for 30 minutes. 1-(3-Dimethylaminopropyl)-3-ethylcarbodiimide (1.27 g, 6.60 mmol) was added and the reaction mixture was stirred for an additional 15 minutes. Dimethylamine hydrochloride (540 mg, 6.60 mmol) was added in one portion and the reaction was stirred for an additional 4 hours. The solution was concentrated under reduced pressure and the resulting oil was dissolved in chloroform (50 mL) and washed with 1% aqueous sodium carbonate (3×25 mL). The combined aqueous washes were extracted with chloroform. The combined organic fractions were purified by chromatography using a HORIZON HPFC system (silica cartridge, eluting with a CMA:chloroform gradient; 0-25% CMA over 1500 mL, followed by 25-30% CMA over 1000 mL) followed by recrystallization from acetonitrile to provide 931 mg of 3-[4-amino-1-(2-hydroxy-2-methylpropyl)-2-(methoxymethyl)-1H-imidazo[4,5-c]quinolin-7-yl]-N,N-dimethylpropanamide as a white solid, mp 142-145° C.

$^1$H NMR (500 MHz, DMSO-$d_6$) δ 8.16 (d, J=8.5 Hz, 1H), 7.45 (d, J=1.7 Hz, 1H), 7.11 (dd, J=8.5, 1.7 Hz, 1H), 6.56 (br s, 2H), 5.11-4.52 (br s, 2H), 4.89 (s, 1H), 4.64 (br s, 2H), 3.30 (s, 3H), 2.94 (s, 3H), 2.91 (t, J=7.7 Hz, 2H), 2.83 (s, 3H), 2.67 (t, J=7.7 Hz, 2H), 1.17 (br s, 6H);

$^{13}$C NMR (125 MHz, DMSO-$d_6$) δ 171.2, 151.9, 150.0, 145.4, 139.7, 134.1, 125.6, 125.1, 121.4, 121.0, 113.2, 70.5, 66.6, 57.5, 54.7, 36.5, 34.7, 33.9, 30.5, 27.5;

MS (APCI) m/z 400 (M+H)$^+$;

Anal. Calcd. for $C_{21}H_{29}N_5O_3 \cdot 0.5H_2O$: C, 61.75; H, 7.40; N, 17.14. Found: C, 61.74; H, 7.47; N, 17.25.

Example 109

N-{3-[4-Amino-1-(2-hydroxy-2-methylpropyl)-2-(methoxymethyl)-1H-imidazo[4,5-c]quinolin-7-yl]propyl}methanesulfonamide

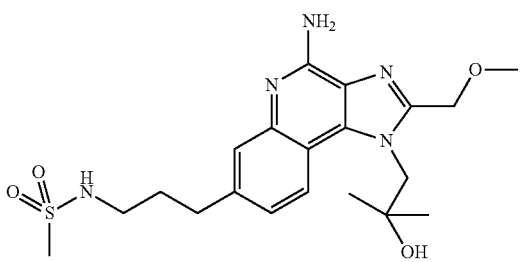 [SMILES: COCc1nc2c(N)nc3cc(CCCNS(C)(=O)=O)ccc3c2n1CC(C)(C)O]

Part A

A thick walled glass tube, equipped with a stir bar, was charged with palladium (II) acetate (225 mg, 1.00 mmol), acetonitrile (50 mL), N,N-dimethylformamide (20 mL) triethylamine (8.25 mL, 59.3 mmol), tri-o-tolylphosphine (900 mg, 2.97 mmol), acrylonitrile (770 mg, 21.8 mmol) and 1-[4-amino-7-bromo-2-(methoxymethyl)-1H-imidazo[4,5-c]quinolin-1-yl)-2-methylpropan-2-ol (7.50 g, 19.8 mmol). The reaction mixture was purged with nitrogen and the tube was sealed and heated at 120° C. in an oil bath for 18 hours. The reaction was cooled to ambient temperature and then concentrated under reduced pressure. The resulting solid was partitioned between chloroform (300 mL) and aqueous 1% sodium carbonate (100 mL). The fractions were separated and the aqueous fraction was extracted with chloroform (4×100 mL). The combined organic fractions were concentrated under reduced pressure and purified by chromatography using a HORIZON HPFC system (silica cartridge, eluting with 0-7% gradient of methanol in dichloromethane) to provide 5.2 g of 3-[4-amino-1-(2-hydroxy-2-methylpropyl)-2-(methoxymethyl)-1H-imidazo[4,5-c]quinolin-7-yl]prop-2-enenitrile as an off-white solid.

MS (ESI) m/z 352 (M+H)$^+$.

Part B

A glass Parr vessel was charged with 10% palladium on carbon (1.0 g), methanol (200 mL), trifluoroacetic acid (5.4 mL, 72.5 mmol) and 3-[4-amino-1-(2-hydroxy-2-methylpropyl)-2-(methoxymethyl)-1H-imidazo[4,5-c]quinolin-7-yl]prop-2-enenitrile (5.1 g, 14.5 mmol). The vessel was evacuated and charged with hydrogen gas (40 psi, 2.8×10$^5$ Pa). The mixture was shaken for approximately 18 hours and then filtered through a 0.2 micron PTFE membrane filter and concentrated under reduced pressure. The resulting yellow oil was dissolved in 10% aqueous hydrochloric acid (100 mL) and stirred for 30 minutes. The solution was made basic (pH 10) by the slow addition of potassium carbonate. Potassium hydroxide was added until pH equaled 13. The solution was then concentrated under reduced pressure. The resulting off-white solid was slurried in hot methanol (300 mL) and filtered. The hot methanol slurry procedure was repeated. The combined filtrates were concentrated and purified by chromatography using a HORIZON HPFC system (silica cartridge, eluting with a CMA:chloroform gradient; 0-30% CMA) to provide 4.7 g of 1-[4-amino-7-(3-aminopropyl)-2-(methoxymethyl)-1H-imidazo[4,5-c]quinolin-1-yl]-2-methylpropan-2-ol as an off-white foam. MS (APCI) m/z 358 (M+H)$^+$.

Part C

To a solution of 1-[4-amino-7-(3-aminopropyl)-2-(methoxymethyl)-1H-imidazo[4,5-c]quinolin-1-yl]-2-methylpropan-2-ol (1.25 g, 3.50 mmol) and triethylamine (2.4 mL, 17.5 mmol) cooled to 0° C. in a ice water bath was added methanesulfonic anhydride (732 mg, 4.20 mmol). The solution was stirred for approximately 18 hours while warming to ambient temperature. The solution was concentrated under reduced pressure and partitioned between 1% aqueous sodium carbonate (125 mL) and chloroform (100 mL). The aqueous fraction was extracted with chloroform until no product was present in the aqueous layer. The combined organic fractions were concentrated and purified by chromatography using a HORIZON HPFC system (silica cartridge, eluting with a CMA:chloroform gradient; 0-25% CMA over 1500 mL, followed by 25-30% CMA over 1000 mL). A final recrystallization from acetonitrile provided 855 mg of N-{3[4-amino-1-(2-hydroxy-2-methylpropyl)-2-(methoxymethyl)-1H-imidazo[4,5-c]quinolin-7-yl]propyl}methanesulfonamide as a white solid, mp 205-207° C.

$^1$H NMR (500 MHz, DMSO-d$_6$) δ 8.17 (d, J=8.5 Hz, 1H), 7.42 (d, J=1.7 Hz, 1H), 7.09 (dd, J=8.5, 1.7 Hz, 1H), 7.05 (t, J=5.6 Hz, 1H), 6.52 (br s, 2H), 5.11-4.57 (br s, 2H), 4.88 (s, 1H), 4.64 (br s, 2H), 3.30 (s, 3H), 2.99 m, 2H), 2.89 (s, 3H), 2.72 (t, J=7.6 Hz, 2H), 1.83 (m, 2H), 1.17 (br s, 6H);

MS (APCI) m/z 435 (M+H)$^+$;

Anal. Calcd. for C$_{20}$H$_{29}$N$_5$O$_4$S.0.25H$_2$O: C, 54.59; H, 6.75; N, 15.91. Found: C, 54.47; H, 6.73; N, 16.20.

Example 110

3-[4-Amino-1-(2-hydroxy-2-methylpropyl)-2-(methoxymethyl)-1H-imidazo[4,5-c]quinolin-7-yl]propanenitrile

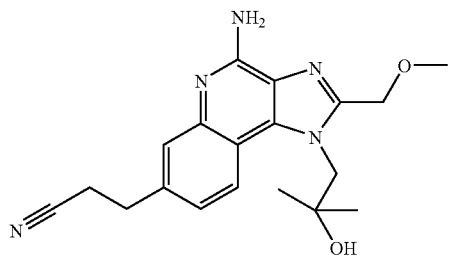 [SMILES: COCc1nc2c(N)nc3cc(CCC#N)ccc3c2n1CC(C)(C)O]

A glass Parr vessel was charged with 10% palladium on carbon catalyst (200 mg), methanol (100 mL), and 3-[4-amino-1-(2-hydroxy-2-methylpropyl)-2-(methoxymethyl)-1H-imidazo[4,5-c]quinolin-7-yl]prop-2-enenitrile (925 mg, 2.63 mmol). The vessel was evacuated and charged with hydrogen gas (40 psi, 2.8×10$^5$ Pa). The mixture was shaken at 50° C. for approximately 18 hours. The reaction mixture was cooled to ambient temperature and then filtered through a 0.2 micron PTFE membrane filter. The filtrate was concentrated under reduced pressure and purified by chromatography using a HORIZON HPFC system (silica cartridge, eluting with a CMA:chloroform gradient; 0-25% CMA over 1500 mL, followed by 25-30% CMA over 500 mL) to provide 760 mg of 3-[4-amino-1-(2-hydroxy-2-methylpropyl)-2-(methoxymethyl)-1H-imidazo[4,5-c]quinolin-7-yl]propanenitrile as a white solid, mp 191-193° C.

$^1$H NMR (500 MHz, DMSO-$d_6$) δ 8.22 (d, J=8.5 Hz, 1H), 7.52 (d, J=1.7 Hz, 1H), 7.14 (dd, J=8.5, 1.7 Hz, 1H), 6.62 (br s, 2H), 5.11-4.57 (br s, 2H), 4.89 (s, 1H), 4.65 (br s, 2H), 3.30 (s, 3H), 2.99 (t, J=7.0 Hz, 2H), 2.89 (t, J=7.0 Hz, 2H), 1.17 (br s, 6H);

$^{13}$C NMR (125 MHz, DMSO-$d_6$) δ 152.0, 150.2, 145.3, 137.0, 134.0, 125.8, 125.4, 121.4, 121.0, 120.3, 113.8, 70.5, 66.6, 57.5, 54.7, 30.4, 27.5, 17.9;

MS (APCI) m/z 354 (M+H)$^+$;

Anal. Calcd. for $C_{19}H_{23}N_5O_2 \cdot 1.0\ CH_3CN$: C, 63.94; H, 6.64; N, 21.31. Found: C, 63.66; H, 6.79; N, 21.12.

Example 111

3-[4-Amino-2-(hydroxymethyl)-1-(2-hydroxy-2-methylpropyl)-1H-imidazo[4,5-c]quinolin-7-yl]-N,N-dimethylpropanamide

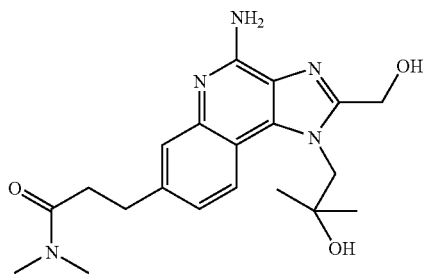 [SMILES: CN(C)C(=O)CCc1ccc2c(c1)nc(N)c1nc(CO)n(CC(C)(C)O)c12]

A stirring solution of 3-[4-amino-1-(2-hydroxy-2-methylpropyl)-2-(methoxymethyl)-1H-imidazo[4,5-c]quinolin-7-yl]-N,N-dimethylpropanamide (523 mg, 1.31 mmol) in dichloromethane (125 mL) was sealed with a septum and purged with nitrogen gas. The solution was cooled in an ice/water bath and a 1.0 M solution of boron tribromide in dichloromethane (6.6 mL) was added via syringe. The resulting mixture was stirred for 18 hours while warming to ambient temperature. Methanol (50 mL) was added and the mixture was concentrated under reduced pressure. The resulting solid was dissolved in a 2.0 M solution of ammonia in methanol (75 mL) and the solution was concentrated under reduced pressure to yield a solid. This step was repeated two more times with silica gel (1 tbsp) being added prior to the final concentration. The sample absorbed on silica was purified by chromatography using a HORIZON HPFC system (silica cartridge, eluting with a CMA:chloroform gradient; 0-25% CMA over 1200 mL, followed by 25-40% CMA over 1300 mL) to provide 298 mg of 3-[4-Amino-2-(hydroxymethyl)-1-(2-hydroxy-2-methylpropyl)-1H-imidazo[4,5-c]quinolin-7-yl]-N,N-dimethylpropanamide as a white crystalline solid, mp 228-230° C.

$^1$H NMR (300 MHz, DMSO-$d_6$) δ 8.15 (d, J=8.5 Hz, 1H), 7.42 (d, J=1.6 Hz, 1H), 7.10 (dd, J=8.5, 1.7 Hz, 1H), 6.43 (br s, 2H), 5.47 (t, J=5.9 Hz, 1H), 4.95 (s, 1H), 4.86 (br s, 2H), 4.68 (br s, 2H), 2.94 (s, 3H), 2.90 (m, 2H), 2.83 (s, 3H), 2.67 (m, 2H), 1.17 (br s, 6H);

MS (ESI) m/z 386 (M+H)$^+$;

Anal. Calcd. for $C_{20}H_{27}N_5O_3 \cdot 0.5H_2O$: C, 60.90; H, 7.16; N, 17.75. Found: C, 60.93; H, 7.42; N, 17.85.

Example 112

1-[4-Amino-2-(hydroxymethyl)-7-(3-morpholin-4-yl-3-oxopropyl)-1H-imidazo[4,5-c]quinolin-1-yl]-2-methylpropan-2-ol

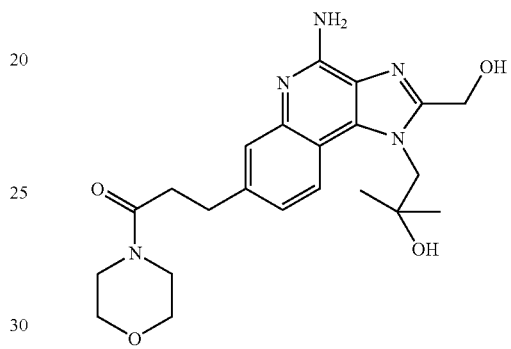

A stirring solution of 1-[4-amino-2-(methoxymethyl)-7-(3-morpholin-4-yl-3-oxopropyl)-1H-imidazo[4,5-c]quinolin-1-yl]-2-methylpropan-2-ol (460 mg, 1.04 mmol) in chloroform (120 mL) was sealed with a septum and purged with nitrogen gas. The solution was cooled in an ice water bath and a solution of 1.0 M boron tribromide in dichloromethane (6.6 mL) was added via syringe. The reaction was stirred for 18 hours while warming to ambient temperature. In order to complete the reaction three additional portions (3 mL, 10 mL, and 10 mL) of 1.0 M boron tribromide in dichloromethane were added at approximately 18 hour intervals. Methanol (75 mL) was added. The reaction was concentrated to a dark purple liquid and then stirred in 10% aqueous hydrochloric acid (100 mL) for three days. Solid sodium carbonate was slowly added until the pH equaled 10. The solution was concentrated to a white solid. The solid was washed with methanol (2×100 mL) and filtered. The filtrate was absorbed onto silica (2 tbsp) and then purified by chromatography using a HORIZON HPFC system (silica cartridge, eluting with a CMA:chloroform gradient; 0-20% CMA over 1400 mL, followed by 20-30% CMA over 1600 mL) to provide 48 mg of 1-[4-amino-2-(hydroxymethyl)-7-(3-morpholin-4-yl-3-oxopropyl)-1H-imidazo[4,5-c]quinolin-1-yl]-2-methylpropan-2-ol as a white crystalline solid, mp 223-225° C.

$^1$H NMR (500 MHz, DMSO-$d_6$) δ 8.15 (d, J=8.5 Hz, 1H), 7.43 (d, J=1.3 Hz, 1H), 7.10 (dd, J=8.5, 1.5 Hz, 1H), 6.44 (br s, 2H), 5.47 (t, J=5.8 Hz, 1H), 4.96 (s, 1H), 4.87 (br s, 2H), 4.68 (br s, 2H), 3.52-3.48 (m, 2H), 3.45-3.38 (m, 6H), 2.92 (t, J=7.6 Hz, 2H), 2.69 (t, J=7.7 Hz, 2H), 1.17 (br s, 6H);

MS (ESI) m/z 428 (M+H)$^+$;

Anal. Calcd. for $C_{22}H_{29}N_5O_4$: C, 61.81; H, 6.84; N, 16.38. Found: C, 61.62; H, 6.77; N, 16.26.

Example 113

3-[4-Amino-1-(2-hydroxy-2-methylpropyl)-2-(methoxymethyl)-1H-imidazo[4,5-c]quinolin-7-yl]propanamide

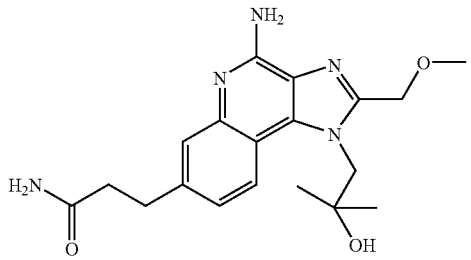 [SMILES: COCc1nc2c(N)nc3cc(CCC(N)=O)ccc3c2n1CC(C)(C)O]

3-[4-Amino-1-(2-hydroxy-2-methylpropyl)-2-(methoxymethyl)-1H-imidazo[4,5-c]quinolin-7-yl]propanenitrile (430 mg, 1.30 mmol) in methanol (75 mL) was heated to 50° C. in an oil bath. Aqueous 10% sodium hydroxide (0.33 mmol) and 30% aqueous hydrogen peroxide (516 mg, 4.55 mmol) were added and the reaction was stirred for 18 hours. The mixture was cooled to ambient temperature and then concentrated under reduced pressure. The resulting solid was slurried in water (70 mL). The aqueous mixture was washed with chloroform (35 mL), concentrated to a wet solid, slurried in methanol (100 mL) and filtered. The filtrate was absorbed onto silica (1 tbsp) and purified by chromatography using a HORIZON HPFC system (silica cartridge, eluting with CMA:chloroform gradient; 0-20% CMA over 1400 mL, followed by 20-25% CMA over 1200 mL). The material was further purified by chromatography using a HORIZON HPFC system (silica cartridge, eluting with a 0-9% gradient of methanol in dichloromethane) to provide 102 mg of 3-[4-amino-1-(2-hydroxy-2-methylpropyl)-2-(methoxymethyl)-1H-imidazo[4,5-c]quinolin-7-yl]propanamide as a white solid, mp 228-230° C.

$^1$H NMR (500 MHz, DMSO-$d_6$) δ 8.15 (d, J=8.4 Hz, 1H), 7.43 (d, J=1.3 Hz, 1H), 7.32 (s, 1H), 7.07 (dd, J=8.4, 1.4 Hz, 1H), 6.77 (s, 1H), 6.49 (br s, 2H), 5.11-4.63 (br s, 2H), 4.87 (s, 1H), 4.63 (br s, 2H), 3.30 (s, 3H), 2.90 (t, J=7.7 Hz, 2H), 2.43 (t, J=7.7 Hz, 2H), 1.16 (br s, 6H);

MS (ESI) m/z 372 (M+H)$^+$;

Anal. Calcd. for $C_{19}H_{25}N_5O_3$: C, 61.44; H, 6.78; N, 18.85. Found: C, 61.27; H, 6.64; N, 18.74.

Example 114

1-[4-Amino-7-[3-(1,1-dioxidothiomorpholin-4-yl)-3-oxopropyl]-2-(hydroxymethyl)-1H-imidazo[4,5-c]quinolin-1-yl]-2-methylpropan-2-ol

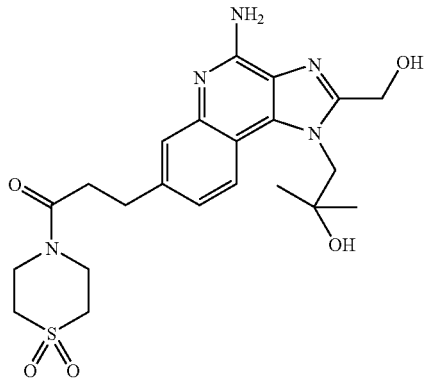 [SMILES: CC(C)(O)Cn1c(CO)nc2c(N)nc3cc(CCC(=O)N4CCS(=O)(=O)CC4)ccc3c21]

To a stirring solution of 1-[4-amino-7-[3-(1,1-dioxidothiomorpholin-4-yl)-3-oxopropyl]-2-(methoxymethyl)-1H-imidazo[4,5-c]quinolin-1-yl]-2-methylpropan-2-ol (655 mg, 1.34 mmol) in dichloromethane (125 mL), sealed with a septum and purged with nitrogen gas, was added a 1.0 M solution of boron tribromide in dichloromethane (6.6 mL) via syringe. The resulting mixture was stirred for 18 hours. Methanol (50 mL) was added and the solution was concentrated under reduced pressure. The resulting solid was dissolved in a 2.0 M solution of ammonia in methanol (75 mL) and then concentrated under reduced pressure to a solid. This step was repeated two more times with silica gel (1 tbsp) being added prior to the final concentration. The crude product absorbed on silica was purified by chromatography using a HORIZON HPFC system (silica cartridge, eluting with a CMA:chloroform gradient; 0-25% CMA over 1200 mL, followed by 25-40% CMA over 1300 mL). The recovered solid was washed with 1% aqueous sodium carbonate and filtered to provide 325 mg of 1-[4-amino-7-[3-(1,1-dioxidothiomorpholin-4-yl)-3-oxopropyl]-2-(hydroxymethyl)-1H-imidazo[4,5-c]quinolin-1-yl]-2-methylpropan-2-ol as an off white semi-solid.

$^1$H NMR (500 MHz, DMSO-$d_6$) δ 8.16 (d, J=8.5 Hz, 1H), 7.45 (d, J=1.4 Hz, 1H), 7.11 (dd, J=8.5, 1.6 Hz, 1H), 6.46 (br s, 2H), 5.48 (br s, 1H), 4.97 (s, 1H), 4.87 (br s, 2H), 4.68 (br s, 2H), 3.91-3.82 (m, 4H), 3.13 (m, 2H), 3.07 (m, 2H), 2.93 (t, J=7.7 Hz, 2H), 2.81 (t, J=7.7 Hz, 2H), 1.17 (br s, 6H);

MS (ESI) m/z 476 (M+H)$^+$;

Anal. Calcd. for $C_{22}H_{29}N_5O_5S \cdot 0.5H_2O$: C, 54.23; H, 6.24; N, 14.45. Found: C, 54.17; H, 6.14; N, 14.68.

Example 115

N-{3-[4-Amino-1-(2-hydroxy-2-methylpropyl)-2-(methoxymethyl)-1H-imidazo[4,5-c]quinolin-7-yl]propyl}acetamide

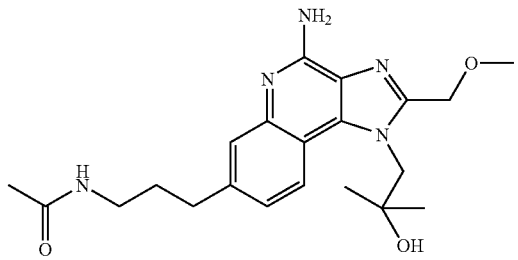 [SMILES: COCc1nc2c(N)nc3cc(CCCNC(C)=O)ccc3c2n1CC(C)(C)O]

A solution of 1-[4-amino-7-(3-aminopropyl)-2-(methoxymethyl)-1H-imidazo[4,5-c]quinolin-1-yl]-2-methylpropan-2-ol (1.25 g, 3.50 mmol) in triethylamine (2.4 mL, 17.5 mmol) was cooled to 0° C. in an ice water bath and acetic anhydride (393 mg, 3.85 mmol) was added. The solution was stirred for approximately 18 hours while warming to ambient temperature. The solution was concentrated under reduced pressure and the residue was partitioned between 1% aqueous sodium carbonate (125 mL) and chloroform (50 mL). Successive chloroform extractions were performed until no product was present in the aqueous layer. The combined organic fractions were concentrated under reduced pressure and dissolved in methanol (100 mL). To this solution was added solid potassium carbonate (3 tsp) and the reaction was heated to reflux temperature for 2 hours. After cooling to ambient temperature, the mixture was filtered, concentrated and partitioned between water (50 mL) and chloroform (50 mL).

Crude product was extracted from the aqueous fraction through successive chloroform extractions until no product remained in the aqueous layer. The combined organic extracts were concentrated and purified by chromatography using a HORIZON HPFC system (silica cartridge, eluting with a CMA:chloroform gradient; 0-30% CMA over 1500 mL, followed by 30% CMA over 1000 mL) to provide 578 mg of N-{3-[4-amino-1-(2-hydroxy-2-methylpropyl)-2-(methoxymethyl)-1H-imidazo[4,5-c]quinolin-7-yl]propyl}acetamide as a white semi-solid.

$^1$H NMR (500 MHz, DMSO-$d_6$) δ 8.17 (d, J=8.5 Hz, 1H), 7.86 (t, J=5.1 Hz, 1H), 7.42 (d, J=1.5 Hz, 1H), 7.07 (dd, J=8.4, 1.6 Hz, 1H), 6.53 (br s, 2H), 5.08-4.57 (br s, 2H), 4.88 (s, 1H), 4.64 (br s, 2H), 3.30 (s, 3H), 3.08 (m, 2H), 2.68 (t, J=7.6 Hz, 2H), 1.81 (s, 3H), 1.77 (m, 2H), 1.17 (br s, 6H);

MS (APCI) m/z 400 (M+H)$^+$;

Anal. Calcd. for $C_{21}H_{29}N_5O_3 \cdot 0.5H_2O$: C, 61.64; H, 7.41; N, 17.11. Found: C, 61.63; H, 7.13; N, 17.31.

Example 116

N-{3-[4-Amino-2-(hydroxymethyl)-1-(2-hydroxy-2-methylpropyl)-1H-imidazo[4,5-c]quinolin-7-yl]propyl}methanesulfonamide

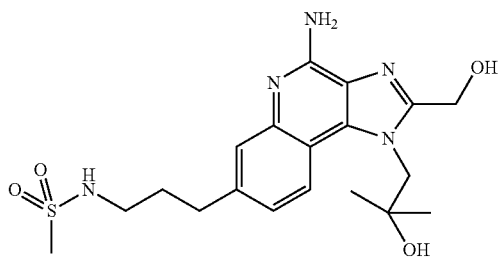 [SMILES: CC(C)(O)Cn1c(CO)nc2c(N)nc3cc(CCCNS(C)(=O)=O)ccc3c21]

A solution of N-{3-[4-amino-1-(2-hydroxy-2-methylpropyl)-2-(methoxymethyl)-1H-imidazo[4,5-c]quinolin-7-yl]propyl}methanesulfonamide (630 mg, 1.45 mmol) in dichloromethane (125 mL) was sealed with a septum and purged with nitrogen gas. A 1.0 M solution of boron tribromide in dichloromethane (7.3 mL) was added via syringe. The resulting mixture was stirred for 18 hours. Methanol (50 mL) was added and the solution was concentrated under reduced pressure. The resulting solid was dissolved in a 2.0 M solution of ammonia in methanol (75 mL) and then concentrated under reduced pressure. This step was repeated two more times with silica gel (1 tbsp) being added prior to final concentration. The crude product absorbed on silica was purified by chromatography using a HORIZON HPFC system (silica cartridge, eluting with CMA:chloroform gradient; 0-25% CMA over 1200 mL, followed by 25-40% CMA over 1900 mL). The solid product was washed with water, filtered, and dried to provide 325 mg of N-{3-[4-amino-2-(hydroxymethyl)-1-(2-hydroxy-2-methylpropyl)-1H-imidazo[4,5-c]quinolin-7-yl]propyl}methanesulfonamide as a white solid, mp 202-205° C.

$^1$H NMR (500 MHz, DMSO-$d_6$) δ 8.18 (d, J=8.5 Hz, 1H), 7.42 (d, J=1.6 Hz, 1H), 7.09 (dd, J=8.5, 1.7 Hz, 1H), 7.05 (t, J=5.4 Hz, 1H), 6.57 (br s, 2H), 5.51 (br s, 1H), 4.97 (s, 1H), 4.87 (br s, 2H), 4.68 (br s, 2H), 3.00 (m, 2H), 2.89 (s, 3H), 2.72 (t, J=7.2 Hz, 2H), 1.84 (m, 2H), 1.17 (br s, 6H);

MS (APCI) m/z 421 (M+H)$^+$;

Anal. Calcd. for $C_{19}H_{27}N_5O_4S$: C, 54.14; H, 6.46; N, 16.61. Found: C, 54.10; H, 6.30; N, 16.66.

Example 117

N-[4-Amino-2-(ethoxymethyl)-1-(2-hydroxy-2-methylpropyl)-1H-imidazo[4,5-c]quinolin-8-yl]-2-methylpropanamide

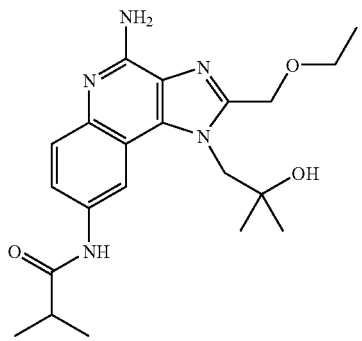 [SMILES: CCOCc1nc2c(N)nc3ccc(NC(=O)C(C)C)cc3c2n1CC(C)(C)O]

Part A

Phosphorous oxychloride (5.45 mL, 58.5 mmol) was added to a slurry of 6-bromo-3-nitroquinolin-4-ol (15 g, 55.7 mmol) in N,N-dimethylformamide (100 mL). The reaction mixture was heated to 100° C. for 10 minutes and then cooled to ambient temperature. The solution was poured into ice water (400 mL) and stirred for 20 minutes. The resulting precipitate was filtered, washed with water, and dried. The recovered solid was transferred to a round bottomed flask and tetrahydrofuran (100 mL) was added. A solution of triethylamine (11.6 mL, 83.5 mmol) and 1-amino-2-methylpropan-2-ol (5.21 g, 58.5 mmol) in tetrahydrofuran (20 mL) was added dropwise. The reaction was stirred for 16 hours. The mixture was poured into water and stirred for 15 minutes. The resulting yellow solid was filtered and dried to provide 17.2 g of 1-[(6-bromo-3-nitroquinolin-4-yl)amino]-2-methylpropan-2-ol as a yellow solid.

Part B

1-[(6-Bromo-3-nitroquinolin-4-yl)amino]-2-methylpropan-2-ol (17.2 g, 50.5 mmol), toluene (150 mL) and isopropanol (20 mL) were added to a Parr flask containing 5% platinum on carbon (1.7 g) wetted with toluene. The flask was evacuated three times, charged with hydrogen to 30 psi, and shaken for 72 hours. The reaction mixture was filtered through a pad of CELITE filter agent. The CELITE was washed with several portions of dichloromethane followed by methanol. The filtrate was concentrated to provide crude 1-[(3-amino-6-bromoquinolin-4-yl)amino]-2-methylpropan-2-ol as a brown oil.

Part C

Ethoxyacetyl chloride (6.2 g, 50.5 mmol) was added dropwise to a solution of crude 1-[(3-amino-6-bromoquinolin-4-yl)amino]-2-methylpropan-2-ol, dichloromethane (500 mL), and triethylamine (7 mL, 50.5 mmol). After stirring for 16 hours, water was added and the mixture was stirred for an additional 2 hours. The fractions were separated. The organic fraction was washed with water, concentrated under reduced pressure and redissolved in ethanol (500 mL). Water (150 mL) and potassium carbonate (10.5 g) were added and the mixture was heated at reflux temperature for 3 hours. The ethanol was removed under reduced pressure. The remaining aqueous fraction was extracted with ethyl acetate (2×500 mL). The organic fractions were combined, washed with water followed by saturated aqueous sodium chloride, dried over anhydrous sodium sulfate, filtered, and concentrated under reduced pressure. Recrystallization from acetonitrile provided 10.4 g of 1-[8-bromo-2-(ethoxymethyl)-1H-imidazo[4,5-c]quinolin-1-yl]-2-methylpropan-2-ol as a tan powder.

Part D

1-[8-Bromo-2-(ethoxymethyl)-1H-imidazo[4,5-c]quinolin-1-yl]-2-methylpropan-2-ol (0.550 g, 1.45 mmol), isobutyramide (0.150 g, 1.74 mmol), copper(I) iodide (0.055 g, 0.290 mmol), potassium phosphate (0.647 g, 3.05 mmol), and 1,4-dioxane (1.5 mL) were added to a scintillation vial. 1,2-(±)-trans-Diaminocyclohexane (0.035 mL, 0.290 mmol) was added. The vial was flushed with nitrogen, sealed with a Teflon-lined cap and heated at 110° C. for 72 hours. The vial was cooled to ambient temperature and the reaction was diluted with dichloromethane and methanol. Purification by chromatography with a HORIZON HPFC system (silica cartridge, eluting with a linear gradient of 1-15% CMA in chloroform) provided 0.38 g of N-[2-(ethoxymethyl)-1-(2-hydroxy-2-methylpropyl)-1H-imidazo[4,5-c]quinolin-8-yl]-2-methylpropanamide as a dark semi-solid.

Part E

3-Chloroperoxybenzoic acid (60% pure, 0.283 g, 1.0 mmol) was added to a solution of N-[2-(ethoxymethyl)-1-(2-hydroxy-2-methylpropyl)-1H-imidazo[4,5-c]quinolin-8-yl]-2-methylpropanamide (0.380 g, 1.0 mmol) in chloroform (10 mL) and the reaction was stirred for 1 hour. The mixture was cooled in an ice bath and ammonium hydroxide (3 mL) was added. After 15 minutes of stirring, p-toluenesulfonyl chloride (0.190 g, 1.0 mmol) was added and the reaction mixture was stirred for 72 hours. The fractions were separated and the aqueous fraction was extracted with chloroform. The combined organic fractions were washed with brine and purified by chromatography using a HORIZON HPFC system (silica cartridge, eluting with a linear gradient of 2-20% CMA in chloroform). Recrystallization from acetonitrile provided 0.231 g of N-[4-amino-2-(ethoxymethyl)-1-(2-hydroxy-2-methylpropyl)-1H-imidazo[4,5-c]quinolin-8-yl]-2-methylpropanamide as an off-white solid, mp 259-261° C.

$^1$H NMR (300 MHz, DMSO-$d_6$) δ 9.88 (s, 1H), 8.86 (d, J=1.7 Hz, 1H), 7.53-7.42 (m, 2H), 6.41 (s, 2H), 5.15-4.73 (m, 2H), 4.90 (s, 1H), 4.63 (s, 2H), 3.51 (q, J=7.0 Hz, 2H), 2.68-2.59 (m, 1H), 1.22 (br s, 6H), 1.14 (d, J=6.9 Hz, 6H), 1.13 (t, J=7.0 Hz, 3H);

MS (ESI) m/z 400.17 (M+H)$^+$;

Anal. Calcd. for $C_{21}H_{29}N_5O_3$: C, 63.14; H, 7.32; N, 17.53. Found: C, 62.78; H, 7.20; N, 17.48.

Example 118

N-{2-[4-Amino-2-ethyl-1-(2-hydroxy-2-methylpropyl)-1H-imidazo[4,5-c]quinolin-7-yl]ethyl}methanesulfonamide

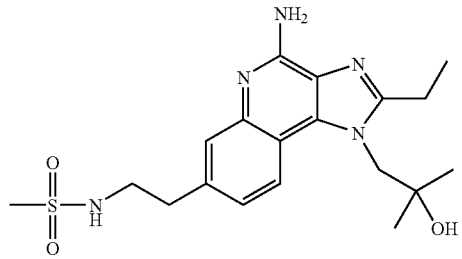 [SMILES: CCc1nc2c(N)nc3cc(CCNS(C)(=O)=O)ccc3c2n1CC(C)(C)O]

Part A

A thick walled glass tube, equipped with a stir bar, was charged with palladium (II) acetate (64 mg, 0.29 mmol), acetonitrile (50 mL), N-vinylphthalimide (1.19 g, 6.89 mmol), triethylamine (2.4 mL, 17 mmol), tri-o-tolylphosphine (260 mg, 0.86 mmol) and 1-(7-bromo-2-ethyl-1H-imidazo[4,5-c]quinolin-1-yl)-2-methylpropan-2-ol (2.00 g, 5.74 mmol). The reaction mixture was purged with nitrogen and the tube was sealed and heated at 120° C. in an oil bath for 16 hours. The reaction was cooled to ambient temperature and silica gel (20 g) was added followed by concentration under reduced pressure. The sample absorbed on silica was purified by chromatography using a HORIZON HPFC system (silica cartridge, eluting with a 0-7% gradient of methanol in dichloromethane). The recovered solid was washed with 1% aqueous sodium carbonate to provide 1.95 g of 2-{2[2-ethyl-1-(2-hydroxy-2-methylpropyl)-1H-imidazo[4,5-c]quinolin-7-yl]ethenyl}-1H-isoindole-1,3(2H)-dione as a bright yellow solid. MS (APCI) m/z 441 (M+H)$^+$.

Part B

A glass Parr vessel was charged with 10% palladium on carbon (0.4 g), methanol (75 mL) and 2-{2-[2-ethyl-1-(2-hydroxy-2-methylpropyl)-1H-imidazo[4,5-c]quinolin-7-yl]ethenyl}-1H-isoindole-1,3(2H)-dione (1.9 g, 4.3 mmol). The vessel was evacuated and charged with hydrogen gas (40 psi, 2.8×10$^5$ Pa). The reaction was shaken at 50° C. for approximately 18 hours and then cooled to ambient temperature. The reaction mixture was filtered followed by concentration under reduced pressure to provide 1.9 g of 2-{2-[2-ethyl-1-(2-hydroxy-2-methylpropyl)-1H-imidazo[4,5-c]quinolin-7-yl]ethyl}-1H-isoindole-1,3(2H)-dione as a bright yellow solid. MS (APCI) m/z 443 (M+H)$^+$.

Part C

2-{2-[2-ethyl-1-(2-hydroxy-2-methylpropyl)-1H-imidazo[4,5-c]quinolin-7-yl]ethyl}-1H-isoindole-1,3(2H)-dione (1.90 g, 4.29 mmol) in dichloromethane (75 mL) was combined with 3-chloroperoxybenzoic acid (60% pure, 1.24 g, 4.72 mmol) and the reaction was stirred for 18 hours. Concentrated ammonium hydroxide (40 mL) was added and the mixture was vigorously stirred for an additional 10 minutes. p-Toluenesulfonyl chloride (900 mg, 4.72 mmol) was added and the mixture was stirred for an additional 1 hour. The fractions were separated and the aqueous fraction was extracted with chloroform (3×50 mL). The combined organic fractions were sequentially dried (MgSO$_4$), filtered, and concentrated under reduced pressure. Purification by chromatography using a HORIZON HPFC system (silica cartridge, eluting with 0-8% gradient of methanol in dichloromethane) provided 1.05 g of 2-{2-[4-amino-2-ethyl-1-(2-hydroxy-2-methylpropyl)-1H-imidazo[4,5-c]quinolin-7-yl]ethyl}-1H-isoindole-1,3(2H)-dione as an off-white foam. MS (APCI) m/z 458 (M+H)$^+$.

Part D:

2-{2-[4-amino-2-ethyl-1-(2-hydroxy-2-methylpropyl)-1H-imidazo[4,5-c]quinolin-7-yl]ethyl}-1H-isoindole-1,3(2H)-dione (1.05 g, 2.29 mmol) was dissolved in 2:1 ethanol: tetrahydrofuran (100 mL), combined with hydrazine hydrate (150 mg, 2.98 mmol) and heated to reflux temperature for three hours. Additional hydrazine hydrate (0.25 mL) was added and solution was refluxed for an additional 18 hours. The reaction mixture was cooled to ambient temperature and filtered. The crude solid was combined with triethylamine (2.1 mL, 15.3 mmol) in dichloromethane (75 mL) and the solution was cooled to 0° C. in an ice/water bath. Methanesulfonic anhydride (585 mg, 3.35 mmol) was added and solution was stirred for approximately 18 hours while warming to ambient temperature. The solution was concentrated under reduced pressure and the residue was slurried in 1% aqueous sodium carbonate (125 mL). The aqueous mixture was extracted with chloroform (50 mL) until no product was present in the aqueous fraction. The combined organic fractions were sequentially dried (MgSO$_4$), filtered, concentrated under reduced pressure, and purified by chromatography using a HORIZON HPFC system (silica cartridge, eluting with a CMA:chloroform gradient; 0-25% CMA over 1200 mL, followed by 25-30% CMA over 1100 mL). A final recrystallization for acetonitrile provided 328 mg of N-{2-[4-amino-2-ethyl-1-(2-hydroxy-2-methylpropyl)-1H-imidazo[4,5-c]quinolin-7-yl]ethyl}methanesulfonamide as an off-white solid, mp 149-152° C.

$^1$H NMR (500 MHz, DMSO-d$_6$) δ 8.18 (d, J=8.5 Hz, 1H), 7.45 (d, J=1.6 Hz, 1H), 7.10 (m, 1H), 7.09 (dd, J=8.5, 1.7 Hz, 1H), 6.37 (br s, 2H), 4.77 (s, 1H), 4.52 (br s, 2H), 3.26 (m, 2H), 3.04 (q, J=7.4 Hz, 2H), 2.87 (t, J=7.4 Hz, 2H), 2.82 (s, 3H), 1.34 (t, J=7.5 Hz, 3H), 1.16 (br s, 6H);

MS (APCI) m/z 406 (M+H)$^+$;

Anal. Calcd. for C$_{19}$H$_{27}$N$_5$O$_3$S: C, 56.28; H, 6.71; N, 17.27. Found: C, 56.00; H, 6.87; N, 17.44.

Example 119

1-{3-[4-Amino-8-(2-aminoethyl)-2-(2-methoxyethyl)-1H-imidazo[4,5-c]quinolin-1-yl]propyl}pyrrolidin-2-one

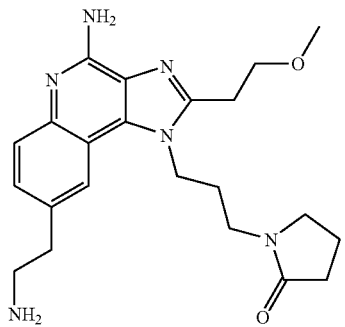 [SMILES: COCCc1nc2c(N)nc3ccc(CCN)cc3c2n1CCCN1CCCC1=O]

Part A

A thick walled glass tube, equipped with a stir bar, was charged with palladium (II) acetate (17 mg, 0.08 mmol), acetonitrile (50 mL), N-vinylphthalimide (716 mg, 4.13 mmol), triethylamine (1.6 mL, 11 mmol), tri-o-tolylphosphine (69 mg, 0.22 mmol) and 1-{3-[8-bromo-2-(2-methoxyethyl)-1H-imidazo[4,5-c]quinolin-1-yl]propyl}pyrrolidin-2-one (1.62 g, 3.76 mmol). The reaction mixture was purged with nitrogen and the tube was sealed and heated at 120° C. in an oil bath for 15 hours. The reaction was cooled to ambient temperature and methanol (50 mL) and chloroform (50 ml) were added. After filtering through a 0.2 micron PTFE membrane, the solution was concentrated under reduced pressure and then purified by chromatography using a HORIZON HPFC system (silica cartridge, eluting with a 0-8% gradient of methanol in dichloromethane) to provide 2.0 g of 2-(2-{2-(2-methoxyethyl)-1-[3-(2-oxopyrrolidin-1-yl)propyl]-1H-imidazo[4,5-c]quinolin-8-yl}ethenyl)-1H-isoindole-1,3(2H)-dione as a bright yellow solid.

MS (APCI) m/z 524 (M+H)$^+$.

Part B

A glass Parr vessel was charged with 10% palladium on carbon (0.2 g), methanol (75 mL) and 2-(2-{2-(2-methoxyethyl)-1-[3-(2-oxopyrrolidin-1-yl)propyl]-1H-imidazo[4,5-c]quinolin-8-yl}ethenyl)-1H-isoindole-1,3(2H)-dione (2.0 g, 3.8 mmol). The vessel was evacuated and charged with hydrogen gas (40 psi, 2.8×10$^5$ Pa). The reaction was shaken at 50° C. for approximately 18 hours. After cooling to ambient temperature, the reaction mixture was filtered followed by concentration under reduced pressure to provide 2.1 g of 2-(2-{2-(2-methoxyethyl)-1-[3-(2-oxo-pyrrolidin-1-yl)propyl]-1H-imidazo[4,5-c]quinolin-8-yl}ethyl)-1H-isoindole-1,3(2H)-dione as a pale yellow solid. MS (ESI) m/z 526 (M+H)$^+$.

Part C 2-(2-{2-(2-Methoxyethyl)-1-[3-(2-oxo-pyrrolidin-1-yl)propyl]-1H-imidazo[4,5-c]quinolin-8-yl}ethyl)-1H-isoindole-1,3(2H)-dione (2.1 g, 3.8 mmol) in dichloromethane (75 mL) was combined with 3-chloroperoxybenzoic acid (60% pure, 2.0 g, 7.5 mmol) and the reaction was stirred for 18 hours. Concentrated ammonium hydroxide (40 mL) was added and the mixture was vigorously stirred for an additional 10 minutes. p-Toluenesulfonyl chloride (791 mg, 4.12 mmol) was added and the mixture was stirred for an additional 1 hour. The fractions were separated and aqueous fraction was extracted with chloroform (10×35 mL). The combined organic fractions were sequentially dried (MgSO$_4$), filtered, and concentrated to provide 2.2 g of 2-(2-{4-amino-2-(2-methoxyethyl)-1-[3-(2-oxopyrrolidin-1-yl)propyl]-1H-imidazo[4,5-c]quinolin-8-yl}ethyl)-1H-isoindole-1,3(2H)dione as an off-white foam. MS (APCI) m/z 541 (M+H)$^+$.

Part D 2-(2-{4-Amino-2-(2-methoxyethyl)-1-[3-(2-oxopyrrolidin-1-yl)propyl]-1H-imidazo[4,5-c]quinolin-8-yl}ethyl)-1H-isoindole-1,3(2H)dione (2.2 g, 4.1 mmol) was dissolved in 2:1 ethanol:tetrahydrofuran (40 mL), combined with hydrazine hydrate (410 mg, 8.2 mmol) and heated at reflux temperature for three hours. Additional hydrazine hydrate (0.25 mL) was added and the solution was refluxed for an additional 1.5 hours. The reaction was cooled to ambient temperature, filtered and the filtrate concentrated under reduce pressure. Purification by chromatography using a HORIZON HPFC system (silica cartridge, eluting with a 0-40% CMA:chloroform gradient over 3.8 L) provided 650 mg of 1-{3-[4-amino-8-(2-aminoethyl)-2-(2-methoxyethyl)-1H-imidazo[4,5-c]quinolin-1-yl]propyl}pyrrolidin-2-one as an off-white solid. MS (ESI) m/z 411 (M+H)$^+$.

Example 120

2-Ethyl-7-[2-(methylsulfonyl)ethyl])-1-(tetrahydro-2H-pyran-4-ylmethyl)-1H-imidazo[4,5-c]quinolin-4-amine

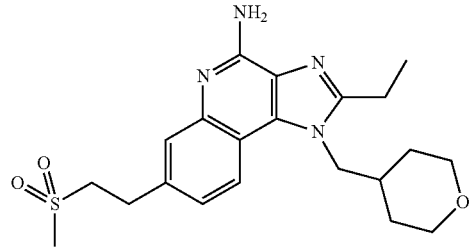 [SMILES: CCc1nc2c(N)nc3cc(CCS(C)(=O)=O)ccc3c2n1CC1CCOCC1]

Part A

A thick walled glass tube, equipped with a stir bar, was charged with palladium (II) acetate (7 mg, 0.03 mmol), acetonitrile (15 mL), N,N-dimethylformamide (15 mL), methyl vinyl sulfone (150 mg, 1.41 mmol), triethylamine (0.53 mL, 3.8 mmol), tri-o-tolylphosphine (23 mg, 0.08 mmol) and 7-bromo-2-ethyl-1-(tetrahydro-2H-pyran-4-ylmethyl)-1H-imidazo[4,5-c]quinolin-4-amine (500 g, 1.28 mmol). The reaction mixture was purged with nitrogen and the tube was sealed and heated at 120° C. in an oil bath for 16 hours. The reaction mixture was cooled to ambient temperature and then concentrated under reduced pressure. The resulting solid was partitioned between chloroform (100 mL) and 1% aqueous sodium carbonate (100 mL). The fractions were separated and the aqueous fraction was extracted with chloroform (2×50 mL). The combined organic fractions were sequentially dried (MgSO$_4$), filtered, and purified by chromatography using a HORIZON HPFC system (silica cartridge, eluting with a CMA:chloroform gradient, 0-15% CMA over 1200 mL followed by 15-20% CMA over 1100 mL). Recrystallization from methanol provided 315 mg of 2-ethyl-7-[2-(methylsulfonyl)ethenyl]-1-(tetrahydro-2H-pyran-4-ylmethyl)-1H-imidazo[4,5-c]quinolin-4-amine as a pale yellow solid.

$^1$H NMR (500 MHz, DMSO-d$_6$) δ 8.08 (d, J=8.6 Hz, 1H), 7.89 (d, J=1.8 Hz, 1H), 7.62-7.53 (m, 3H), 6.65 (br s, 2H), 4.46 (d, J=7.1 Hz, 2H), 3.82 (m, 2H), 3.15-3.12 (m, 2H), 3.12 (m, 3H), 2.96 (q, J=7.4 Hz, 2H), 2.07 (m, 1H), 1.51-1.40 (m, 4H), 1.38 (t, J=7.4 Hz, 3H);

MS (ESI) m/z 415 (M+H)$^+$.

Part B

A glass Parr vessel was charged with 10% palladium on carbon (0.2 g), methanol (25 mL), ethanol (25 mL) and 2-ethyl-7-[2-(methylsulfonyl)ethenyl]-1-(tetrahydro-2H-pyran-4-ylmethyl)-1H-imidazo[4,5-c]quinolin-4-amine (315 mg, 0.76 mmol). The vessel was evacuated and charged with hydrogen gas (40 psi, 2.8×10$^5$ Pa). The reaction was shaken at 50° C. for approximately 18 hours and then cooled to ambient temperature. The reaction mixture was sequentially filtered, concentrated under reduced pressure, and purified by chromatography using a HORIZON HPFC system (silica cartridge, eluting with CMA:chloroform gradient, 0-10% CMA over 1000 mL followed by 10-25% CMA over 1000 mL). A final recrystallization from acetonitrile provided 125 mg of 2-ethyl-7-[2-(methylsulfonyl)ethyl])-1-(tetrahydro-2H-pyran-4-ylmethyl)-1H-imidazo[4,5-c]quinolin-4-amine as a white crystalline solid, mp 246.5-249.0° C.

$^1$H NMR (500 MHz, DMSO-d$_6$) δ 7.97 (d, J=8.5 Hz, 1H), 7.52 (d, J=1.7 Hz, 1H), 7.21 (dd, J=8.4, 1.8 Hz, 1H), 6.48 (br s, 2H), 4.42 (d, J=7.0 Hz, 2H), 3.83-3.80 (m, 2H), 3.53-3.50 (m, 2H), 3.17-3.11 (m, 4H), 3.02 (s, 3H), 2.94 (q, J=7.4 Hz, 2H), 2.07 (m, 1H), 1.51-1.40 (m, 4H), 1.37 (t, J=7.4 Hz, 3H);

$^{13}$C NMR (125 MHz, DMSO-d$_6$) δ 154.2, 151.7, 144.9, 136.1, 132.3, 126.2, 125.6, 121.7, 120.2, 113.3, 66.4, 54.3, 49.6, 40.1, 35.6, 29.5, 27.6, 20.0, 11.9;

MS (ESI) m/z 417 (M+H)$^+$;

Anal. Calcd. for $C_{21}H_{28}N_4O_3S$: C, 60.55; H, 6.78; N, 13.45. Found: C, 60.63; H, 6.70; N, 13.76.

Example 121

3-[4-Amino-2-ethyl-1-(tetrahydro-2H-pyran-4-ylmethyl)-1H-imidazo[4,5-c]quinolin-7-yl]propanenitrile

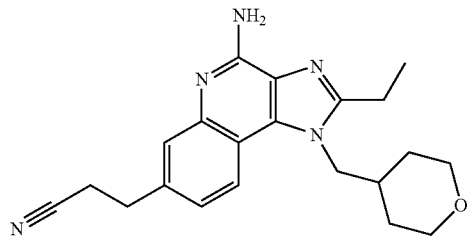 [SMILES: CCc1nc2c(N)nc3cc(CCC#N)ccc3c2n1CC1CCOCC1]

Part A

A thick walled glass tube, equipped with a stir bar, was charged with palladium (II) acetate (225 mg, 1.00 mmol), acetonitrile (15 mL), N,N-dimethylformamide (15 mL), acrylonitrile (1.20 g, 22.6 mmol), triethylamine (8.6 mL, 62 mmol), tri-o-tolylphosphine (935 mg, 3.10 mmol) and 7-bromo-2-ethyl-1-(tetrahydro-2H-pyran-4-ylmethyl)-1H-imidazo[4,5-c]quinolin-4-amine (8.00 g, 20.5 mmol). The reaction mixture was purged with nitrogen and the tube was sealed and heated at 120° C. for approximately 18 hours. The reaction was cooled to ambient temperature and methanol (100 mL) was added. The reaction was filtered and the filtrate concentrated under reduced pressure. The resulting solid was washed with 1% aqueous sodium carbonate (100 mL) followed by washing with water (2×100 mL). Purification by chromatography using a HORIZON HPFC system (silica cartridge, eluting with a CMA:chloroform gradient, 0-15% CMA over 1500 mL followed by 15-25% CMA over 2.4 L) provided 5.2 g of a mixture of cis and trans isomers of 3-[4-amino-2-ethyl-1-(tetrahydro-2H-pyran-4-ylmethyl)-1H-imidazo[4,5-c]quinolin-7-yl]prop-2-enenitrile as a yellow solid. MS (APCI) m/z 362 (M+H)$^+$.

Part B

A glass Parr vessel was charged with 10% palladium on carbon (0.05 g), methanol (20 mL), and 3-[4-amino-2-ethyl-1-(tetrahydro-2H-pyran-4-ylmethyl)-1H-imidazo[4,5-c]quinolin-7-yl]prop-2-enenitrile (100 mg, 0.27 mmol). The vessel was evacuated and charged with hydrogen gas (40 psi, 2.8×10$^5$ Pa). The reaction was shaken at 50° C. for approximately 18 hours and then cooled to ambient temperature. The reaction mixture was sequentially filtered, concentrated under reduced pressure, and purified by chromatography using a HORIZON HPFC system (silica cartridge, eluting with a CMA:chloroform gradient, 0-30% CMA). A final recrystallization from acetonitrile provided 71 mg of 3-[4-amino-2-ethyl-1-(tetrahydro-2H-pyran-4-ylmethyl)-1H-imidazo[4,5-c]quinolin-7-yl]propanenitrile as a white solid, mp 273-275° C.

$^1$H NMR (500 MHz, DMSO-d$_6$) δ 7.97 (d, J=8.4 Hz, 1H), 7.53 (d, J=1.7 Hz, 1H), 7.20 (dd, J=8.4, 1.8 Hz, 1H), 6.45 (br s, 2H), 4.42 (d, J=7.2 Hz, 2H), 3.82 (m, 2H), 3.15 (m, 2H), 3.00-2.88 (m, 6H), 2.08 (m, 1H), 1.51-1.40 (m, 4H), 1.37 (t, J=7.4 Hz, 3H);

$^{13}$C NMR (125 MHz, DMSO-d$_6$) δ 154.2, 151.7, 144.8, 136.6, 132.3, 126.2, 125.5, 121.6, 120.3, 120.1, 113.4, 66.4, 49.6, 35.6, 30.4, 29.5, 20.0, 17.9, 11.9;

MS (ESI) m/z 364 (M+H)$^+$;

Anal. Calcd. for $C_{21}H_{25}N_5O$: C, 69.40; H, 6.93; N, 19.27. Found: C, 69.16; H, 6.87; N, 19.25.

Example 122

3-[4-Amino-2-ethyl-1-(tetrahydro-2H-pyran-4-ylmethyl)-1H-imidazo[4,5-c]quinolin-7-yl]propanamide

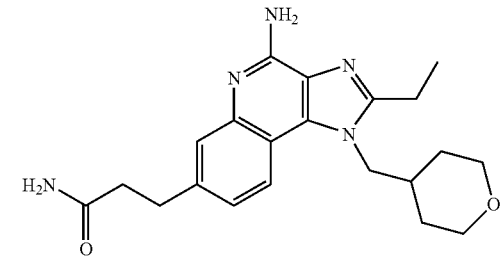 [SMILES: CCc1nc2c(N)nc3cc(CCC(N)=O)ccc3c2n1CC1CCOCC1]

3-[4-Amino-2-ethyl-1-(tetrahydro-2H-pyran-4-ylmethyl)-1H-imidazo[4,5-c]quinolin-7-yl]propanenitrile (590 mg, 1.6 mmol), 10% aqueous sodium hydroxide (132 mg, 0.33 mmol), and 30% aqueous hydrogen peroxide (516 mg, 4.55 mmol) were combined in methanol (75 mL) and the reaction was heated at 50° C. for 18 hours. The mixture was concentrated under reduced pressure and then partitioned between chloroform (75 mL) and water (75 mL). The fractions were separated and the aqueous fraction was extracted with chloroform (3×25 mL). The combined organic fractions were sequentially dried (MgSO$_4$), filtered, concentrated to dryness and purified by chromatography using a HORIZON HPFC system (silica cartridge, eluting with 2 L of 10% methanol in dichloromethane). A final recrystallization from acetonitrile provided 35 mg of 3-[4-amino-2-ethyl-1-(tetrahydro-2H-pyran-4-ylmethyl)-1H-imidazo[4,5-c]quinolin-7-yl]propanamide as an off-white solid, mp 197-199° C.

$^1$H NMR (500 MHz, DMSO-d$_6$) δ 7.92 (d, J=8.4 Hz, 1H), 7.44 (d, J=1.4 Hz, 1H), 7.32 (s, 1H), 7.13 (dd, J=8.4, 1.7 Hz, 1H), 6.77 (s, 1H), 6.39 (br s, 2H), 4.40 (d, J=7.0 Hz, 2H), 3.82 (m, 2H), 3.15 (m, 2H), 2.95-2.90 (m, 4H), 2.44 (t, J=7.6 Hz, 2H), 2.08 (m, 1H), 1.51-1.40 (m, 4H), 1.37 (t, J=7.4 Hz, 3H);

$^{13}$C NMR (125 MHz, DMSO-d$_6$) δ 173.3, 154.1, 151.5, 144.8, 139.4, 132.5, 125.9, 125.0, 121.9, 119.8, 112.8, 66.4, 49.6, 36.3, 35.6, 30.6, 29.5, 20.0, 11.9;

MS (ESI) m/z 382 (M+H)$^+$;

Anal. Calcd. for C$_{21}$H$_{27}$N$_5$O$_2$.0.30H$_2$O: C, 65.20; H, 7.19; N, 18.10. Found: C, 65.19; H, 7.14; N, 18.24.

Example 123

7-(3-Aminopropyl)-2-ethyl-1-(tetrahydro-2H-pyran-4-ylmethyl)-1H-imidazo[4,5-c]quinolin-4-amine

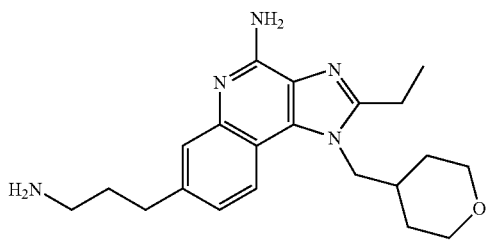 [SMILES: CCc1nc2c(N)nc3cc(CCCN)ccc3c2n1CC1CCOCC1]

A glass Parr vessel was charged with 10% palladium on carbon (1 g), methanol (50 mL), 3-[4-amino-2-ethyl-1-(tetrahydro-2H-pyran-4-ylmethyl)-1H-imidazo[4,5-c]quinolin-7-yl]prop-2-enenitrile (4.0 g, 11.1 mmol) and trifluoroacetic acid (6.3 g, 55 mmol). The vessel was evacuated, charged with hydrogen gas (40 psi, 2.8×10$^5$ Pa) and shaken for approximately 18 hours. The mixture was filtered and concentrated under reduced pressure to a yellow oil. The oil was dissolved in 10% aqueous hydrochloric acid and stirred for 18 hours. Chloroform (100 mL) was added followed by slow addition of potassium carbonate until the pH equaled 11. The fractions were separated and the aqueous fraction was extracted with chloroform (4×50 mL). The combined organic fractions were sequentially dried (MgSO$_4$), filtered, and concentrated under reduced pressure. Recrystallization from acetonitrile provided 3.55 g of the desired product as a white solid. A small amount of this material was further purified by chromatography using a HORIZON HPFC system (silica cartridge, eluting with a CMA:chloroform gradient, 0-30% CMA over 1000 mL followed by 30% CMA over 1000 mL). A final recrystallization from acetonitrile provided 7-(3-aminopropyl)-2-ethyl-1-(tetrahydro-2H-pyran-4-ylmethyl)-1H-imidazo[4,5-c]quinolin-4-amine as a white solid, mp 217-220° C.

$^1$H NMR (500 MHz, DMSO-d$_6$) δ 7.92 (d, J=8.4 Hz, 1H), 7.42 (d, J=1.5 Hz, 1H), 7.12 (dd, J=8.4, 1.7 Hz, 1H), 6.38 (br s, 2H), 4.40 (d, J=7.0 Hz, 2H), 3.82 (m, 2H), 3.16 (m, 2H), 2.93 (q, J=7.4 Hz, 2H), 2.70 (t, J=7.6 Hz, 2H), 2.59 (t, J=6.8 Hz, 2H), 2.09 (m, 1H), 1.71 (m, 2H), 1.51-1.36 (m, 6H), 1.37 (t, J=7.4 Hz, 3H);

$^{13}$C NMR (125 MHz, DMSO-d$_6$) δ 154.0, 151.5, 144.9, 140.2, 132.5, 125.9, 125.2, 122.0, 119.8, 112.7, 66.4, 49.6, 41.2, 35.6, 34.9, 32.4, 29.5, 20.0, 11.9;

MS (ESI) m/z 368 (M+H)$^+$;

Anal. Calcd. for C$_{21}$H$_{29}$N$_5$O.0.25H$_2$O: C, 67.81; H, 7.99; N, 18.83. Found: C, 68.00; H, 8.03; N, 18.75.

Example 124

N-{3-[4-Amino-2-ethyl-1-(tetrahydro-2H-pyran-4-ylmethyl)-1H-imidazo[4,5-c]quinolin-7-yl]propyl}methanesulfonamide

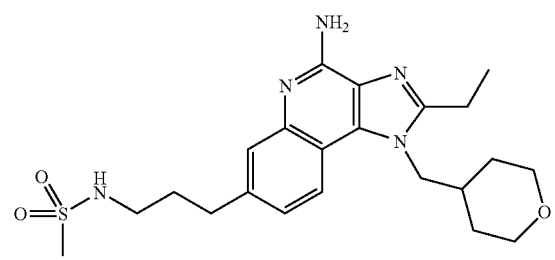 [SMILES: CCc1nc2c(N)nc3cc(CCCNS(C)(=O)=O)ccc3c2n1CC1CCOCC1]

7-(3-Aminopropyl)-2-ethyl-1-(tetrahydro-2H-pyran-4-ylmethyl)-1H-imidazo[4,5-c]quinolin-4-amine (500 mg, 1.4 mmol), triethylamine (410 mg, 4.1 mmol), and methanesulfonic anhydride (260 mg, 1.5 mmol) were combined in dichloromethane (50 mL) at 0° C. and the reaction was stirred for approximately 18 hours. Aqueous sodium carbonate (1%, 50 mL) was added and the reaction mixture was stirred for one additional hour. The fractions were separated and the aqueous fraction was extracted with chloroform (3×20 mL). The combined organic fractions were sequentially dried (MgSO$_4$), filtered and purified by chromatography using a HORIZON HPFC system (silica cartridge, eluting with a CMA:chloroform gradient, 0-20% CMA over 1500 mL followed by 20% CMA over 500 mL). A final recrystallization from acetonitrile provided 165 mg of N-{3-[4-amino-2-ethyl-1-(tetrahydro-2H-pyran-4-ylmethyl)-1H-imidazo[4,5-c]quinolin-7-yl]propyl}methanesulfonamide as a white solid, mp 168-170° C.

$^1$H NMR (500 MHz, DMSO-d$_6$) δ 7.93 (d, J=8.4 Hz, 1H), 7.44 (d, J=1.6 Hz, 1H), 7.14 (dd, J=8.4, 1.7 Hz, 1H), 7.05 (t, J=5.5 Hz, 1H), 6.40 (br s, 2H), 4.40 (d, J=7.0 Hz, 2H), 3.82 (m, 2H), 3.16 (m, 2H), 3.00 (m, 2H), 2.93 (q, J=7.4 Hz, 2H), 2.89 (s, 3H), 2.73 (t, J=7.6 Hz, 2H), 2.09 (m, 1H), 1.85 (m, 2H), 1.51-1.40 (m, 4H), 1.37 (t, J=7.4 Hz, 3H);

$^{13}$C NMR (125 MHz, DMSO-d$_6$) δ 154.0, 151.6, 144.9, 139.4, 132.4, 126.0, 125.3, 121.9, 119.9, 112.8, 66.4, 49.6, 42.0, 39.1, 35.6, 32.1, 31.0, 29.5, 20.0, 11.9;

MS (ESI) m/z 446 (M+H)$^+$;

Anal. Calcd. for C$_{22}$H$_{31}$N$_5$O$_3$S: C, 59.30; H, 7.01; N, 15.72. Found: C, 59.22; H, 7.29; N, 15.68.

Example 125

N-{3-[4-amino-2-ethyl-1-(tetrahydro-2H-pyran-4-ylmethyl)-1H-imidazo[4,5-c]quinolin-7-yl]propyl}acetamide

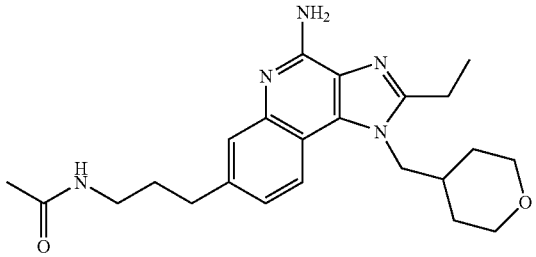 [SMILES: CCc1nc2c(N)nc3cc(CCCNC(C)=O)ccc3c2n1CC1CCOCC1]

7-(3-Aminopropyl)-2-ethyl-1-(tetrahydro-2H-pyran-4-ylmethyl)-1H-imidazo[4,5-c]quinolin-4-amine (500 mg, 1.4 mmol), triethylamine (410 mg, 4.1 mmol), and acetic anhydride (153 mg, 1.5 mmol) were combined in dichloromethane (50 mL) at 0° C. and the reaction was stirred for approximately 18 hours. Aqueous sodium carbonate (1%, 50 mL) was added and the reaction mixture was stirred for one additional hour. The fractions were separated and the aqueous fraction was extracted with chloroform (3×20 mL). The combined organic fractions were sequentially dried (MgSO$_4$), filtered and purified by chromatography using a HORIZON HPFC system (silica cartridge, eluting with a CMA:chloroform gradient, 0-15% CMA over 2000 mL followed by 15-20% CMA over 500 mL). The desired product was further purified by chromatography using a HORIZON HPFC system (silica cartridge, eluting with a 0-8% gradient of methanol in dichloromethane). A final recrystallization from acetonitrile provided 142 mg of N-{3-[4-amino-2-ethyl-1-(tetrahydro-2H-pyran-4-ylmethyl)-1H-imidazo[4,5-c]quinolin-7-yl]propyl}acetamide as a white solid, mp 209-211° C.

$^1$H NMR (500 MHz, DMSO-d$_6$) δ 7.92 (d, J=8.4 Hz, 1H), 7.87 (t, J=5.1 Hz, 1H), 7.44 (d, J=1.5 Hz, 1H), 7.13 (dd, J=8.4, 1.7 Hz, 1H), 6.39 (br s, 2H), 4.40 (d, J=7.0 Hz, 2H), 3.82 (m, 2H), 3.16 (m, 2H), 3.09 (m, 2H), 2.93 (q, J=7.4 Hz, 2H), 2.69 (t, J=7.6 Hz, 2H), 2.09 (m, 1H), 1.81 (s, 3H), 1.77 (m, 2H), 1.51-1.40 (m, 4H), 1.37 (t, J=7.4 Hz, 3H);

$^{13}$C NMR (125 MHz, DMSO-d$_6$) δ 168.8, 154.0, 151.5, 144.9, 139.6, 132.4, 125.9, 125.3, 121.9, 119.8, 112.8, 66.4, 49.6, 38.1, 35.6, 32.4, 30.6, 29.5, 22.5, 20.0, 11.9;

MS (ESI) m/z 410 (M+H)$^+$;

Anal. Calcd. for C$_{23}$H$_{31}$N$_5$O$_2$: C, 67.46; H, 7.63; N, 17.10. Found: C, 67.18; H, 7.37; N, 17.14.

Example 126

N-{3-[4-amino-2-ethyl-1-(tetrahydro-2H-pyran-4-ylmethyl)-1H-imidazo[4,5-c]quinolin-7-yl]propyl}-N'-isopropylurea

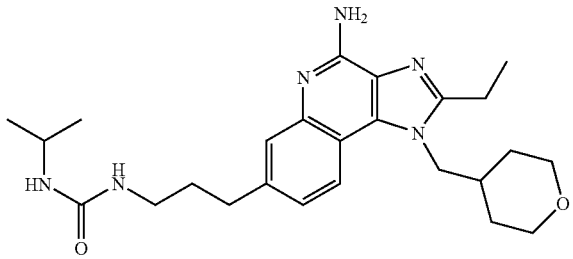 [SMILES: CCc1nc2c(N)nc3cc(CCCNC(=O)NC(C)C)ccc3c2n1CC1CCOCC1]

7-(3-Aminopropyl)-2-ethyl-1-(tetrahydro-2H-pyran-4-ylmethyl)-1H-imidazo[4,5-c]quinolin-4-amine (500 mg, 1.4 mmol), triethylamine (410 mg, 4.1 mmol), and isopropyl isocyanate (128 mg, 1.5 mmol) were combined in dichloromethane (50 mL) at 0° C. and the reaction was stirred for approximately 18 hours. Aqueous sodium carbonate (1%, 50 mL) was added and the reaction mixture was stirred for one additional hour. The fractions were separated and the aqueous fraction was extracted with chloroform (3×20 mL). The combined organic fractions were sequentially dried (MgSO$_4$), filtered and purified by chromatography using a HORIZON HPFC system (silica cartridge, eluting with a CMA:chloroform gradient, 0-20% CMA over 2000 mL). The desired product was further purified by chromatography using a HORIZON HPFC system (silica cartridge, eluting with 10% methanol in dichloromethane over 1500 mL). A final purification by recrystallization from acetonitrile provided 142 mg of N-{3-[4-amino-2-ethyl-1-(tetrahydro-2H-pyran-4-ylmethyl)-1H-imidazo[4,5-c]quinolin-7-yl]propyl}-N'-isopropylurea as a white solid, mp 213-216° C.

$^1$H NMR (500 MHz, DMSO-d$_6$) δ 7.93 (d, J=8.4 Hz, 1H), 7.43 (d, J=1.6 Hz, 1H), 7.13 (dd, J=8.4, 1.7 Hz, 1H), 6.40 (br s, 2H), 5.76 (t, J=5.6 Hz, 1H), 5.61 (d, J=7.7 Hz, 1H), 4.40 (d, J=7.0 Hz, 2H), 3.82 (m, 2H), 3.65 (m, 1H), 3.16 (m, 2H), 3.02 (m, 2H), 2.93 (q, J=7.4 Hz, 2H), 2.67 (t, J=7.6 Hz, 2H), 2.09 (m, 1H), 1.73 (m, 2H), 1.51-1.40 (m, 4H), 1.37 (t, J=7.4 Hz, 3H), 1.02 (d, J=6.5 Hz, 6H);

$^{13}$C NMR (125 MHz, DMSO-d$_6$) δ 157.3, 154.1, 151.5, 144.7, 139.7, 132.5, 125.9, 125.1, 122.0, 119.9, 112.7, 66.4, 49.6, 40.7, 38.7, 35.6, 32.4, 31.5, 29.5, 23.1, 20.0, 11.9;

MS (ESI) m/z 453 (M+H)$^+$;

Anal. Calcd. for C$_{25}$H$_{36}$N$_6$O$_2$·0.33H$_2$O: C, 65.41; H, 8.06; N, 18.31. Found: C, 65.41; H, 8.26; N, 18.30.

Example 127

1-Isobutyl-8-{[(3-methoxybenzyl)amino]methyl}-1H-imidazo[4,5-c]quinolin-4-amine

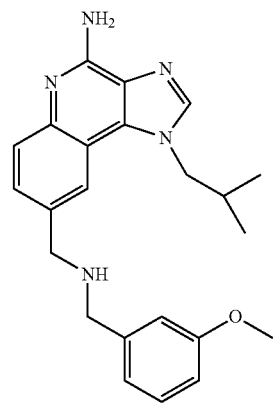 [SMILES: COc1cccc(CNCc2ccc3nc(N)c4ncn(CC(C)C)c4c3c2)c1]

Part A

A solution of 1-isobutyl-8-vinyl-1H-imidazo[4,5-c]quinolin-4-amine (500 mg, 1.9 mmol) in dichloromethane (30 mL) and methanol (5 mL) was cooled to −78° C. Ozone was bubbled through the solution for 10 minutes. While still cold, the reaction was purged with oxygen for 15 minutes and dimethyl sulfide (0.7 mL, 9.4 mmol) was added. The reaction was warmed to ambient temperature and then concentrated under reduced pressure. The residue was dissolved in dichloromethane (50 mL) and washed with 1% aqueous sodium carbonate (2×15 mL). The combined aqueous fractions were extracted with chloroform (3×20 mL) and sequentially dried (MgSO$_4$), filtered, and purified by chromatography using a HORIZON HPFC system (silica cartridge, eluting with a gradient of 0-6% methanol in dichloromethane) to provide 237 mg of 4-amino-1-isobutyl-1H-imidazo[4,5-c]quinoline-8-carbaldehyde as an off-white solid. MS (ESI) m/z 269 (M+H)$^+$.

Part B

4-Amino-1-isobutyl-1H-imidazo[4,5-c]quinoline-8-carbaldehyde (237 mg, 0.66 mmol) and 3-methoxybenzylamine (100 mg, 1.3 mmol) were combined in methanol (25 mL) and dichloromethane (1 mL). The solution was purged with nitrogen gas and a 1M solution of sodium cyanoborohydride in THF (2 mL) was added. The reaction was stirred for 30 minutes. Additional sodium cyanoborohydride in THF (1M, 1 mL) was added and the reaction was stirred for an additional 15 minutes. Aqueous sodium carbonate (1%, 0.25 mL) was added and the reaction was stirred for 7 days. The solvent was removed under reduced pressure and approximately equal portions of chloroform and water were added. The fractions were separated and the organic fraction was sequentially dried (MgSO$_4$), filtered, and purified by chromatography using a HORIZON HPFC system (silica cartridge, eluting with a CMA:chloroform gradient, 0-20% CMA). Recrystallization from acetonitrile provided 25 mg of 1-isobutyl-8-{[(3-methoxybenzyl)amino]methyl}-1H-imidazo[4,5-c]quinolin-4-amine as an off-white solid, mp 125-126° C.

$^1$H NMR (500 MHz, DMSO-d$_6$) δ 8.15 (s, 1H), 7.92 (d, J=1.2 Hz, 1H), 7.57 (d, J=8.5 Hz, 1H), 7.41 (dd, J=8.5, 1.7 Hz, 1H), 7.22 (t, J=7.4 Hz, 1H), 6.95-6.92 (m, 2H), 6.79 (m, 1H), 6.46 (br s, 2H), 4.37 (d, J=7.3 Hz, 2H), 3.82 (s, 2H), 3.73 (s, 3H), 3.71 (s, 2H), 2.69 (br s, 1H), 2.18 (septet, J=6.8 Hz, 1H), 0.90 (d, J=6.6 Hz, 6H);

MS (ESI) m/z 390 (M+H)$^+$;

Anal. Calcd. for C$_{23}$H$_{27}$N$_5$O: C, 70.93; H, 6.99; N, 17.98. Found: C, 70.64; H, 6.92; N, 18.01.

Example 128

(2E)-3-[4-Amino-2-ethyl-1-(tetrahydro-2H-pyran-4-ylmethyl)-1H-imidazo[4,5-c]quinolin-7-yl]-N,N-dimethylprop-2-enamide

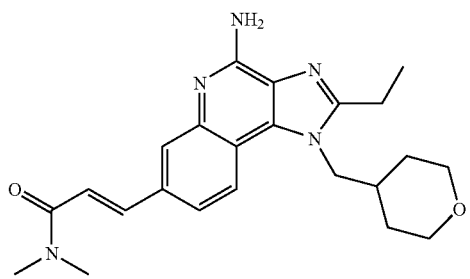 [SMILES: CCc1nc2c(N)nc3cc(/C=C/C(=O)N(C)C)ccc3c2n1CC1CCOCC1]

A thick walled glass vessel, equipped with a stir bar, was charged with a warmed solution of 7-bromo-2-ethyl-1-(tetrahydro-2H-pyran-4-ylmethyl)-1H-imidazo[4,5-c]quinolin-4-amine (0.58 g, 1.5 mmol) in N,N-dimethylformamide (10 mL). To the solution was added in succession, a solution of palladium acetate (37 mg, 0.15 mmol) and tri-ortho-tolylphosphine (91 mg, 0.3 mmol) in N,N-dimethylformamide (5 mL), triethylamine (3.0 eq. 0.6 mL), and a solution of N,N-dimethylacrylamide (178 mg, 1.8 mmol) in N,N-dimethylformamide (2 mL). The reaction mixture was purged with nitrogen. The vessel was sealed and heated at 120° C. for 18 hours. The reaction was cooled to ambient temperature and then concentrated to dryness under reduced pressure. The resulting solid was dissolved in dichloromethane (100 mL) and washed with saturated aqueous potassium carbonate (50 mL). The fractions were separated and the organic fraction was concentrated to dryness. The resulting off-white solid was purified by chromatography using a HORIZON HPFC system, (silica cartridge, 0-15% CMA/chloroform). A final recrystallization from acetonitrile provided 390 mg of (2E)-3-[4-amino-2-ethyl-1-(tetrahydro-2H-pyran-4-ylmethyl)-1H-imidazo[4,5-c]quinolin-7-yl]-N,N-dimethylprop-2-enamide as an off-white crystalline solid, mp>260° C.

$^1$H NMR (500 MHz, CDCl$_3$) δ 8.01 (d, J=8.5 Hz, 1H), 7.81 (d, J=1.6 Hz, 1H), 7.68 (dd, J=8.5, 1.9 Hz, 1H), 7.56 (d, J=15.1 Hz, 1H), 7.27 (d, J=15.4 Hz, 1H) 6.52 (s, 2H), 4.47-4.41 (m, 2H), 3.85-3.79 (m, 2H), 3.21-3.13 (m, 5H), 2.98-2.92 (m, 5H) 2.09 (s, 1H), 1.51-1.35 (m, 4H), 1.38 (t, J=7.6 Hz, 3H);

MS (APCI) m/z 408 (M+H)$^+$;

Anal. Calcd. for C$_{23}$H$_{29}$N$_5$O$_2$: C, 67.79; H, 7.17; N, 17.19. Found: C, 67.55; H, 7.10; N, 17.05.

Example 129

3-[4-Amino-2-ethyl-1-(tetrahydro-2H-pyran-4-ylmethyl)-1H-imidazo[4,5-c]quinolin-7-yl]-N,N-dimethylpropanamide

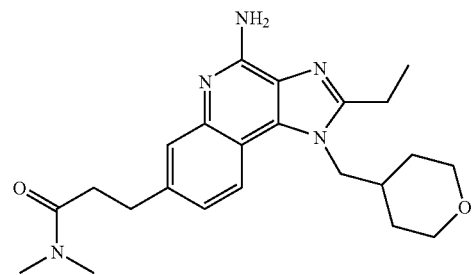 [SMILES: CCc1nc2c(N)nc3cc(CCC(=O)N(C)C)ccc3c2n1CC1CCOCC1]

A glass Parr bottle was charged with 10% palladium on carbon (0.1 g) wetted with ethanol (10 mL) and a slurry of (2E)-3-[4-amino-2-ethyl-1-(tetrahydro-2H-pyran-4-ylmethyl)-1H-imidazo[4,5-c]quinolin-7-yl]-N,N-dimethylprop-2-enamide (0.32 g, 0.78 mmol) in methanol (200 mL). The vessel was placed on Parr apparatus, evacuated and charged with hydrogen (55 psi). The mixture was shaken at ambient temperature for 48 hours. The reaction mixture was filtered through a 0.2 micron PTFE membrane filter and the filter was rinsed with methanol (100 mL). The filtrate was concentrated to dryness under reduced pressure. The resulting solid was recrystallized from acetonitrile to provide 220 mg of 3-[4-amino-2-ethyl-1-(tetrahydro-2H-pyran-4-ylmethyl)-1H-imidazo[4,5-c]quinolin-7-yl]-N,N-dimethylpropanamide as a white crystalline solid, mp 219-220° C.

$^1$H NMR (500 MHz, CDCl$_3$) δ 7.92 (d, J=8.4 Hz, 1H), 7.45 (d, J=1.6 Hz, 1H), 7.16 (dd, J=8.3, 1.6 Hz, 1H), 6.36 (s, 2H), 4.43-4.37 (m, 2H), 3.84-3.78 (m, 2H), 3.19-3.12 (m, 2H), 2.96 (s, 3H), 2.95-2.89 (m, 4H), 2.83 (s, 3H), 2.68 (t, J=8.2 Hz, 2H), 2.08 (s, 1H), 1.51-1.34 (m, 4H), 1.37 (t, J=7.6 Hz, 3H);

MS (APCI) m/z 410 (M+H)$^+$;

Anal. Calcd. for C$_{23}$H$_{31}$N$_5$O$_2$H$_2$O: C, 64.61; H, 7.78; N, 16.38. Found: C, 64.63; H, 7.51; N, 16.23.

Example 130

2-Ethyl-7-[(1E)-3-morpholin-4-yl-3-oxoprop-1-enyl]-1-(tetrahydro-2H-pyran-4-ylmethyl)-1H-imidazo[4,5-c]quinolin-4-amine

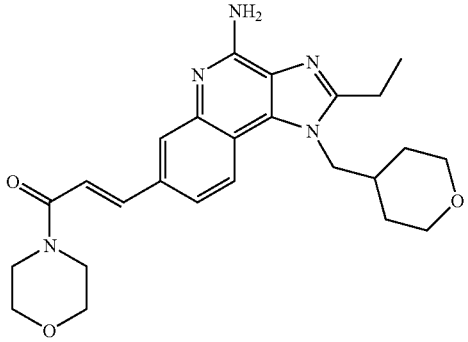 [SMILES: CCc1nc2c(N)nc3cc(/C=C/C(=O)N4CCOCC4)ccc3c2n1CC1CCOCC1]

A thick walled glass vessel, equipped with a stir bar, was charged with a warmed solution of 7-bromo-2-ethyl-1-(tetrahydro-2H-pyran-4-ylmethyl)-1H-imidazo[4,5-c]quinolin-4-amine (584 mg, 1.5 mmol) in N,N-dimethylformamide (10 mL). To the solution was added in succession, a solution of palladium acetate (37 mg, 0.15 mmol) and tri-ortho-tolylphosphine (91 mg, 0.3 mmol) in N,N-dimethylformamide (5 mL), triethylamine (0.6 mL), and a solution of 4-acryloylmorpholine (254 mg 1.8 mmol) in N,N-dimethylformamide (2 mL). The reaction mixture was purged with nitrogen. The vessel was sealed and heated at 120° C. for 18 hours. The reaction was cooled to ambient temperature and then concentrated to dryness under reduced pressure. The resulting solid was dissolved in dichloromethane (100 mL) and washed with saturated aqueous potassium carbonate (50 mL). The fractions were separated and the organic fraction was concentrated to dryness under reduced pressure. The resulting solid was purified by chromatography using a HORIZON HPFC system (silica cartridge, 0-15% CMA/chloroform). A final recrystallization from acetonitrile provided 345 mg of 2-ethyl-7-[(1E)-3-morpholin-4-yl-3-oxoprop-1-enyl]-1-(tetrahydro-2H-pyran-4-ylmethyl)-1H-imidazo[4,5-c]quinolin-4-amine as a white crystalline solid, mp>260° C.

$^1$H NMR (500 MHz, CDCl$_3$) δ 8.01 (d, J=8.5 Hz, 1H), 7.83 (d, J=1.6 Hz, 1H), 7.70 (dd, J=8.5, 1.6 Hz, 1H), 7.61 d, J=15.4, 1H), 7.32 (d, J=15.4 Hz, 1H), 6.52 (s, 2H), 4.47-4.42 (m, 2H), 3.84-3.78 (m, 2H), 3.78-3.72 (m, 2H) 3.65-3.55 (m, 6H) 3.19-3.11 (m, 2H), 2.95 (q, J=7.3 Hz, 2H), 2.08 (s, 1H), 1.52-1.36 (m, 4H), 1.38 (t, J=7.6 Hz, 3H);

MS (APCI) m/z 450 (M+H)$^+$.

Example 131

Ethyl (2E)-3-[4-amino-2-ethyl-1-(tetrahydro-2H-pyran-4-ylmethyl)-1H-imidazo[4,5-c]quinolin-7-yl]prop-2-enoate

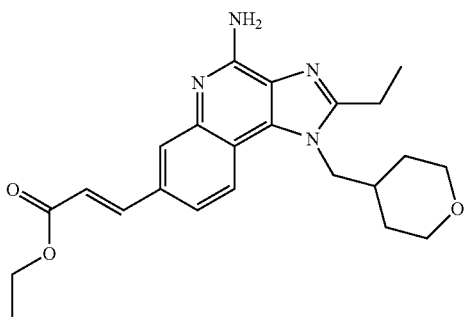 [SMILES: CCOC(=O)/C=C/c1ccc2c(c1)nc(N)c1nc(CC)n(CC3CCOCC3)c12]

A thick walled glass vessel, equipped with a stir bar, was charged with a warmed solution of 7-bromo-2-ethyl-1-(tetrahydro-2H-pyran-4-ylmethyl)-1H-imidazo[4,5-c]quinolin-4-amine (2.5 g, 6.42 mmol) in N,N-dimethylformamide (50 mL). To the solution was added in succession, a solution of palladium acetate (144 mg, 0.642 mmol) and tri-ortho-tolylphosphine (390 mg, 1.28 mmol) in N,N-dimethylformamide (5 mL), triethylamine (2.7 mL) and a solution of ethyl acrylate (0.77 g, 7.7 mmol) in N,N-dimethylformamide (2 mL). The reaction mixture was purged with nitrogen. The vessel was sealed and heated at 120° C. for 18 hours. The reaction was cooled to ambient temperature and then concentrated to dryness under reduced pressure. The resulting solid was dissolved in dichloromethane (150 mL) and washed with saturated aqueous potassium carbonate (100 mL). The fractions were separated and the organic fraction was concentrated to dryness under reduced pressure. The resulting off-white solid was purified by chromatography using a HORIZON HPFC system (silica cartridge, 0-15% CMA/chloroform). A final recrystallization from acetonitrile provided 1.9 g of ethyl (2E)-3-[4-amino-2-ethyl-1-(tetrahydro-2H-pyran-4-ylmethyl)-1H-imidazo[4,5-c]quinolin-7-yl]prop-2-enoate as an off-white crystalline solid, mp 209-210° C.

$^1$H NMR (500 MHz, CDCl$_3$) δ 8.04 (d, J=8.5 Hz, 1H), 7.84 (d, J=1.6 Hz, 1H), 7.77 (d, J=16.1 Hz, 1H), 7.64 (dd, J=8.5, 1.6 Hz, 1H), 6.67 (d, J=16.1 Hz, 1H), 6.62 (s, 2H), 4.48-4.41 (m, 2H), 4.25-4.18 (m, 2H) 3.85-3.78 (m, 2H) 3.20-3.13 (m, 2H), 2.95 (q, J=7.6 Hz, 2H), 2.12-2.05 (m, 1H), 1.51-1.38 (m, 4H), 1.38 (t, J=7.6 Hz, 3H), 1.28 (t, J=7.3 Hz, 3H);

MS (APCI) m/z 409 (M+H)$^+$;

Anal. Calcd. for C$_{23}$H$_{28}$N$_4$O$_3$: C, 67.63; H, 6.91; N, 13.72. Found: C, 67.58; H, 6.71; N, 13.98.

Example 132

Ethyl 3-[4-amino-2-ethyl-1-(tetrahydro-2H-pyran-4-ylmethyl)-1H-imidazo[4,5-c]quinolin-7-yl]propanoate

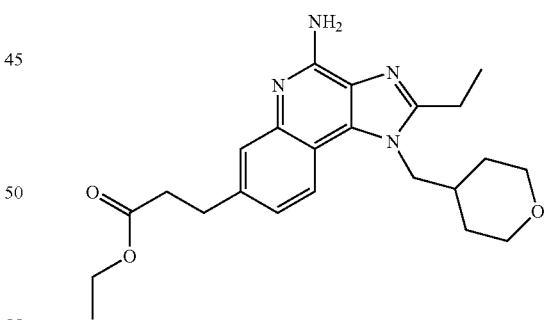

A glass Parr bottle was charged with 10% palladium on carbon (0.2 g) wetted with ethanol (10 mL) and a slurry of ethyl (2E)-3-[4-amino-2-ethyl-1-(tetrahydro-2H-pyran-4-ylmethyl)-1H-imidazo[4,5-c]quinolin-7-yl]prop-2-enoate (1.81 g, 4.4 mmol) in ethanol (250 mL). The vessel was placed on a Parr apparatus, evacuated and charged with hydrogen (55 psi). The mixture was shaken at ambient temperature for 48 hours. The reaction mixture was filtered through a 0.2 micron PTFE membrane filter and the filter was rinsed with ethanol (300 ml). The filtrate was concentrated to dryness under reduced pressure. Recrystallization from acetonitrile provided 1.51 g of ethyl 3-[4-amino-2-ethyl-1-(tetrahydro-2H-pyran-4-ylmethyl)-1H-imidazo[4,5-c]quinolin-7-yl]propanoate as a white crystalline solid, mp 172-173° C.

$^1$H NMR (500 MHz, CDCl$_3$) δ 7.93 (d, J=8.5 Hz, 1H), 7.44 (d, J=1.7 Hz, 1H), 7.14 (dd, J=8.5, 1.7 Hz, 1H), 6.40 (s, 2H), 4.43-4.37 (m, 2H), 4.08-4.02 (m, 2H), 3.84-3.78 (m, 2H), 3.18-3.11 (m, 2H), 2.98-2.90 (m, 4H), 2.69 (t, J=7.6 Hz, 2H), 2.07 (m, 1H), 1.50-1.34 (m, 4H), 1.37 (t, J=7.6 Hz, 3H), 1.15 (t, J=7.3 Hz, 3H);

$^{13}$C NMR (125 MHz, CDCl$_3$) δ 172.7, 154.6, 152.1, 145.4, 138.9, 132.9, 126.5, 125.7, 122.3, 120.4, 113.5, 67.0, 60.2, 50.1, 36.1, 35.3, 30.7, 30.0, 20.5, 14.5, 12.4;

MS (APCI) m/z 411 (M+H)$^+$;

Anal. Calcd. for C$_{23}$H$_{30}$N$_4$O$_3$: C, 67.29; H, 7.37; N, 13.65. Found: C, 67.25; H, 7.53; N, 13.71.

Example 133

4-Amino-2-(ethoxymethyl)-1-(2-hydroxy-2-methylpropyl)-1H-imidazo[4,5-c]quinoline-7-carbaldehyde

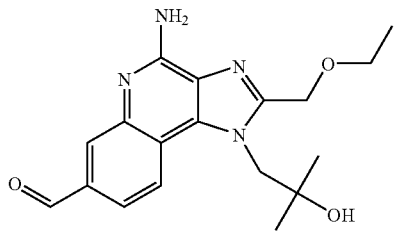 [SMILES: CCOCc1nc2c(N)nc3cc(C=O)ccc3c2n1CC(C)(C)O]

Part A

A round bottom flask, equipped with a stir bar, was charged with 1-[4-amino-7-bromo-2-(ethoxymethyl)-1H-imidazo[4,5-c]quinolin-1-yl]-2-methylpropan-2-ol (1.18 g, 3.0 mmol), 1-propanol (30 mL), potassium vinyltrifluoroborate (0.4 g, 3.0 mmol), triethylamine (1.25 mL, 9.0 mmol) and dichloro[1,1'-bis(diphenylphosphino)ferrocene]palladium (II) dichloromethane adduct (Pd(dppf)), (11 mg, 0.015 mmol). The reaction mixture was heated at 80° C. for 66 hours. The reaction mixture was cooled to ambient temperature and then concentrated to dryness under reduced pressure. The solid was dissolved in dichloromethane (100 mL) and washed with saturated aqueous potassium carbonate (50 mL). The fractions were separated and the organic fraction was concentrated to dryness. The off-white solid was purified by chromatography using a HORIZON HPFC system (silica cartridge, 0-15% CMA/chloroform). Recrystallization from acetonitrile provided 0.31 g of 1-[4-amino-2-(ethoxymethyl)-7-vinyl-1H-imidazo[4,5-c]quinolin-1-yl]-2-methylpropan-2-ol as an off-white crystalline solid. MS (APCI) m/z 341 (M+H)$^+$.

Part B

A round bottom flask was charged with 1-[4-amino-2-(ethoxymethyl)-7-vinyl-1H-imidazo[4,5-c]quinolin-1-yl]-2-methylpropan-2-ol (0.26 g, 0.76 mmol) and dichloromethane (100 mL). The resulting solution was cooled in a dry ice/acetone bath. Ozone was bubbled through the reaction mixture for 10 minutes. The reaction mixture was purged with oxygen for 5 minutes followed by a nitrogen purge for an additional 10 minutes. A solution of triphenylphosphine (0.4 g, 1.52 mmol) in dichloromethane (10 mL) was added in one portion. The dry ice/acetone bath was removed and the reaction mixture was allowed to warm to ambient temperature for 18 hours. The reaction mixture was concentrated to dryness under reduced pressure. The resulting solid was purified by chromatography using a HORIZON HPFC system (silica cartridge, 0-15% CMA/chloroform). A final recrystallization from acetonitrile provided 30 mg of 4-amino-2-(ethoxymethyl)-1-(2-hydroxy-2-methylpropyl)-1H-imidazo[4,5-c]quinoline-7-carbaldehyde as an off-white crystalline solid, mp 203-205° C.

$^1$H NMR (500 MHz, CDCl$_3$) δ 10.09 (s, 1H), 8.47 (d, J=8.5 Hz, 1H), 8.11 (d, J=1.6 Hz, 1H), 7.64 (dd, J=8.5, 1.6 Hz, 1H), 6.85 (s, 2H), 4.92-4.85 (m, 2H), 4.89 (s, 1H), 4.71 (s, 2H) 3.53 (q, J=7.1 Hz, 2H), 1.18 (br s, 6H), 1.14 (t, J=6.9 Hz, 3H);

MS (APCI) m/z 343 (M+H)$^+$;

Anal. Calcd. for C$_{18}$H$_{22}$N$_4$O$_3$: C, 63.14; H, 6.48; N, 16.36. Found: C, 63.13; H, 6.46; N, 16.40.

Example 134

3-[4-Amino-2-(ethoxymethyl)-1-(2-hydroxy-2-methylpropyl)-1H-imidazo[4,5-c]quinolin-7-yl]propan-1-ol

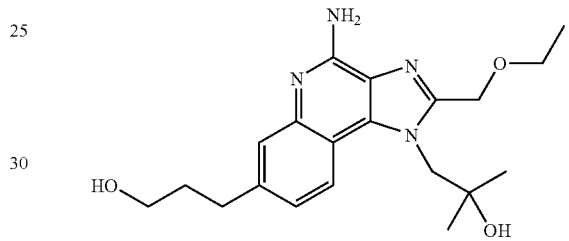

A round bottom flask, equipped with a stir bar, was charged with ethyl 3-[4-amino-2-(ethoxymethyl)-1-(2-hydroxy-2-methylpropyl)-1H-imidazo[4,5-c]quinolin-7-yl]propanoate (1.0 g, 2.4 mmol) and anhydrous tetrahydrofuran (20 mL). The reaction mixture was cooled in an ice bath. Lithium aluminum hydride (92 mg, 2.4 mmol) was added in one portion. After 2 hours additional lithium aluminum hydride (92 mg, 2.4 mmol) was added in one portion. The ice bath was removed and the reaction mixture was allowed to warm to ambient temperature. The reaction was quenched by successive dropwise addition of water (1 mL), 10% sodium hydroxide solution (1 mL) and water (3 mL). The reaction mixture was maintained at ambient temperature for 18 hours and then diluted with diethyl ether and water. The fractions were separated and the aqueous fraction was extracted with diethyl ether (3×25 mL). All of the organic fractions were combined and then concentrated to dryness under reduced pressure. Purification by chromatography using a HORIZON HPFC system (silica cartridge, 0-20% CMA/chloroform) provided 0.8 g of 3-[4-amino-2-(ethoxymethyl)-1-(2-hydroxy-2-methylpropyl)-1H-imidazo[4,5-c]quinolin-7-yl]propan-1-ol as a white crystalline solid, mp 177-178° C.

$^1$H NMR (500 MHz, CDCl$_3$) δ 8.21 (d, J=8.5 Hz, 1H), 7.45 (s, 1H), 7.12 (d, J=8.5 Hz, 1H), 6.54 (s, 2H), 4.97 (br s, 2H), 4.94 (s, 1H), 4.71 (br s, 2H), 4.54 (t, J=5.2 Hz, 1H), 3.56 (q, J=6.9 Hz, 2H), 3.51 (q, J=6.3 Hz, 2H), 2.76 (t, J=7.7 Hz, 2H), 1.88-1.81 (m, 2H), 1.29-1.20 (m, 6H), 1.19 (t, J=7.1 Hz, 3H)

$^{13}$C NMR (125 MHz, DMSO-d$_6$) δ 152.3, 150.8, 145.9, 140.8, 134.6, 126.1, 125.6, 121.9, 121.5, 113.6, 71.0 65.6, 65.3, 60.6, 55.2, 34.5, 32.0, 28.1, 15.4 MS (APCI) m/z 373 (M+H)$^+$;

Anal. calcd for C$_{20}$H$_{28}$N$_4$O$_3$·0.3H$_2$O: C, 63.57; H, 7.63; N, 14.83. Found: C, 63.71; H, 7.32; N, 14.88.

Example 135

1-[4-Amino-2-(ethoxymethyl)-7-(3-morpholin-4-ylpropyl)-1H-imidazo[4,5-c]quinolin-1-yl]-2-methylpropan-2-ol

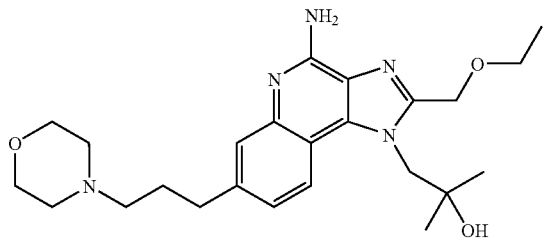 [SMILES: CCOCc1nc2c(N)nc3cc(CCCN4CCOCC4)ccc3c2n1CC(C)(C)O]

Part A

A stirred solution of 3-[4-amino-2-(ethoxymethyl)-1-(2-hydroxy-2-methylpropyl)-1H-imidazo[4,5-c]quinolin-7-yl]propan-1-ol (0.39 g, 1.05 mmol) in pyridine (10 mL) was cooled in an ice bath. 4-Dimethylaminopyridine (12.8 mg, 0.105 mmol) and methanesulfonic anhydride (204 mg, 1.15 mmol) were added. After stirring for one hour, the reaction was not complete and additional methanesulfonic anhydride was added (204 mg, 1.15 mmol). After another 2 hours of stirring the reaction was still incomplete and additional methanesulfonic anhydride was added (204 mg, 1.15 mmol). The cooling bath was removed and the reaction was stirred for 18 hours. The reaction mixture was concentrated to dryness under reduced pressure. The resulting solid was dissolved in dichloromethane (100 mL) and washed with saturated aqueous potassium carbonate (25 mL). The fractions were separated and the organic fraction was concentrated to provide 0.3 g of 3-[4-amino-2-(ethoxymethyl)-1-(2-hydroxy-2-methylpropyl)-1H-imidazo[4,5-c]quinolin-7-yl]propyl methanesulfonate as a pale gold solid. MS (APCI) m/z 451 (M+H)$^+$.

Part B

A round bottom flask, equipped with a stir bar, was charged with 3-[4-amino-2-(ethoxymethyl)-1-(2-hydroxy-2-methylpropyl)-1H-imidazo[4,5-c]quinolin-7-yl]propyl methanesulfonate (0.24 g, 0.53 mmol) and acetonitrile (10 mL). Morpholine (0.23 g, 2.7 mmol) was added in one portion. The reaction mixture was heated at 75° C. for 18 hours and then cooled to ambient temperature. After concentrating under reduced pressure, the resulting solid was dissolved in dichloromethane (50 mL) and washed with saturated aqueous potassium carbonate (50 mL). The fractions were separated and the organic fraction was concentrated to dryness. The solid was purified by chromatography using a HORIZON HPFC system (silica cartridge, 0-25% CMA/chloroform). The material was further purified by a second chromatography treatment using a HORIZON HPFC system (silica cartridge, 10% methanol/dichloromethane). A final recrystallization from acetonitrile provided 0.1 g of 1-[4-amino-2-(ethoxymethyl)-7-(3-morpholin-4-ylpropyl)-1H-imidazo[4,5-c]quinolin-1-yl]-2-methylpropan-2-ol as a white crystalline solid, mp 132-133° C.

$^1$H NMR (500 MHz, DMSO-d$_6$) δ 8.16 (d, J=8.5 Hz, 1H), 7.39 (d, J=1.6 Hz, 1H), 7.07 (dd, J=8.4, 1.7 Hz, 1H), 6.48 (br s, 2H), 4.89 (br s, 2H), 4.87 (s, 1H), 4.65 (br s, 2H), 3.59-3.55 (m, 4H), 3.50 (q, J=4.7 Hz, 2H), 2.69 (t, J=7.3 Hz, 2H), 2.36-2.30 (m, 4H) 2.30 (t, J=7.3 Hz, 2H) 1.82-1.75 (m, 2H), 1.25-1.13 (m, 6H), 1.13 (t, J=7.3 Hz, 3H);

MS (APCI) m/z 442 (M+H)$^+$;

Anal. calcd for $C_{24}H_{35}N_5O_3 \cdot 0.3H_2O$: C, 64.49; H, 8.03; N, 15.67. Found: C, 64.26; H, 8.16; N, 15.69.

Exemplary Compounds

Certain exemplary compounds, including some of those described above in the Examples, have the following Formulas (IIc, IId, IIe, or IIf) and the following $R_1$ and $R_2$ substituents, wherein each line of the table is matched with Formula IIc, IId, IIe, or IIf to represent a specific embodiment of the invention.

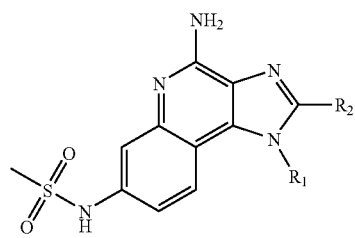
IIc

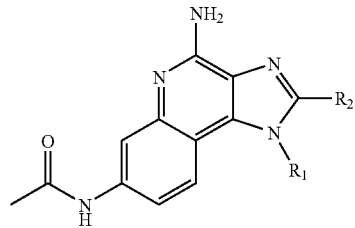
IId

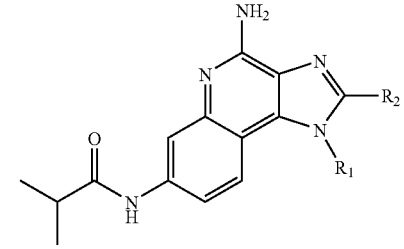
IIe

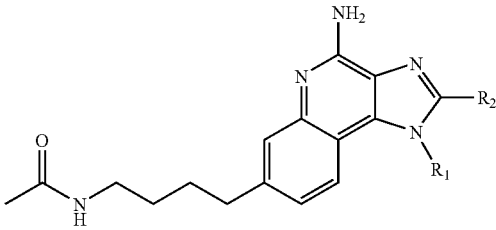
IIf

| $R_1$ | $R_2$ |
|---|---|
| 2-methylpropyl | methyl |
| 2-hydroxy-2-methylpropyl | methyl |
| tetrahydro-2H-pyran-4-ylmethyl | methyl |
| 3-isopropoxypropyl | methyl |
| 2-methylpropyl | ethyl |
| 2-hydroxy-2-methylpropyl | ethyl |
| tetrahydro-2H-pyran-4-ylmethyl | ethyl |
| 3-isopropoxypropyl | ethyl |
| 2-methylpropyl | n-propyl |
| 2-hydroxy-2-methylpropyl | n-propyl |
| tetrahydro-2H-pyran-4-ylmethyl | n-propyl |
| 3-isopropoxypropyl | n-propyl |
| 2-methylpropyl | n-butyl |
| 2-hydroxy-2-methylpropyl | n-butyl |
| tetrahydro-2H-pyran-4-ylmethyl | n-butyl |
| 3-isopropoxypropyl | n-butyl |

-continued

| | |
|---|---|
| 2-methylpropyl | 2-methoxyethyl |
| 2-hydroxy-2-methylpropyl | 2-methoxyethyl |
| tetrahydro-2H-pyran-4-ylmethyl | 2-methoxyethyl |
| 3-isopropoxypropyl | 2-methoxyethyl |
| 2-methylpropyl | ethoxymethyl |
| 2-hydroxy-2-methylpropyl | ethoxymethyl |
| tetrahydro-2H-pyran-4-ylmethyl | ethoxymethyl |
| 3-isopropoxypropyl | ethoxymethyl |
| 2-methylpropyl | 2-hydroxyethyl |
| 2-hydroxy-2-methylpropyl | 2-hydroxyethyl |
| tetrahydro-2H-pyran-4-ylmethyl | 2-hydroxyethyl |
| 3-isopropoxypropyl | 2-hydroxyethyl |
| 2-methylpropyl | hydroxymethyl |
| 2-hydroxy-2-methylpropyl | hydroxymethyl |
| tetrahydro-2H-pyran-4-ylmethyl | hydroxymethyl |
| 3-isopropoxypropyl | hydroxymethyl |
| 2-methylpropyl | methoxymethyl |
| 2-hydroxy-2-methylpropyl | methoxymethyl |
| tetrahydro-2H-pyran-4-ylmethyl | methoxymethyl |
| 3-isopropoxypropyl | methoxymethyl |

Certain exemplary compounds, including some of those described above in the Examples, have the following Formulas (IIi, IIj, IIk, IIm, IIn, IIo, IIp, IIq, IIr, or IIs) and the following $R_1$ and $R_2$ substituents, wherein each line of the table is matched with Formula IIi, IIj, IIk, IIm, IIn, IIo, IIp, IIq, IIr, or IIs to represent a specific embodiment of the invention.

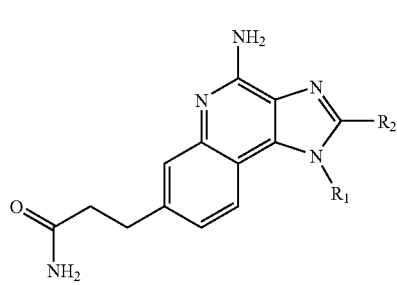

IIi

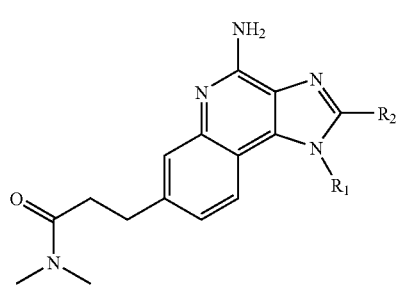

IIj

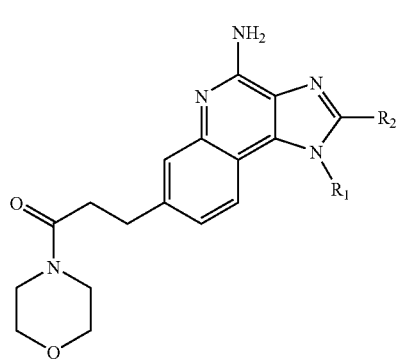

IIk

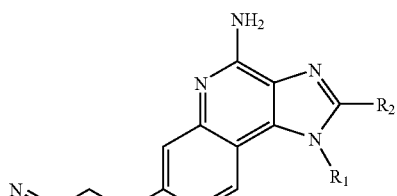

IIm

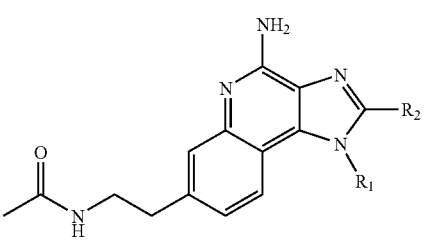

IIn

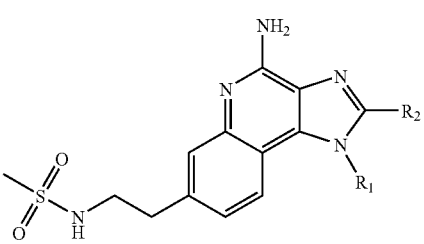

IIo

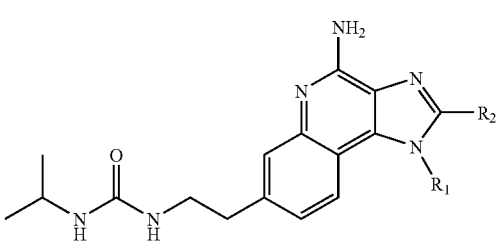

IIp

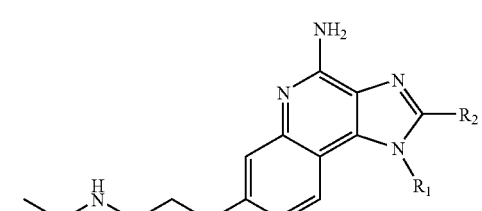

IIq

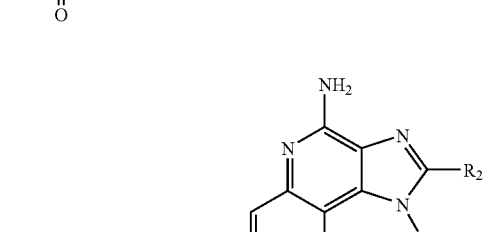

IIr

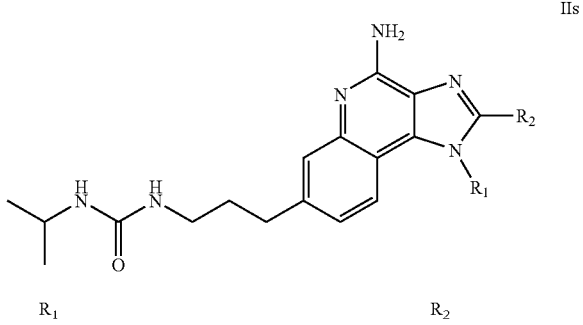

IIs

| R₁ | R₂ |
|---|---|
| 2-methylpropyl | hydrogen |
| 2-methylpropyl | methyl |
| 2-methylpropyl | ethyl |
| 2-methylpropyl | n-propyl |
| 2-methylpropyl | n-butyl |
| 2-methylpropyl | hydroxymethyl |
| 2-methylpropyl | 2-hydroxyethyl |
| 2-methylpropyl | methoxymethyl |
| 2-methylpropyl | ethoxymethyl |
| 2-methylpropyl | 2-methoxyethyl |
| 2-hydroxy-2-methylpropyl | hydrogen |
| 2-hydroxy-2-methylpropyl | methyl |
| 2-hydroxy-2-methylpropyl | ethyl |
| 2-hydroxy-2-methylpropyl | n-propyl |
| 2-hydroxy-2-methylpropyl | n-butyl |
| 2-hydroxy-2-methylpropyl | hydroxymethyl |
| 2-hydroxy-2-methylpropyl | 2-hydroxyethyl |
| 2-hydroxy-2-methylpropyl | methoxymethyl |
| 2-hydroxy-2-methylpropyl | ethoxymethyl |
| 2-hydroxy-2-methylpropyl | 2-methoxyethyl |
| tetrahydro-2H-pyran-4-ylmethyl | hydrogen |
| tetrahydro-2H-pyran-4-ylmethyl | methyl |
| tetrahydro-2H-pyran-4-ylmethyl | ethyl |
| tetrahydro-2H-pyran-4-ylmethyl | n-propyl |
| tetrahydro-2H-pyran-4-ylmethyl | n-butyl |
| tetrahydro-2H-pyran-4-ylmethyl | hydroxymethyl |
| tetrahydro-2H-pyran-4-ylmethyl | 2-hydroxyethyl |
| tetrahydro-2H-pyran-4-ylmethyl | methoxymethyl |
| tetrahydro-2H-pyran-4-ylmethyl | ethoxymethyl |
| tetrahydro-2H-pyran-4-ylmethyl | 2-methoxyethyl |
| 2-methyl-2-[(methylsulfonyl)amino]propyl | hydrogen |
| 2-methyl-2-[(methylsulfonyl)amino]propyl | methyl |
| 2-methyl-2-[(methylsulfonyl)amino]propyl | ethyl |
| 2-methyl-2-[(methylsulfonyl)amino]propyl | n-propyl |
| 2-methyl-2-[(methylsulfonyl)amino]propyl | n-butyl |
| 2-methyl-2-[(methylsulfonyl)amino]propyl | hydroxymethyl |
| 2-methyl-2-[(methylsulfonyl)amino]propyl | 2-hydroxyethyl |
| 2-methyl-2-[(methylsulfonyl)amino]propyl | methoxymethyl |
| 2-methyl-2-[(methylsulfonyl)amino]propyl | ethoxymethyl |
| 2-methyl-2-[(methylsulfonyl)amino]propyl | 2-methoxyethyl |
| 2-[(methylsulfonyl)amino]ethyl | hydrogen |
| 2-[(methylsulfonyl)amino]ethyl | methyl |
| 2-[(methylsulfonyl)amino]ethyl | ethyl |
| 2-[(methylsulfonyl)amino]ethyl | n-propyl |
| 2-[(methylsulfonyl)amino]ethyl | n-butyl |
| 2-[(methylsulfonyl)amino]ethyl | hydroxymethyl |
| 2-[(methylsulfonyl)amino]ethyl | 2-hydroxyethyl |
| 2-[(methylsulfonyl)amino]ethyl | methoxymethyl |
| 2-[(methylsulfonyl)amino]ethyl | ethoxymethyl |
| 2-[(methylsulfonyl)amino]ethyl | 2-methoxyethyl |
| 4-[(methylsulfonyl)amino]butyl | hydrogen |
| 4-[(methylsulfonyl)amino]butyl | methyl |
| 4-[(methylsulfonyl)amino]butyl | ethyl |
| 4-[(methylsulfonyl)amino]butyl | n-propyl |
| 4-[(methylsulfonyl)amino]butyl | n-butyl |
| 4-[(methylsulfonyl)amino]butyl | hydroxymethyl |
| 4-[(methylsulfonyl)amino]butyl | 2-hydroxyethyl |
| 4-[(methylsulfonyl)amino]butyl | methoxymethyl |
| 4-[(methylsulfonyl)amino]butyl | ethoxymethyl |
| 4-[(methylsulfonyl)amino]butyl | 2-methoxyethyl |
| 2-{[(isopropylamino)carbonyl]amino}ethyl | hydrogen |
| 2-{[(isopropylamino)carbonyl]amino}ethyl | methyl |
| 2-{[(isopropylamino)carbonyl]amino}ethyl | ethyl |
| 2-{[(isopropylamino)carbonyl]amino}ethyl | n-propyl |
| 2-{[(isopropylamino)carbonyl]amino}ethyl | n-butyl |
| 2-{[(isopropylamino)carbonyl]amino}ethyl | hydroxymethyl |
| 2-{[(isopropylamino)carbonyl]amino}ethyl | 2-hydroxyethyl |
| 2-{[(isopropylamino)carbonyl]amino}ethyl | methoxymethyl |
| 2-{[(isopropylamino)carbonyl]amino}ethyl | ethoxymethyl |
| 2-{[(isopropylamino)carbonyl]amino}ethyl | 2-methoxyethyl |
| 2-(1,1-dioxidoisothiazolidin-2-yl)ethyl | hydrogen |
| 2-(1,1-dioxidoisothiazolidin-2-yl)ethyl | methyl |
| 2-(1,1-dioxidoisothiazolidin-2-yl)ethyl | ethyl |
| 2-(1,1-dioxidoisothiazolidin-2-yl)ethyl | n-propyl |
| 2-(1,1-dioxidoisothiazolidin-2-yl)ethyl | n-butyl |
| 2-(1,1-dioxidoisothiazolidin-2-yl)ethyl | hydroxymethyl |
| 2-(1,1-dioxidoisothiazolidin-2-yl)ethyl | 2-hydroxyethyl |
| 2-(1,1-dioxidoisothiazolidin-2-yl)ethyl | methoxymethyl |
| 2-(1,1-dioxidoisothiazolidin-2-yl)ethyl | ethoxymethyl |
| 2-(1,1-dioxidoisothiazolidin-2-yl)ethyl | 2-methoxyethyl |

Certain exemplary compounds, including some of those described above in the Examples, have the following Formula IIt and the following $R_2$ and $R_3$ substituents, wherein each line of the table is matched with Formula IIt to represent a specific embodiment of the invention.

IIt

| R₂ | R₃ |
|---|---|
| hydrogen | 2-(acetylamino)ethyl |
| methyl | 2-(acetylamino)ethyl |
| ethyl | 2-(acetylamino)ethyl |
| n-propyl | 2-(acetylamino)ethyl |
| n-butyl | 2-(acetylamino)ethyl |
| hydroxymethyl | 2-(acetylamino)ethyl |
| 2-hydroxyethyl | 2-(acetylamino)ethyl |
| methoxymethyl | 2-(acetylamino)ethyl |
| ethoxymethyl | 2-(acetylamino)ethyl |
| 2-methoxyethyl | 2-(acetylamino)ethyl |
| hydrogen | 2-[(methylsulfonyl)amino]ethyl |
| methyl | 2-[(methylsulfonyl)amino]ethyl |
| ethyl | 2-[(methylsulfonyl)amino]ethyl |
| n-propyl | 2-[(methylsulfonyl)amino]ethyl |
| n-butyl | 2-[(methylsulfonyl)amino]ethyl |
| hydroxymethyl | 2-[(methylsulfonyl)amino]ethyl |
| 2-hydroxyethyl | 2-[(methylsulfonyl)amino]ethyl |
| methoxymethyl | 2-[(methylsulfonyl)amino]ethyl |
| ethoxymethyl | 2-[(methylsulfonyl)amino]ethyl |
| 2-methoxyethyl | 2-[(methylsulfonyl)amino]ethyl |
| hydrogen | 2-{[(isopropylamino)carbonyl]amino}ethyl |
| methyl | 2-{[(isopropylamino)carbonyl]amino}ethyl |
| ethyl | 2-{[(isopropylamino)carbonyl]amino}ethyl |
| n-propyl | 2-{[(isopropylamino)carbonyl]amino}ethyl |
| n-butyl | 2-{[(isopropylamino)carbonyl]amino}ethyl |
| hydroxymethyl | 2-{[(isopropylamino)carbonyl]amino}ethyl |
| 2-hydroxyethyl | 2-{[(isopropylamino)carbonyl]amino}ethyl |
| methoxymethyl | 2-{[(isopropylamino)carbonyl]amino}ethyl |
| ethoxymethyl | 2-{[(isopropylamino)carbonyl]amino}ethyl |
| 2-methoxyethyl | 2-{[(isopropylamino)carbonyl]amino}ethyl |
| hydrogen | 2-(benzoylamino)ethyl |
| methyl | 2-(benzoylamino)ethyl |
| ethyl | 2-(benzoylamino)ethyl |

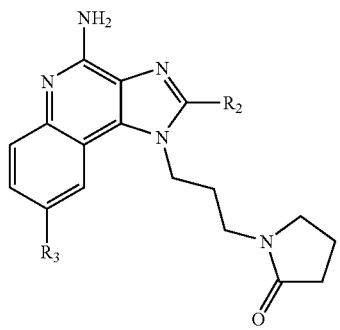

IIt

| $R_2$ | $R_3$ |
|---|---|
| n-propyl | 2-(benzoylamino)ethyl |
| n-butyl | 2-(benzoylamino)ethyl |
| hydroxymethyl | 2-(benzoylamino)ethyl |
| 2-hydroxyethyl | 2-(benzoylamino)ethyl |
| methoxymethyl | 2-(benzoylamino)ethyl |
| ethoxymethyl | 2-(benzoylamino)ethyl |
| 2-methoxyethyl | 2-(benzoylamino)ethyl |
| hydrogen | 2-cyanoethyl |
| methyl | 2-cyanoethyl |
| ethyl | 2-cyanoethyl |
| n-propyl | 2-cyanoethyl |
| n-butyl | 2-cyanoethyl |
| hydroxymethyl | 2-cyanoethyl |
| 2-hydroxyethyl | 2-cyanoethyl |
| methoxymethyl | 2-cyanoethyl |
| ethoxymethyl | 2-cyanoethyl |
| 2-methoxyethyl | 2-cyanoethyl |
| hydrogen | 2-(aminocarbonyl)ethyl |
| methyl | 2-(aminocarbonyl)ethyl |
| ethyl | 2-(aminocarbonyl)ethyl |
| n-propyl | 2-(aminocarbonyl)ethyl |
| n-butyl | 2-(aminocarbonyl)ethyl |
| hydroxymethyl | 2-(aminocarbonyl)ethyl |
| 2-hydroxyethyl | 2-(aminocarbonyl)ethyl |
| methoxymethyl | 2-(aminocarbonyl)ethyl |
| ethoxymethyl | 2-(aminocarbonyl)ethyl |
| 2-methoxyethyl | 2-(aminocarbonyl)ethyl |
| hydrogen | 2-[(pyridin-3-ylcarbonyl)amino]ethyl |
| methyl | 2-[(pyridin-3-ylcarbonyl)amino]ethyl |
| ethyl | 2-[(pyridin-3-ylcarbonyl)amino]ethyl |
| n-propyl | 2-[(pyridin-3-ylcarbonyl)amino]ethyl |
| n-butyl | 2-[(pyridin-3-ylcarbonyl)amino]ethyl |
| hydroxymethyl | 2-[(pyridin-3-ylcarbonyl)amino]ethyl |
| 2-hydroxyethyl | 2-[(pyridin-3-ylcarbonyl)amino]ethyl |
| methoxymethyl | 2-[(pyridin-3-ylcarbonyl)amino]ethyl |
| ethoxymethyl | 2-[(pyridin-3-ylcarbonyl)amino]ethyl |
| 2-methoxyethyl | 2-[(pyridin-3-ylcarbonyl)amino]ethyl |

Compounds of the invention have been found to modulate cytokine biosynthesis by inducing the production of interferon α and/or tumor necrosis factor α in human cells when tested using one of the methods described below.

Cytokine Induction in Human Cells

An in vitro human blood cell system is used to assess cytokine induction. Activity is based on the measurement of interferon (α) and tumor necrosis factor (α) (IFN-α and TNF-α, respectively) secreted into culture media as described by Testerman et. al. in "Cytokine Induction by the Immunomodulators Imiquimod and S-27609", *Journal of Leukocyte Biology,* 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 μM. Controls include cell samples with media only, cell samples with DMSO only (no compound), and cell samples with reference compound.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (usually 30-0.014 μM). The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multisubtype colorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (1 molar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

Cytokine Induction in Human Cells

High Throughput Screen

The CYTOKINE INDUCTION IN HUMAN CELLS test method described above was modified as follows for high throughput screening.

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete (2-fold the final cell density). The PBMC suspension is added to 96-well flat bottom sterile tissue culture plates.

Compound Preparation

The compounds are solubilized in dimethyl sulfoxide (DMSO). The compounds are generally tested at concentrations ranging from 30-0.014 μM. Controls include cell samples with media only, cell samples with DMSO only (no compound), and cell samples with a reference compound 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) on each plate. The solution of test compound is added at 7.5 mM to the first well of a dosing plate and serial 3 fold dilutions are made for the 7 subsequent concentrations in DMSO. RPMI Complete media is then added to the test compound dilutions in order to reach a final compound concentration of 2-fold higher (60-0.028 μM) than the final tested concentration range.

Incubation

Compound solution is then added to the wells containing the PBMC suspension bringing the test compound concentrations to the desired range (usually 30-0.014 μM) and the DMSO concentration to 0.4%. The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200 g) at 4° C. 4-plex Human Panel MSD MULTI-SPOT 96-well plates are pre-coated with the appropriate capture antibodies by MesoScale Discovery, Inc. (MSD, Gaithersburg, Md.). The cell-free culture supernatants are removed and transferred to the MSD plates. Fresh samples are typically tested, although they may be maintained at −30 to −70° C. until analysis.

Interferon-α and Tumor Necrosis Factor-α Analysis

MSD MULTI-SPOT plates contain within each well capture antibodies for human TNF-α and human IFN-α that have been pre-coated on specific spots. Each well contains four spots: one human TNF-α capture antibody (MSD) spot, one human IFN-α a capture antibody (PBL Biomedical Laboratories, Piscataway, N.J.) spot, and two inactive bovine serum albumin spots. The human TNF-α capture and detection antibody pair is from MesoScale Discovery. The human IFN-α multi-subtype antibody (PBL Biomedical Laboratories) captures all IFN-α subtypes except IFN-α F (IFNA21). Standards consist of recombinant human TNF-α (R&D Systems, Minneapolis, Minn.) and IFN-α (PBL Biomedical Laboratories). Samples and separate standards are added at the time of analysis to each MSD plate. Two human IFN-α detection antibodies (Cat. Nos. 21112 & 21100, PBL) are used in a two to one ratio (weight:weight) to each other to determine the IFN-α concentrations. The cytokine-specific detection antibodies are labeled with the SULFO-TAG reagent (MSD). After adding the SULFO-TAG labeled detection antibodies to the wells, each well's electrochemoluminescent levels are read using MSD's SECTOR HTS READER. Results are expressed in pg/mL upon calculation with known cytokine standards.

Assay Data and Analysis

In total, the data output of the assay consists of concentration values of TNF-α or IFN-α (y-axis) as a function of compound concentration (x-axis).

A plate-wise scaling is performed within a given experiment aimed at reducing plate-to-plate variability associated within the same experiment. First, the greater of the median DMSO (DMSO control wells) or the experimental background (usually 20 pg/mL for IFN-α and 40 pg/mL for TNF-α) is subtracted from each reading. Negative values that may result from background subtraction are set to zero. Each plate within a given experiment has a reference compound that serves as a control. This control is used to calculate a median expected area under the curve across all plates in the assay. A plate-wise scaling factor is calculated for each plate as a ratio of the area of the reference compound on the particular plate to the median expected area for the entire experiment. The data from each plate are then multiplied by the plate-wise scaling factor for all plates. Only data from plates bearing a scaling factor of between 0.5 and 2.0 (for both cytokines IFN-α, TNF-α) are reported. Data from plates with scaling factors outside the above mentioned interval are retested until they bear scaling factors inside the above mentioned interval. The above method produces a scaling of the y-values without altering the shape of the curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91). The median expected area is the median area across all plates that are part of a given experiment.

A second scaling may also be performed to reduce inter-experiment variability (across multiple experiments). All background-subtracted values are multiplied by a single adjustment ratio to decrease experiment-to-experiment variability. The adjustment ratio is the area of the reference compound in the new experiment divided by the expected area of the reference compound based on an average of previous experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α- dimethyl-1H-imidazo[4,5-c]quinolin-1-yl]ethanol hydrate (U.S. Pat. No. 5,352,784; Example 91) and the expected area is the sum of the median dose values from an average of previous experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the Formula II:

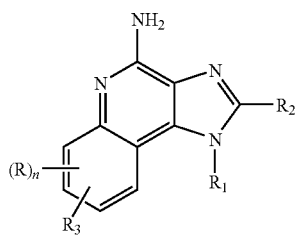

II wherein:
$R_3$ is selected from the group consisting of:
-Z-Y-$R_4$, and
-Z-$R_5$;
R is selected from the group consisting of alkyl, alkoxy, hydroxy, halogen, and trifluoromethyl;
n is 0 or 1;
$R_1$ is selected from the group consisting of alkyl, alkoxyalkylenyl, dihydroxyalkylenyl, hydroxyalkylenyl, and alkyl substituted by a group selected from the group consisting of —NH—C(O)-alkyl, —NH—S(O)$_2$-alkyl, —NH—C(O)—NH-alkyl, tetrahydropyranyl, phenoxy, 1,1-dioxidoisothiazolidin-2-yl, and 2-oxo-pyrroldin-1-yl;:
$R_2$ is selected from the group consisting of hydrogen, alkyl, alkoxyalkylenyl, and hydroxyalkylenyl;
Z is selected from the group consisting of a bond, and alkylene;
Y is selected from the group consisting of:
—S(O)$_{0-2}$—,
—S(O)$_2$—N($R_8$)—,
—C($R_6$)—,
—N($R_8$)-Q-,
—C($R_6$)—N($R_8$)—, and
—O—C($R_6$)—N($R_8$)—,
$R_4$ is selected from the group consisting of hydrogen, alkyl, and heterocyclyl wherein the alkyl, and heterocyclyl groups can be unsubstituted or substituted by one or more substituents independently selected from the group consisting of alkyl, alkoxy, hydroxyalkyl, haloalkyl, haloalkoxy, halogen, hydroxy, amino, alkylamino, dialkylamino, and in the case of alkyl, and heterocyclyl, oxo;
$R_5$ is selected from the group consisting of:

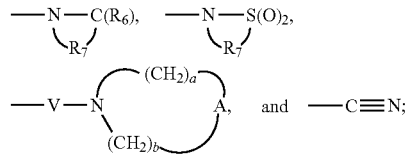

$R_6$ is =O;
$R_7$ is $C_{2-7}$ alkylene;
$R_8$ is selected from the group consisting of hydrogen, alkyl, alkoxyalkylenyl, and hydroxyalkylenyl;
A is selected from the group consisting of —O—, —CH$_2$—, —C(O)—, —S(O)$_{0-2}$—, and —N($R_4$)—;
Q is selected from the group consisting of a bond, —C($R_6$)—, —S(O)$_2$—, —C($R_6$)—N($R_8$)—W—, —S(O)$_2$—N($R_8$)—, —C($R_6$)—O—, and
V is selected from the group consisting of —C($R_6$)—, —O—C($R_6$)—, —N($R_8$)—C($R_6$)—, and —S(O)$_2$—;
W is a bond; and
a and b are independently integers from 1 to 6 with the proviso that a+b is ≤7;
with the proviso that when $R_3$ is -Z-Y-$R_4$ and Z is a bond, then Y is selected from the group consisting of —N($R_8$)-Q-, S(O)$_{0-2}$, and —C($R_6$)— wherein Q is selected from the group consisting of —C($R_6$)—, S(O)$_2$—, —C($R_6$)—N($R_8$)—W—; and
with the further proviso that when $R_3$ is -Z-$R_5$, then Z is alkylene or alkenylene;
or a pharmaceutically acceptable salt thereof.

2. The compound or salt of claim 1 wherein n is 0.
3. The compound or salt of claim 1 wherein $R_3$ is -Z-Y-$R_4$.
4. The compound or salt of claim 3 wherein Y is —N($R_8$)-Q-, and $R_4$ is alkyl, or heterocyclyl.
5. The compound or salt of claim 1 wherein Z is $C_{1-4}$ alkylene.
6. The compound or salt of claim 1 wherein $R_3$ is at the 7-position.
7. A pharmaceutical composition comprising a therapeutically effective amount of a compound or salt of claim 1 and a pharmaceutically acceptable carrier.
8. The compound or salt of claim 1 wherein $R_1$ is selected from the group consisting of 2-hydroxy-2-methylpropyl, 2-methylpropyl, propyl, ethyl, methyl, 2,3-dihydroxypropyl, 3-isopropoxypropyl, 2-phenoxyethyl, 4-[(methylsulfonyl)amino]butyl, 2-methyl-2-[(methylsulfonyl)amino]propyl, 2-(acetylamino)-2-methylpropyl, 2-{[(isopropylamino)carbonyl]amino}-2-methylpropyl, 4-{[(isopropylamino)carbonyl]amino}butyl, 4-(1,1-dioxidoisothiazolidin-2-yl)butyl, and tetrahydro-2H-pyran-4-ylmethyl.
9. The compound or salt of claim 1 wherein $R_2$ is selected from the group consisting of hydrogen, methyl, ethyl, propyl, butyl, ethoxymethyl, methoxymethyl, 2-methoxyethyl, hydroxymethyl, and 2-hydroxyethyl.
10. The compound or salt of claim 4 wherein Q is —C($R_6$)—, —S(O)$_2$—, or —C($R_6$)—N($R_8$)—.
11. The compound or salt of claim 1 wherein $R_1$ is selected from the group consisting of alkyl, hydroxyalkylenyl, alkoxyalkylenyl, and alkyl substituted by tetrahydropyranyl.

12. The compound or salt of claim 1 wherein $R_1$ is alkyl substituted by —NH—S(O)$_2$-alkyl.

13. The compound or salt of claim 1 wherein $R_1$ is selected from the group consisting of 2-hydroxy-2-methylpropyl, 2-methylpropyl, 4-[(methylsulfonyl)amino]butyl, 2-methyl-2-[(methylsulfonyl)amino]propyl, tetrahydro-2H-pyran-4-ylmethyl, and 3-isopropoxypropyl.

14. The compound or salt of claim 11 wherein $R_1$ is selected from the group consisting of 2-hydroxy-2-methylpropyl, 2-methylpropyl, tetrahydro-2H-pyran-4-ylmethyl, and 3-isopropoxypropyl.

15. A compound selected from the group consisting of:
2-ethyl-7-[2-(methylsulfonyl)ethyl]-1-(tetrahydro-2H-pyran-4-ylmethyl)-1H-imidazo[4,5-c]quinolin-4-amine;
N-{3-[4-amino-2-ethyl-1-(tetrahydro-2H-pyran-4-ylmethyl)-1H-imidazo[4,5-c]quinolin-7-yl]propyl}methane sulfonamide;
N-{3-[4-amino-2-ethyl-1-(tetrahydro-2H-pyran-4-ylmethyl)-1H-imidazo[4,5-c]quinolin-7-yl]propyl}acetamide;
N-{3-[4-amino-2-ethyl-1-(tetrahydro-2H-pyran-4-ylmethyl)-1H-imidazo[4,5-c]quinolin-7-yl]propyl}-N'-isopropylurea;
3-[4-amino-2-ethyl-1-(tetrahydro-2H-pyran-4-ylmethyl)-1H-imidazo[4,5-c]quinolin-7-yl]-N,N-dimethylpropanamide;
or a pharmaceutically acceptable salt thereof.

16. A compound selected from the group consisting of:
3-[4-amino-2-ethyl-1-(2-hydroxy-2-methylpropyl)-1H-imidazo[4,5-c]quinolin-7-yl]-1-(morpholin-4-yl)propan-1-one;
1-{4-amino-7-[2-(methylsulfonyl)ethyl]-1H-imidazo[4,5-c]quinolin-1-yl}-2-methylpropan-2-ol;
3-[4-amino-2-ethyl-1-(2-hydroxy-2-methylpropyl)-1H-imidazo[4,5-c]quinolin-7-yl]-N,N-dimethylpropanamide;
1-{4-amino-2-(methoxymethyl)-7-[2-(methylsulfonyl)ethyl]-1H-imidazo[4,5-c]quinolin-1-yl}-2-methylpropan-2-ol;
1-{4-amino-2-(hydroxymethyl)-7-[2-(methylsulfonyl)ethyl]-1H-imidazo[4,5-c]quinolin-1-yl}-2-methylpropan-2-ol;
1-[4-amino-2-(methoxymethyl)-7-(3-morpholin-4-yl-3-oxopropyl)-1H-imidazo[4,5-c]quinolin-1-yl]-2-methylpropan-2-ol;
1-[4-amino-7-[3-(1,1-dioxidothiomorpholin-4-yl)-3-oxopropyl]-2-(methoxymethyl)-1H-imidazo[4,5-c]quinolin-1-yl]-2-methylpropan-2-ol;
3-[4-amino-1-(2-hydroxy-2-methylpropyl)-2-(methoxymethyl)-1H-imidazo[4,5-c]quinolin-7-yl]-N,N-dimethylpropanamide;
N-{3-[4-amino-1-(2-hydroxy-2-methylpropyl)-2-(methoxymethyl)-1H-imidazo[4,5-c]quinolin-7-yl]propyl}methanesulfonamide;
3-[4-amino-2-(hydroxymethyl)-1-(2-hydroxy-2-methylpropyl)-1H-imidazo[4,5-c]quinolin-7-yl]-N,N-dimethylpropanamide;
1-[4-amino-2-(hydroxymethyl)-7-(3-morpholin-4-yl-3-oxopropyl)-1H-imidazo[4,5-c]quinolin-1-yl]-2-methylpropan-2-ol;
3-[4-amino-1-(2-hydroxy-2-methylpropyl)-2-(methoxymethyl)-1H-imidazo[4,5-c]quinolin-7-yl]propanamide;
1-[4-amino-7-[3-(1,1-dioxidothiomorpholin-4-yl)-3-oxopropyl]-2-(hydroxymethyl)-1H-imidazo[4,5-c]quinolin-1-yl]-2-methylpropan-2-ol;
N-{3-[4-amino-1-(2-hydroxy-2-methylpropyl)-2-(methoxymethyl)-1H-imidazo[4,5-c]quinolin-7-yl]propyl}acetamide;
N-{3-[4-amino-2-(hydroxymethyl)-1-(2-hydroxy-2-methylpropyl)-1H-imidazo[4,5-c]quinolin-7-yl]propyl}methanesulfonamide;
N-{2-[4-amino-2-ethyl-1-(2-hydroxy-2-methylpropyl)-1H-imidazo[4,5-c]quinolin-7-yl]ethyl}methanesulfonamide;
1-[4-amino-2-(ethoxymethyl)-7-(3-morpholin-4-yl-3-oxopropyl)-1H-imidazo[4,5-c]quinolin-1-yl]-2-methylpropan-2-ol;
or a pharmaceutically acceptable salt thereof.

17. A compound selected from the group consisting of:
1-{3-[4-amino-2-(2-methoxyethyl)-8-(3-morpholin-4-yl-3-oxo-propyl)-1H-imidazo[4,5-c]quinolin-1-yl]propyl}pyrrolidin-2-one;
3-{4-amino-2-(2-methoxyethyl)-1-[3-(2-oxo-pyrrolidin-1-yl)propyl]-1H-imidazo[4,5-c]quinolin-8-yl}-N,N-dimethylpropanamide;
N-[4-amino-2-ethoxymethyl-1-(2-hydroxy-2-methylpropyl)-1H-imidazo[4,5-c]quinolin-7-yl]ethanesulfonamide;
or a pharmaceutically acceptable salt thereof.

18. The compound or salt of claim 4 wherein $R_8$ is hydrogen; Q is —C(O)—, —S(O)$_2$—, or —C(O)—NH—; and $R_4$ is alkyl.

19. The compound or salt of claim 1 wherein $R_3$ is -Z-$R_5$.

20. The compound or salt of claim 19 wherein Z is $C_{2-4}$ alkylene and $R_5$ is

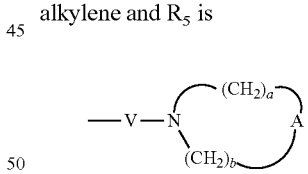

wherein a and b are both 2.

* * * * *

UNITED STATES PATENT AND TRADEMARK OFFICE
CERTIFICATE OF CORRECTION

| | | |
|---|---|---|
| PATENT NO. | : 8,658,666 B2 | Page 1 of 4 |
| APPLICATION NO. | : 11/884191 | |
| DATED | : February 25, 2014 | |
| INVENTOR(S) | : Michael Rice | |

It is certified that error appears in the above-identified patent and that said Letters Patent is hereby corrected as shown below:

Title Page, References Cited

Page 3, Column 2 (Other Publications)
Line 5, Delete "3-aminopryidines.""" and insert -- 3-aminopyridines." --, therefor.
Line 18, Delete "DeClerq," and insert -- DeClercq, --, therefor.

In the Specification

Column 4
Line 6, Delete "substitutents;" and insert -- substituents; --, therefor.

Column 5
Line 19-20, Delete "heteroarylalklenyl;" and insert -- heteroarylalkylenyl; --, therefor.
Line 28, Delete "-S(O)$_2$-N(R$_9$)-," and insert -- -S(O)2-N(R$_8$)-, --, therefor.
Line 29, Delete "-N(OR$_5$)-;" and insert -- -N(OR$_9$)-; --, therefor.

Column 7
Line 14, Delete "allylamino," and insert -- alkylamino, --, therefor.
Line 14-15, Delete "diallylamino," and insert -- dialkylamino, --, therefor.
Line 57-58, Delete "heteroarylalklenyl;" and insert -- heteroarylalkylenyl; --, therefor.

Column 10
Line 21, Delete "hydroxyallyl," and insert -- hydroxyalkyl, --, therefor.
Line 22-23, Delete "diallylamino," and insert -- dialkylamino, --, therefor.
Line 66-67, Delete "heteroarylalklenyl;" and insert -- heteroarylalkylenyl; --, therefor.

Column 14
Line 16-17, Delete "heteroarylalklenyl;" and insert -- heteroarylalkylenyl; --, therefor.

Signed and Sealed this
Twenty-third Day of December, 2014

Michelle K. Lee
*Deputy Director of the United States Patent and Trademark Office*

CERTIFICATE OF CORRECTION (continued)

Column 16
Line 47-48, Delete "heteroarylalklenyl;" and insert -- heteroarylalkylenyl; --, therefor.
Line 57, Delete "-N(OR₅)-;" and insert -- -N(OR₉)-; --, therefor.
Line 63, Delete "≤7;" and insert -- ≤7, --, therefor.

Column 17
Line 32, Delete "substitutent." and insert -- substituent. --, therefor.

Column 20
Line 21, Delete "non-interfereing" and insert -- non-interfering --, therefor.

Line 46-49, Delete " " and insert -- .--, therefor.

Column 21
Line 30, Delete "amino)}" and insert -- amino} --, therefor.
Line 42, Delete "then" and insert -- than --, therefor.

Column 23
Line 38, Delete "dihydroisoquinolin-(1)-yl," and insert -- dihydroisoquinolin-(1H)-yl, --, therefor.
Line 42, Delete "substitutents." and insert -- substituents. --, therefor.
Line 46, Delete "substitutents." and insert -- substituents. --, therefor.

Column 25
Line 52, Delete "-CH(OC₁₄" and insert -- -CH(OC₁₋₄ --, therefor.

Column 26
Line 34, Delete "-N(R₉)-," and insert -- -N(R₈)-, --, therefor.
Line 38, Delete "-N(R₅)-," and insert -- -N(R₈)-, --, therefor.
Line 41, Delete "-N(R₅)-Q-." and insert -- -N(R₈)-Q-. --, therefor.

Column 28
Line 44, Delete "diallylamino," and insert -- dialkylamino, --, therefor.
Line 53, Delete "substitutents." and insert -- substituents. --, therefor.

Column 29
Line 7, Delete "substitutents." and insert -- substituents. --, therefor.

Column 30
Line 47, Delete "allyl" and insert -- alkyl --, therefor.

Column 37
Line 54, Delete "C₁-R₇S(O)₂Cl" and insert -- Cl-R₇S(O)₂Cl --, therefor.

CERTIFICATE OF CORRECTION (continued)
U.S. Pat. No. 8,658,666 B2

Line 55, Delete "$C_1$-$R_7C(O)_2Cl$." and insert -- $Cl$-$R_7C(O)_2Cl$. --, therefor.

Column 38
Line 3, Delete "$R_4N=C=O$," and insert -- $R_4N=C=O$. --, therefor.

Column 55
Line 11-12, Delete "pneumocystis carnii" and insert -- pneumocystis carinii --, therefor.
Line 26, Delete "Ommen's" and insert -- Omenn's --, therefor.
Line 29, Delete "greata;" and insert -- areata; --, therefor.
Line 47, Delete "hemophilus" and insert -- haemophilus --, therefor.

Column 62
Line 31, Delete "-H-imi-" and insert -- -1H-imi- --, therefor.

Column 71
Line 66, Delete "$C_{18}H_{20}N_4O_3$ 0.5 $CH_3OH$:" and insert -- $C_{18}H_{20}N_4O_3 \cdot 0.5\ CH_3OH$: --, therefor.

Column 73
Line 36, Delete "$C_{20}H_{24}N_4O_3$ 1.0 $CH_3OH$:" and insert -- $C_{20}H_{24}N_4O_3 \cdot 1.0\ CH_3OH$: --, therefor.

Column 78
Line 20, Before "  " delete " ".

Column 79
Line 20, Before "  " delete " ".

Column 80
Line 20, Before "  " delete " ".

Column 86
Line 21, Delete "isocyante" and insert -- isocyanate --, therefor.
Line 30, Delete "isocyante" and insert -- isocyanate --, therefor.

Column 105
Line 30, Delete "-IH-imidazo" and insert -- 1H-imidazo --, therefor.

Column 128
Line 66, Delete "$C_{23}H_{31}N_5O_2H_2O$:" and insert -- $C_{23}H_{31}N_5O_2 \cdot H_2O$: --, therefor.

Column 141
Line 10, Delete "(1 molar)" and insert -- (μmolar) --, therefor.

CERTIFICATE OF CORRECTION (continued)
U.S. Pat. No. 8,658,666 B2

In the Claims

Column 143
Line 53, In Claim 1, delete "yl;" and insert -- yl; --, therefor.